(12) United States Patent
Whiteford et al.

(10) Patent No.: US 7,368,564 B2
(45) Date of Patent: May 6, 2008

(54) BRIDGED MACROCYCLIC MODULE COMPOSITIONS

(75) Inventors: Jeffery A. Whiteford, Belmont, CA (US); William Freeman, Anaheim, CA (US); Joshua W. Kriesel, San Francisco, CA (US)

(73) Assignee: Covalent Partners, LLC, Hayward, CA (US)

( * ) Notice: Subject to any disclaimer, the term of this patent is extended or adjusted under 35 U.S.C. 154(b) by 277 days.

(21) Appl. No.: 10/913,634

(22) Filed: Aug. 6, 2004

(65) Prior Publication Data

US 2005/0154199 A1 Jul. 14, 2005

Related U.S. Application Data

(60) Provisional application No. 60/492,808, filed on Aug. 6, 2003.

(51) Int. Cl.
*C07K 1/10* (2006.01)
*C07D 487/22* (2006.01)
*C07D 491/14* (2006.01)

(52) U.S. Cl. ............... 540/145; 525/327.4; 525/329.5; 205/751

(58) Field of Classification Search ............... 540/145; 525/327.4, 329.5; 205/751
See application file for complete search history.

(56) References Cited

OTHER PUBLICATIONS

Kwit et al, Tetrahedron: Asymmetry, vol. 14, pp. 1303-1308, 2003.*
Korupoju et al, Inorganic Chemistry, vol. 41, No. 16, 2002, pp. 4099-4101.*
Coope et al. "Predictive blood glucose lowering efficacy by glucokinase activators in high fat fed female Zucker rats" British Journal of Pharmacology 149:328-335 (2006).
Gill et al. "Stimulation of insulin release in MIN6 cells and isolated rodent islets by a small molecule glucokinase activator (GKA50)" poster presented at 42nd EASD Meeting Copenhagen (2006).
Gill et al. "Upregulation of key β-cell genes and improvement of function in rodent islets following chronic in vitro treatment with a glucokinase activator" poster presented at 43rd EASD Meeting, Amsterdam (Sep. 17-21, 2007).
Gorman et al. "Effect of high-fat diet on glucose homeostasis and gene expression in glucokinase (GK) Heterozygous Knock-Outs" Abstract No. 0108-OR, 67th Annual ADA Scientific Sessions (2007).
Johnson et al. "Glucose-dependent modulation of insulin secretion and intracellular calcium ions by GKA50 - A glucokinase activator" Abstract No. 0592-P, 67th Annual ADA Scientific Sessions (2007).
Leighton et al. "Improved glycemic control after sub-acute administration of a glucokinase activator to male zucker (fa/fa) rats" Abstract No. 0377-OR, 67th Annual ADA Scientific Sessions (2007).
McKerrecher et al. "Design and synthesis of novel glucokinase activators as potention treatments for type 2 diabetes" 233rd National Meeting and Exposition, Chicago, IL (Mar. 25-29, 2007).
McKerrecher et al. "Identification of orally bioavailable small molecule activators of glucokinase" Abstract, 12th SCI-RSC Medicinal Chemistry Symposium, Cambridge, UK, Sep. 7-10, 2003 (poster 21) and 227th American Chemical Society National Meeting and Exposition, San Francisco, California, Mar. 28-Apr. 1, 2004 (paper 341).
Winzell et al. "Glucokinase activation reduces glycemia and improves glucose tolerance in mice with high-fat diet-induced insulin resistance" Abstract No. 1482-P, 67th Annual Scientific Sessions (2007).
RAJCA et al., "Biphenylene dimer. Molecular fragment of a two-dimensional carbon net and double-stranded polymer," *J. Am. Chem. Soc.*, 118:7272-7279 (1996).
Kanamathareddy et al., "Conformational characteristics of *p-tert*-Butylcalix[6]arene ethers," *J. Org. Chem.*, 59:3871-3879 (1994).
Hendel et al., "Assembly and Disassembly of Langmuir-Blodgett Films on Poly[1-(trimethylsilyl)-1-propyne]: The Uniqueness of Calix[6]arene Multilayers as Permeation-Selective Membranes," *J. Am. Chem. Soc.*, 119:6909-6918 (1997).

* cited by examiner

*Primary Examiner*—Shailendra Kumar
(74) *Attorney, Agent, or Firm*—Finnegan, Henderson, Farabow, Garrett & Dunner, LLP

(57) ABSTRACT

This invention is related to the fields of organic chemistry and nanotechnology. In particular, it relates to materials and methods for the preparation of organic synthons and bridged macrocyclic module compounds. The bridged macrocyclic module compounds may be used to prepare macrocyclic compositions such as nanofilms, which may be useful for filtration.

34 Claims, 6 Drawing Sheets

BRIDGED MACROCYCLIC MODULE COMPOSITIONS

CROSS-REFERENCE TO RELATED APPLICATIONS

This application claims the benefit under 35 U.S.C. §119 (e) of U.S. Provisional Application No. 60/492,808 filed on Aug. 6, 2003, the disclosure of which is hereby incorporated by reference in its entirety.

TECHNICAL FIELD

This invention is related to the fields of organic chemistry and nanotechnology. In particular, it relates to materials and methods for the preparation of organic synthons and bridged macrocyclic module compositions. The bridged macrocyclic module compositions may be used to prepare macromolecular compositions such as nanofilms, which may be useful for filtration.

BACKGROUND OF THE INVENTION

One area of nanotechnology is to develop chemical building blocks from which hierarchical macrcmolecules of predicted properties can be assembled. An approach to making chemical building blocks or nanostructures begins at the atomic and molecular level by designing and synthesizing starting materials with highly tailored properties. Precise control at the atomic level is the foundation for development of rationally tailored synthesis-structure-property relationships which can provide materials of unique structure and predictable properties. This approach to nanotechnology is inspired by nature where, for example, from twenty common amino acids found in natural proteins, more than $10^5$ stable and unique proteins are made.

Nanotechnology has also been described by K. Eric Drexler in *Engines of Creation* as "the knowledge and means for designing, fabricating and employing molecular scale devices by the manipulation and placement of individual atoms and molecules with precision on the atomic scale." A quest of nanotechnology is to prepare molecular architectures capable of performing on a nanometer scale functions normally observed for large-scale constructs. For example, rotaxanes and polyrotaxanes are molecules that are interlocked, but not chemically bound to one another, which act like nano-machines. In other examples, carbon nanotubes and similar constructs have been created which may function as molecular scaffold units, or as transport channels, storage units, or encapsulators for various atoms and molecules. The use of biological processes is also being studied as an approach to the assembly of non-biological nano-devices.

A hurdle in developing "building block" nanotechnology is creating the ability to program the final output of a chemical reaction between the reactants from which the building blocks are formed. In other words, it is desirable to control the geometry of the building block reactants in order to predetermine which product will be built from the reactants. The product will be the thermodynamically favored product in most cases, however, the programming of geometrical constraints into the reactants overrides the random statistics of bulk phase macroscopic interactions and effectively limits the reaction at the atomic level.

Entropically driven self assembly processes may be used to produce hierarchical products which are typically well-organized aggregates. Although such processes may be robust in tolerating a range of conditions, they are generally very limited in synthetic accessibility and produce a narrow range of products.

Most conventional methods of preparation of organic compounds involve stepwise attachment of species to form a product. Step-by-step synthesis can be an arduous route to prepare molecules, even some relatively simple molecules. Random statistics plays a role in every step and can make it impossible to achieve multistep products. For example, a collection of cyclic synthons may be coupled in stepwise synthesis to yield macrocyclic modules, however, the yield in many cases is relatively low, or may even be prohibitive.

One application that will benefit from nanotechnology is filtration using membranes. Conventional membranes used in a variety of separation processes can be made selectively permeable to various molecular species. The permeation properties of conventional membranes generally depend on the pathways of transport of species through the membrane structure. While the diffusion pathway in conventional selectively permeable materials can be made tortuous in order to control permeation, porosity is not well defined or controlled by conventional methods. The ability to fabricate regular or unique pore structures of membranes is a long-standing goal of separation technology.

Thus, what is needed is an approach to making chemical entities in the form of bridged macrocyclic module compositions from which to create nanostructures with desirable properties.

All documents referenced herein, including applications for patent, patent references, publications, articles, books, and treatises, are specifically incorporated by reference herein in their entirety.

BRIEF SUMMARY OF THE INVENTION

A bridged macrocyclic module compound of the formula:

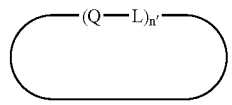

wherein the compound further comprises a bridge moiety A having two or more termini, wherein at least two of said two or more termini are coupled to the compound; wherein each Q is a synthon independently selected from the group consisting of: benzene, cyclohexadiene, cyclopentadiene, naphthalene, anthracene, phenylene, phenanthracene, pyrene, triphenylene, phenanthrene, pyridine, pyrimidine, pyridazine, biphenyl, bipyridyl, cyclohexane, cyclohexene, decalin, piperidine, pyrrolidine, morpholine, piperazine, pyrazolidine, quinuclidine, tetrahydropyran, dioxane, tetrahydrothiophene, tetrahydrofuran, pyrrole, cyclopentane, cyclopentene, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, spiro[4.4]nonane, —OCH$_2$CH$_2$—, —(CH$_2$)$_n$C≡C(CH$_2$)$_{n'}$—, —(CH$_2$)$_n$CH═CH(CH$_2$)$_{n'}$—,

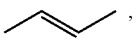

$-(CH_2)_n-$, $-C(O)O(CH_2)_n-$, $-(CH_2)_nC(O)NR-$; $-S_m-$, $-(CH_2)_nSiMe_2(CH_2)_n-$, $-(CH_2)_nNR(CH_2)_n-$, and $-(CH_2)_nCH(OH)-$; wherein each synthon Q may optionally be substituted with one or more functional groups for coupling the synthon to at least a second bridged macrocyclic module or to a substrate; wherein each synthon may optionally be substituted with one or more lipophilic and/or hydrophilic groups; wherein each L is a linkage moiety independently selected from the group consisting of a direct bond, $-NRC(O)-$, $-OC(O)-$, $-O-$, $-S-S-$, $-S-$, $-NR-$, $-(CRR)_p-$, $-CH_2NH-$, $-C(O)S-$, $-C(O)O-$, $-C\equiv C-$, $-C\equiv C-C\equiv C-$, $-CH(OH)-$, $-HC=CH-$, $-NHC(O)NH-$, $-NHC(O)O-$, $-NHCH_2NH-$, $-NHCH_2CH(OH)CH_2NH-$, $-N=CH(CH_2)_pCH=N-$, $-CH_2CH(OH)CH_2-$, $-N=CH(CH_2)_nCH=N-$, $-CH=N-NH-$, $-OC(O)O-$, $-OP(O)(OH)O-$, $-CH(OH)CH_2NH-$, $-CH(OH)CH_2-$, $-CH(OH)C(CH_3)_2C(O)O-$,

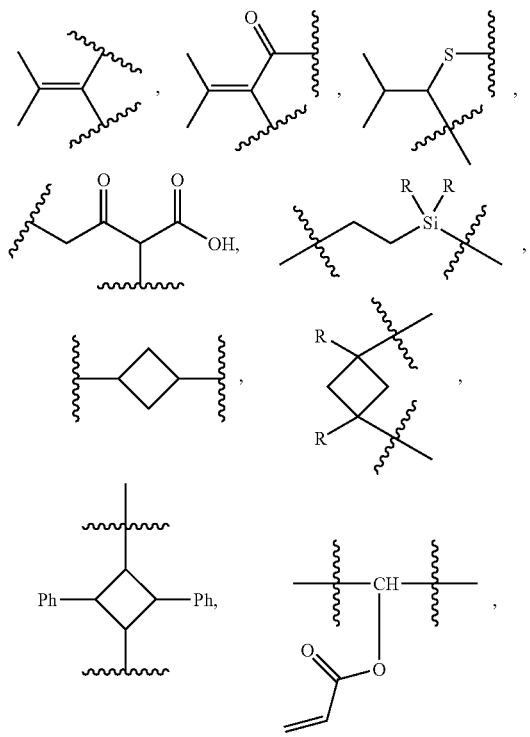

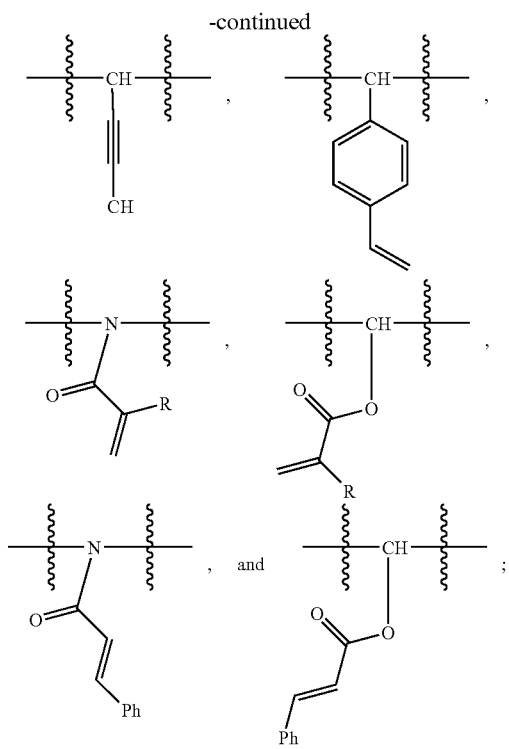

wherein the linkage is independently configured in either of two possible configurations, forward and reverse, with respect to the synthons it couples together; wherein the bridge moiety A is selected from the group consisting of:

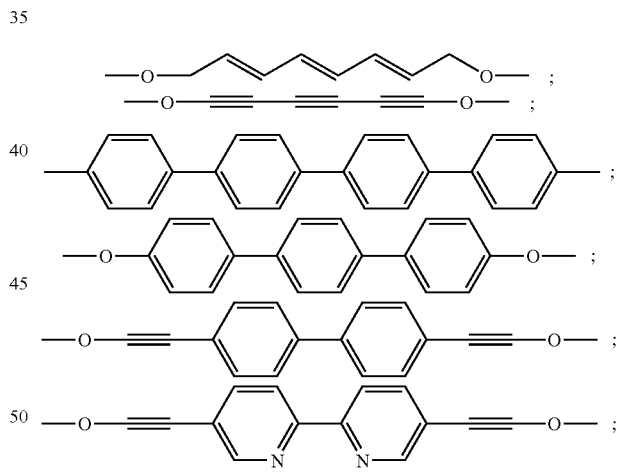

$-O-(CH_2)_m-O-$;   $-\{NH-CHR-(CO)\}_m-O-$;
$-O-(CF_2)_m-O-$;   $-(S)_m-$;   $-O(CH_2CH_2O)_m-$;
$-(OCH(CH_3)CH_2)_mO-$;

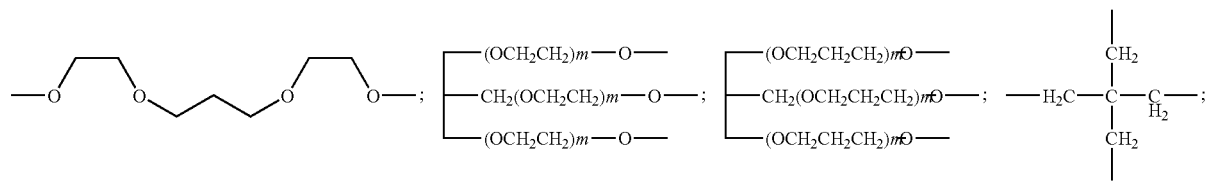

-continued
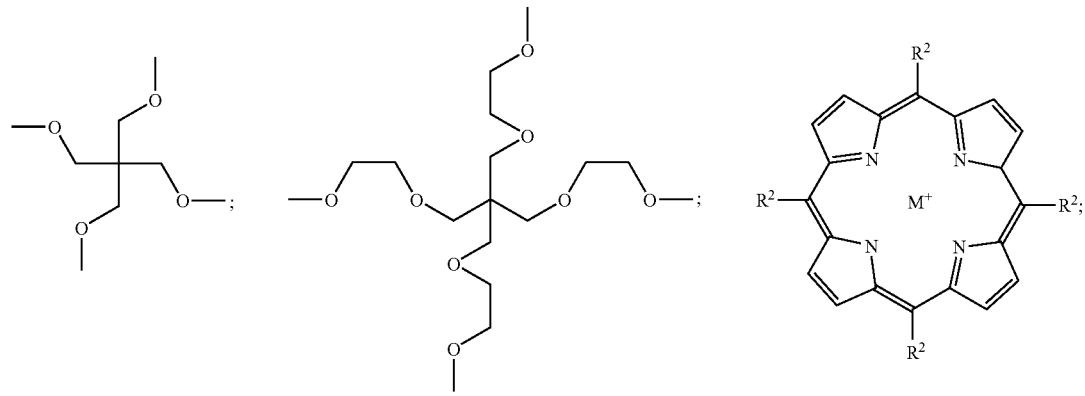
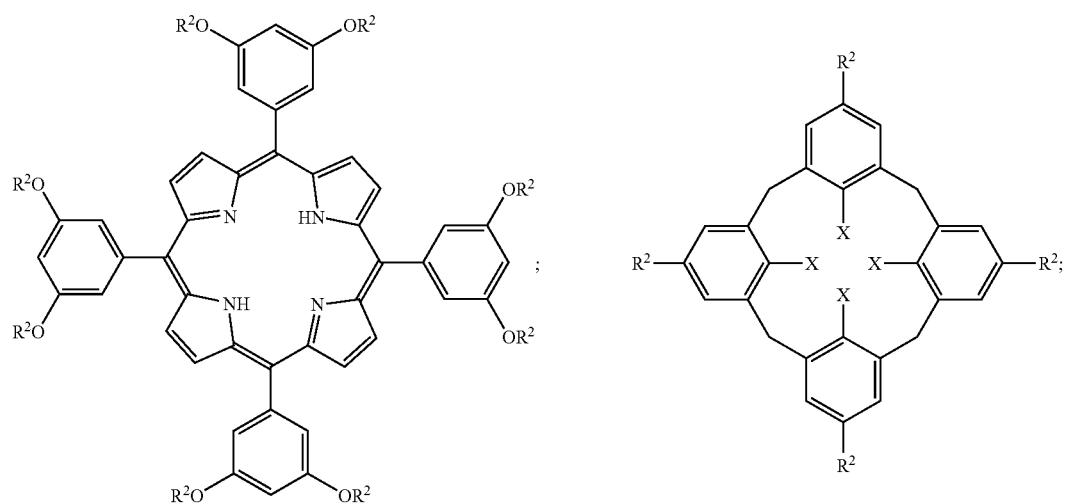
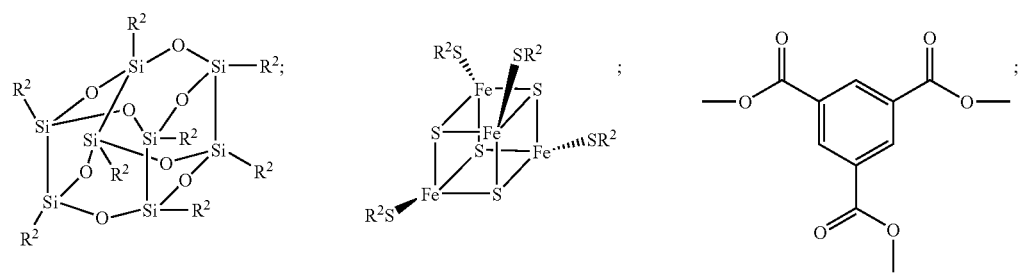
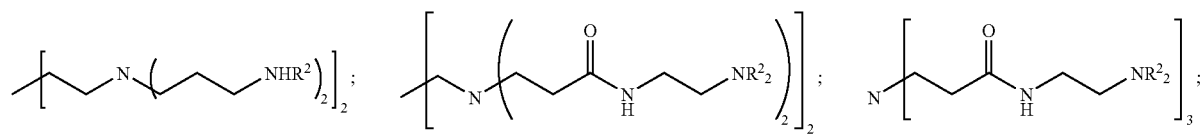
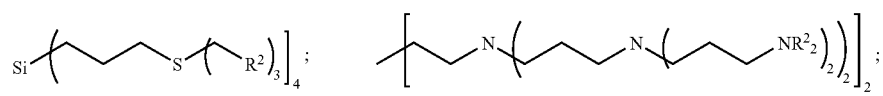
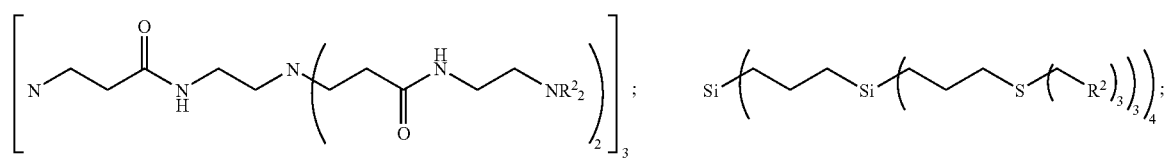

-continued
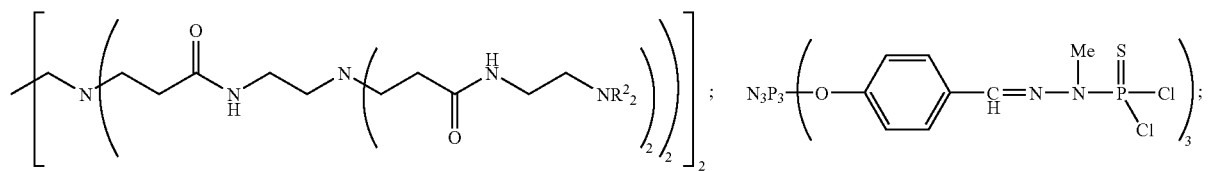
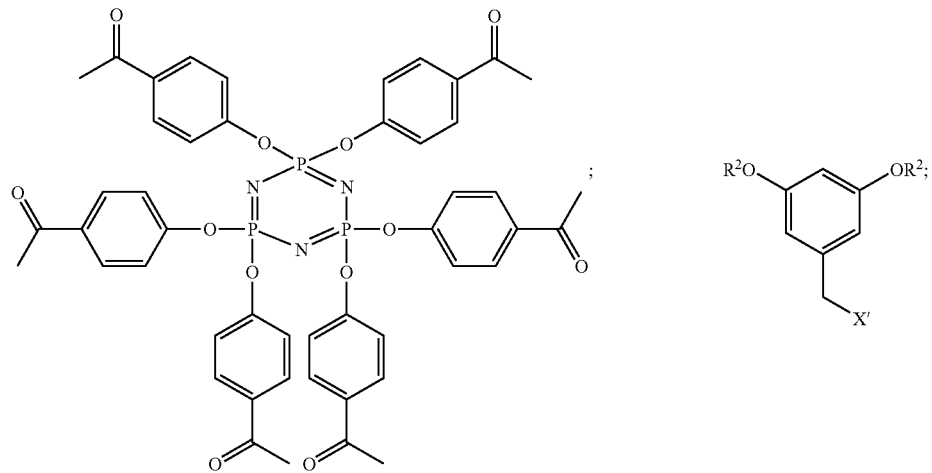
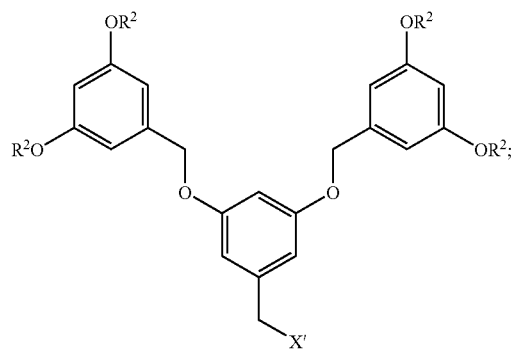
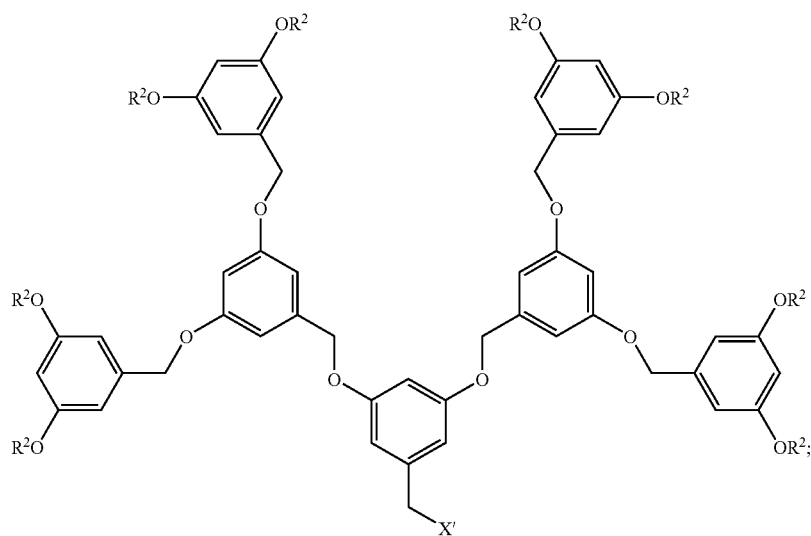

-continued
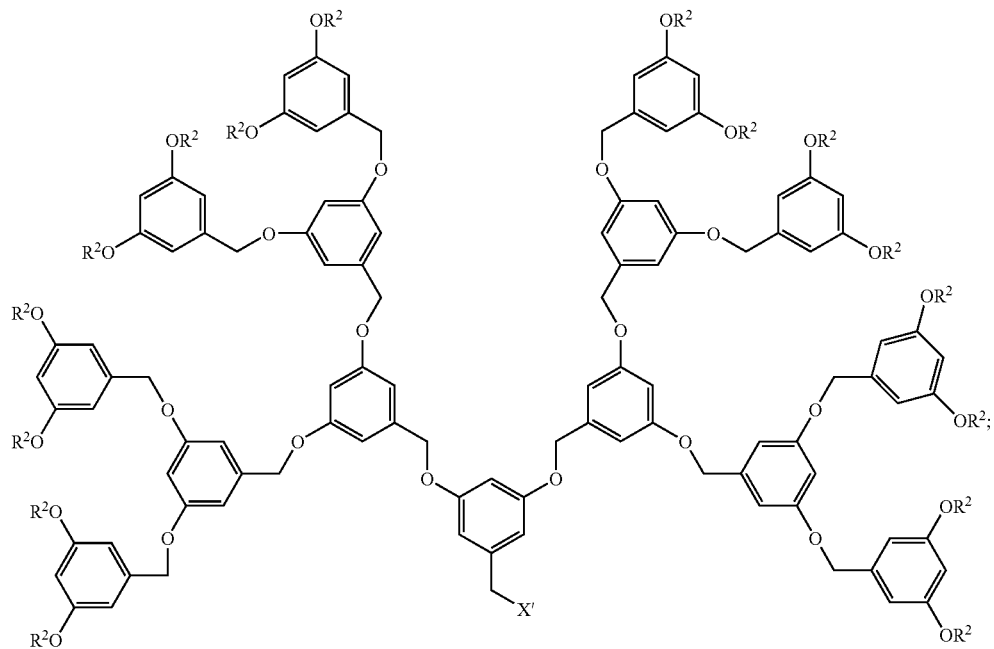
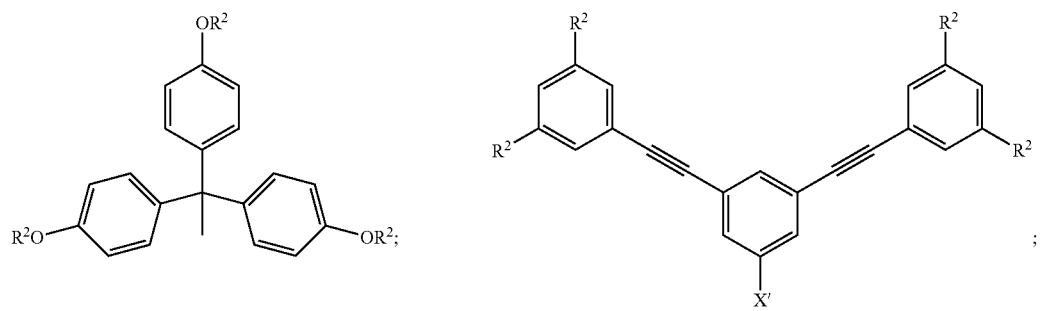
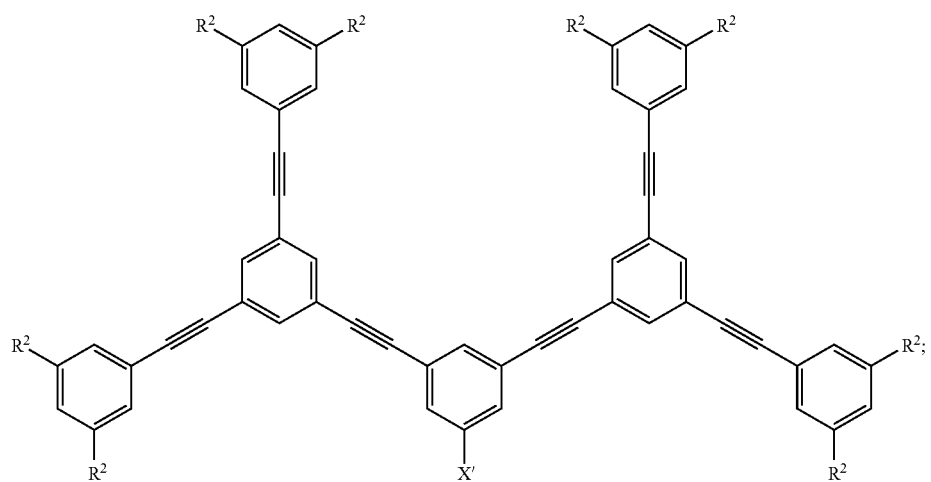

-continued

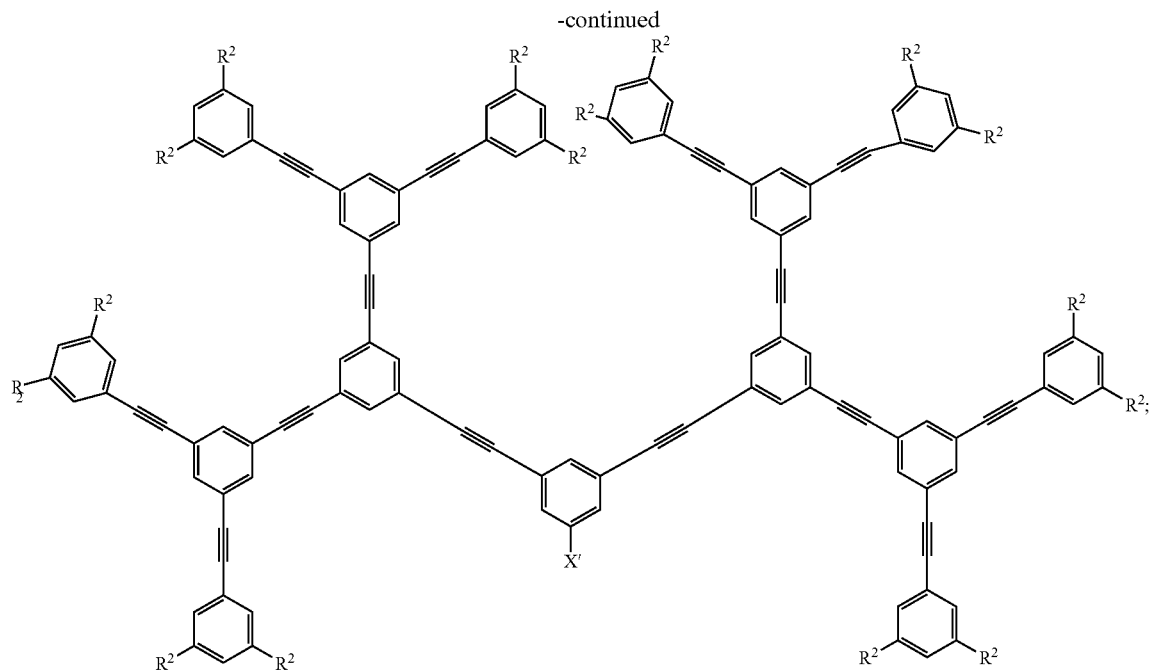

wherein the at least two termini of the bridge moiety may be conjugated to the compound through a linkage moiety L, wherein L is as defined above; wherein R is independently selected from the group consisting of hydrogen and alkyl; wherein Ph is phenyl; wherein X is selected from the group consisting of F, Cl, Br, and I; wherein X' is H or a functional group for linking to at least a second bridged macrocyclic moiety or a substrate; wherein each $R^2$ is independently selected from a bond for linking to a synthon or a functional group selected from the group consisting of hydrogen, an activated acid, —OH, —C(O)OH, —C(O)H, —C(O)OCH$_3$, —C(O)Cl, —NRR, —NRRR$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR, —CH=CRR, 4-vinylaryl, —C(O)CH=CH$_2$, —NHC(O)CH=CH$_2$, —C(O)CH=CH(C$_6$H$_5$),

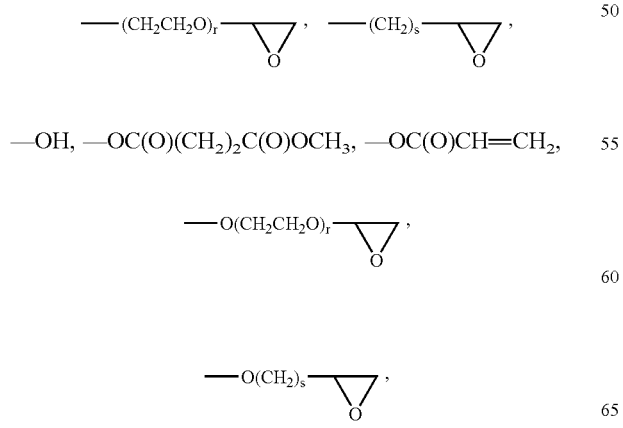

—P(O)(OH)(OX), or —P(=O)(O$^-$)O(CH$_2$)$_s$NR$_3^+$; wherein n' is from 4 to 50; wherein n is 1-22; wherein m is 2-14; wherein p is 1-6; wherein h is 1-4; wherein r is 1-50; and wherein s is 1-4.

In one embodiment, the two or more termini of said bridge moiety are coupled to synthons. In another embodiment, the two or more termini of said bridge moiety are coupled to L moieties, with the proviso that said L moieties to which the termini are coupled are not direct bonds.

In one embodiment, n is from 4 to 24. In another embodiment, n is from 6 to 16. In another embodiment, n is from 6 to 12. In other embodiments, n may be, for example, 4, 6, 8, 10, 12, 14, or 16.

In another embodiment, the bridged macrocyclic module compound has the formula:

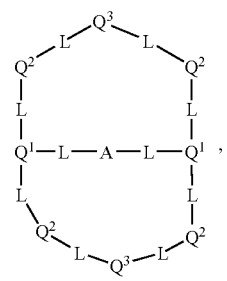

wherein $Q^1$, $Q^2$ and $Q^3$ are as defined for Q above, L is as defined above, and A is a bridge moiety as defined above. In another embodiment, the bridged macrocyclic module compound has the formula:

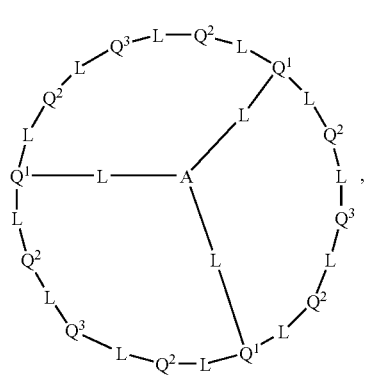

wherein $Q^1$, $Q^2$ and $Q^3$ are as defined for Q above, L is as defined above, and A is a bridge moiety as defined above. In another embodiment, the bridged macrocyclic module compound has the formula:

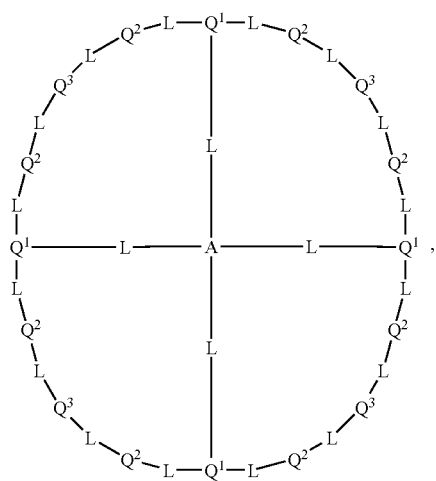

wherein $Q^1$, $Q^2$ and $Q^3$ are as defined for Q above, L is as defined above, and A is a bridge moiety as defined above.

In another embodiment, each $Q^1$ is the same synthon. In another embodiment, each $Q^2$ is the same synthon. In another embodiment, each $Q^3$ is the same synthon.

In another embodiment, $Q^1$, $Q^2$, and $Q^3$ are synthons independently selected from the group consisting of

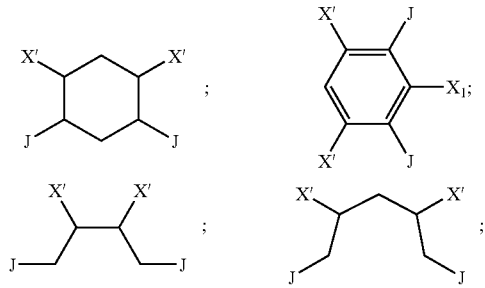

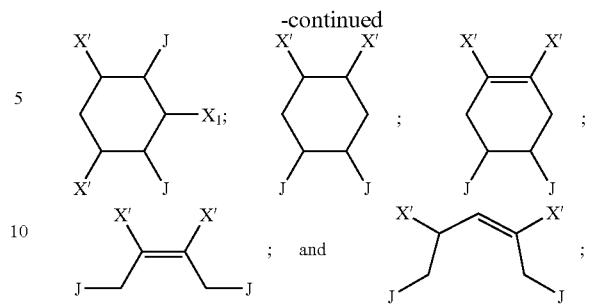

wherein each X' is independently H or a functional group for coupling the synthon to at least a second bridged macrocyclic module or to a substrate, wherein each J is an independently selected functional group for coupling the synthon to an adjacent synthon within said bridged macrocyclic module, and wherein each $X_1$ is an independently selected functional group which may couple the synthon to the bridge moiety. In another embodiment, each $Q^1$, $Q^2$, and $Q^3$ is independently selected from the group consisting of

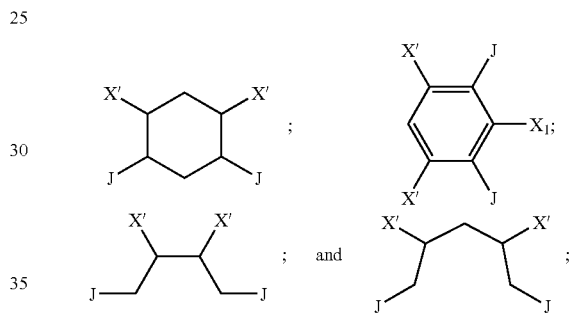

wherein each X' is independently H or a functional group for coupling the synthon to at least a second bridged macrocyclic module or to a substrate, wherein each J is an independently selected functional group for coupling the synthon to an adjacent synthon within said bridged macrocyclic module, and wherein each $X_1$ is an independently selected functional group which may couple the synthon to the bridge moiety. In a preferred embodiment, each $Q^1$, $Q^2$, and $Q^3$ is independently selected from the group consisting of

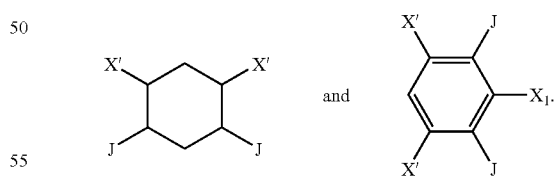

In another embodiment, each linker moiety L between the synthons is the same. In another embodiment, each linker moiety L between the bridge moiety and the synthons is the same.

In another embodiment, the synthons are cyclic synthons. In another embodiment, the synthons are acyclic synthons. In another embodiment, the synthons alternate between cyclic and acyclic synthons. In one embodiment, the synthons are independently selected from the group consisting of benzene, cyclohexadiene, cyclopentadiene, naphthalene, anthracene, phenylene, phenanthracene, pyrene, triphenylene, phenanthrene, pyridine, pyrimidine, pyridazine, biphenyl, bipyridyl, cyclohexane, cyclohexene, decalin, piperidine, pyrrolidine, morpholine, piperazine, pyrazolidine, quinuclidine, tetrahydropyran, dioxane, tetrahydrothiophene, tetrahydrofuran, pyrrole, cyclopentane, cyclopentene, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, spiro[4.4]nonane. In another embodiment, the synthons are independently selected from the group consisting of —OCH$_2$CH$_2$—, —(CH$_2$)$_n$C≡C(CH$_2$)$_n$—, —(CH$_2$)$_n$CH═CH(CH$_2$)$_n$—

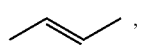,

—(CH$_2$)$_n$—, —C(O)O(CH$_2$)$_n$—, —(CH$_2$)$_n$C(O)NR—; —S$_m$—, —(CH$_2$)$_n$SiMe$_2$(CH$_2$)$_n$—, —(CH$_2$)$_n$NR(CH$_2$)$_n$—, and —(CH$_2$)$_n$CH(OH)—. In a preferred embodiment, the synthons are independently selected from benzene, piperidine, and cyclohexane. In another preferred embodiment, the synthons are independently selected from benzene and cyclohexane.

In one embodiment, each L is a bond. In another embodiment, L is a linkage independently selected from the group consisting of —NRC(O)—, —OC(O)—, —O—, —S—S—, —S—, —NR—, —(CRR)$_p$—, —CH$_2$NH—, —CH═N—, —C(O)S—, —C(O)O—, —C≡C—, —C≡C—C≡C—, —CH(OH)—, —HC═CH—, —NHC(O)NH—, —NHC(O)O—, —NHCH$_2$NH—, —NHCH$_2$CH(OH)CH$_2$NH—, —N═CH(CH$_2$)$_p$CH═N—, —CH$_2$CH(OH)CH$_2$—, —N═CH(CH$_2$)$_h$CH═N—, —CH═N—NH—, —OC(O)O—, —OP(O)(OH)O—, —CH(OH)CH$_2$NH—, —CH(OH)CH$_2$—, —CH(OH)C(CH$_3$)$_2$C(O)O—,

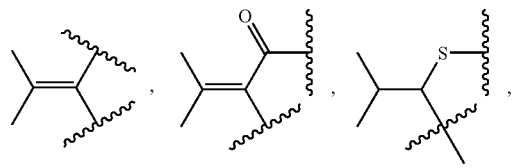

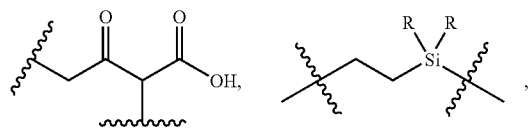

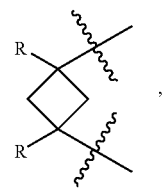

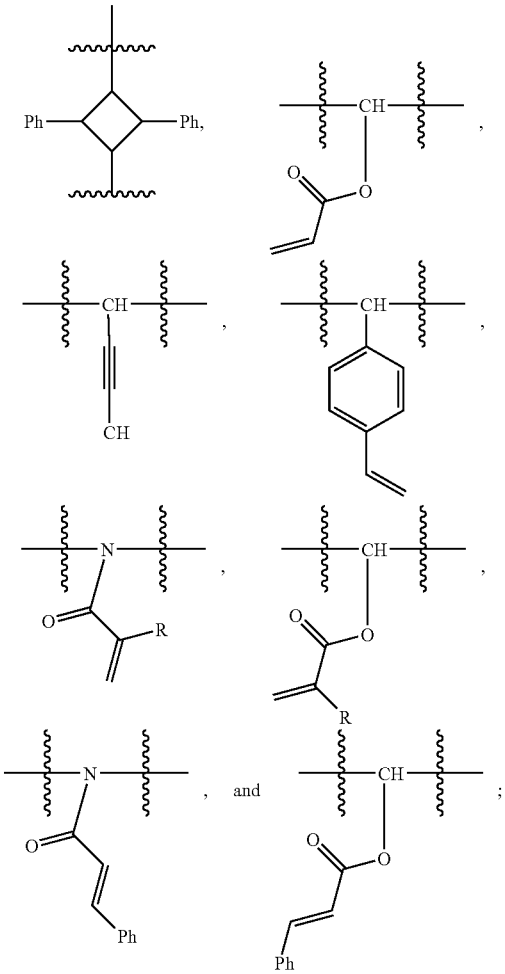

wherein p is 1-6; wherein h is 1-4; wherein Ph is phenyl; wherein each R is independently selected from the group of hydrogen and alkyl; wherein the linkage is independently configured in either of two possible configurations, forward and reverse, with respect to the synthons it couples together. In a preferred embodiment, each L is independently selected from the group consisting of —NH—C(O)—, —N═CH$_2$—, and —NH—CH$_2$—. In one embodiment, L is not —CH$_2$—. In another embodiment, L is not —CH$_2$NHCO—.

In one embodiment, the bridge moiety further comprises a surface attachment group. In another embodiment, the bridge moiety further comprises a lipophilic group. In another embodiment, the bridge moiety comprises a functional group for coupling the compound to at least a second bridged macrocyclic module compound. In another embodiment, the bridge moiety comprises a polymerization center. In one embodiment, the bridge moiety is not a polyethylene glycol moiety. In another embodiment, the bridge moiety does not comprise ethylene glycol moieties. In one embodiment, X' is H. In another embodiment, X' is a functional group.

In a preferred embodiment, the bridge moiety is selected from the group consisting of:

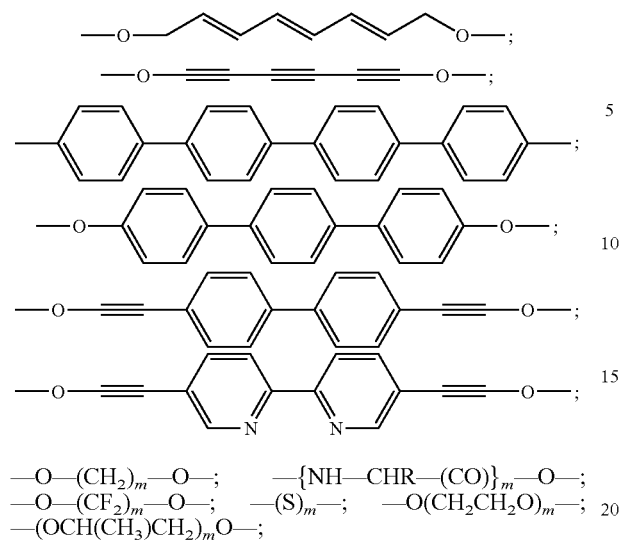
Non-limiting examples of bridged macrocyclic module compounds include the following:
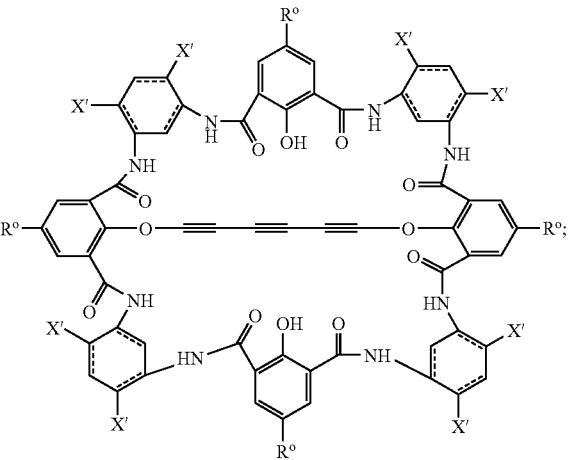
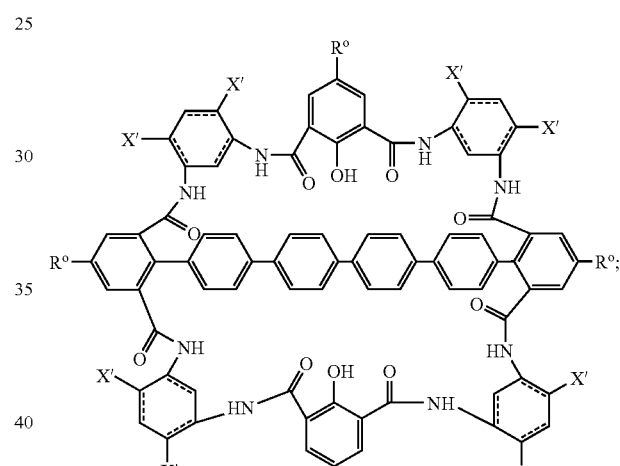
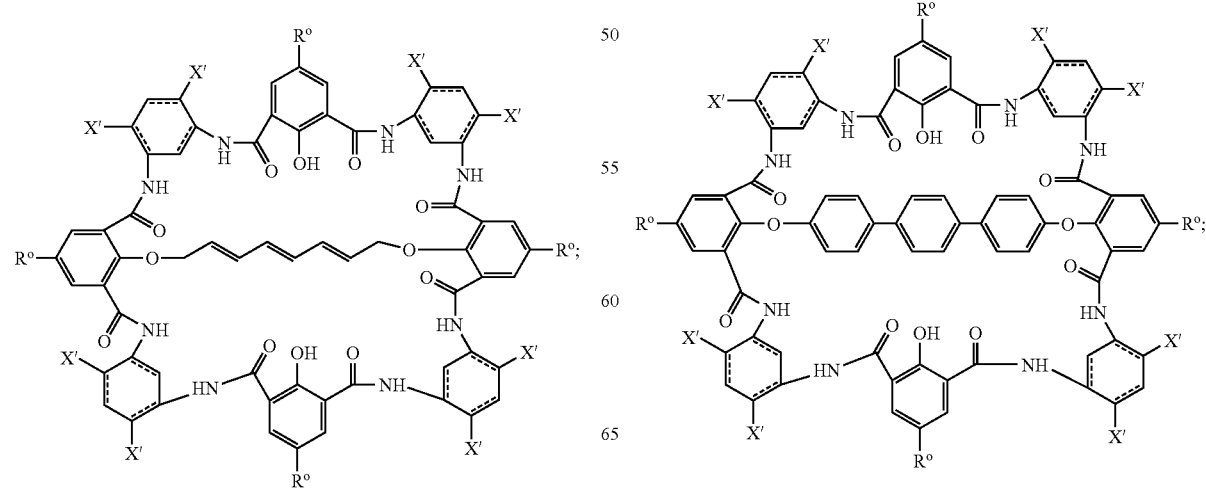

-continued
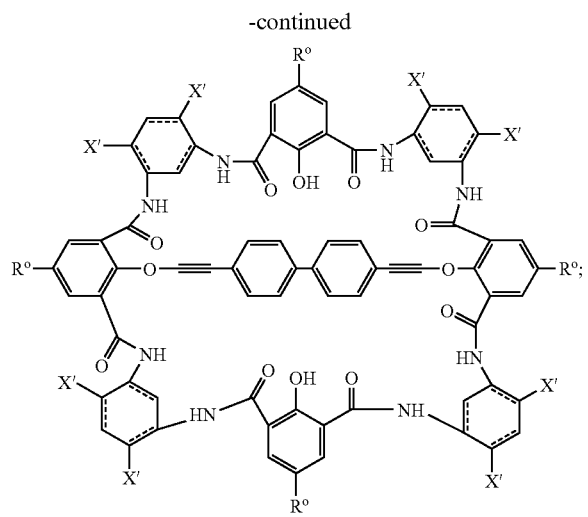
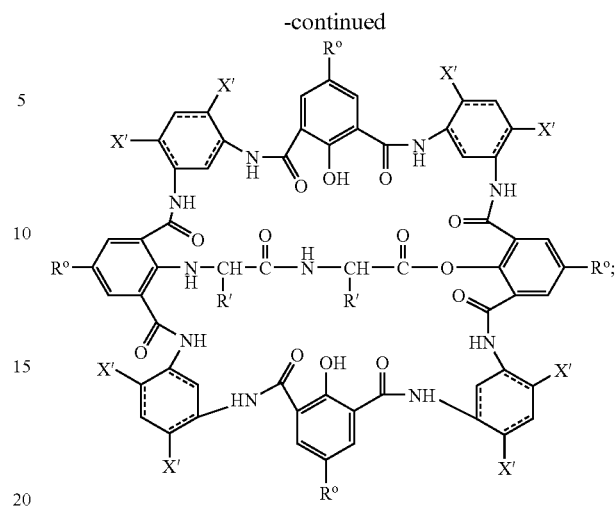
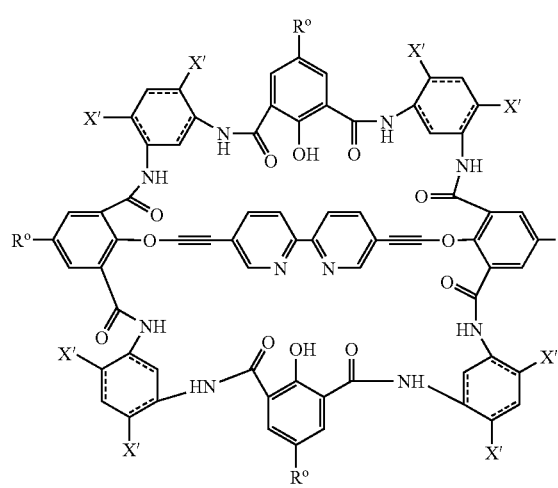
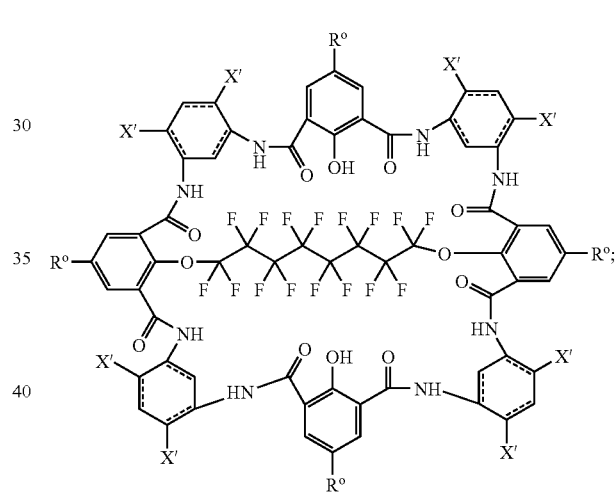
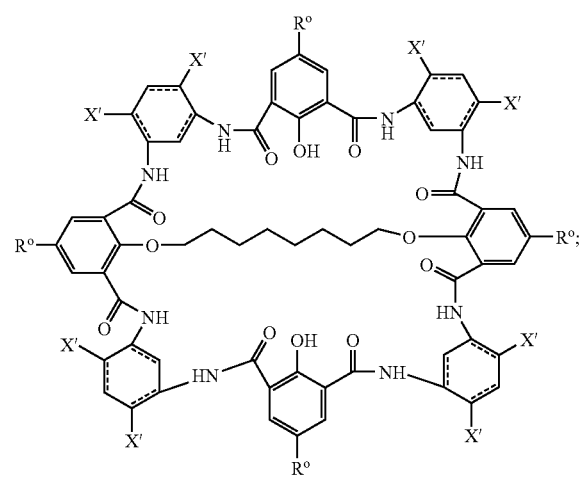
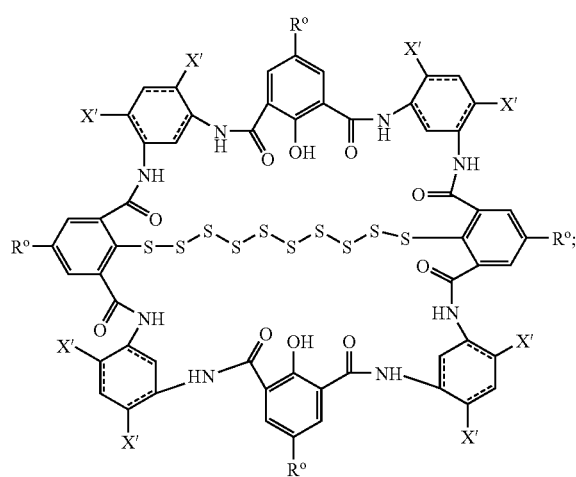

-continued
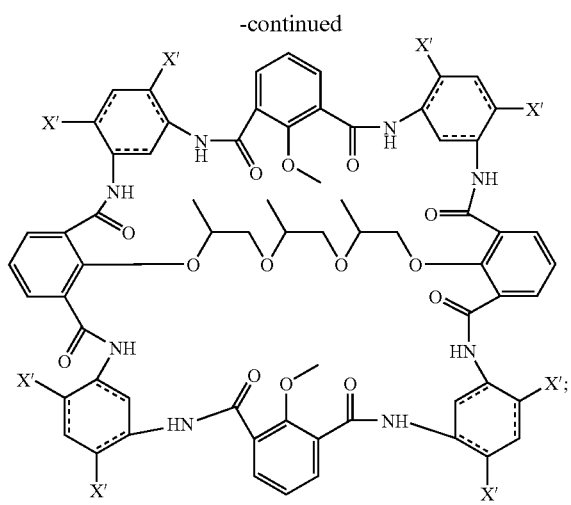
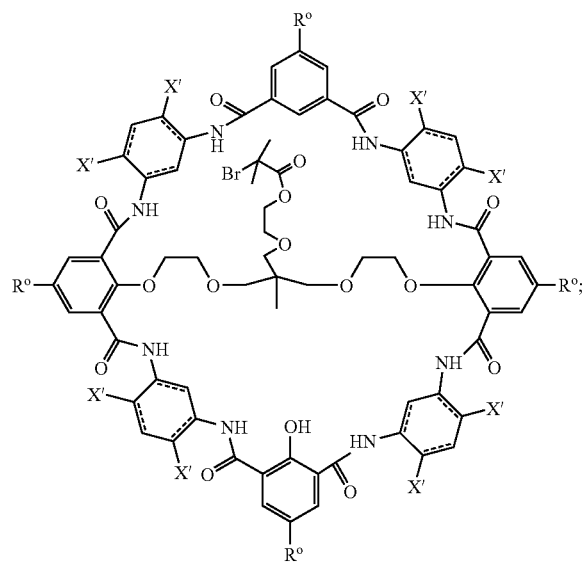
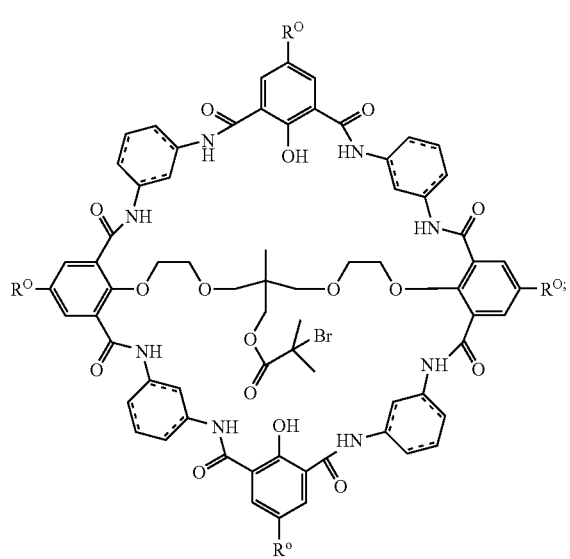
-continued
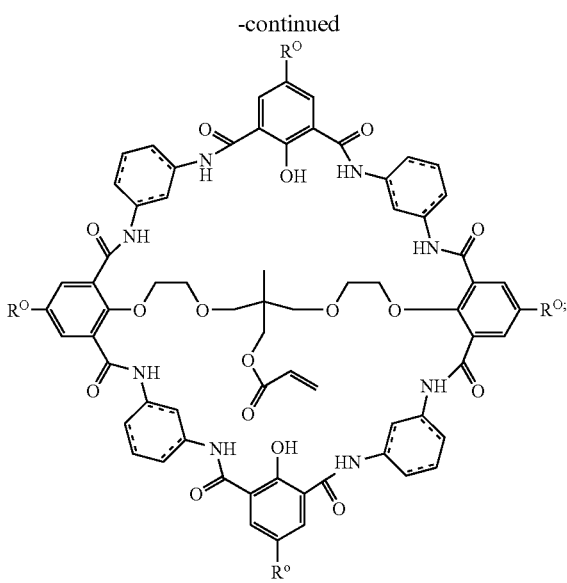
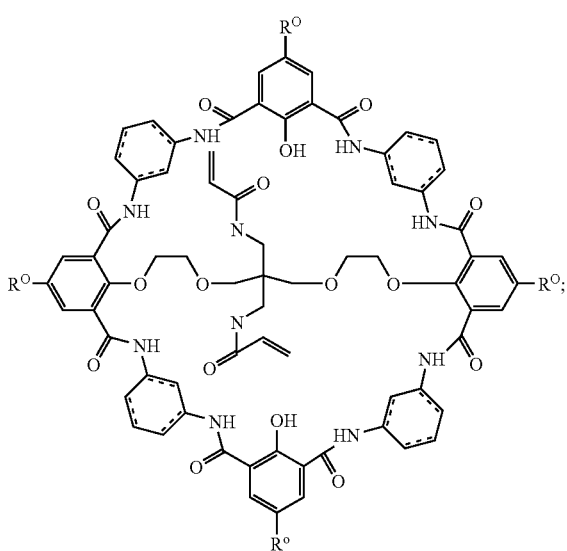
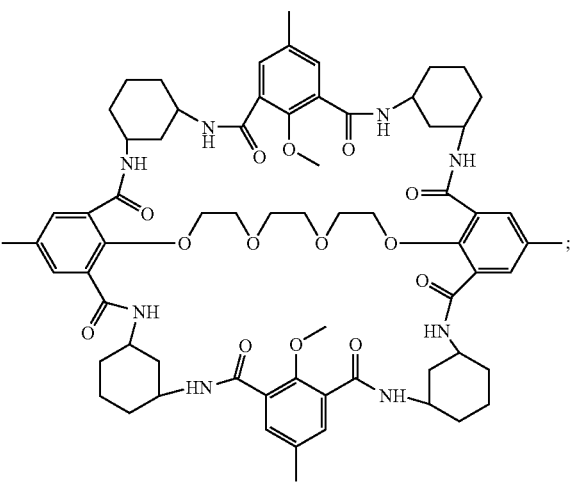

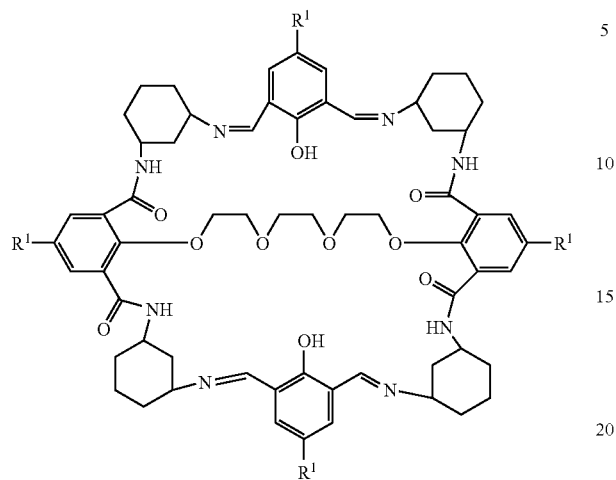
wherein $R^1$ is $CH_2CO_2(CH_2)_{15}CH_3$;
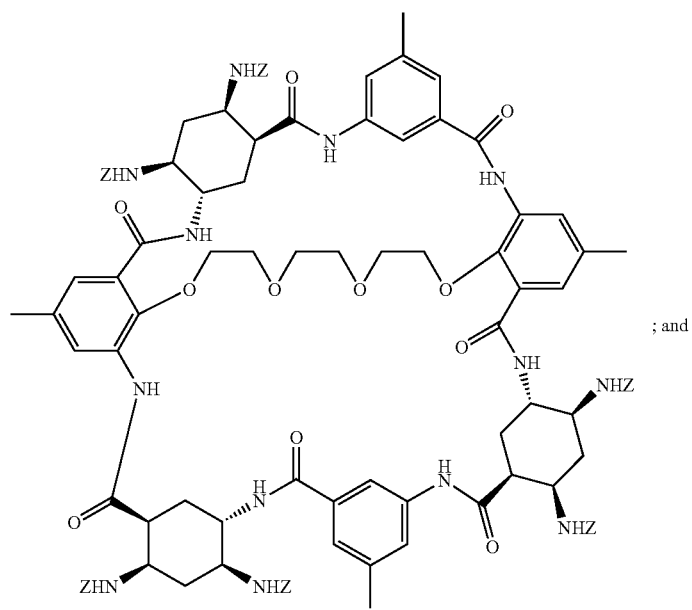
; and

-continued

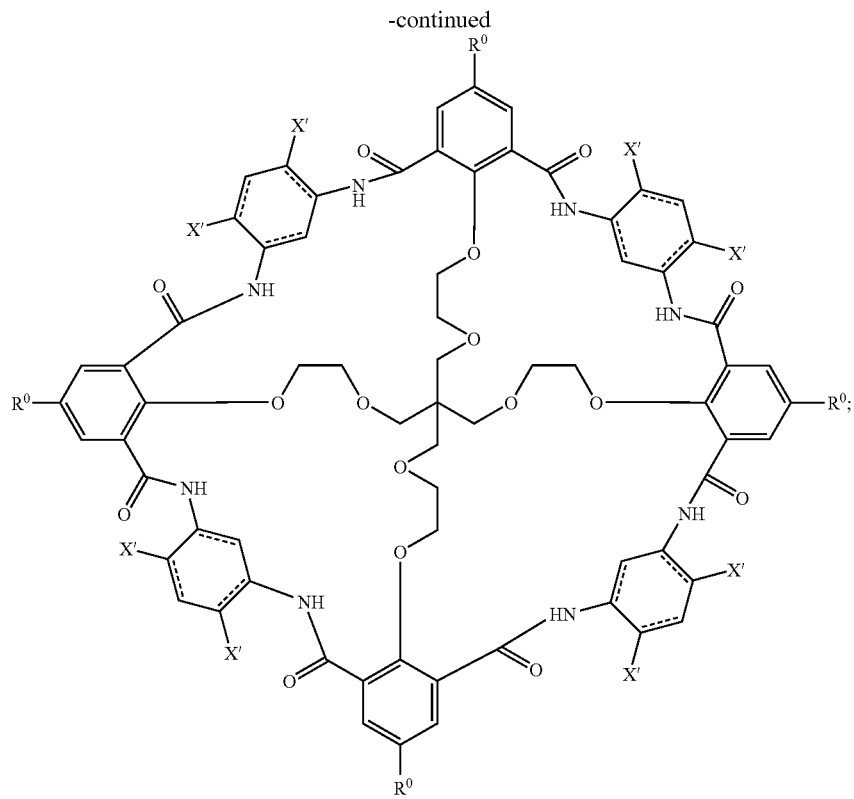

wherein R⁰ is H, alkyl, or a lipophilic group; wherein R' is a natural α-amino acid side chain; and wherein the structure

may be either benzene or cyclohexane. In one embodiment,

is benzene. In another embodiment,

is cyclohexane.

In another aspect are nanofilms comprising a plurality of a bridged macrocyclic module as defined herein. In one embodiment, the thickness of the nanofilm composition is less than about 30 nanometers. In another embodiment, the thickness of the nanofilm composition is less than about 6 nanometers. In another embodiment, the nanofilm is impermeable to viruses and larger species. In another embodiment, the nanofilm is impermeable to immunoglobulin G and larger species. In another embodiment, the nanofilm is impermeable to albumin and larger species. In another embodiment, the nanofilm is impermeable to β2-Microglobulin and larger species. In another embodiment, the nanofilm is permeable only to water and smaller species. In another embodiment, the nanofilm has a molecular weight cut-off of 13 kDa. In another embodiment, the nanofilm has a molecular weight cut-off of 190 Da. In another embodiment, the nanofilm has a molecular weight cut-off of 100 Da. In another embodiment, the nanofilm has a molecular weight cut-off of 45 Da. In another embodiment, the nanofilm has a molecular weight cut-off of 20 Da. In another embodiment, the nanofilm has high permeability for water molecules and Na+, K+, and Cs+ in water. In another embodiment, the nanofilm has low permeability for glucose and urea. In another embodiment, the nanofilm has high permeability for water molecules and Cl– in water. In another embodiment, the nanofilm has high permeability for water molecules and K+ in water, and low permeability for Na+ in water. In another embodiment, the nanofilm has high permeability for water molecules and Na+ in water, and low permeability for K+ in water. In another embodiment, the nanofilm has low permeability for urea, creatinine, Li+, Ca2+, and Mg2+ in water. In another embodiment, the nanofilm has high permeability for Na+, K+, hydrogen phosphate, and dihydrogen phosphate in water. In another embodiment, the nanofilm has high permeability for Na+, K+, and glucose in water. In another embodiment, the nanofilm has low permeability for myoglobin, ovalbumin, and albumin in water. In another embodiment, the nanofilm has high permeability for organic compounds and low permeability for water. In another embodiment, the nanofilm has low permeability for organic compounds and high permeability for water. In another embodiment, the nanofilm has low permeability for water molecules and high permeability for helium and hydrogen gases. In another embodiment is a nanofilm composition comprising at least two layers of a nanofilm defined herein. In another embodiment, the nanofilm composition comprises at least one spacing layer between any two of the nanofilm layers. In one embodiment, the spacing layer comprises a layer of a polymer, a gel, or inorganic particles. In another embodiment, the nanofilm is deposited on a substrate. In one embodiment, the substrate is porous. In another embodiment, the nanofilm is coupled to the substrate through biotin-strepavidin mediated interaction.

In another aspect is a method of filtration comprising using a nanofilm of the invention to separate components from fluid.

In another aspect is a method for making a bridged macrocyclic module compound of the invention, comprising: (a) providing a bridged program director compound of the structure:

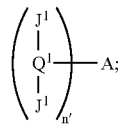

wherein each $J^1$ is a functional group for coupling an adjacent synthon; and (b) reacting a synthon or a synthon multimer with said bridged program director compound to form a bridged macrocyclic module compound.

In another aspect is a method for making a bridged macrocyclic module compound of the invention, comprising: (a) providing a macrocyclic moiety compound, wherein the macrocyclic moiety compound contains from 4 to 50 synthons; and (b) reacting a bridge moiety comprising at least two termini with said macrocyclic moiety compound to form a bridged macrocyclic module compound.

This invention further includes the rational design of bridged macrocyclic module compounds that may be assembled into larger constructions. Bridged macrocyclic module compounds may be used from which hierarchical molecules approaching macroscopic dimension having predicted properties can be assembled. These bridged macrocyclic modules may have functional groups which couple to complementary functional groups on other bridged macrocyclic modules to create larger structures.

DETAILED DESCRIPTION OF THE INVENTION

Definitions

Figure 1:
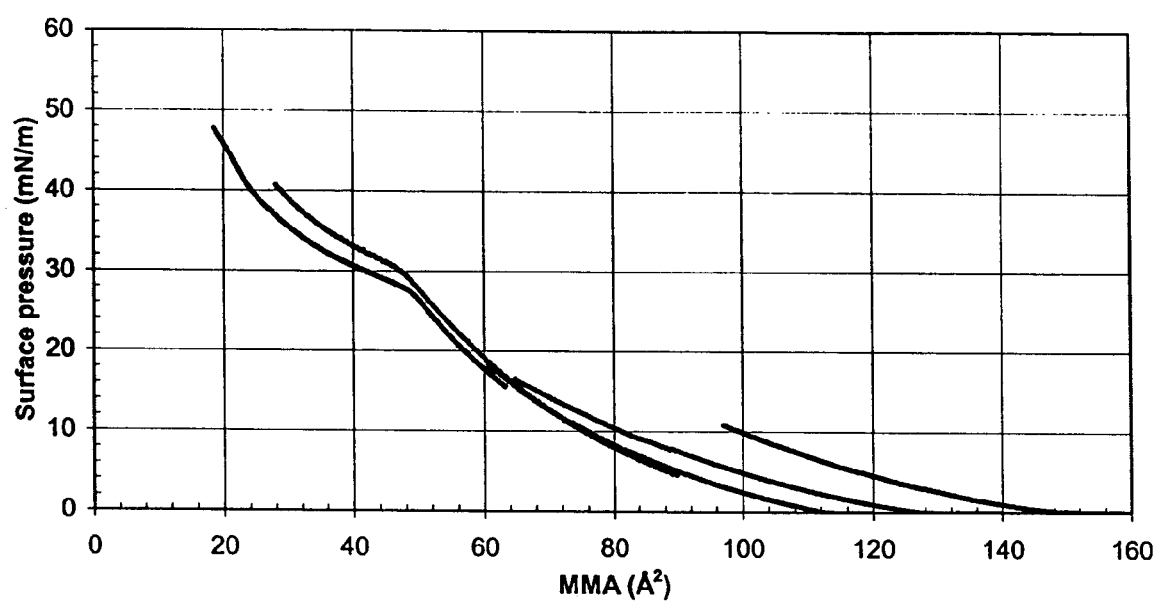
FIG. 1 shows examples of surface pressure vs. area isotherms of a nanofilm of Octamer IV pjs.

The term "synthon" is used herein to indicate a monomeric molecular unit from which a macrocyclic module may be made; a macrocyclic module is a closed ring of coupled synthons, for example, from 4 to 50, or more synthons. Structures and syntheses of synthons and macrocyclic modules are described in greater detail hereinbelow.

A macrocyclic module may be coupled with a molecular bridge ("bridge moiety"), which comprises at least two termini, to form a bridged macrocyclic module. When part of a bridged macrocylic module, the macrocyclic module portion may be termed "macrocyclic moiety."

The term "bridge moiety" is used herein to indicate a molecular bridge. The bridge moiety may have two termini, resulting in a bicyclic structure when the two termini of the bridge moiety are coupled to the macrocyclic moiety. The bridge may have three or more termini, resulting in a polycyclic structure when at least three termini are coupled to the macrocyclic moiety. The bridge may have, for example, 3, 4, 5, 6, 8, 12, 16, 32, 64 or more termini, at least two of which may couple to the macrocyclic moiety.

The terms "bridged macrocyclic module" and "bridged macrocyclic module compound" are used interchangeably herein and are used to indicate a compound comprising a macrocyclic moiety and a bridge moiety. The bridge moiety comprises at least two termini, resulting in a bicyclic or polycyclic structure when the two or greater termini are coupled to the macrocyclic moiety. In a "bridged macrocyclic module", not all termini of the bridge moiety must be coupled to the macrocyclic moiety, however, a minimum of two termini must be coupled to the macrocyclic moiety. Bridged macrocyclic modules may be coupled to each other to form macromolecular structures, for example, a nanofilm.

The term "synthon multimer" is used herein to indicate a linear coupling of two or more synthons. For example, "synthon trimer" is used to indicate a molecule of the general formula: synthon-synthon-synthon.

The term "activated synthon multimer" is used herein to indicate a synthon multimer with functional groups for coupling the activated synthon multimer to additional synthons or to a bridged program director, preferably in a specific orientation.

The term "bridged program director" is used herein to indicate a compound comprising a bridge moiety and at least two synthons, wherein the bridge moiety has 2 or more termini, and wherein each synthon is coupled to a terminus of the bridge moiety, and wherein the compound comprises functional groups to permit the coupling of additional synthons or synthon multimers to the bridged program director, preferably in a specific orienation.

The term "component" is used herein to refer to the molecules used in producing the bridged macrocyclic module compounds and 2-D and 3-D hierarchical structures produced therefrom, e.g., synthons, bridge moieties, macrocyclic moieties, macrocyclic modules, bridged macrocyclic modules, and substrates.

As used herein, the terms "amphiphile" or "amphiphilic" refer to a molecule or species which exhibits both hydrophilic and lipophilic character. In general, an amphiphile contains a lipophilic moiety and a hydrophilic moiety. The terms "lipophilic" and "hydrophobic" are interchangeable as used herein. An amphiphile may form a Langmuir film.

Non-limiting examples of hydrophobic groups or moieties include lower alkyl groups, alkyl groups having 7, 8, 9, 10, 11, 12, or more carbon atoms, including alkyl groups with 14-30, or 30 or more carbon atoms, substituted alkyl groups, alkenyl groups, alkynyl groups, aryl groups, substituted aryl groups, saturated or unsaturated cyclic hydrocarbons, heteroaryl, heteroarylalkyl, heterocyclic, and corresponding substituted groups. A hydrophobic group may contain some hydrophilic groups or substituents insofar as the hydrophobic character of the group is not outweighed. In further variations, a hydrophobic group may include substituted silicon atoms, and may include fluorine atoms. The hydrophobic moieties may be linear, branched, or cyclic. Non-limiting examples of preferred groups which may be coupled to a synthon or macrocyclic module as a lipophilic group include alkyls, —CH=CH—R$^3$, —C≡C—R$^3$, —OC(O)—R$^3$, —C(O)O—R$^3$, —NHC(O)—R$^3$, —C(O)NH—R$^3$, —O—R$^3$, and —CH$_2$COOR$^3$, where R$^3$ is 4-18C alkyl.

Non-limiting examples of hydrophilic groups or moieties include hydroxyl, methoxy, phenyl, carboxylic acids and salts thereof, methyl, ethyl, and vinyl esters of carboxylic acids, amides, amino, cyano, isocyano, nitrile, ammonium salts, sulfonium salts, phosphonium salts, mono- and di-alkyl substituted amino groups, polypropyleneglycols, polyethylene glycols, epoxy groups, acrylates, sulfonamides, nitro, —OP(O)(OCH$_2$CH$_2$N$^+$RRR)O$^-$, guanidinium, aminate, acrylamide, pyridinium, piperidine, and combinations thereof, wherein each R is independently selected from H or alkyl. Further examples include polymethylene chains substituted with alcohol, carboxylate, acrylate, methacrylate, or

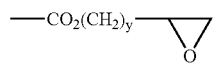

groups, where y is 1-6. Hydrophilic moieties may also include alkyl chains having internal amino or substituted amino groups, for example, internal —NH—, —NC(O)R—, or —NC(O)CH=CH$_2$— groups, wherein R is H or alkyl. Hydrophilic moieties may also include polycaprolactones, polycaprolactone diols, poly(acetic acid)s, poly(vinyl acetate)s, poly(2-vinyl pyridine)s, cellulose esters, cellulose hydroxylethers, poly(L-lysine hydrobromide)s, poly(itaconic acid)s, poly(maleic acid)s, poly(styrenesulfonic acid)s, poly(aniline)s; or poly(vinyl phosphonic acid)s. A hydrophilic group may contain some hydrophobic groups or substituents insofar as the hydrophilic character of the group is not outweighed.

As used herein, the terms "coupling" and "coupled" with respect to molecular moieties or species, atoms, synthons, macrocyclic modules and bridged macrocyclic modules refers to their attachment or association with other molecular moieties or species, atoms, synthons, macrocyclic modules and bridged macrocyclic modules. The attachment or association may be specific or non-specific, reversible or non-reversible, the result of chemical reaction, or complexation or charge transfer. The bonds formed by a coupling reaction are often covalent bonds, or polar-covalent bonds, or mixed ionic-covalent bonds, and may sometimes be Coulombic forces, ionic or electrostatic forces or interactions. In preferred embodiments, the coupling is covalent.

As used herein, the terms "R," "R'," "R''," and "R'''" in a chemical formula refer to a hydrogen or a functional group, each independently selected, unless stated otherwise. In some embodiments the functional group may be an organic group. In some embodiments the functional group may be an alkyl group. In some embodiment, the functional group may be a lipophilic group.

As used herein, the term "functional group" includes, but is not limited to, chemical groups, biochemical groups, organic groups, inorganic groups, organometallic groups, aryl groups, heteroaryl groups, cyclic hydrocarbon groups, amino (—NH$_2$), hydroxyl (—OH), cyano (—C≡N), nitro (NO$_2$), carboxyl (—COOH), formyl (—CHO), keto (—CH$_2$C(O)CH$_2$—), alkenyl (—C=C—), alkynyl, (—C≡C—), and halo (F, Cl, Br and I) groups. In some embodiments, the functional group is an organic group.

As used herein, the term "alkyl" refers to a branched or unbranched monovalent hydrocarbon radical. An "n-mC" alkyl or "(nC-mC)alkyl" refers to all alkyl groups containing from n to m carbon atoms. For example, a 1-4C alkyl refers to a methyl, ethyl, propyl, or butyl group. All possible isomers of an indicated alkyl are also included. Thus, propyl includes isopropyl, butyl includes n-butyl, isobutyl and t-butyl, and so on. An alkyl group with from 1-6 carbon atoms is referred to as "lower alkyl." The term alkyl includes substituted alkyls.

As used herein, the term "substituted alkyl" refers to an alkyl group with an additional group or groups attached to any carbon of the alkyl group. Substituent groups may include one or more functional groups such as alkyl, lower alkyl, aryl, acyl, halogen, alkylhalo, hydroxy, amino, alkoxy, alkylamino, acylamino, acyloxy, aryloxy, aryloxyalkyl, mercapto, both saturated and unsaturated cyclic hydrocarbons, heterocycles, and other organic groups.

As used herein, the term "alkenyl" refers to any structure or moiety having the unsaturation C=C. As used herein, the term "alkynyl" refers to any structure or moiety having the unsaturation C≡C.

As used herein, the term "aryl" refers to an aromatic group which may be a single aromatic ring or multiple aromatic rings which are fused together, coupled covalently, or coupled to a common group such as a methylene, ethylene, or carbonyl, and includes polynuclear ring structures. An aromatic ring or rings may include substituted or unsubstituted phenyl, naphthyl, biphenyl, diphenylmethyl, and benzophenone groups, among others. The term "aryl" includes substituted aryls.

As used herein, the term "substituted aryl" refers to an aryl group with an additional group or groups attached to any carbon of the aryl group. Additional groups may include one or more functional groups such as lower alkyl, aryl, acyl, halogen, alkylhalos, hydroxy, amino, alkoxy, alkylamino, acylamino, acyloxy, aryloxy, aryloxyalkyl, thioether, heterocycles, both saturated and unsaturated cyclic hydrocarbons which are fused to the aromatic ring(s), coupled covalently or coupled to a common group such as a methylene or ethylene group, or a carbonyl coupling group such as in cyclohexyl phenyl ketone, and others.

As used herein, the term "heteroaryl" refers to an aromatic ring(s) in which one or more carbon atoms of the aromatic ring(s) are substituted by a heteroatom such as nitrogen, oxygen, or sulfur. Heteroaryl refers to structures which may include a single aromatic ring, multiple aromatic rings, or one or more aromatic rings coupled to one or more nonaromatic rings. It includes structures having multiple rings, fused or unfused, coupled covalently, or coupled to a common group such as a methylene or ethylene group, or coupled to a carbonyl as in phenyl pyridyl ketone. As used herein, the term "heteroaryl" includes rings such as thiophene, pyridine, isoxazole, phthalimide, pyrazole, indole, furan, or benzo-fused analogues of these rings.

As used herein, the term "acyl" refers to a carbonyl substituent, —C(O)R$^6$, where R$^6$ is alkyl or substituted alkyl, aryl or substituted aryl, which may be called an alkanoyl substituent when R$^6$ is alkyl.

As used herein, the term "amino" refers to a group —NR$^4$R$^5$, where R$^4$ and R$^5$ may independently be hydrogen, lower alkyl, substituted lower alkyl, aryl, substituted aryl or acyl.

As used herein, the term "alkoxy" refers to an —OR$^7$ group, where R$^7$ is an alkyl, substituted lower alkyl, aryl, substituted aryl. Alkoxy groups include, for example, methoxy, ethoxy, phenoxy, substituted phenoxy, benzyloxy, phenethyloxy, t-butoxy, and others.

As used herein, the term "thioether" refers to the general structure R$^8$—S—R$^9$ in which R$^8$ and R$^9$ are the same or different and may be alkyl, aryl or heterocyclic groups. The group —SH may also be referred to as "sulfhydryl" or "thiol" or "mercapto."

As used herein, the term "saturated cyclic hydrocarbon" refers to ring structures cyclopropyl, cyclobutyl, cyclopentyl groups, and others, including substituted groups. Substituents to saturated cyclic hydrocarbons include substituting one or more carbon atoms of the ring with a heteroatom such as nitrogen, oxygen, or sulfur. Saturated cyclic hydrocarbons include bicyclic structures such as bicycloheptanes and bicyclooctanes, and multicyclic structures.

As used herein, the term "unsaturated cyclic hydrocarbon" refers to a monovalent nonaromatic group with at least one double bond, such as cyclopentenyl, cyclohexenyl, and others, including substituted groups. Substituents to unsaturated cyclic hydrocarbons include substituting one or more carbon atoms of the ring with a heteroatom such as nitrogen, oxygen, or sulfur. Unsaturated cyclic hydrocarbons include bicyclic structures such as bicycloheptenes and bicyclooctenes, and multicyclic structures.

As used herein, the term "cyclic hydrocarbon" includes substituted and unsubstituted, saturated and unsaturated cyclic hydrocarbons, and multicyclic structures.

As used herein, the term "heteroarylalkyl" refers to -alkyl-heteroaryl.

As used herein, the term "heterocyclic" refers to a monovalent saturated or unsaturated nonaromatic group having a single ring or multiple condensed rings having from 1-12 carbon atoms and from 1-4 heteroatoms selected from nitrogen, phosphorous, sulfur, or oxygen within the ring. Examples of heterocycles include tetrahydrofuran, morpholine, piperidine, pyrrolidine, and others.

As used herein, each chemical term described above expressly includes the corresponding substituted group. For example, the term "heterocyclic" includes substituted heterocyclic groups.

As used herein, the term "activated acid" refers to a —C(O)X$^2$ moiety, where X$^2$ is a leaving group, in which the X$^2$ group is readily displaced by a nucleophile to form a covalent bond between the —C(O)— and the nucleophile. Examples of activated acids include acid chlorides, acid fluorides, p-nitrophenyl esters, pentafluorophenyl esters, and N-hydroxysuccinimide esters.

As used herein, the term "amino acid residue" refers to the product formed when a species comprising at least one amino (—NH$_2$) and at least one carboxyl (—C(O)O—) group couples through either of its amino or carboxyl groups with an atom or functional group of a synthon. Whichever of the amino or carboxyl groups is not involved in the coupling may be blocked with a removable protective group.

Bridged Macrocyclic Module Compounds

In one aspect of the invention are compounds of the formula:

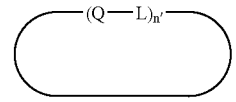

wherein each Q is an independently selected synthon, each L is independently a bond or a linker molecule, n' is from 4 to 50, and wherein the compound further comprises a bridge moiety having two or more termini, wherein at least two of said two or more termini are coupled to the compound. The termini of the bridge moiety may each be independently coupled to either a synthon Q or a linker molecule L. In one embodiment, the bridge moiety termini are coupled to the synthons Q. In another embodiment, the bridge moiety termini are coupled to the linker molecules L. In a preferred embodiment, n is from 4 to 30, more preferably 4 to 24, still more preferably 4 to 12.

In other embodiments are bridged macrocyclic module compounds of one of the following formulas:

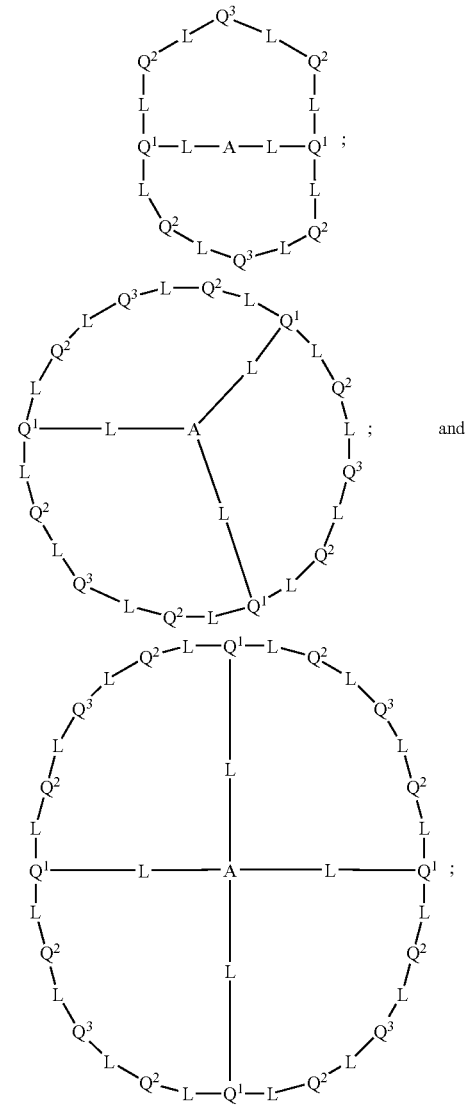

and wherein: A is a bridge moiety as defined herein; each $Q^1$ is an independently selected synthon as defined herein; each $Q^2$ is an independently selected synthon as defined herein; each $Q^3$ is an independently selected synthon as defined herein, and each L is an independently selected bond or a linker molecule as defined herein.

In some embodiments, each $Q^1$ is the same synthon. In some embodiments, each $Q^2$ is the same synthon. In some embodiments, each $Q^3$ is the same synthon. In some embodiments, the synthons are directly coupled (L is a bond). In other embodiments, the synthons are coupled to each other through linker molecules.

In some embodiments, the bridge moiety may be connected to synthons directly, for example:

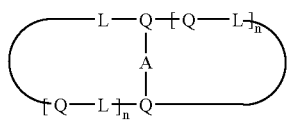

wherein A is a bridge moiety, each Q is an independently selected synthon, each L is an independently selected linker molecule or a bond, and each n is independently from 1 to 24.

The bridge moiety may also be connected to the synthons through a linker molecule, for example:

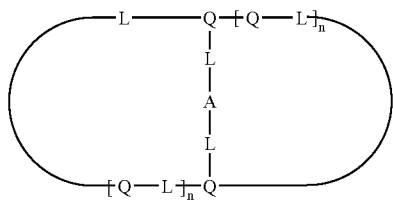

In other embodiments, the bridge moiety may be connected to a linker between synthons, or to combinations of synthons and linkers, for example:

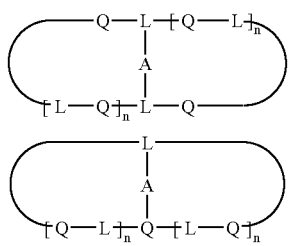

These bridged macrocyclic modules may comprise functional groups which couple to complementary functional groups on other bridged macrocyclic modules to create larger structures. These bridged macrocyclic modules may comprise functional groups for coupling the module to a substrate.

Exemplary, non-limiting, bridged macrocyclic module compounds include the following:

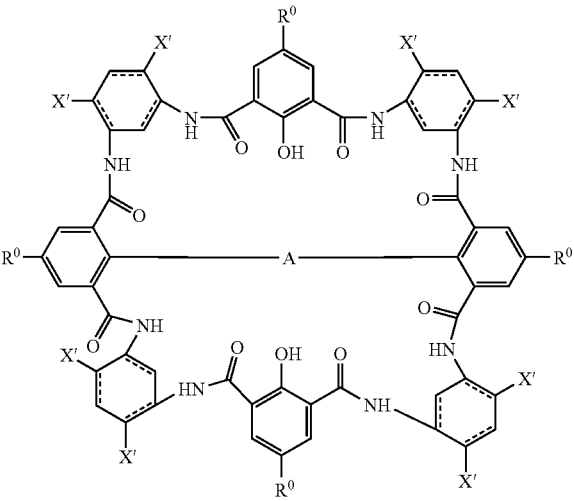

wherein A is a bridge moiety comprising one or more of the following structural units:

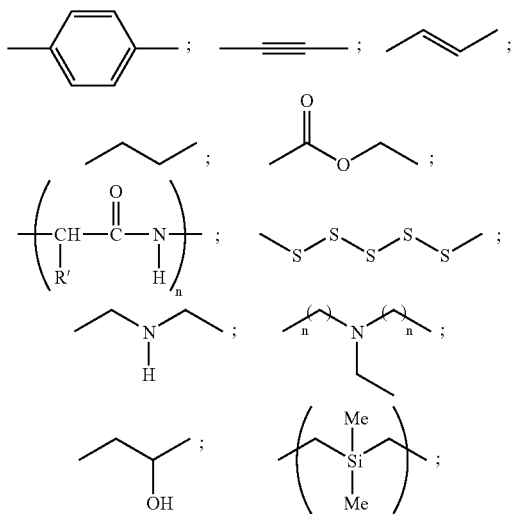

wherein each $R^0$ comprises H, an alkyl group, or a lipophilic group; wherein R' comprises a natural α-amino acid side chain; and wherein X' is H or a functional group for coupling the bridged macrocyclic module to another bridged macrocyclic module or to a substrate.

Additional non-limiting examples of bridged macrocyclic module compounds may be found in the Examples and claims.

Bridged Program Directors

In another aspect, this invention relates to bridged program director compounds, and compounds useful in the synthesis of bridged program director compounds. A bridged program director is a discrete product molecule which has built-in directionality to control coupling reactions of the terminal synthons to additional synthons.

In one aspect of the invention are compounds of the formula:

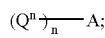

wherein A is a bridge moiety as defined herein; each $Q^n$ is an independently selected synthon as defined herein; and n is from 2 to 30. These compounds may be useful in the synthesis of bridged program director compounds.

In another aspect of the invention are bridged program director compounds of one of the following formula:

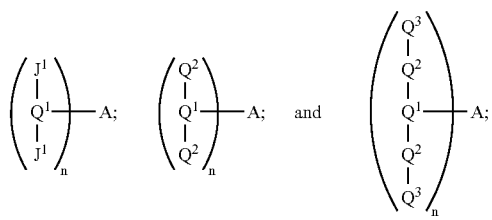

wherein A is a bridge moiety as defined herein; each $Q^1$ is an independently selected synthon as defined herein; each $J^1$, if present, is an independently selected functional group for coupling one or more additional synthons; each $Q^2$, if present, is an independently selected synthon as defined herein; each $Q^3$, if present, is an independently selected synthon as defined herein; and n is from 2 to 30.

In some embodiments, A is coupled to the synthons $Q^1$ directly. In other embodiments, A is coupled to $Q^1$ through a linker molecule. In some embodiments, the synthons are coupled directly to each other (e.g., $Q^1$ is coupled directly to $Q^2$, $Q^2$ is coupled directly to $Q^3$). In other embodiments, the synthons may be coupled through linker molecules (e.g., $Q^1$ is coupled to $Q^2$ through a linker molecule, $Q^2$ is coupled to $Q^3$ through a linker molecule). In some embodiments, some sythons may be connected through linker molecules, while other synthons are directly coupled.

In a preferred embodiment, n is from 2 to 5. In a more preferred embodiment, n is from 2 to 3.

The use of bridged program directors may be advantageous in the synthesis of bridged macrocyclic modules. The use of bridged program directors may allow for convergent synthesis methods of some bridged macrocyclic modules, which may result in fewer synthesis steps and, in general, higher yields. Examples of convergent synthesis methods may be found hereinbelow and in, for example, Example 4. In some embodiments, the functional groups on the synthons may be tailored to only bind to a particular additional synthon in a particular orientation. Further, the positioning of functional groups on the synthons may be useful in limiting side reactions.

Synthons

A general formula for a cyclic or an acyclic synthon may be written:

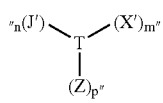

wherein T is a cyclic or an acyclic core synthon having attached functional groups J', X', and Z; each J' is an independently selected functional group for coupling the synthon to one or more other synthons or to a bridge moiety, wherein n" is at least 2; each X' is independently H or a functional group for coupling the synthon to another bridged macrocyclic module or to a substrate, wherein m" is 0, 1, or greater than 1; and each Z is independently either H, a lipophilic group, or a hydrophilic group, wherein p" is 0, 1, or greater than 1. Functional groups J' and X' may be selected, for example, from those listed in Tables 6-8. Preferred lipophilic groups Z include, for example, alkyls, —CH=CH—$R^3$, —C≡C—$R^3$, —OC(O)—$R^3$, —C(O)O—$R^3$, —NHC(O)—$R^3$, —C(O)NH—$R^3$, —CH$_2$COOR$^3$, and —O—$R^3$, where $R^3$ is 4-18C alkyl.

In one embodiment, the X' group on a synthon is H. In another embodiment, the X' group on a synthon is a functional group. In some embodiments, a synthon may be substantially one isomeric configuration, for example, a single enantiomer.

Cyclic Synthons

As used herein, the term "cyclic synthon" refers to a synthon having one or more ring structures. Examples of ring structures include aryl, heteroaryl, and cyclic hydrocarbon structures including bicyclic ring structures and multicyclic ring structures. Examples of core cyclic synthons include benzene, cyclohexadiene, cyclopentadiene, naphthalene, anthracene, phenylene, phenanthracene, pyrene, triphenylene, phenanthrene, pyridine, pyrimidine, pyridazine, biphenyl, bipyridyl, cyclohexane, cyclohexene, decalin, piperidine, pyrrolidine, morpholine, piperazine, pyrazolidine, quinuclidine, tetrahydropyran, dioxane, tetrahydrothiophene, tetrahydrofuran, pyrrole, cyclopentane, cyclopentene, triptycene, adamantane, bicyclo[2.2.1]heptane, bicyclo[2.2.1]heptene, bicyclo[2.2.2]octane, bicyclo[2.2.2]octene, bicyclo[3.3.0]octane, bicyclo[3.3.0]octene, bicyclo[3.3.1]nonane, bicyclo[3.3.1]nonene, bicyclo[3.2.2]nonane, bicyclo[3.2.2]nonene, bicyclo[4.2.2]decane, 7-azabicyclo[2.2.1]heptane, 1,3-diazabicyclo[2.2.1]heptane, and spiro[4.4]nonane. A core synthon comprises all isomers or arrangements of coupling the core synthon to other synthons. For example, the core synthon benzene includes synthons such as 1,2- and 1,3-substituted benzenes, where the linkages between synthons are formed at the 1,2- and 1,3-positions of the benzene ring, respectively. For example, the core synthon benzene includes 1,3-substituted synthons such as

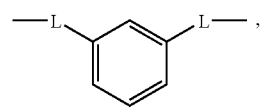

where L is a linkage between synthons and the 2,4,5,6 positions of the benzene ring may also have substituents. A condensed linkage between synthons involves a direct coupling between a ring atom of one cyclic synthon to a ring atom of another cyclic synthon, for example, where synthons Q-X and Q-X couple to form Q-Q, where Q is a cyclic synthon and X is halogen; as for example when Q is phenyl resulting in the condensed linkage

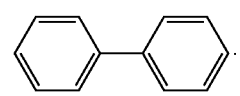

Examples of synthons and their syntheses are further described in U.S. patent application Ser. Nos. 10/071,377 and 10/226,400 filed Feb. 7, 2002 and Aug. 23, 2002, respectively, and in PCT Application No. PCT/US03/03830, filed Feb. 7, 2003.

Acyclic Synthons

Examples of formulas representing acyclic synthons are shown in Table 1.

TABLE 1

Examples of acyclic synthons

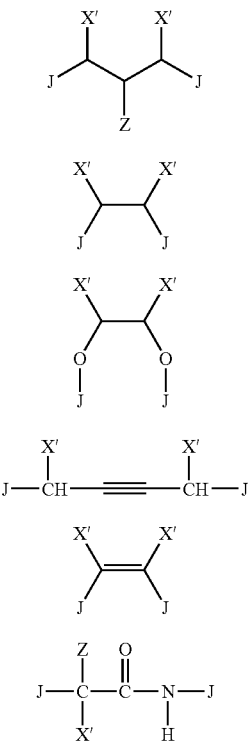

J and X' may be a functional group selected, for example, from those found in Tables 6-8. Z may be any lipophilic group. Preferred lipophilic groups include alkyls, —CH=CH—$R^3$, —C≡C—$R^3$, —OC(O)—$R^3$, —C(O)O—$R^3$, —NHC(O)—$R^3$, —C(O)NH—$R^3$, —CH$_2$COOR$^3$, and —O—$R^3$, where $R^3$ is 4-18C alkyl. The synthons may further comprise functional groups for coupling with a bridge moiety; nonlimiting examples of suitable functional groups and linkages formed may be found in Tables 6-8.

Non-limiting examples of acyclic core synthons are shown in Table 2.

TABLE 2

Examples of acyclic core synthons

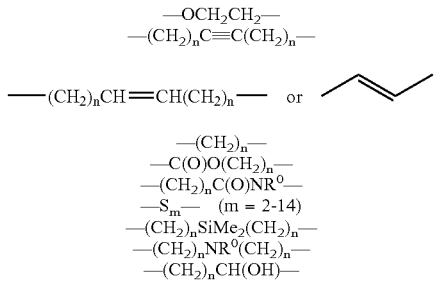

—OCH$_2$CH$_2$—
—(CH$_2$)$_n$C≡C(CH$_2$)$_n$—
—(CH$_2$)$_n$CH=CH(CH$_2$)$_n$— or
—(CH$_2$)$_n$—
—C(O)O(CH$_2$)$_n$—
—(CH$_2$)$_n$C(O)NR$^0$—
—S$_m$— (m = 2-14)
—(CH$_2$)$_n$SiMe$_2$(CH$_2$)$_n$—
—(CH$_2$)$_n$NR$^0$(CH$_2$)$_n$—
—(CH$_2$)$_n$CH(OH)—

In Table 2, $R^0$ is H or a lipophilic group, and n is 1-22.

The examples of acyclic synthons in Table 2 may further comprise the groups X', J and Z as described above, as well as functional groups for coupling to the bridge moiety.

Suitable acyclic synthons may be purchased from, for example, Aldrich Chemical Company (St. Louis, Mo.). Alternatively, one skilled in the art may synthesize appropriate acyclic synthons.

Preferred synthons for the bridged macrocyclic module compounds include:

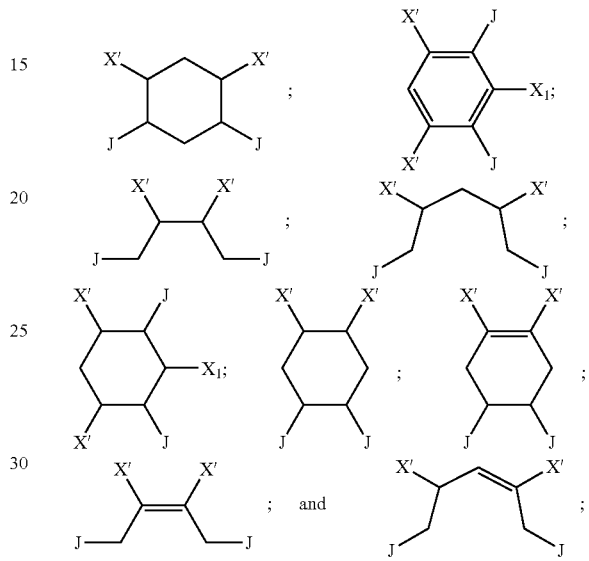

wherein each X' are independently H or a functional group for coupling the synthon to another bridged macrocyclic moiety ("cross-linking groups"), each J are independently selected functional groups for coupling the synthons to additional synthons within the same bridged macrocyclic moiety, and $X_1$ are functional groups for coupling the synthon to a bridge moiety. In a preferred embodiment, each X' within a synthon is the same. In another preferred embodiment, each J within a synthon is the same.

Particularly preferred synthons for a bridged macrocyclic module include

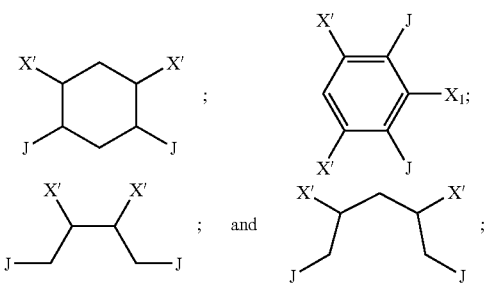

wherein each X' are independently H or a functional group for coupling the synthon to another bridged macrocyclic moiety ("cross-linking groups"), each J are independently selected functional groups for coupling the synthons to additional synthons within the same bridged macrocyclic moiety, and $X_1$ are functional groups for coupling the synthon to a bridge moiety. In a preferred embodiment, each X' within a synthon is the same. In another preferred embodiment, each J within a synthon is the same.

Macrocyclic Modules

A macrocyclic module is a closed ring of 4-50 coupled synthons. The synthons may be coupled using, for example, the functional groups in Tables 6-8. A macrocyclic module may be coupled to a bridge moiety having at least two termini to produce a bridged macrocyclic module, as further described herein.

The preparation of macrocyclic modules beginning with a set of synthons is described in U.S. patent application Ser. Nos. 10/071,377 and 10/226,400, and in the PCT Application PCT/US03/03830, incorporated by reference herein in their entirety. The assembly of molecular building blocks, beginning with a set of synthons assembled to make macrocyclic modules, which, in turn, are combined to form a nanofilm are described in U.S. Ser. No. 60/383,236, filed May 22, 2002, and in U.S. patent application Ser. No. 10/359,894, filed Feb. 7, 2003, incorporated by reference herein in their entirety. Examples and syntheses of synthons, macrocyclic modules, and amphiphilic macrocyclic modules are further described hereinbelow.

Examples of macrocyclic modules which may be modified with a bridge moiety to produce a bridged macrocyclic module include those shown in Table 3.

TABLE 3

Examples of macrocyclic modules

| MODULE | STRUCTURE |
|---|---|
| Hexamer 1a | 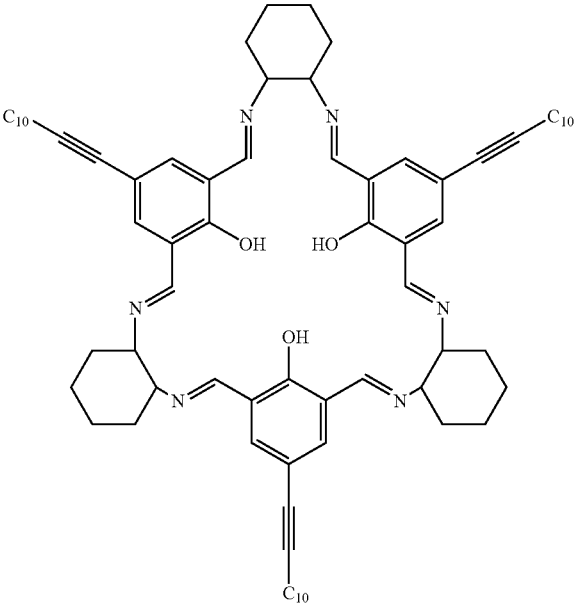 |
| Hexamer 1dh | 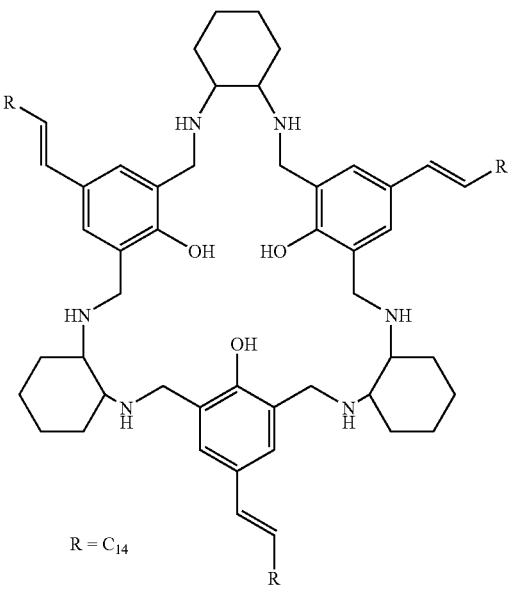 |

TABLE 3-continued
Examples of macrocyclic modules
| MODULE | STRUCTURE |
| --- | --- |
| Hexamer 3j-amine | 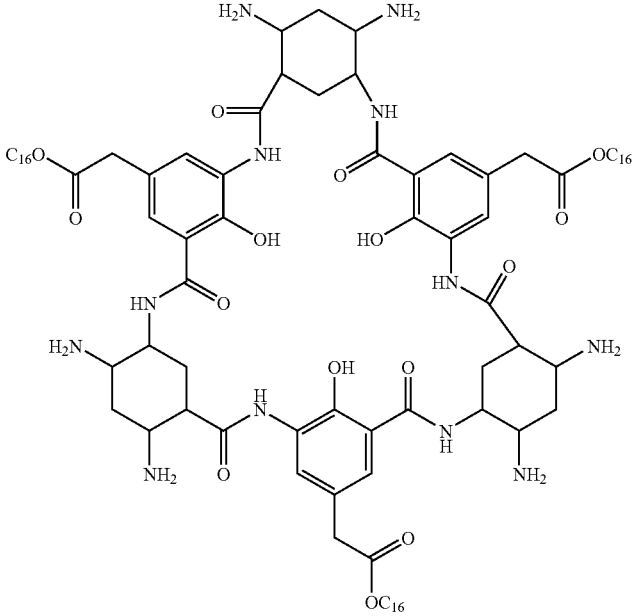 |
| Hexamer 1jh-AC | 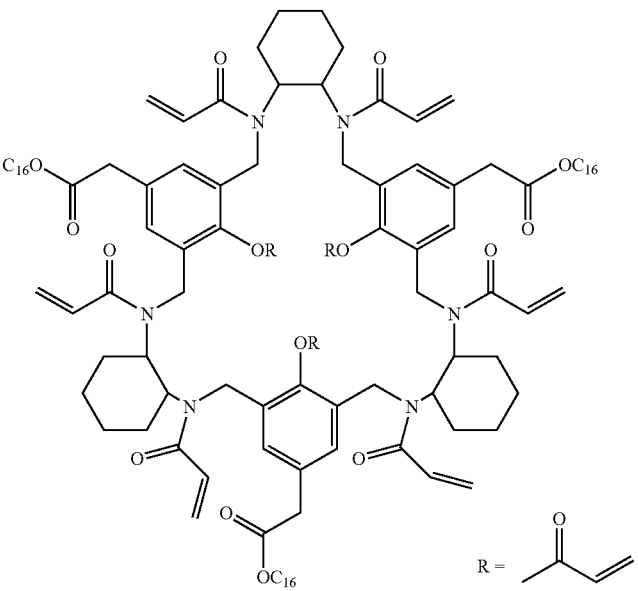
Hexamer 1jh-Ac |

TABLE 3-continued
Examples of macrocyclic modules
| MODULE | STRUCTURE |
| --- | --- |
| Hexamer 1jh | 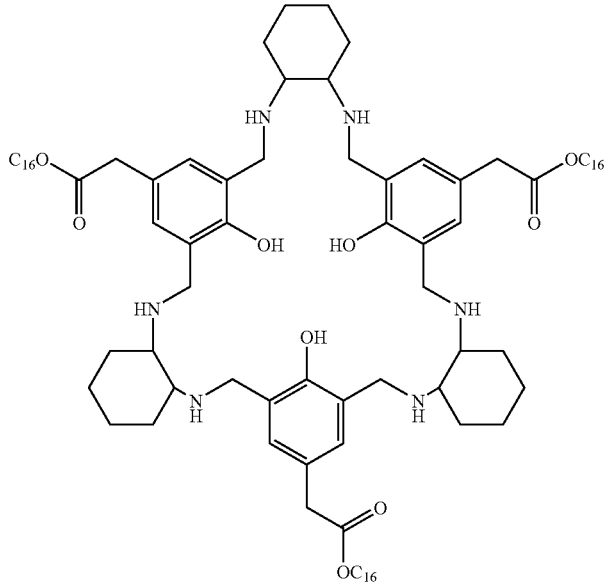 |
| Hexamer 2j-amine/ester | 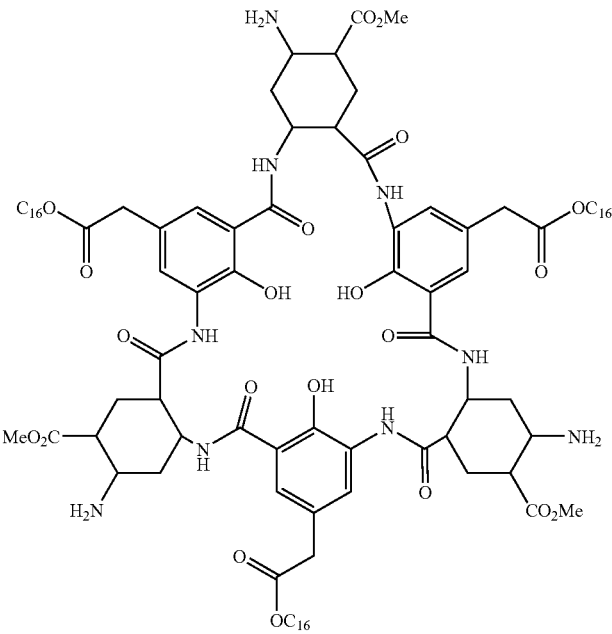 |

TABLE 3-continued
Examples of macrocyclic modules
| MODULE | STRUCTURE |
| --- | --- |
| Hexamer 1dh-acryl | 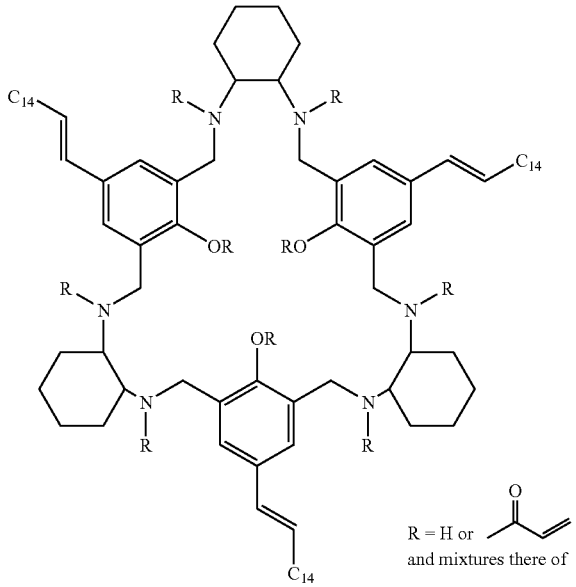 R = H or  and mixtures there of |
| Octamer 5jh-aspartic | 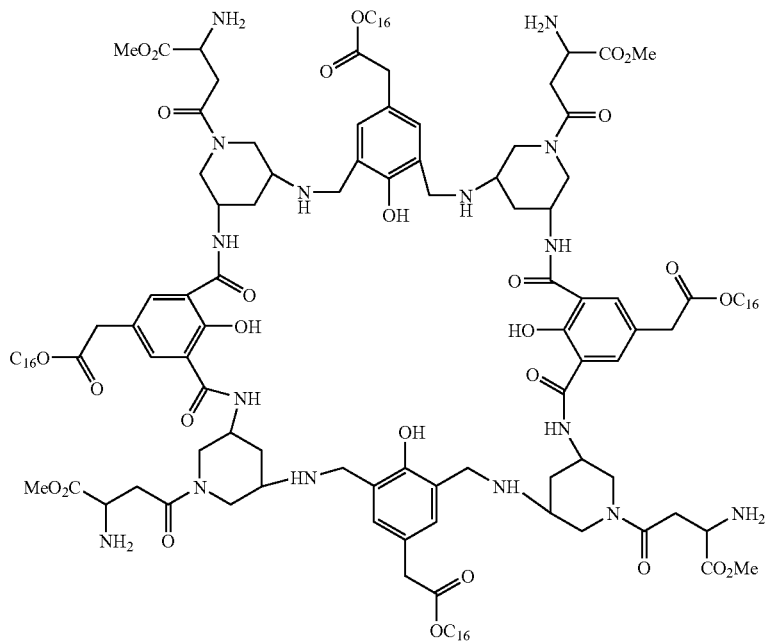 |

TABLE 3-continued

Examples of macrocyclic modules

| MODULE | STRUCTURE |
|---|---|
| Octamer 4jh-acryl | 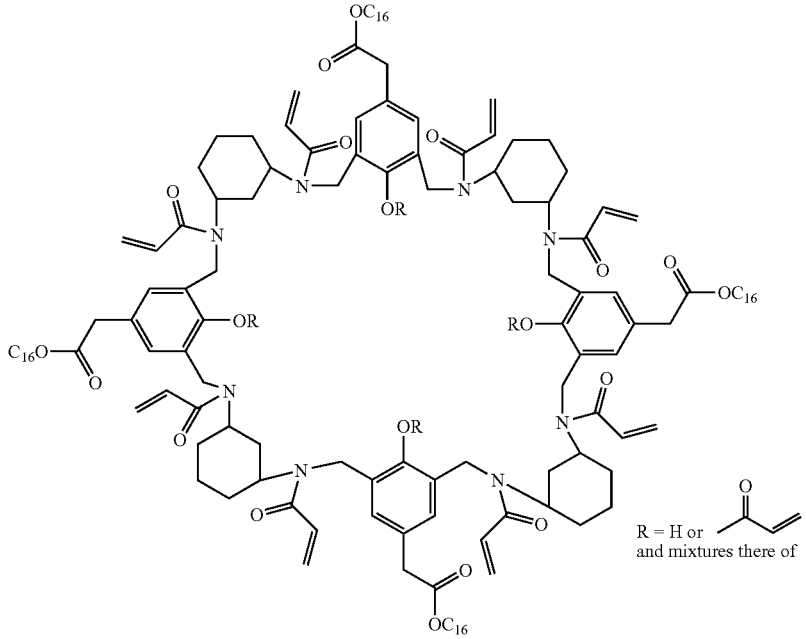 R = H or 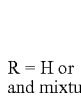 and mixtures there of |

An individual macrocyclic module may include a pore in its structure, which has a particular size depending on the conformation and state of the module. Addition of a bridge moiety to the module to form a bridged macrocyclic module may result in pores with different sizes and properties.

Macrocyclic modules and bridged macrocyclic modules may have varying degrees of flexibility in their structures. In general, addition of a bridge moiety to a macrocyclic module decreases the flexibility of the module. Increased flexibility of the macrocyclic modules or bridged macrocyclic modules may allow the modules to more easily form linkages with other modules by coupling reactions. Flexibility of a macrocyclic module or bridged macrocyclic module may also play a role in regulating passage of species through the pore of the module. For example, flexibility may affect the dimension of the pore of an individual module since various conformations may be available to the structure. For example, a module may have a certain pore dimension in one conformation when one group of substituents are located at the pore, and have a different pore dimension in a different conformation when a different group of substituents are located at the pore. For example, the "one group" of substituents located at the pore may be three alkoxy groups arranged in one regioisomer, while the "different group" of substituents may be two alkoxy groups arranged in another regioisomer. The effect of the "one group" of substituents located at the pore and the "different group" of substituents located at the pore is to provide a bridged macrocyclic module composition which may regulate transport and filtration, in conjunction with other regulating factors.

Bridge Moieties

Examples of bridge moieties include polymers, biopolymers, chain structures, and various other chemical groups and structures. Bridge moieties may also be comprised of multimeric cores.

Examples of polymers and biopolymers which may be used as a bridge moiety include poly(maleic anhydrides), a copolymer of maleic anhydride, poly(ethylene-co-maleic anhydride), poly(maleic anhydride-co-alpha olefin), polyacrylates, a polymer or copolymer having acrylate side groups, a polymer or copolymer having oxacyclopropane side groups, polyethyleneimides, polyetherimides, polyethylene oxides, polypropylene oxides, polystyrenes, poly(vinyl acetate)s, polytetrafluoroethylenes, polyolefins, polyethylenes, polypropylenes, ethylene-propylene copolymers, polyisoprenes, neopropenes, polyanilines, polyacetylenes, polyvinylchlorides, polyvinylidene chlorides, polyvinylidene fluorides, polyvinylalcohols, polyurethanes, polyamides, polyimides, polysulfones, polyethersulfones, polysulfonamides, polysulfoxides, polyglycolic acids, polyacrylamides, polyvinylalcohols, polyesters, polyester ionomers, polyethylene terephthalates, polybutylene terephthalates, polycarbonates, polysorbates, polylysines, polypeptides, poly(amino acids), polyvinylpyrrolidones, polylactic acids, gels, hydrogels, carbohydrates, polysaccharides, agarose, amylose, amylopectin, glycogen, dextran, cellulose, cellulose acetates, chitin, chitosan, peptidoglycan, and glycosaminoglycan. Further examples include amino-branched, amino-substituted, and amino-terminal derivatives of the preceding example polymers. Further examples include polynucleotides, synthetic or naturally-occurring polynucleotides, for example, poly(T) and poly(A), nucleic acids, as well as proteoglycans, glycoproteins, and glycolipids.

Examples of polymerizable monomers which can be used to form the polymeric bridge moiety include vinyl halide compounds such as vinyl chloride; vinylidene monomers such as vinylidene chloride; unsaturated carboxylic acids such as acrylic acid, methacrylic acid, maleic acid, itaconic acid, and salts thereof; acrylates such as methyl acrylate, ethyl acrylate, butyl acrylate, octyl acrylate, methoxyethyl acrylate, phenyl acrylate and cyclohexyl acrylate; methacrylates such as methyl methacrylate, ethyl methacrylate, butyl methacrylate, octyl methacrylate, phenyl methacrylate and cyclohexyl methacrylate; unsaturated ketones such as methyl vinyl ketone, ethyl vinyl ketone, phenyl vinyl ketone, methyl isobutenyl ketone and methyl isopropenyl ketone; vinyl esters such as vinyl formate, vinyl acetate, vinyl propionate, vinyl butyrate, vinyl benzoate, vinyl monochloroacetate, vinyl dichloroacetate, vinyl trichloroacetate, vinyl monofluoroacetate, vinyl difluoroacetate and vinyl trifluoroacetate; vinyl ethers such as methyl vinyl ether and ethyl vinyl ether; acrylamide and alkyl substituted compounds thereof; acid compounds containing a vinyl group and salts, anhydrides and derivatives thereof such as vinylsulfonic acid, allylsulfonic acid, methallylsulfonic acid, styrenesulfonic acid, 2-acrylamido-2-methylpropane-sulfonic acid, sulfopropyl methacrylate, vinylstearic acid and vinylsulfinic acid; styrene or alkyl- or halogen-substituted compounds thereof such as styrene, methylstyrene and chlorostyrene; allyl alcohol or esters or ethers thereof; vinylimides such as N-vinylphthalimide and N-vinylsucci-noimide; basic vinyl compounds such as vinylpyridine, vinylimidazole, dimethylaminoethyl methacrylate, N-vi-nylpyrrolidone, N-vinylcarbazole and vinylpyridine; unsaturated aldehydes such as acrolein and methacrolein; and cross-linking vinyl compounds such as glycidyl methacrylate, N-methylolacrylamide, hydroxyethyl methacrylate, triallyl isocyanurate, triallyl cyanurate, divinylbenzene, ethylene glycol di(meth)acrylate, diethylene glycol di(meth)acrylate, triethylene glycol di(meth)acrylate, trimethylolpropane tri(meth)acrylate, and methylene bisacrylamide.

Examples of chain structures which may be used as a bridge moiety include chains containing one or more aryl groups, alkynyl groups, alkenyl groups, alkyl groups, ester groups, ether groups, amino acid residues, sulfur atoms, substituted amine groups, alcohol groups, or silicon atoms.

Non-limiting examples of mulfimeric cores include silsesquioxanes, dendrimers, and porphyrins. Silsesquioxanes (POSS) multimeric cores may be obtained from, for example, Aldrich Chemical Company (Milwaukee, Wis.) and Hybrid Plastics (Fountain Valley, Calif.). Dendrimers and dendrimeric macromolecules may be obtained from, for example, Aldrich Chemical Company (Milwaukee, Wis.) and Dendritech, Inc. (Midland, Mich.). Porphyrins may be obtained from, for example, Aldrich Chemical Company (Milwaukee, Wis.) and Frontier Scientific Inc. (Logan, Utah).

Non-limiting examples of bridge moieties are shown in Table 4.

TABLE 4

Examples of bridge moieties

—O—CH=CH—CH=CH—CH=CH—O—

—O—C≡C—C≡C—C≡C—O—

[tetraphenyl structure]

—O—[triphenyl]—O—

—O—C≡C—[biphenyl]—C≡C—O—

—O—C≡C—[bipyridyl]—C≡C—O—

—O—(CH$_2$)$_n$—O—
—{NH—CHR—(CO)}$_3$—O—
—O—(CF$_2$)$_n$—O—
—(S)$_m$— m=2–14
—O(CH$_2$CH$_2$O)$_n$—
—(OCH(CH$_3$)CH$_2$)$_n$O—

⎡—(OCH$_2$CH$_2$)$_n$—O—
⎢—CH$_2$(OCH$_2$CH$_2$)$_n$—O—
⎣—(OCH$_2$CH$_2$)$_n$—O—

⎡—(OCH$_2$CH$_2$CH$_2$)$_n$—O—
⎢—CH$_2$(OCH$_2$CH$_2$CH$_2$)$_n$—O—
⎣—(OCH$_2$CH$_2$CH$_2$)$_n$—O—

H$_2$C—C(CH$_2$)(CH$_2$)—CH$_2$

HO—CH$_2$—C(CH$_2$OH)(CH$_2$OH)—CH$_2$—OH

In Table 4, n is 2–14.
Further example of bridge moieties include:

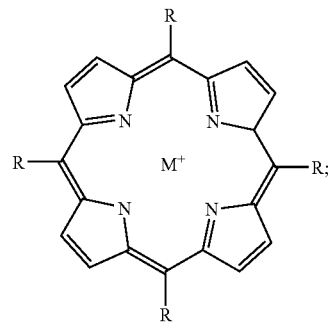
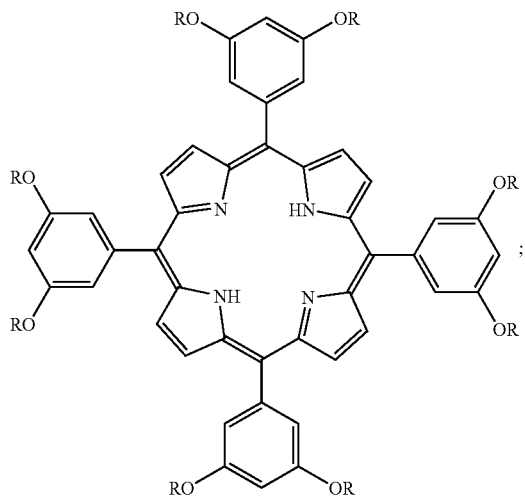
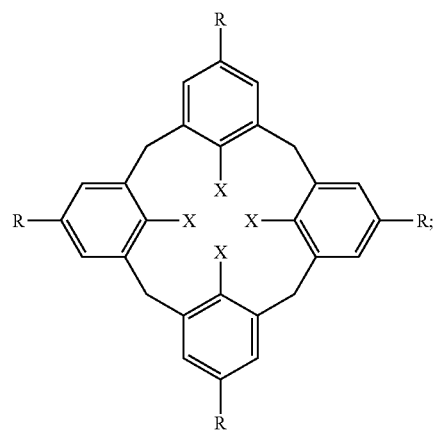
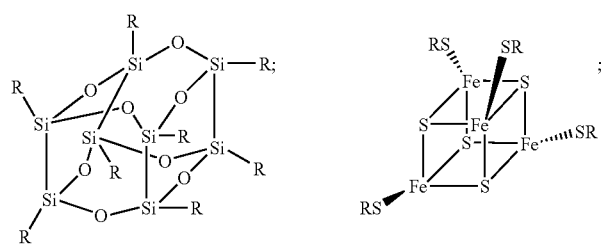
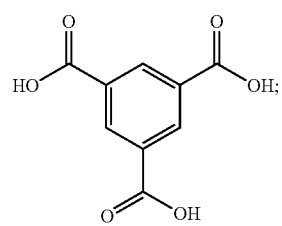
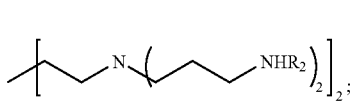
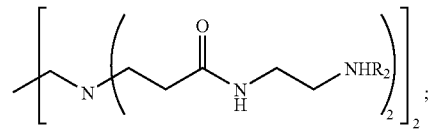
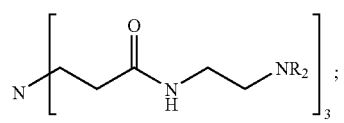
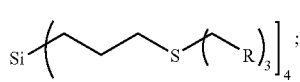
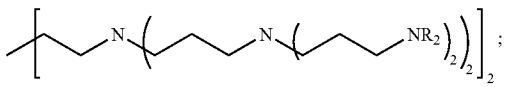
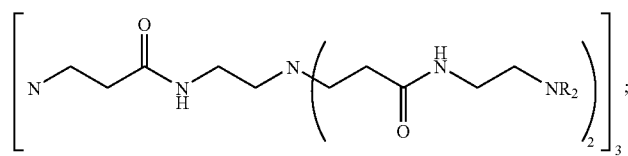

53
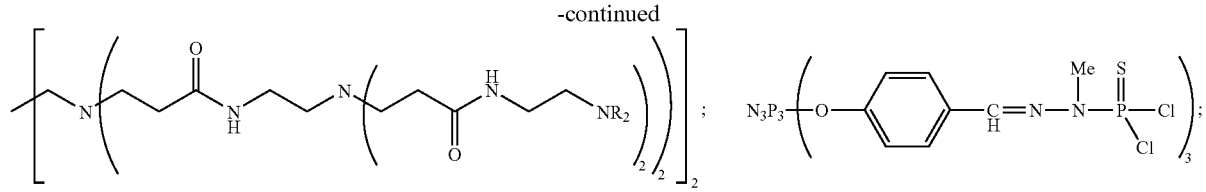
54
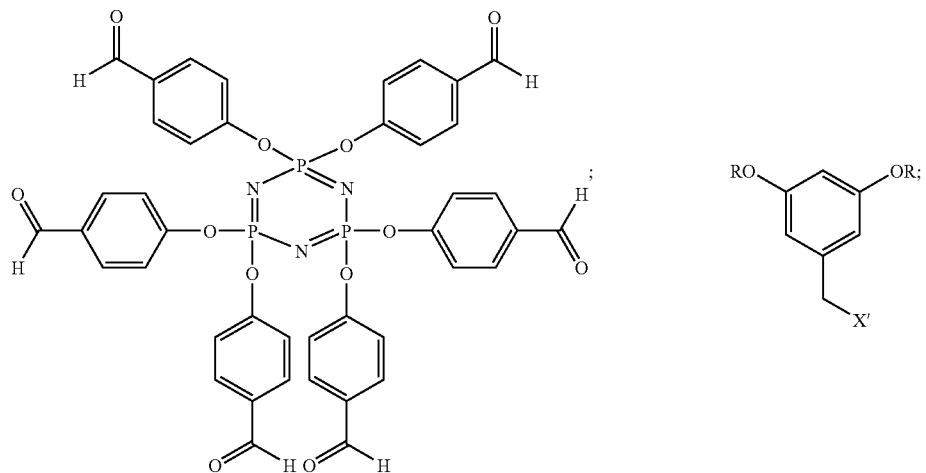
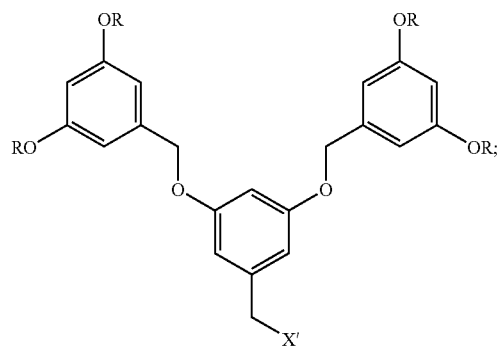
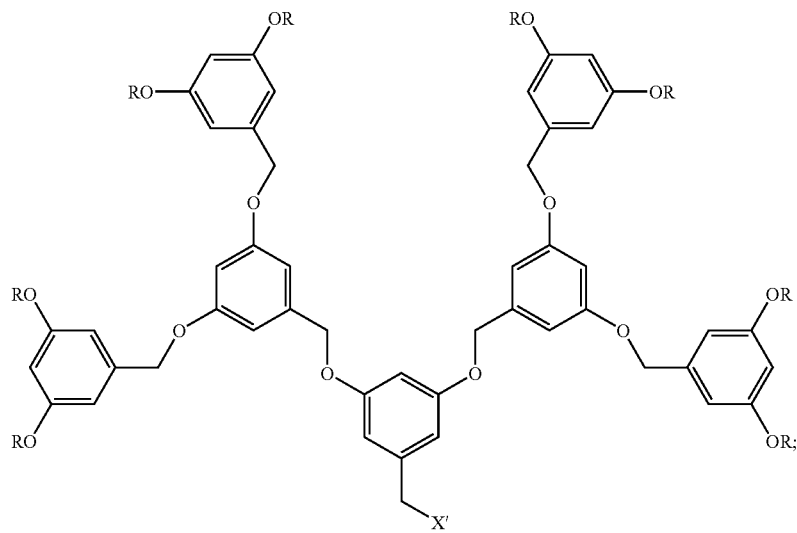

-continued
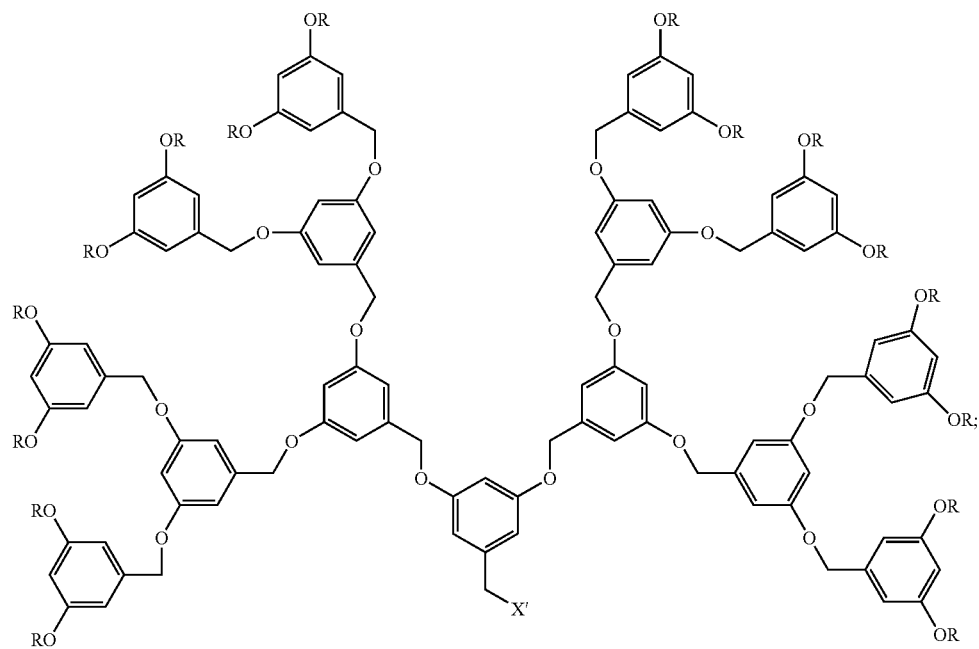
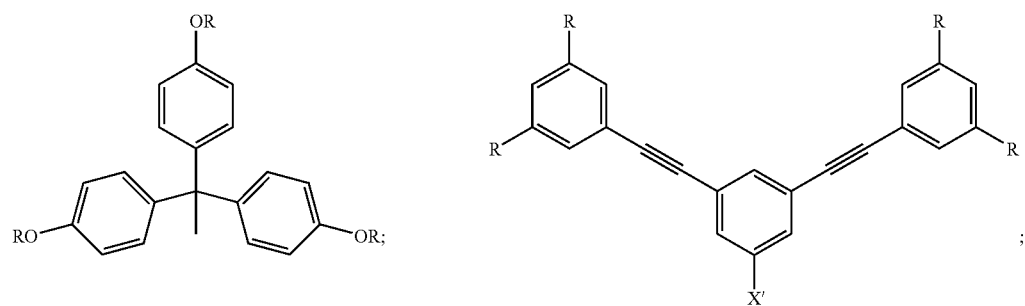
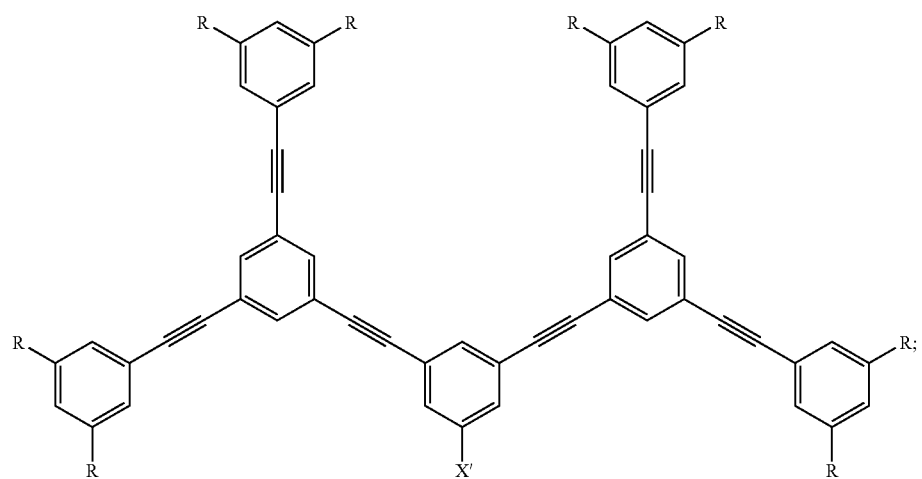

-continued

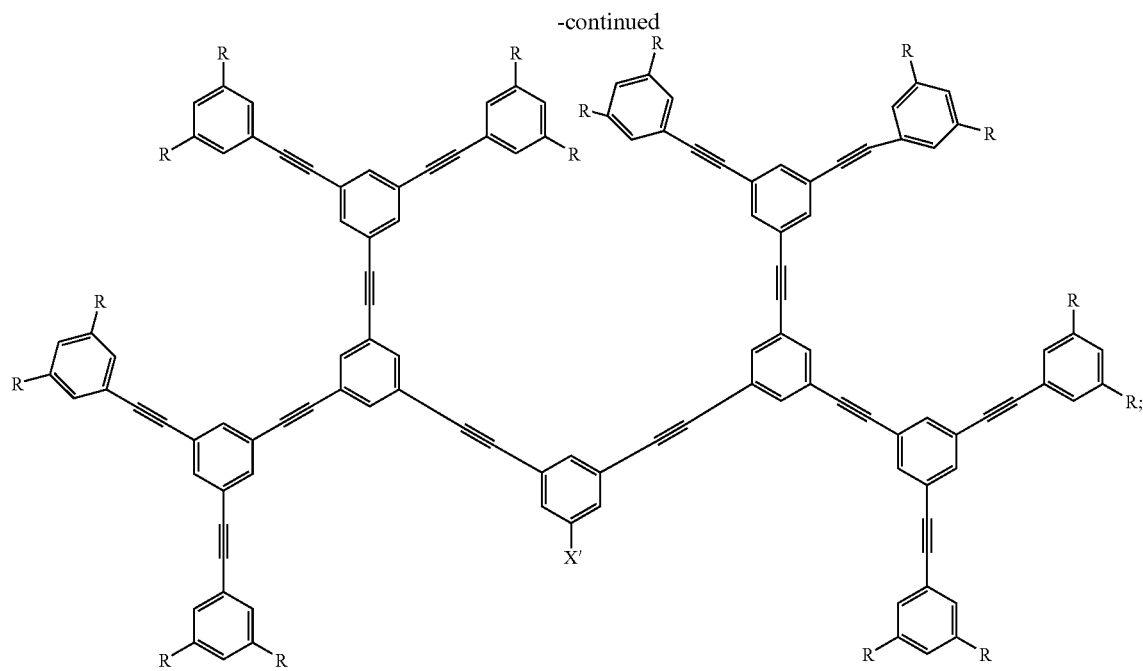

wherein X' is independently H or a functional group for linking to another bridged macrocyclic moiety or to other moieties, such as hydrophobic groups, biocompatibility groups, etc; and wherein R may be a functional group for coupling the bridge moiety to a macrocyclic module, or may be an additional functional group, such as hydrogen, an activated acid, —OH, —C(O)OH, —C(O)H, —C(O)OCH$_3$, —C(O)Cl, —NR'R', —NR'R'R'$^+$, —MgX, —Li, —OLi, —OK, —ONa, —SH, —C(O)(CH$_2$)$_2$C(O)OCH$_3$, —NH-alkyl-C(O)CH$_2$CH(NH$_2$)CO$_2$-alkyl, —CH=CH$_2$, —CH=CHR', —CH=CR'$_2$, 4-vinylaryl, —C(O)CH=CH$_2$, —NHC(O)CH=CH$_2$, —C(O)CH=CH(C$_6$H$_5$),

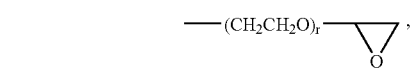

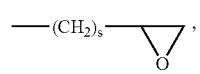

—OH, —OC(O)(CH$_2$)$_2$C(O)OCH$_3$, —OC(O)CH=CH$_2$,

—P(O)(OH)(OX), or —P(=O)(O-)O(CH$_2$)$_s$NR'$_3^+$;

wherein R' are each independently selected from the group consisting of hydrogen and 1-6C alkyl; X is selected from the group consisting of Cl, Br, and I; r is 1-50; and s is 1-4.

In further variations, the bridge moiety may be star-shaped or dendrimeric. In these variations, a synthon is coupled to each of the termini.

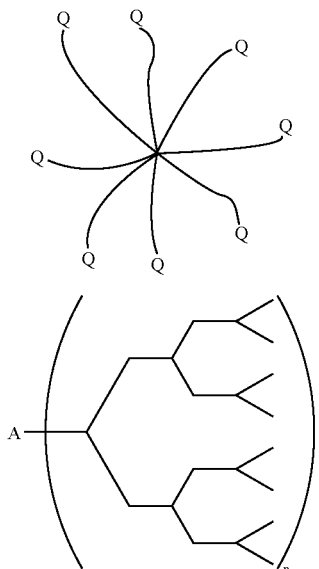

Preferred bridge moieties include

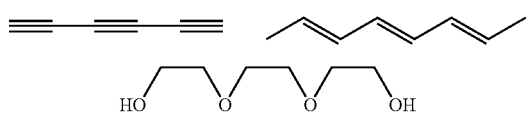

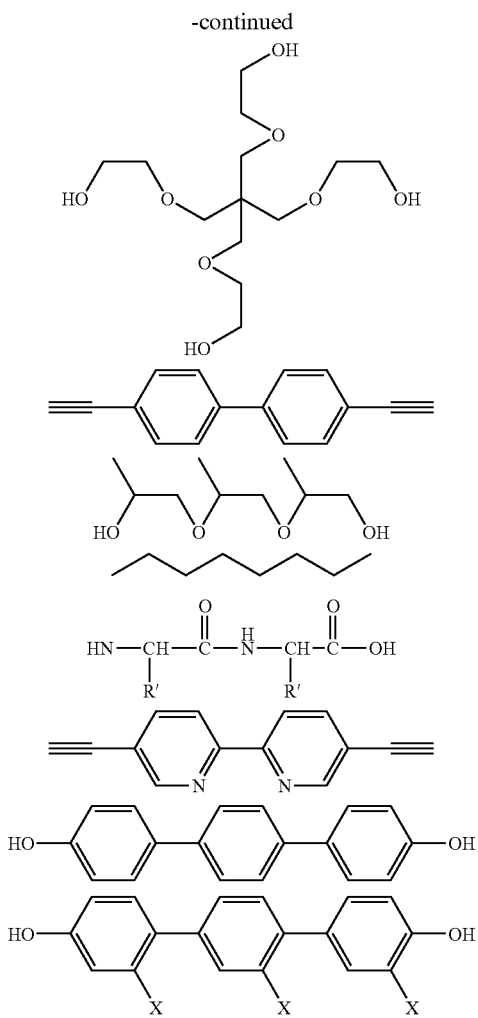

wherein X is a funotional group for coupling the bridge moiety to a surface, and wherein R' is a natural amino acid side chain.

Particularly preferred bridge moieties for the bridged macrocyclic modules of the invention include

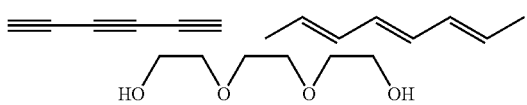

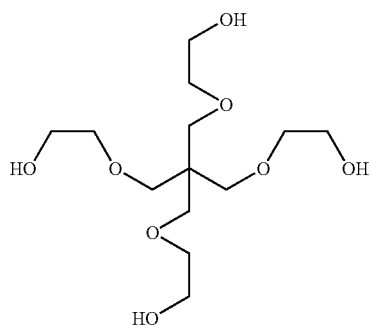

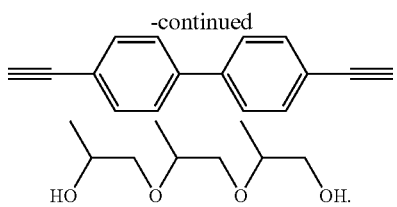

In one variation, the termini of a bridge moiety may be coupled to synthons to form a bridged program director. The synthons coupled to a bridged program director may have protection groups for directing the addition of other synthons to the bridged program director. The bridged program director has a built-in directionality which may control the coupling of the synthons at the termini to other synthons.

In another variation, the bridge moiety may also be directly coupled to a macrocyclic module to form a bridged macrocyclic module.

Other variations on methods for producing bridged macrocyclic modules from bridge moieties will be apparent from the methods and Examples herein, as well as further variations apparent to those of skill in the art.

The bridge moiety may provide a variety of functions. For example, the bridge moiety may comprise functional groups for attachment of the module to a surface. The chemical and steric properties of the bridge moiety may affect transport modification and selectivity, through chemical or electronic interaction with and/or steric inhibition of components of a fluid in contact with the bridged mcarocyclic module. For example, adding steric bulk to the bridge might be expected to decrease effective pore size of the module. For example, use of a polypropylene glycol (PPG) bridge moiety versus a polyethylene glycol (PEG) bridge may result in a dramatically different solute size exclusion.

The bridge moiety may further comprise groups which help with biocompatibility. In one example, PEG may be used as a bridge moiety, which may help to decrease plasma buildup. The bridge moiety may provide the module with amphiphilic character, which may, for example, facilitate the orientation of the modules on a surface to form a nanofilm.

The bridge moieties may help to constrain the geometry of the molecule. For example, in comparison with a similar macrocylic module which does not contain a bridge moiety, the structure of the bridged macrocyclic moiety may be more rigid.

Polymerizable Groups of Bridge Moieties

A bridge moiety may contain a polymerizable group, which may be useful in the production of 2-D and 3-D arrays of bridged macrocyclic modules. For example, a polymerizable group may participate in anionic, cationic, radical, condensation, ring opening or other types of polymerizations. A polymerizable group may have more than one polymerizable moiety, and several polymerizable groups may be attached to one bridge moiety. Examples of polymerization groups include those shown in Table 5.

TABLE 5

| Examples of polymerizable groups of bridge moieties |
|---|
| 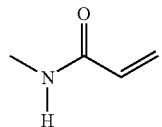 |
| 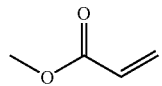 |
| 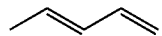 |
| 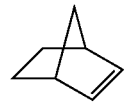 |

TABLE 5-continued

| Examples of polymerizable groups of bridge moieties |
|---|
| 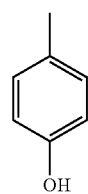 |
| 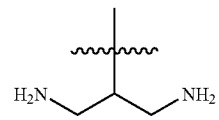 |
| 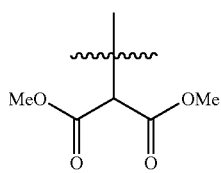 |
| ⸺⸺ |

A non-limiting example of a bridged macrocyclic moiety with a polymerization groups is the structure:

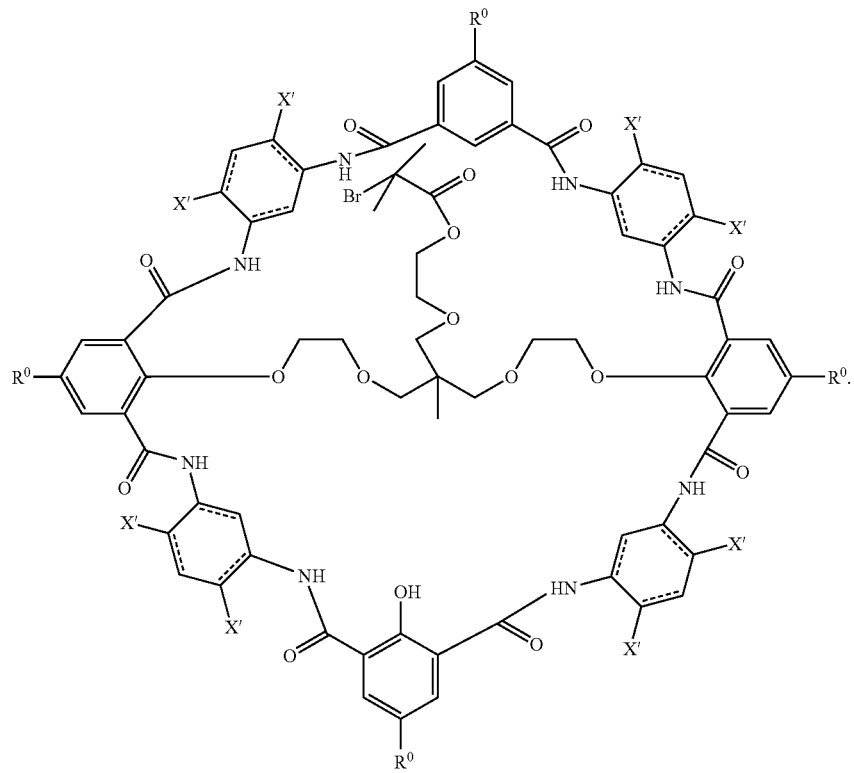

Various monomers may be mixed with a bridged macrocyclic module which contains a polymerizable group and a polymerization may be performed, coupling the bridged macrocyclic modules together (see examples in Schemes 1 and 2). In Scheme 1, R indicates H or a lipophilic group.

Scheme 1
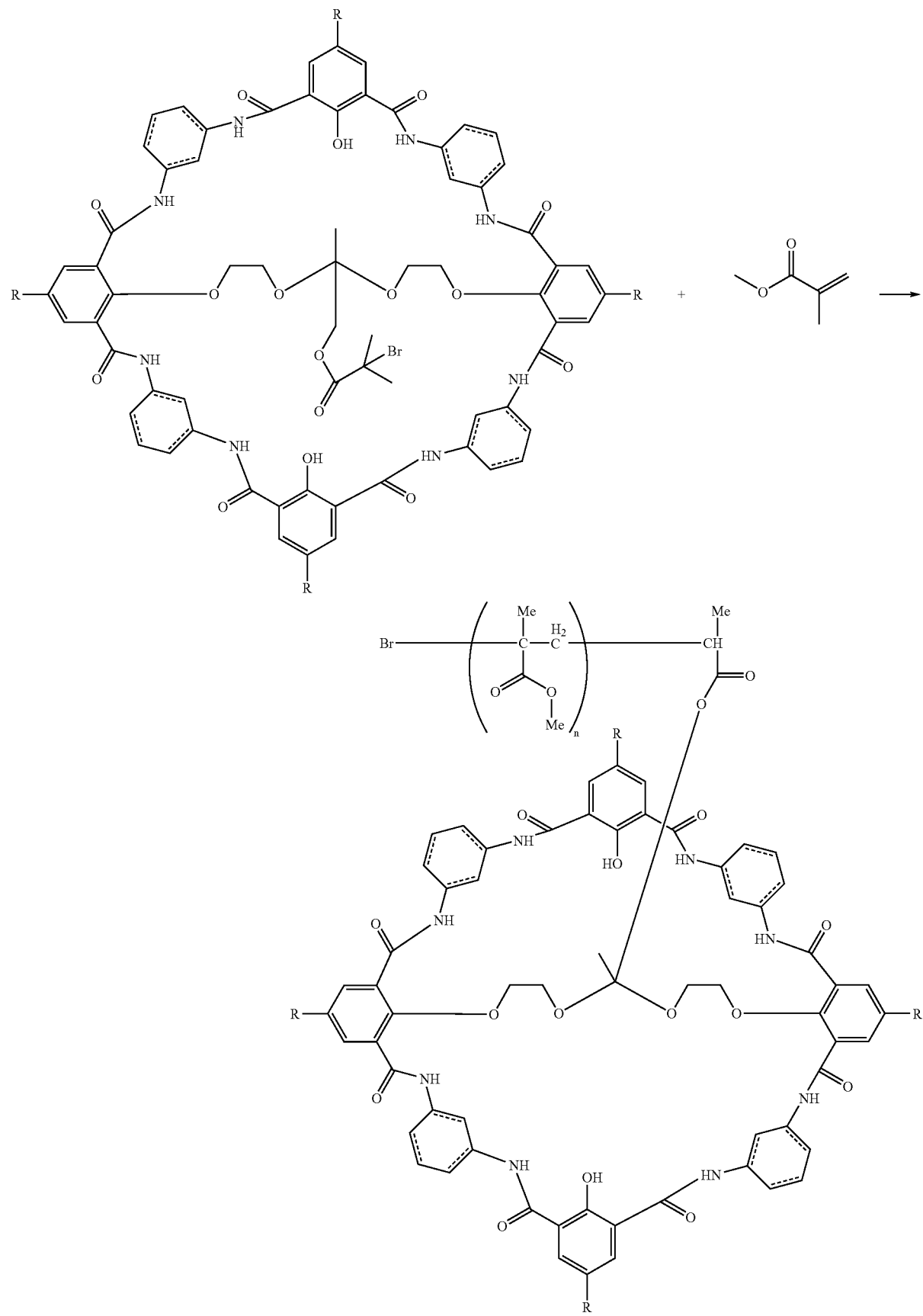

Scheme 2
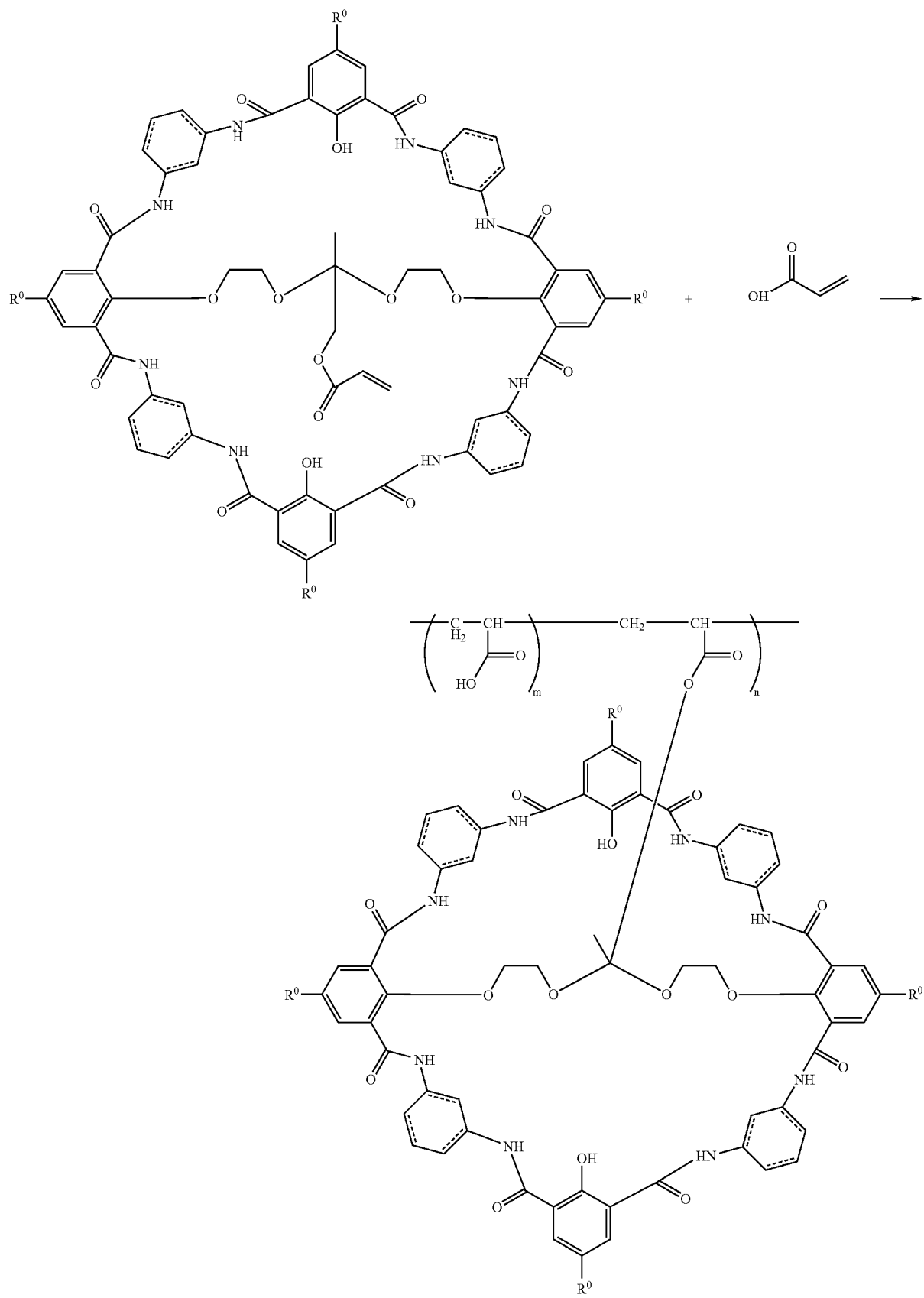

Formation of 2-D versus 3-D structures may be controlled by the type of polymerizable group added, as well as by the relative ratios of monomer to bridged macrocyclic modules. For example, in the schematic above, relatively higher amounts, or ratios, of 2-methyl-acrylic acid methyl ester versus the bridged macrocyclic module may favor formation of a 2-dimensional structure rather than a 3-dimensional structure.

Network structures with higher 3-D cross-linking density may also be achieved by using bridged macrocyclic modules or monomers which are multi-functional. For example, an acrylamide polymerization scheme below illustrates a bridged macrocyclic module with multiple polymerization groups and an analogous multi-functional cross-linking monomer:

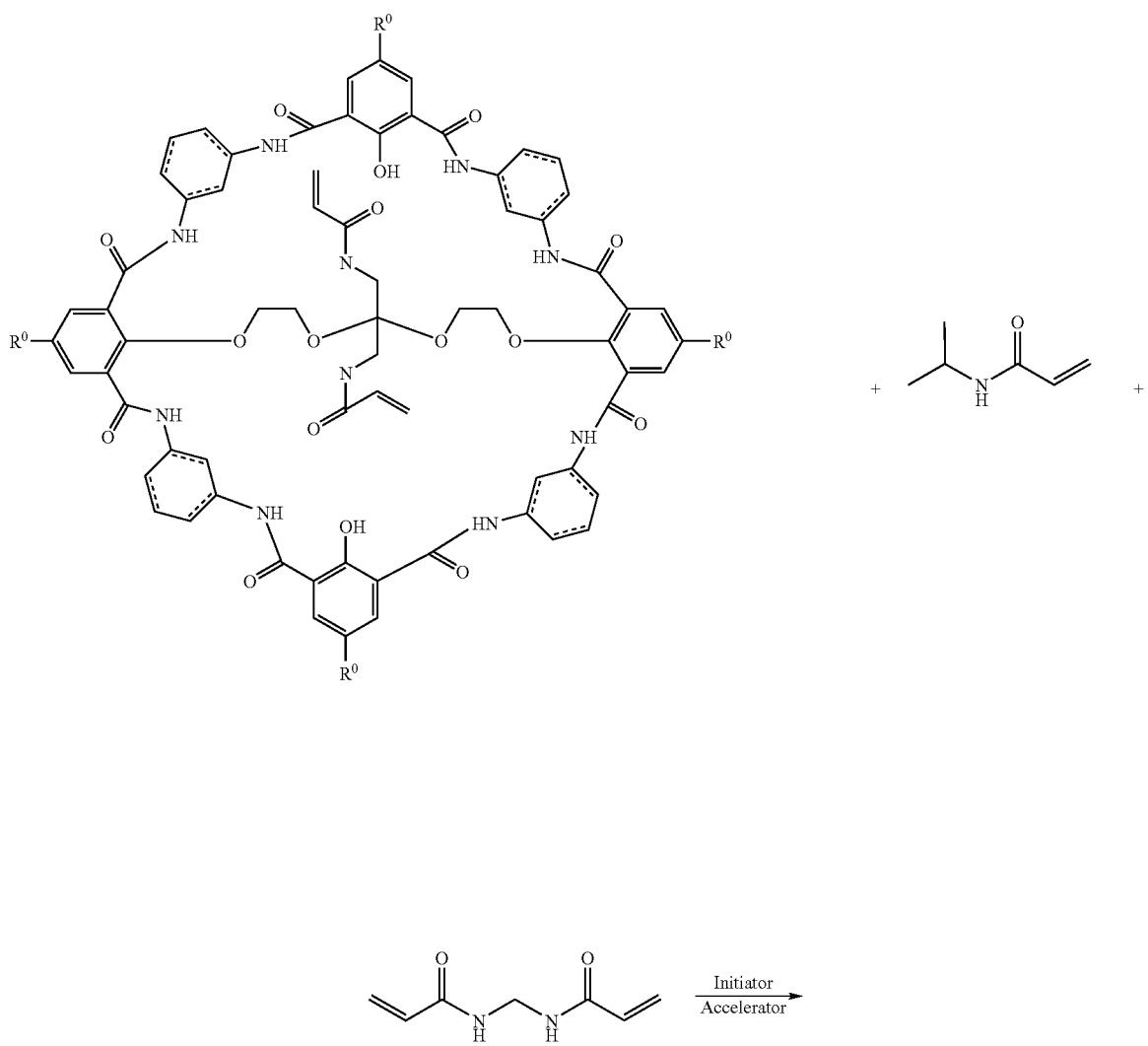

Scheme 3

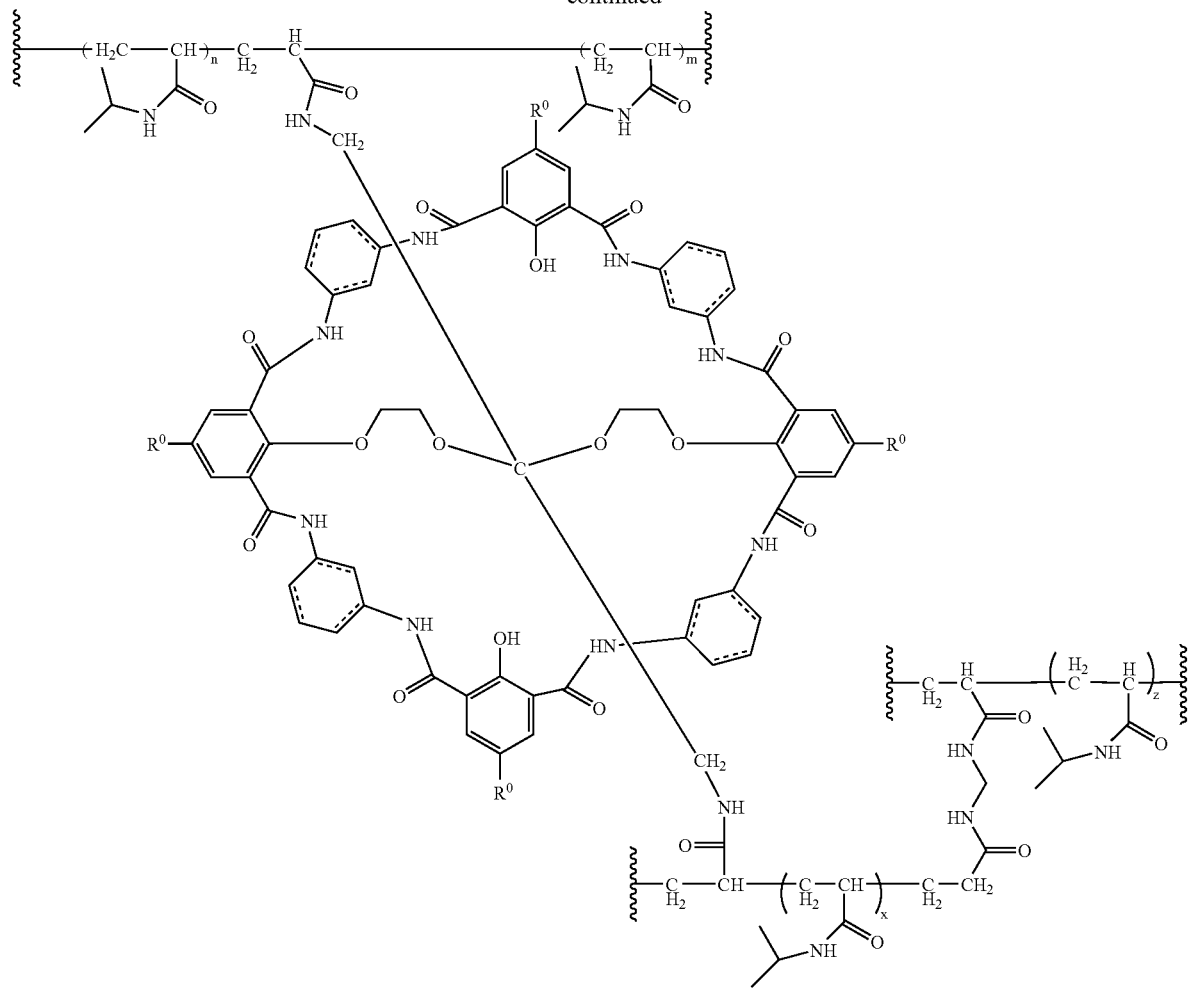

40

In addition to the multi-component schemes above, a bridged macrocyclic module could also be self-polymerized. Such a polymerization would form a more discrete network of bridged macrocyclic modules with narrower pore size distribution.

Coupling Methods

A variety of coupling schemes may be used in coupling the various components of the compositions of the invention. For example, synthons may possess functional groups for coupling of the synthon to other synthons on the same or different bridged macrocyclic module, for coupling of the synthon to bridge moieties on the same or different bridged macrocyclic module, or for coupling of the synthon to a substrate. Bridge moieties may possess functional groups for coupling of the bridge moiety to synthons, to other bridge moieties, or to a substrate.

In one type of coupling, the linkage may be the product of the direct coupling of one functional group from each component. For example, a hydroxyl group of a first synthon may couple with an acid group or acid halide group of a second synthon to form an ester linkage between the two synthons. Another example is an imine linkage, —CH=N—, resulting from the reaction of an aldehyde, —CH=O, on one synthon with an amine, —NH2, on another synthon. Non-limiting examples of suitable linkages between, e.g., bridged macrocyclic modules, are shown in Table 6.

TABLE 6

Examples of functional groups and linkages formed

| Functional Group A | Functional Group B | Linkage Formed |
|---|---|---|
| —NH$_2$ | —C(O)H | —N=CH— |
| —NH$_2$ | —CO$_2$H | —NHC(O)— |
| —NHR | —CO$_2$H | —NRC(O)— |
| —OH | —CO$_2$H | —OC(O)— |
| —X | —ONa | —O— |
| —SH | —SH | —S—S— |

TABLE 6-continued

Examples of functional groups and linkages formed

| Functional Group A | Functional Group B | Linkage Formed |
|---|---|---|
| —X | —(NR)Li | —NR— |
| —X | —SNa | —S— |
| —X | —NHR | —NR— |
| module-X |  | 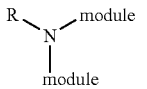 |
| —X | —CH$_2$CuLi | —CH$_2$— |
| —X | —(CRR)$_{n=1-6}$CuLi | —(CRR)$_n$— |
| module-X | module-X | module-module |
| —CH$_2$X | —CH$_2$X | —CH$_2$CH$_2$— |
| —ONa | —C(O)OR | —C(O)O— |
| —SNa | —C(O)OR | —C(O)S— |
| —X | —C≡CH | —C≡C— |
| —C≡CH | —C≡CH | —C≡C—C≡C— |
| —MgX | —C(O)H | —CH(OH)— |
| Module-NH$_2$ | 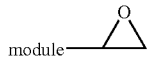 | 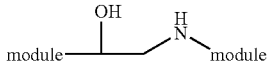 |
| Module-MgX |  | 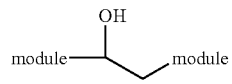 |
| 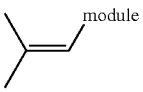 | module-X | 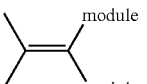 |
| —C(O)H | —C(O)H | —HC=CH— |
| (CH$_3$)$_2$C=CH-module | module-C(O)Cl | 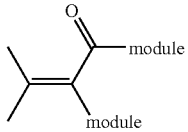 |
| —N=C=O | —NH$_2$ | —NHC(O)NH— |
| —N=C=O | HO— | —NHC(O)O— |
| —C(O)H | —NHNH$_2$ | —CH=N—NH— |
| —OH | —OC(O)X | —OC(O)O— |
| (CH$_3$)$_2$C=CH-module | Module-SH | 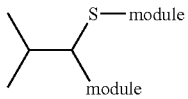 |
| (CH$_3$)$_2$CHC(O)O-module | module-CH(O) | 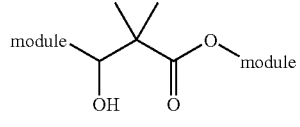 |
| module-CH$_2$C(O)OH | module-CH$_2$C(O)OH | 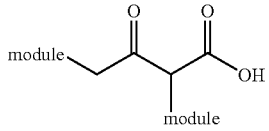 |
| 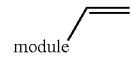 | R$_2$SiH-module | 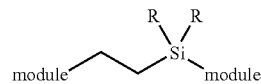 |

TABLE 6-continued
Examples of functional groups and linkages formed
| Functional Group A | Functional Group B | Linkage Formed |
|---|---|---|
| 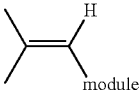 | 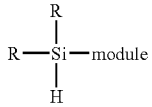 | 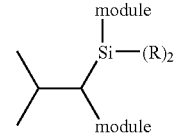 |
| 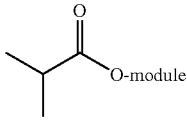 | 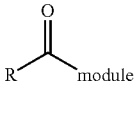 | 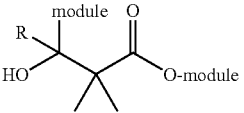 |
|  | 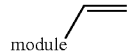 |  |
| 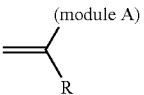 | 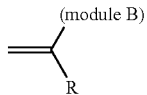 | 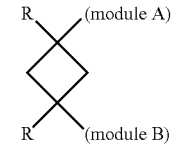 |
| 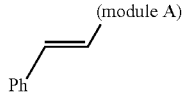 | 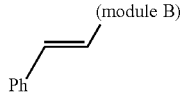 | 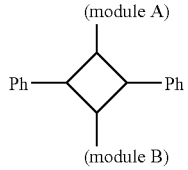 |
|  | 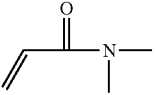 | 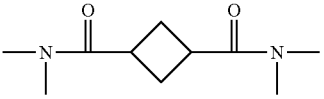 |
| 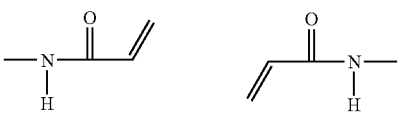 | 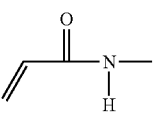 | 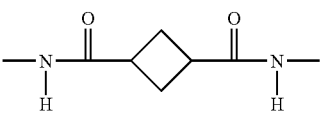 |
| 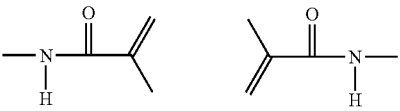 | 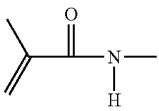 | 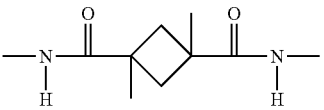 |
|  | 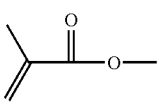 | 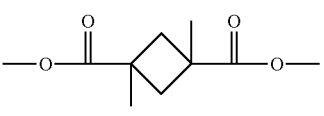 |
|  | 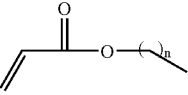 | 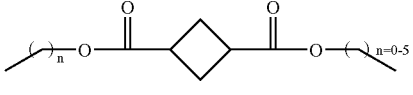 |
| —OP(O)(OH)$_2$ | —OH | —OP(O)(OH)O— |
|  | 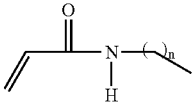 | 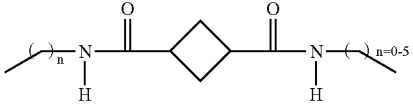 |

TABLE 6-continued

Examples of functional groups and linkages formed

| Functional Group A | Functional Group B | Linkage Formed |
|---|---|---|

In Table 6, R independently represents a hydrogen or an alkyl group, and X is halogen or other good leaving group. It is to be understood that the functional groups and resulting linkages in Table 6 are not limited to coupling modules to each other, but may also be used to couple other various components, for example, coupling a synthon to a substrate, coupling a synthon to a bridge moiety, etc.

In one variation, the functional group may be added to a component after initial preparation of that component. For example, a bridged macrocyclic module may have functional groups for coupling to other bridged macrocyclic modules wherein the functional groups are coupled to the bridged macrocyclic module after initial preparation of the closed ring of the module. For example, an amine linkage between the synthons of a bridged macrocyclic module may be substituted with one of various functional groups to produce a substituted linkage. Examples of such linkages between synthons of a bridged macrocyclic module having functional groups for coupling other bridged macrocyclic modules are shown in Table 7.

TABLE 7

Examples of macrocyclic module linkages

| Macrocyclic Module Linkage | Reagent | Substituted Linkage |
|---|---|---|
| $Q_1-NH-Q_2$ | acryloyl chloride | acrylamide linkage |
| $Q_1-CH_2-NH-Q_2$ | acryloyl chloride | acrylamide linkage |
| $Q_1-CH(OH)-Q_2$ | acryloyl chloride | acrylate ester linkage |
| $Q_1-CHX-Q_2$ | $X-C\equiv C-H$ | alkyne linkage |
| $Q_1-CHX-Q_2$ | $X$-styrene | styrene linkage |
| $Q_1-NH-Q_2$ | 2-alkylacryloyl chloride (R=alkyl) | methacrylamide linkage |
| $Q_1-CH(OH)-Q_2$ | 2-alkylacryloyl chloride (R=alkyl) | methacrylate ester linkage |
| $Q_1-NH-Q_2$ | cinnamoyl chloride | cinnamamide linkage |

TABLE 7-continued

Examples of macrocyclic module linkages

| Macrocyclic Module Linkage | Reagent | Substituted Linkage |
|---|---|---|
| $Q_1-CH(OH)-Q_2$ | cinnamoyl chloride | cinnamate ester linkage |

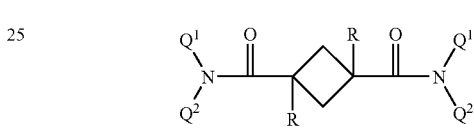

In Table 7, X is halogen, and Q represents a synthon in a bridged macrocyclic module.

Referring to Table 7, the substituted linkage of a bridged macrocyclic module may couple to a substituted linkage of another module. In some variations, the coupling of these linkages is done by initiating 2+2 cycloaddition. For example, acrylamide linkages may couple to produce by 2+2 cycloaddition. In other variations, coupling of these reactive substituted linkages may be initiated by other chemical, thermal, photochemical, electrochemical, and irradiative methods to provide a variety of coupled structures.

It is to be understood that the functional groups and substituted linkages formed included in Table 7 may also be used to couple other components.

The functional groups used to form linkages between components may be separated from the component by a spacer. A spacer can be any atom or group of atoms which couples the functional group to the component, and does not interfere with the linkage-forming reaction. A spacer is part of the functional group, and becomes part of the linkage between components. An example of a spacer is a polymethylene group, —$(CH_2)n$-, where n is 1-6. The spacer may be said to extend the linkage between the components. Other examples of spacer groups are alkylene, aryl, acyl, alkoxy, saturated or unsaturated cyclic hydrocarbon, heteroaryl, heteroarylalkyl, heterocyclic, and corresponding substituted groups. Further examples of spacer groups are polymer, copolymer, or oligomer chains, for example, polyethylene oxides, polypropylene oxides, polysaccharides, polylysines, polypeptides, poly(amino acids), polyvinylpyrrolidones, polyesters, polyacrylates, polyamines, polyimines, polystyrenes, poly(vinyl acetate)s, polytetrafluoroethylenes, polyisoprenes, neopropene, polycarbonate, polyvinylchlorides, polyvinylidene fluorides, polyvinylalcohols, polyurethanes, polyamides, polyimides, polysulfones, polyethersulfones, polysulfonamides, polysulfoxides, and copolymers thereof. Examples of polymer chain spacer structures include linear, branched, comb and dendrimeric polymers, random and block copolymers, homo- and heteropolymers, flexible and rigid chains. The spacer may be any group which does not interfere with formation of the linkage. A spacer group may be substantially longer or shorter than the functional group to which it is attached.

Coupling of components to each other may occur through coupling of functional groups of the components to linker molecules. The functional groups involved may be, for example, those exemplified in Table 8. For example, modules may couple to at least one other module through a linker molecule. A linker molecule is a discrete molecular species used to couple at least two components. Each module may have 1 to 30 or more functional groups which may couple to a linker molecule. Linker molecules may have 1 to 20 or more functional groups which may couple to, for example, a module.

In one variation, a linker molecule has at least two functional groups, each of which can couple to a module and/or other component. In these variations, linker molecules may include a variety of functional groups for coupling modules and/or other components. Non-limiting examples of functional groups of modules and linker molecules are illustrated in Table 8.

TABLE 8

Examples of functional groups of modules and linker molecules

| Functional Group of Module A | Functional Group of Module B | Linker Molecule | Linkage |
|---|---|---|---|
| —NHR or —NH$_2$ | —NHR or —NH$_2$ | [structure] | [structure] |
| —NHR or —NH$_2$ | —NHR or —NH$_2$ | [structure] | [structure] |
| —NHR or —NH$_2$ | —NHR or —NH$_2$ | [structure] | [structure] |
| —NHR or —NH$_2$ | —NHR or —NH$_2$ | [structure] | [structure] |
| —OH | —OH | [structure] | [structure] |
| —OH | —OH | [structure] | [structure] |
| —OH | —OH | (RO)$_2$BR'B(OR)$_2$ | —O(HO)BR'B(OH)O— |
| —NHR or —NH$_2$ | —NHR or —NH$_2$ | (RO)$_2$BR'B(OR)$_2$ | —NH(HO)BR'B(OH)NH— |
| —OH | —OH | X—(CH$_2$)$_n$—X | —O—(CH$_2$)$_n$—O— |
| —OH | —OH | ClC(O)—(CH$_2$)$_n$—C(O)Cl | [structure] |
| —NHR or —NH$_2$ | —NHR or —NH$_2$ | [formaldehyde structure] | —NH—CH$_2$—NH— |

TABLE 8-continued

Examples of functional groups of modules and linker molecules

| Functional Group of Module A | Functional Group of Module B | Linker Molecule | Linkage |
|---|---|---|---|
| —NHR or —NH$_2$ | —NHR or —NH$_2$ | | |
| | | | |
| | | | |
| | | | |
| | | | |
| —OH | —OH | | —OCH$_2$CH(OH)CH$_2$O— |
| —OH | —NH$_2$ | | —OCH$_2$CH(OH)CH$_2$NH— |
| —NH$_2$ | —NH$_2$ | | —NHCH$_2$CH(OH)CH$_2$NH— |
| —NRH | —NRH | | —NHCH$_2$CH(OH)CH$_2$NR— |

In Table 8, n is 1-6, m is 1-10, R is —CH$_3$ or —H, R' is —(CH$_2$)$_n$— or phenyl, R" is —(CH$_2$)—, polyethylene glycol (PEG), or polypropylene glycol (PPG), and X is Br, Cl, I, or other good leaving groups which are organic groups containing atoms selected from the group of carbon, oxygen, nitrogen, halogen, silicon, phosphorous, sulfur, and hydrogen. A module may have a combination of the various functional groups exemplified in Table 8. It is to be understood that the functional groups and linkers included in Table 8 may also be used to link other components together. Preferred linkers include DEM and ethylene diamine. Further examples of suitable linkers are found in the Examples.

Methods of initiating coupling of the components to linker molecules include chemical, thermal, photochemical, electrochemical, and irradiative methods.

Other methods for linking the components will be apparent to one of skill in the art.

Methods for Preparing Bridged Program Directors from Bridge Moieties

Scheme 4 illustrates an example of a general scheme for preparing bridged program director compounds.

Scheme 4

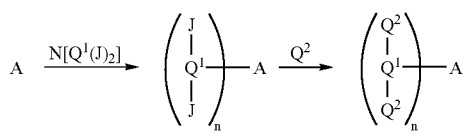

In Scheme 4, A is a bridge moiety which provides at least two termini, each $Q^1$ is an independently selected synthon as defined herein, and each J is an independently selected functional group for further coupling to an independently selected synthon $Q^2$. Synthons $Q^2$ may be coupled to synthons $Q^1$ directly, or through linkers. Examples of suitable functional groups and resulting linkages may be found in Tables 6-8.

The bridge moiety termini may comprise functional groups for coupling synthons $Q^1$ to the termini. Alternatively, suitable functional groups may be added to the termini for coupling to the synthons. The synthons may be directly coupled to the termini, or may be coupled through linker molecules. Examples of suitable functional groups and resulting linkages are found in Tables 6-8. The termini may independently include protection groups.

In Scheme 4, synthons $Q^1$ are shown having functional groups J attached, before coupling to bridge moiety A. In an alternate scheme, synthons $Q^1$ are coupled to bridge moiety A, and then synthons $Q^1$ are subsequently derivatized with functional groups J for coupling of additional synthons $Q^2$.

Non-limiting examples for preparation of bridged program director compounds (compounds 4 and 5) may be found in Example 1. Additional schemes and syntheses for preparing bridged program directors will be apparent to those of skill in the art.

Methods for Preparation of Activated Synthon Multimer Compounds:

Activated synthon multimers may be prepared by concerted and/or step-wise methods. A general scheme for a concerted-approach is shown in Scheme 5.

Scheme 5

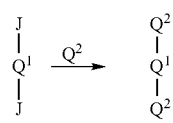

A non-limiting example for preparation of an activated synthon multimer A according to a concerted-approach may be found in Scheme 18 of Example 4. Activated synthon multimers may also be prepared by step-wise methods. Additional schemes and syntheses for preparing activated synthon multimer compounds will be apparent to those of skill in the art.

Methods for Preparing Bridged Macrocyclic Module Compounds

Various coupling schemes for preparing bridged macrocyclic module compounds may be used. A bridged macrocyclic module may be made via a stepwise methodology, a pseudo-concerted approach, convergent methods, or a variety of other synthetic schemes that will be apparent to one skilled in the art.

Pseudoconcerted Methods

A bridged macrocyclic module may be prepared by pseudoconcerted methods. For example, a bridged macrocyclic module may be prepared from a bridged program director compound according to Scheme 6.

Scheme 6

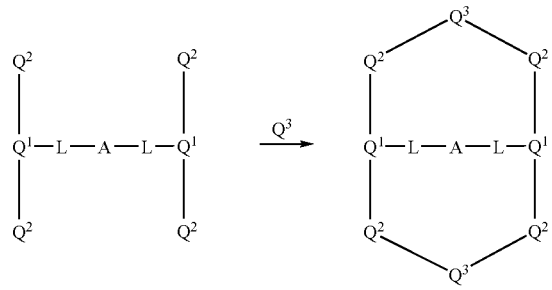

In Scheme 6, A is a bridge moiety, L are optional linker molecules, each $Q^1$ is an independently selected synthon, each $Q^2$ is an independently selected synthon, and each $Q^3$ is an independently selected synthon. Complementary functional groups present on synthons $Q^2$ and $Q^3$ may react to form the bicyclic bridged macrocyclic module. $Q^2$ and $Q^3$ may be directly coupled or may be coupled through linker molecules. Examples of suitable functional groups, linkers and the resulting linkages for coupling $Q^2$ to $Q^3$ are found in Tables 6-8.

Non-limiting examples of the synthesis of bridged macrocyclic modules according to this method may be found in Examples 1 and 2. It is to be understood that this approach may also be used for synthesizing polycyclic bridged macrocyclic modules, wherein the bridge moiety comprises more than two termini. For example, Scheme 7 shows a general approach for the synthesis of a bridged macrocyclic module from a bridged program director, wherein the bridged program director comprises three termini.

Scheme 7

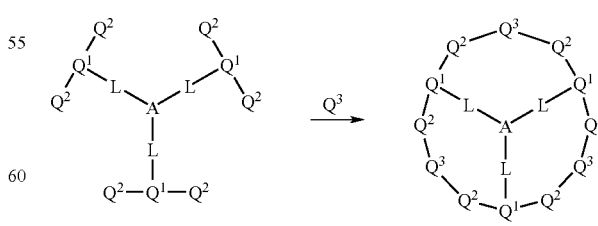

A specific example of a pseudo-concerted synthesis of a bridged macrocyclic module having a bridge moiety with four termini is shown in Example 5. Other variations on this method will be apparent to those of skill in the art.

Stepwise Methods

In another variation, a bridged macrocyclic module may be synthesized by stepwise ring closure using a bridge moiety with appropriate functional groups, as shown in Scheme 8:

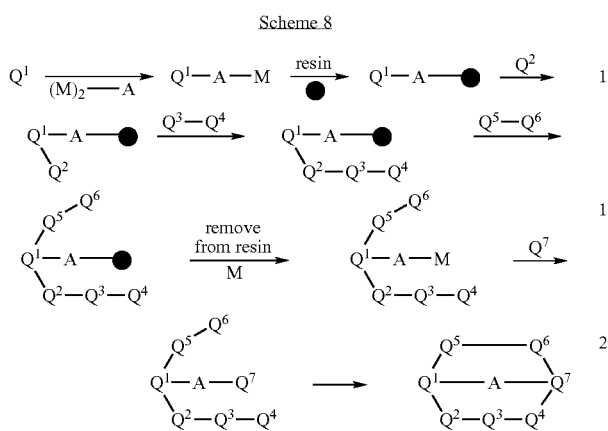

Scheme 8

In Scheme 8, each synthon may be coupled directly to its adjacent synthons, or may also be linked through a linker molecule. Examples of suitable functional groups, linkers and the resulting linkages are found in Tables 6-8. A non-limiting example of the synthesis of a bridged macrocyclic module according to this method may be found in Example 3.

This approach may be of particular use in synthesizing asymmetrical bridged macrocyclic modules, although other methods may also be useful. It is to be understood that the method shown in Scheme 8 may also be used to produce a symmetrical bridged macrocyclic module. Further variations on this approach will be apparent to those of skill in the art.

Convergent Methods

A bridged macrocyclic module may also be prepared by convergent methods. For example, a bridged macrocyclic module is prepared from a bridged program director and an activated synthon trimer according to Scheme 9.

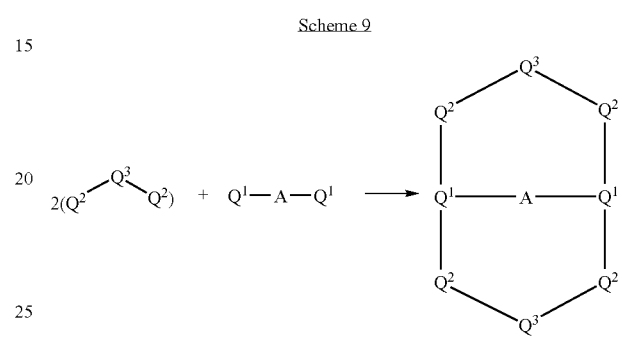

Scheme 9

In Scheme 9, an activated synthon multimer is reacted with a bridged program director containing appropriate reactive functional groups, forming the bridged macrocyclic module.

Schemes 10 and 11 illustrate a specific example of a synthesis of this type.

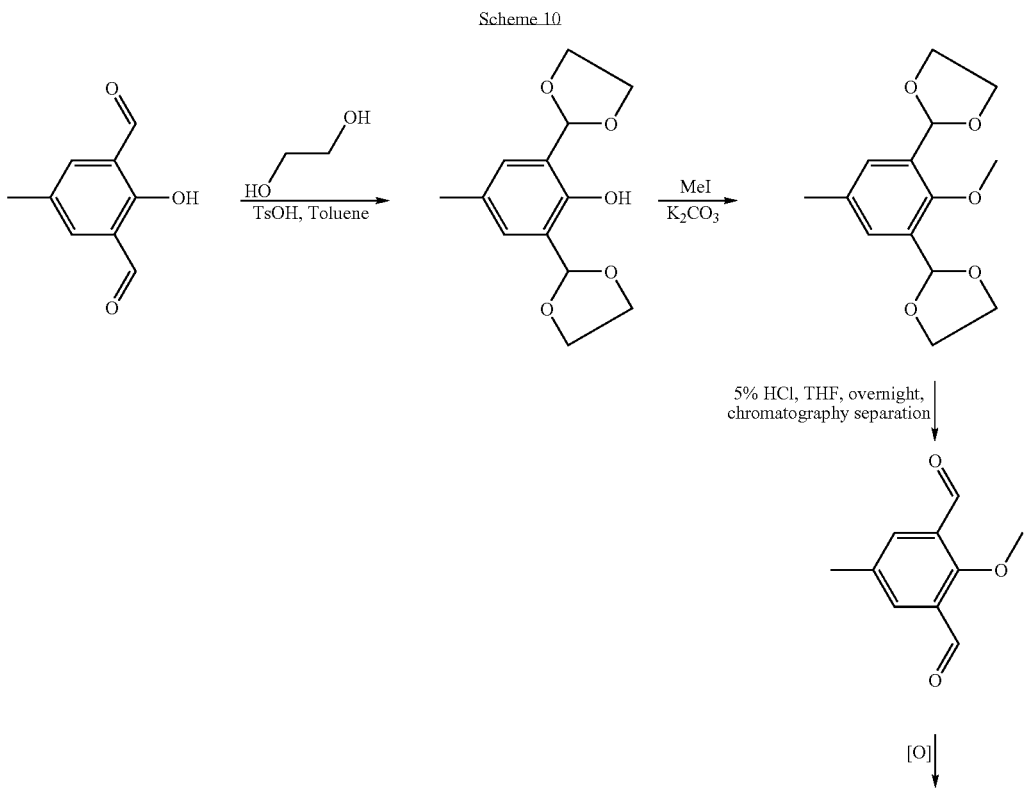

Scheme 10

-continued

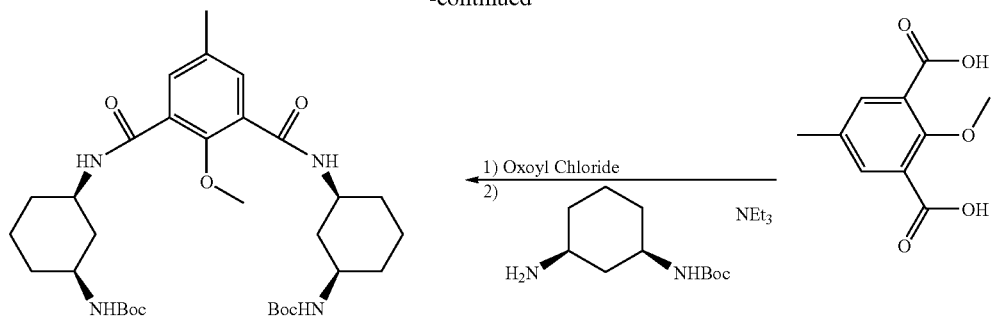

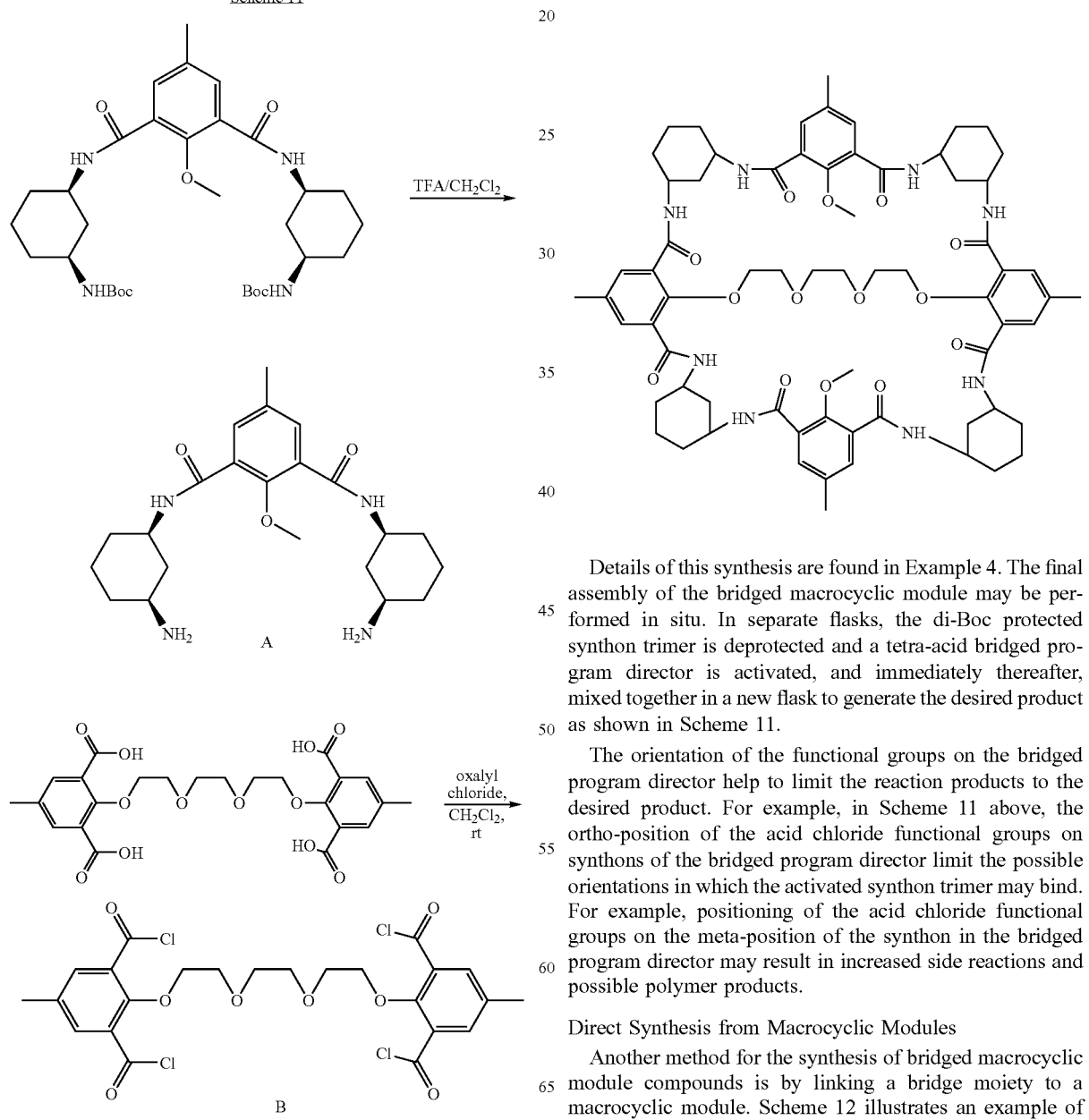

Details of this synthesis are found in Example 4. The final assembly of the bridged macrocyclic module may be performed in situ. In separate flasks, the di-Boc protected synthon trimer is deprotected and a tetra-acid bridged program director is activated, and immediately thereafter, mixed together in a new flask to generate the desired product as shown in Scheme 11.

The orientation of the functional groups on the bridged program director help to limit the reaction products to the desired product. For example, in Scheme 11 above, the ortho-position of the acid chloride functional groups on synthons of the bridged program director limit the possible orientations in which the activated synthon trimer may bind. For example, positioning of the acid chloride functional groups on the meta-position of the synthon in the bridged program director may result in increased side reactions and possible polymer products.

Direct Synthesis from Macrocyclic Modules

Another method for the synthesis of bridged macrocyclic module compounds is by linking a bridge moiety to a macrocyclic module. Scheme 12 illustrates an example of this type of synthesis:

Scheme 12

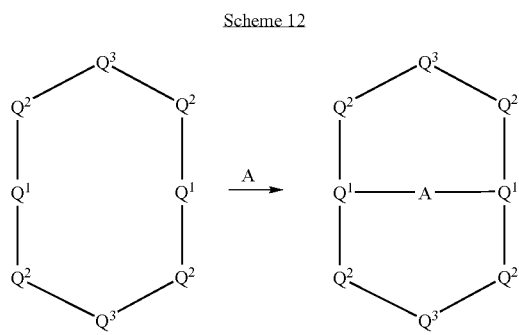

In Scheme 12, the bridge moiety A may be directly coupled to the synthons $Q^1$, or may be linked to the $Q^1$ synthons through linker molecules.

Nanofilms and Membranes from Bridged Macrocyclic Modules

In one aspect of the invention, bridged macrocyclic modules may be coupled to form a two-dimensional array or nanofilm. These nanofilms may have regions in which unique structures exist, which may repeat at regular intervals to provide a lattice of pores having substantially uniform dimensions. The unique structures may have a variety of shapes and sizes, thereby providing pores of various shapes and sizes. Because the unique structures may be formed in a monolayer of molecular thickness, the pores defined by the unique structures may include a cavity, opening, or chamber-like structure of molecular size. In general, pores of atomic to molecular size defined by those unique structures may be used for selective permeation or molecular sieving functions. Some aspects of nanotechnology are given in *Nanostructured Materials*, J. Ying, ed., Academic Press, San Diego, 2001.

Methods of Preparing Nanofilms

In one variation, bridged macrocyclic modules can be oriented on a surface or subphase by providing functional groups on the modules which impart amphiphilic character to the modules. For example, when the module is deposited on a hydrophilic surface, hydrophobic substituent groups or hydrophobic tails attached to the module may cause the module to reorient on the surface so that the hydrophobic substituents are oriented away from the surface, leaving a more hydrophilic facet of the module oriented toward the surface.

The amphiphilic character may arise from, e.g., atoms in the synthons, the linkages between the synthons, functional groups coupled to the synthons or linkages, and the bridge moiety. For example, lipophilic and/or hydrophilic moieties may be coupled to the same or different synthon or linkage in an amphiphilic bridged macrocyclic module. Lipophilic and hydrophilic moieties may be coupled to the macrocyclic module or moiety before or after formation of the closed ring of the macrocyclic module or moiety. For example, lipophilic or hydrophilic moieties may be added to the macrocyclic module after formation of the closed ring by substitution of a synthon or linkage, followed by coupling of a bridge moiety to produce a bridged macrocyclic module. Examples of functional groups added to the components to impart amphiphilic character to the modules include alkyl groups, alkoxy groups, —NHR, —OC(O)R, —C(O)OR, —NHC(O)R, —C(O)NHR, —CH═CHR, and —C≡CR, where the carbon atoms of an alkyl group may be interrupted by one or more —S—, double bond, triple bond or —SiRR— group(s), or substituted with one or more fluorine atoms, or any combination thereof, wherein each R is independently hydrogen or alkyl.

The amphiphilicity of a bridged macrocyclic module may be characterized in part by its ability to form a stable Langmuir film. A Langmuir film may be formed on a Langmuir trough at a particular surface pressure measured in milliNewtons per meter (mN/m) with a particular barrier speed measured in millimeters per minute (mm/min), and the isobaric creep or change in film area at constant surface pressure can be measured to characterize stability of the film. For example, a stable Langmuir film of bridged macrocyclic modules on a water subphase may have an isobaric creep at 5-15 mN/m such that the majority of the film area is retained over a period of time of about one hour. Examples of stable Langmuir films of bridged macrocyclic modules on a water subphase may have isobaric creep at 5-15 mN/m such that at least about 70% of the film area is retained over a period of time of about 30 minutes, sometimes at least about 70% of the film area is retained over a period of time of about 40 minutes, sometimes at least about 70% of the film area is retained over a period of time of about 60 minutes, and sometimes at least about 70% of the film area is retained over a period of time of about 120 minutes. In other embodiments, a stable Langmuir film of bridged macrocyclic modules on a water subphase may have an isobaric creep at 5-15 mN/m such that at least about 80% of the film area is retained over a period of time of about thirty minutes, sometimes at least about 85% of the film area is retained over a period of time of about thirty minutes, sometimes at least about 90% of the film area is retained over a period of time of about thirty minutes, sometimes at least about 95% of the film area is retained over a period of time of about thirty minutes, and sometimes at least about 98% of the film area is retained over a period of time of about thirty minutes.

In one example, the amphiphilic components may be dissolved in a solvent and deposited on an air-subphase interface in a Langmuir trough to form the monolayer. Typically, movable plates or barriers are used to compress the monolayer and decrease its surface area to form a more dense monolayer. At various degrees of compression, having corresponding surface pressures, the monolayer may reach various condensed states. The conformation of a module on a surface may depend on the loading, density, or state of the phase or layer in which the module resides on the surface. Surfaces which may be used to orient modules or other molecules include interfaces such as gas-liquid, air-water, immiscible liquid-liquid, liquid-solid, or gas-solid interfaces.

Surface pressure versus film area isotherms are obtained by the Wilhelmy balance method to monitor the state of the film. Extrapolation of the isotherm to zero surface pressure reveals the average surface area per component, or mean molecular area, before the components are coupled. The isotherm gives an empirical indication of the state of the thin film. Surface-oriented macrocyclic modules and/or other components in a nanofilm layer may be in an expanded state, a liquid state, or a liquid-expanded state, or may be condensed, collapsed, or a solid phase or close-packed state.

Oriented bridged macrocyclic modules may be coupled to form a nanofilm. The modules may be oriented on the surface before or during the process of coupling. The bridged macrocyclic modules may be directly coupled to each other, or may be coupled through linker molecules. The bridged macrocyclic module compounds may be coupled to one another via functional groups located on the synthons or on the bridge moiety. Examples of suitable functional groups and resulting linkages are shown in Tables 6-8. A bridge moiety having functional groups for coupling bridged macrocyclic module compounds may be mono-functional or multi-functional. In one variation, a general scheme for coupling bridged macrocyclic module compounds includes coupling the functional groups located on the bridge moieties, as shown in Scheme 13.

Scheme 13

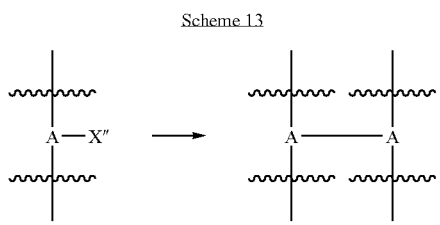

wherein A indicates a bridge moiety, and X" indicates a functional group for coupling complementary functional groups on other bridge moieties.

The nanofilm may be prepared from a single type of bridged macrocyclic module. In other variations, the nanofilm may be prepared from two or more types of bridged macrocyclic modules.

Nanofilms may be prepared by various alternative methods. For example, linker molecules may be added to the solution containing the modules, which is subsequently deposited on the surface of the Langmuir subphase. Alternatively, the linker molecules may be added to the water subphase of the Langmuir trough, and subsequently transfer to the layer phase containing the bridged macrocyclic modules for coupling. In some instances, macrocyclic modules may be added to the subphase of the Langmuir trough, and subsequently transfer to the interface. In general, water soluable components (such as linker molecules) may be added to the subphase for the formation of a nanofilm.

When two or more types of bridged macrocyclic modules are used in forming the nanofilm, the modules may be mixed prior to or during orientation on a surface.

Other variations will be apparent to those of skill in the art.

In general, coupling of the components of a nanofilm may be initiated by chemical, thermal, photochemical, electrochemical, and irradiative methods. In some variations of this invention, the type of coupling of the components of a nanofilm may depend on the type of initiation and the chemical process involved.

Functional groups added to the modules to impart amphiphilic character may in some embodiments be removed during or after formation of the nanofilm. The method of removal depends on the functional group. The groups attached to the modules which impart amphiphilic character to the module may include functional groups which can be used to remove the groups at some point during or after the process of formation of a nanofilm. Acid or base hydrolysis may be used to remove groups attached to the module via a carboxylate or amide linkage. An unsaturated group located in the functional group which imparts amphiphilic character to the module may be oxidized and cleaved by hydrolysis. Photolytic cleavage of the functional group which imparts amphiphilic character to the module may also be done. Examples of cleavable functional groups include

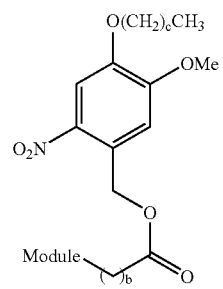

where n is zero to four, which is cleavable by light activation, and

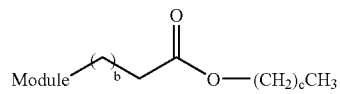

where b is zero to four, and c is 7 to 27, which is cleavable by acid or base catalyzed hydrolysis.

A variety of functional groups may be used in coupling the nanofilms. The nature of the nanofilm product formed by coupling bridged macrocyclic modules depends, e.g., on the specific functional groups used, and the relative orientations of the functional groups with respect to the module structure. The functional groups may in some cases contribute to the amphiphilic character of the module before or after coupling, and may be covalently or non-covalently attached to the modules. In a preferred embodiment, the functional groups are covalently attached to the modules. The functional groups may be attached to the modules before, during, or after orientation of the modules on a surface or subphase.

The coupling of modules in a nanofilm may attach two or more components by a linkage or linkages. The coupling may attach more than two modules, for example, by an array of linkages each formed between the modules. Each module may form one or more linkages to one or more modules, and each module may form several types of linkages, including those exemplified in Tables 6-8. A module may have direct linkages, linkages through a linker molecule, and linkages which include spacers, in any combination. A linkage may connect any portion of a module to any portion of another module. An array of linkages and an array of modules may be described in terms of the theory of Bravais lattices and theories of symmetry.

Coupling of modules may be complete or incomplete, providing a variety of structural variations useful as nanofilm membranes. A portion of each of the components of a nanofilm may be coupled, while the remainder of each is not coupled. The modules may interact through, for example, hydrogen bonding, van der Waals, and other interactions. The arrangement of linkages formed in a nanofilm may be represented by a type of symmetry, or may be substantially unordered.

The types of coupling between the bridged macrocyclic modules and the phase and domain behaviour of the modules, as described herein, may influence the composition and properties of the product nanofilm. A macrocyclic module may participate in more than one type of coupling.

Structure of Nanofilms

Generally, the nanofilms formed are one molecule thick throughout, but may vary locally due to physical and chemical forces. In some embodiments, pores are supplied through the structure of the nanofilm. In some embodiments, pores are supplied through the structure of the bridged macrocyclic modules.

A wide variety of structural features and properties such as amorphous, glassy, semicrystalline or crystalline structures, and elastomeric, pliable, thermoplastic, or deformation properties may be exhibited by the nanofilms.

The composition of the nanofilm may be solid, gel, or liquid. The modules of the nanofilm may be in an expanded state, a liquid state, or a liquid-expanded state. The state of the modules of the nanofilm may be condensed, liquid-condensed, collapsed, or may be a solid phase or close-packed state. The modules of the nanofilm may interact with each other by weak forces of attraction. Alternatively, they may be coupled through, for example, covalent bonds. For example, the modules of a nanofilm prepared from surface-oriented bridged macrocyclic modules need not be linked by any strong interaction or coupling. Alternatively, for example, the modules of the nanofilm may be linked through, for example, covalent bonds.

The thickness of nanofilms described herein, whether through coupled or non-coupled bridged macrocyclic modules, is exceptionally small, often being less than about 30 nanometers, sometimes less than about 20 nanometers, and sometimes from about 1-15 nanometers. The thickness of a nanofilm depends partly on the structure and nature of the groups on the modules which impart amphiphilic character to the modules. The thickness may be dependent on temperature, and the presence of solvent on the surface or located within the nanofilm. The thickness may be modified if the groups on the modules which impart amphiphilic character, in particular the lipophilic moiety, are removed or modified after the modules have been coupled, or at other points during or after the process of preparation of a nanofilm. The thickness of a nanofilm may also depend on the structure and nature of the surface attachment groups on the components. The thickness of nanofilms may be less than about 300, 250, 200, 150, 100, 90, 80, 70, 60, 50, 40, 30, 20, 10 or 5 Å.

Nanofilm structures define pores through which atoms, molecules, or particles of only up to a certain size and composition may pass. One variation of a nanofilm structure includes an area of nanofilm able to face a fluid medium, either liquid or gaseous, and provide pores or openings through which atoms, ions, small molecules, biomolecules, or other species are able to pass. The dimensions of the pores defined by nanofilm structures may be exemplified by quantum mechanical calculations and evaluations, and physical tests, as further described in the following Examples.

The dimensions of the pores defined by nanofilm structures are described by actual atomic and chemical structural features of the nanofilm. The approximate diameters of pores formed in the structure of a nanofilm are from about 1-150 Å, or more. In some embodiments, the dimensions of the pores are about 1-10 Å, about 3-15 Å, about 10-15 Å, about 15-20 Å, about 20-30 Å, about 30-40 Å, about 40-50 Å, about 50-75 Å, about 75-100 Å, about 100-125 Å, about 125-150 Å, about 150-300 Å, about 600-1000 Å. The approximate dimensions of pores formed in the structure of a nanofilm are useful to understand the porosity of the nanofilm. On the other hand, the porosity of conventional membranes is normally quantified by empirical results such as molecular weight cut-off, which reflects complex diffusive and other transport characteristics.

In one variation, a nanofilm structure may comprise an array of coupled modules which provides an array of pores of substantially uniform size. The pores of uniform size may be defined by the individual modules themselves. Each module defines one or more pores of a particular size, depending on the conformation and state of the module. For example, the conformation of the coupled module of the nanofilm may be different from the nascent, pure module in a solvent, and both may be different from the conformation of the amphiphilic module oriented on a surface before coupling.

Modules of various composition and structure may be prepared which define pores of different sizes. Thus, nanofilms having pores of various dimensions are provided, depending on the particular module used to prepare the nanofilm.

In other instances, nanofilm structures define pores in the matrix of coupled modules. Pores defined by nanofilm structures may have a wide range of dimensions, for example, dimensions capable of selectively blocking the passage of small molecules or large molecules. For example, nanofilm structures may be formed from the coupling of two or more modules, in which an interstitial pore is defined by the combined structure of the linked modules. A nanofilm may have an extended matrix of pores of various dimensions and characteristics. Interstitial pores may be, for example, less than about 5 Å, less than about 10 Å, about 3-15 Å, about 10-15 Å, about 15-20 Å, about 20-30 Å, about 30-40 Å, about 40-50 Å, about 50-75 Å, about 75-100 Å, about 100-125 Å, about 125-150 Å, about 150-300 Å, about 300-600 Å, about 600-1000 Å.

The coupling process may result in a nanofilm in which regions of the nanofilm are not precisely monomolecular layers. Various types of local structures are possible which do not prevent use of the nanofilm in a variety of applications. Local structural features may include amphiphilic modules which are flipped over relative to their neighbors, or turned in a different orientation, having their hydrophobic and hydrophilic facets oriented differently than neighboring species. Local structural features may also include overlaying or stacking of molecules in which the nanofilm is two or more molecular layers thick, local regions in which the interlinking of the modules is not complete so that some of the available coupling groups are not coupled to other species, or local regions in which there is an absence of a particular molecule. Other local structural features may include grain boundaries and orientational faults. In one variation, the nanofilm has a thickness of up to 30 nanometers due to the layering of nanofilm structures.

The nanofilms disclosed herein may be substantially uniform with respect to the orientation of their amphiphilic modules, but may in some embodiments comprise regions of local structural features as indicated hereinabove. Local structural features may comprise, for example, greater than about 30%, less than about 30%, less than about 20%, less than about 15%, less than about 10%, less than about 5%, less than about 3%, less than about 1% of the surface area of the nanofilm.

A nanofilm may have an array of coupled modules in which the positional ordering of the modules is random, or is non-random with regions in which one type of species is predominant.

In alternative variations, the nanofilm may include additives, dispersants, surfactants, excipients, compatiblizers, emulsifiers, suspension agents, plasticizers, or other species which modify the properties of the nanofilm. In some instances, the nanofilm may be derivatized to provide biocompatability or reduce fouling of the nanofilm by attachment or adsorption of biomolecules.

Substrates

Nanofilms may be deposited on a substrate by various methods, such as Langmuir-Schaefer, Langmuir-Blodgett, or other methods used with Langmuir systems. In one variation, a nanofilm is deposited on a substrate in a Langmuir tank by locating the substrate in the subphase beneath the air-water interface, and lowering the level of the subphase until the nanofilm lands gently on the substrate and is therefore deposited. A description of Langmuir films and substrates is given in U.S. Pat. Nos. 6,036,778, 4,722,856, 4,554,076, and 5,102,798, and in R. A. Hendel et al., Vol. 119, *J. Am. Chem. Soc.* 6909-18 (1997). A description of films on substrates is given in Munir Cheryan, *Ultrafiltration and Microfiltration Handbook* (1998).

Other methods for preparing nanofilms include forced removal of solvent to prepare a film, such as spin coating methods and spray coating methods, as well as coating and deposition methods including interfacial, dip coating, knife-edge coating, grafting, casting, phase inversion, or electroplating or other plating methods.

Nanofilms deposited on a substrate may be cured or annealed by chemical, thermal, photochemical, electrochemical, irradiative or drying methods during or after deposition on a substrate. For example, chemical methods include reactions with vapor phase reagents such as ethylenediamine or solution phase reagents. A nanofilm treated by any method to attach or couple it to a substrate may be said to be cured.

The deposition may result in non-covalent or weak attachment of the nanofilm to the substrate through physical interactions and weak chemical forces such as van der Waals forces and weak hydrogen bonding. The nanofilm may in some embodiments be bound to the substrate through ionic or covalent interaction, or other type of interaction.

The substrate may be any surface of any material. Substrates may be porous or non-porous, and may be made from polymeric and inorganic substances. Examples of porous substrates include plastics or polymers, track-etch polycarbonate, track-etch polyester, polyethersulfone, polysulfone, gels, hydrogels, cellulose acetate, polyamide, PVDF, polyethylene terephthalate or polybutylene terephthalate, polyvinyl chloride, polyvinylidene chloride, polytetrafluoroethylene, polyethylene or polypropylene, ceramics, anodic alumina, laser ablated and other porous polyimides, and UV etched polyacrylate. Examples of non-porous substrates include silicon, germanium, glass, metals such as platinum, nickel, palladium, aluminum, chromium, niobium, tantalum, titanium, steel, or gold, glass, silicates, aluminosilicates, non-porous polymers, and mica. Further examples of substrates include diamond and indium tin oxide. Preferred substrates include silicon, gold, $SiO_2$, polyethersulfone, and track etch polycarbonate. In some embodiments, the substrate is $SiO_2$. In other embodiments, the substrate is polycarbonate track etch membrane.

Substrates may have any physical shape or form including films, sheets, plates, or cylinders, and may be particles of any shape or size.

A nanofilm deposited on a substrate may serve as a membrane. Any number of layers of nanofilm may be deposited on the substrate to form a membrane. In some variations, a nanofilm is deposited on both sides of a substrate.

A layer or layers of various spacing materials may be deposited or attached in between layers of a nanofilm, and a spacing layer may also be used in between the substrate and the first deposited layer of nanofilm. Examples of spacing layer compositions include polymeric compositions, hydrogels (acrylates, poly vinyl alcohols, polyurethanes, silicones), thermoplastic polymers (polyolefins, polyacetals, polycarbonates, polyesters, cellulose esters), polymeric foams, thermosetting polymers, hyperbranched polymers, biodegradable polymers such as polylactides, liquid crystalline polymers, polymers made by atom transfer radical polymerization (ATRP), polymers made by ring opening metathesis polymerization (ROMP), polyisobutylenes and polyisobutylene star polymers, and amphiphilic polymers. Other examples of spacing layer compositions include inorganics, such as inorganic particles such as inorganic microspheres, colloidal inorganics, inorganic minerals, silica spheres or particles, silica sols or gels, clays or clay particles, and the like. Examples of amphiphilic molecules include amphiphiles containing polymerizable groups such as diynes, enes, or amino-esters. The spacing layers may serve to modify barrier properties of the nanofilm, or may serve to modify transport, flux, or flow characteristics of the membrane or nanofilm. Spacing layers may serve to modify functional characteristics of the membrane or nanofilm, such as strength, modulus, or other properties.

In some variations, a nanofilm may be deposited on a surface and adhere to the surface to a degree sufficient for many applications, such as filtration and membrane separations, without coupling to the surface.

In other variations, a nanofilm may be, for example, covalently coupled to a substrate surface. Surface attachment groups may be provided on the bridge moiety or synthons of a bridged macrocyclic module, which may be used to couple the nanofilm to the substrate.

Examples of functional groups which may be used as surface attachment groups to couple a nanofilm to a substrate include amine groups, carboxylic acid groups, carboxylic ester groups, alcohol groups, glycol groups, vinyl groups, styrene groups, olefin styryl groups, epoxide groups, thiol groups, magnesium halo or Grignard groups, acrylate groups, acrylamide groups, diene groups, aldehyde groups, and mixtures thereof.

A substrate may have functional groups which couple to the functional groups of a nanofilm. The functional groups of the substrate may be surface groups or linking groups bound to the substrate, which may be formed by reactions which bind the surface groups or linking groups to the substrate. Surface groups may also be created on the substrate by a variety of treatments such as cold plasma treatment, surface etching methods, solid abrasion methods, or chemical treatments. Some methods of plasma treatment are given in Inagaki, *Plasma Surface Modification and Plasma Polymerization*, Technomic, Lancaster, Pa., 1996. In some embodiments, the substrate is derivatized with APTES. In other embodiments, the substrate is derivatized with methylacryloxymethyltrimethoxysilane (MAOMTMOS). In other embodiments, the substrate is derivatized with acryloxypropyltrimethoxy-silane (AOPTMOS).

Surface attachment groups of the nanofilm and the surface may be blocked with protecting groups until needed. Non-limiting examples of suitable functional groups for coupling the nanofilm to the substrate and the resulting linkages may be found in Tables 6-8.

Surface attachment groups may be connected to a nanofilm by spacer groups. Likewise, substrate functional groups may be connected to the substrate by spacer groups. Spacer groups for surface attachment groups may be polymeric. Examples of polymeric spacers include polyethylene oxides, polypropylene oxides, polysaccharides, polylysines, polypeptides, poly(amino acids), polyvinylpyrrolidones, polyesters, polyvinylchlorides, polyvinylidene fluorides, polyvinylalcohols, polyurethanes, polyamides, polyimides, polysulfones, polyethersulfones, polysulfonamides, and polysulfoxides. Examples of polymeric spacer structures include linear, branched, comb and dendrimeric polymers, random and block copolymers, homo- and heteropolymers, flexible and rigid chains. Spacer groups for surface attachment groups may also include bifunctional linker groups or heterobifunctional linker groups used to couple biomolecules and other chemical species.

In one variation, a photoreactive group such as a benzophenone or other light activated cross-linker is bound to the substrate. The photoreactive group may be activated with light, for example, ultraviolet light, to provide a reactive species which couples to a nanofilm.

Surface attachment of modules may also be achieved through ligand-receptor mediated interactions, such as biotin-streptavidin. For example, the substrate may be coated with streptavidin, and biotin may be attached to the modules, for example, through linker groups such as PEG or alkyl groups.

Membranes and Filtration Function

The nanofilms described herein may be useful, for example, as membranes. The membrane may be brought into contact with a fluid or solution, separating a species or component from that fluid or solution, for example, for purposes of filtration. Normally, a membrane is a substance which acts as a barrier to block the passage of some species, while allowing restricted or regulated passage of other species. In general, permeants may traverse the membrane if they are smaller than a cut-off size, or have a molecular weight smaller than a so-called cut-off molecular weight. The membrane may be called impermeable to species which are larger than the cut-off molecular weight. The cut-off size or molecular weight is a characteristic property of the membrane. Selective permeation is the ability of the membrane to cut-off, restrict, or regulate passage of some species, while allowing smaller species to pass. Thus, the selective permeation of a membrane may be described functionally in terms of the largest species able to pass the membrane under given conditions. The size or molecular weight of various species may also be dependent on the conditions in the fluid to be separated, which may determine the form of the species. For example, species may have a sphere of hydration or solvation in a fluid, and the size of the species in relation to membrane applications may or may not include the water of hydration or the solvent molecules. Thus, a membrane is permeable to a species of a fluid if the species can traverse the membrane in the form in which it normally would be found in the fluid. Permeation and permeability may be affected by interaction between the species of a fluid and the membrane itself. While various theories may describe these interactions, the empirical measurement of pass/no-pass information relating to a nanofilm, membrane, or module is a useful tool to describe permeation properties. A membrane is impermeable to a species if the species cannot pass through the membrane.

Pores may be provided in the nanofilms described herein, for example, pores may be supplied in the structure of the nanofilm. Pores may be supplied in the structure of the bridged macrocyclic modules. The type and degree of crosslinking between modules may influence pore size.

The nanofilms may have molecular weight species cut offs of, for example, greater than about 15 kDa, greater than about 10 kDa, greater than about 5 kDa, greater that about 1 kDa, greater than about 800 Da, greater than about 600 Da, greater than about 400 Da, greater than about 200 Da, greater than about 100 Da, greater than about 50 Da, greater than about 20 Da, less than about 15 kDa, less than about 10 kDa, less than about 5 kDa, less that about 1 kDa, less than about 800 Da, less than about 600 Da, less than about 400 Da, less than about 200 Da, less than about 100 Da, less than about 50 Da, less than about 20 Da, about 13 kDa, about 190 Da, about 100 Da, about 45 Da, about 20 Da.

"High permeability" indicates a clearance of, for example, greater than about 70%, greater than about 80%, or greater than about 90% of the solute. "Medium permeability" indicates a clearance of, for example, less than about 50%, less than about 60%, or less than about 70% of the solute. "Low permeability" indicates a clearance of less than, for example, about 10%, less than about 20%, or less than about 30% of the solute. A membrane is impermeable to a species if it has a very low clearance (for example, less than about 5%, less than about 3%) for the species, or if it has very high rejection for the species (for example, greater than about 95%, greater than about 98%). The passage or exclusion of a solute is measured by its clearance, which reflects the portion of solute that actually passes through the membrane. For example, the no pass symbol in Tables 12-13 indicates that the solute is partly excluded by the module, sometimes less than about 90% rejection, often at least about 90% rejection, sometimes at least about 98% rejection. The pass symbol indicates that the solute is partly cleared by the module, sometimes less than about 90% clearance, often at least about 90% clearance, sometimes at least about 98% clearance.

Examples of processes in which nanofilms may be useful include processes involving liquid or gas as a continuous fluid phase, filtration, clarification, fractionation, pervaporation, reverse osmosis, dialysis, hemodialysis, affinity separation, oxygenation, and other processes. Filtration applications may include ion separation, desalinization, gas separation, small molecule separation, separation of enantiomers, ultrafiltration, microfiltration, hyperfiltration, water purification, sewage treatment, removal of toxins, removal of biological species such as bacteria, viruses, or fungus.

Networked Arrays from Bridged Macrocyclic Module Compounds

In another aspect of the invention, bridged macrocyclic modules may be coupled to form a networked array, such as a 3-D array. The 3-D arrays may also be useful as nanofilms.

In one variation, a general scheme for coupling bridged macrocyclic module compounds in a network includes coupling the functional groups located on the bridge moieties, as shown in Scheme 14.

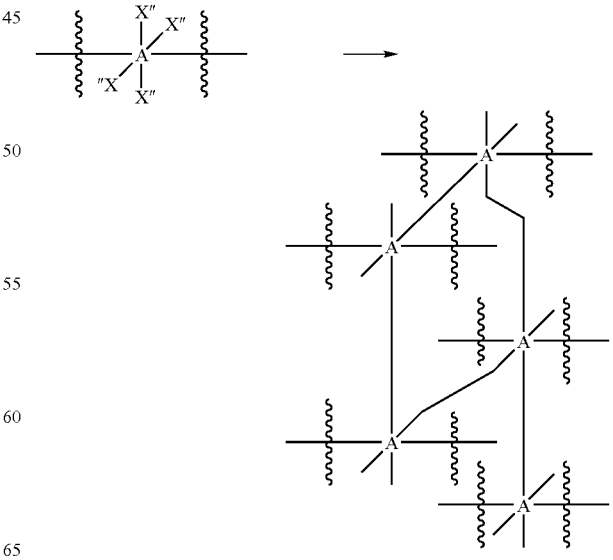

Scheme 14

In Scheme 14, A is a bridge moiety, and X" are independently selected functional groups for coupling to corresponding functional groups on other bridged macrocyclic modules. Suitable examples of functional groups, linkers, and the resulting linkages may be found in Tables 6-8.

Networked arrays may be made, for example, through polymerization schemes, such as those shown in Schemes 1-3.

The following examples further describe and demonstrate variations within the scope of the present invention. All examples described in this specification, both in the description above and the examples below, are given solely for the purpose of illustration and are not to be construed as limiting the present invention. While there have been described illustrative variations of this invention, those skilled in the art will recognize that they may be changed or modified without departing from the spirit and scope of this invention, and it is intended to cover all such changes, modifications, and equivalent arrangements that fall within the true scope of the invention as set forth in the appended claims.

All documents referenced herein, including applications for patent, patent references, publications, articles, books, and treatises, are specifically incorporated by reference herein in their entirety.

EXAMPLES

Reagents were obtained from Aldrich Chemical Company (St. Louis, Mo.). The Langmuir trough used was a KSV minitrough (KSV Instruments, Trumbull, Conn.). Rates of surface compression are reported as the linear rate of barrier movement. Atomic force microscopy (AFM) images may be obtained with a PicoSPM (Molecular Imaging, Pheonix Ariz.). Contact Mode images may be recorded under flowing nitrogen with an Si point probe tip.

Example 1

Bridged macrocyclic module compound 6 was prepared as shown in Scheme 15.

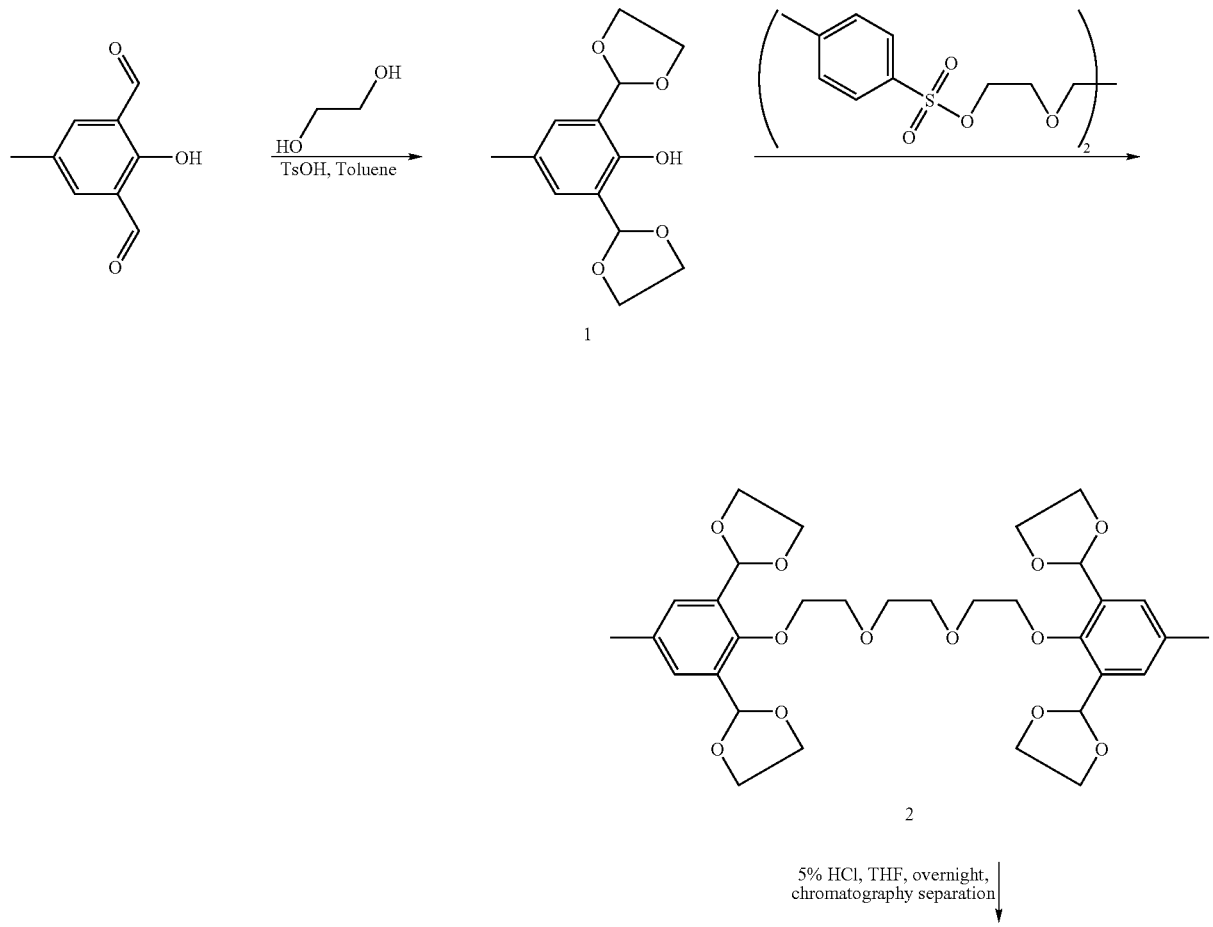

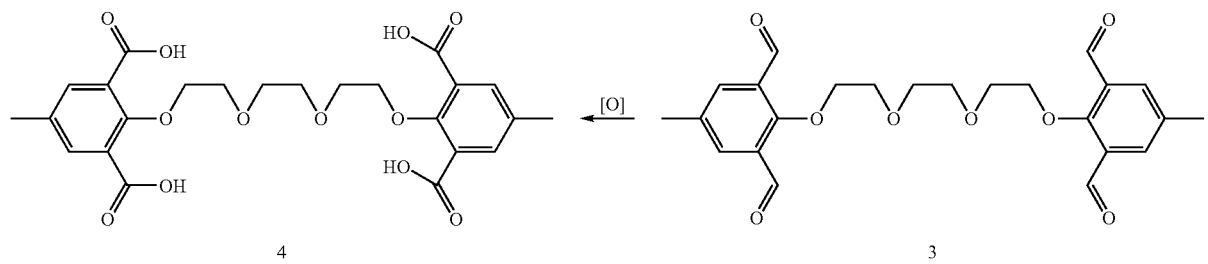
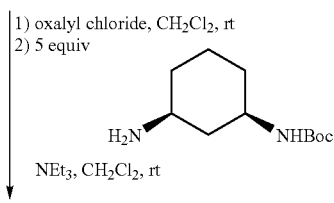
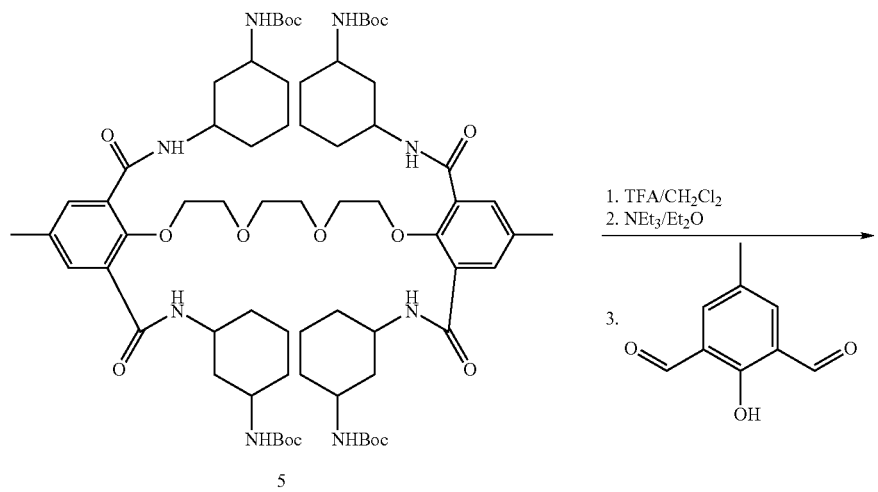
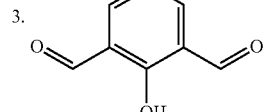
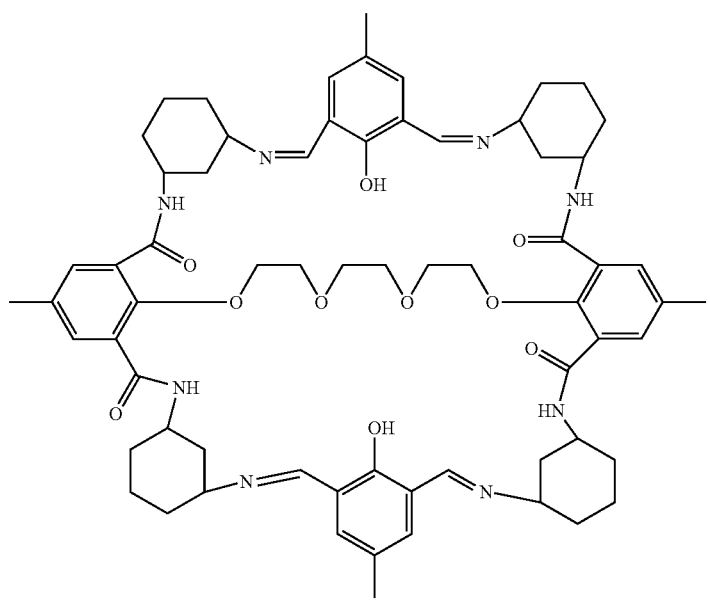

Diprotected 4-methyldialdehyde phenyl (1). To a 250 mL Schlenk flask with stirbar under argon 2-hydroxy-5-methyl-1,3-benzenedicarboxaldehyde (15.2 mmol, 2.5 g) was added and the flask evacuated and backfilled with argon 3×. Anhydrous benzene (80 mL) was cannula transferred followed by stirring at ambient temperature. Next, anhydrous ethylene glycol (91.4 mmol, 5.67 g) was added via syringe under argon followed by TsOH (0.167 mmol, 0.032 g). The reaction vessel was fitted with a Dean-Stark trap and reflux condenser and the reaction refluxed for ca. 23 h. The reaction was diluted with ethyl acetate (300 mL) washed with 1M $NaHCO_3$ (50 mL), $H_2O$ (50 mL), then brine (50 mL). The organic layer was separated and dried over $Na_2SO_4$, filtered and the solvent removed by rotovaporation. Purification by silica gel chromatography (2:1 hexane:ethyl acetate) afforded a white solid (2.34 g; 61% yield). IR ($cm^{-1}$) 3329, 2917, 2895, 1627, 1496, 1478, 1408, 928, 873; $^1$H NMR (400 MHz, $CDCl_3$) δ 8.07 (s, 1H, OH), 7.18 (s, 2H, ArH), 6.03 (s, 2H, $ArCHO_2$), 4.20-4.00 (m, 8H, $OCH_2CH_2O$), 2.26 (s, 3H, ArMe); {$^1$H} $^{13}$C NMR (100 MHz, $CDCl_3$) 151.8, 129.1, 122.0, 102.1, 65.3, 20.8.

Triethylene glycol tethered diprotected 2-hydroxy-5-methyl-1,3-benzenedicarboxaldehyde (2). To a 25 mL schlenk flask with Kontes valve and stirbar under argon 1 (1.67 mmol, 0.423 g) was added and the flask evacuated and backfilled with argon 3×. Anhydrous DMF (12.2 mL) was added via syringe and the solution stirred at rt. Next, anhydrous $CsCO_3$ (3.52 mmol, 1.15 g) was added followed by triethylene glycol ditosylate (0.808 mmol, 0.371 g) and the mixture stirred at rt. The vessel was closed, stirred and heated to 70° C. for ca. 12 h. The reaction was allowed to cool to rt then diluted with ethyl acetate (10 mL), filtered and the solid washed with ethyl acetate (3×100 mL) and filtered. The organic extracts were combined and washed with saturated $NH_4Cl$(aq) (25 mL) then washed with brine (3×25 mL) dried over $Na_2SO_4$, filtered and the solvent removed by rotovaporation to afford the crude product. Purification by silica plug (ethyl acetate) afforded a white solid (0.464 g; 89% yield). IR ($cm^{-1}$) 2947, 2884, 1683, 1601, 1476, 1397, 1110; $^1$H NMR (400 MHz, $CDCl_3$) δ 7.38 (s, 4H, ArH), 6.13 (s, 4H, $ArCHO_2$), 4.18 (m, 4H, $ArOCH_2$—), 4.02 (m, 16H, $OCH_2CH_2O$), 3.84 (m, 4H, $ArOCH_2CH_2$—), 3.78 (s, 4H, $ArOCH_2CH_2OCH_2CH_2OCH_2CH_2OAr$), 2.33 (s, 6H, $ArCH_3$); {$^1$H} $^{13}$C NMR (100 MHz, $CDCl_3$) 154.5, 134.2, 130.8, 129.0, 99.1, 76.0, 70.9, 70.5, 65.5, 21.2.

Triethylene glycol tethered 2-hydroxy-5-methyl-1,3-benzenedicarboxaldehyde (3). To a 1000 mL pear-shaped flask and 100 mL pear shaped flask and stirbar under argon 2 (3.20 mmol, 1.98 g and 0.488 mmol, 0.302 g, respectively) were added. The substrate was dissolved in THF (160 mL, 24.4 mL, respectively) then 5% HCl(aq)(56.8 mL, 8.7 mL) was added and the mixture stirred for 12 h resulting in a white precipitate. The reactions were combined and poured into a separatory funnel containing 50 mL of $NaHCO_3$ (sat, aq) the reaction vessel rinsed with 100 mL of ethyl acetate poured into the separatory funnel with an additional 250 mL of ethyl acetate and the aqueous layer extracted, separated and washed with brine (3×50 mL). The organic layer was dried over $Na_2SO_4$, filtered and the filter and drying agent washed with $CHCl_3$, the solvents combined and volatiles removed by rotovaporation. Purification by silica gel plug (dissolve in $CHCl_3$, ethyl acetate as mobile phase) afforded a white solid (1.63 g, 99%). IR ($cm^{-1}$) 3347, 2947, 2911, 2856, 2760, 1678, 1580, 1465, 1404, 1130; $^1$H NMR (400 MHz, $CDCl_3$) δ 10.43 (s, 4H, ArCHO), 7.87 (s, 4H, ArH), 4.31 (m, 4H, $ArOCH_2$—), 3.67 (s, 4H, $ArOCH_2CH_2OCH_2CH_2OCH_2CH_2OAr$), 2.40 (s, 6H, $ArCH_3$); {$^1$H} $^{13}$C NMR (100 MHz, $CDCl_3$) 189.6, 162.5, 135.4, 135.0, 130.1, 78.6, 71.0, 70.4, 20.8.

Triethylene glycol tethered 2-hydroxy-5-methyl-1,3-benzenedicarboxylic acid (4). To a 100 mL round bottom flask and stirbar under argon 3 (2.43 mmol, 1.08 g) was added. The substrate was dissolved in 1,4-dioxane (186 mL) then sonicated until homogeneous. Buffer, $NaH_2PO_4$ (37.9 mmol, 4.55 g) and sulfamic acid (14.6 mmol, 1.42 g) were dissolved in de-ionized $H_2O$ in a 41.1 mL Erlenmeyer flask with a stirbar, then transferred to the stirring solution of the substrate by syringe. The heterogeneous solution was sonicated again until the mixture was nearly homogeneous. Sodium chlorite ($NaClO_2$, 12.6 mmol, 1.14 g) was dissolved in a de-ionized $H_2O$ (12.6 mL) and added dropwise via syringe to the stirring solution resulting in a yellow homogeneous solution. After ca. 3.5 h the reaction was complete as assessed by TLC. Sodium sulfite (11.7 mmol, 1.47 g) was added, and the reaction stirred for ca. 1 h giving a colorless solution. The reaction mixture was diluted with $CH_2Cl_2$ (500 mL), poured into a separatory funnel, $H_2O$ (200 mL) was added, and the pH adjusted to ca. 1-2 with 4 M HCl. The organic layer was separated and washed with brine (3×50 mL). The organic layer was again separated, and the solvent removed by rotovaporation and put under vacuo to remove the remaining $H_2O$ affording a white solid (1.22 g, 99% yield). IR ($cm^{-1}$) 3060, 2960, 2923, 2853, 2687, 2568, 1678, 1604, 1578, 1467, 1450, 1257, 1244, 1118, 1102; $^1$HNMR (400 MHz, DMSO-$d_6$) δ 13.04 (s, 4H, ArCOOH), 7.60 (s, 4H, ArH), 4.06 (m, 4H, $ArOCH_2$—), 4.06 (m, 4H, $ArOCH_2CH_2$—), 3.54 (s, 4H, $ArOCH_2CH_2OCH_2CH_2OCH_2CH_2OAr$), 2.30 (s, 6H, $ArCH_3$); {$^1$H} $^{13}$C NMR (100 MHz, DMSO-$d_6$) 167.1, 154.4, 133.7, 132.9, 127.5, 74.3, 69.6, 69.4, 66.4, 19.9.

Triethylene glycol tethered 2-hydroxy-5-methyl-1,3-benzenediamide tetra-cis-1,3-diaminocyclohexane (5). To a 50 mL round bottom Schlenk flask with Kontes valve and stirbar under argon 4 (0.096 mmol, 0.100 g) was added. The vessel was evacuated and backfilled with argon (3×). Oxalyl chloride (2.0 M) in dichloromethane (0.985 mmol, 0.480 mL) was added via syringe. Next a catalytic amount of DMF (0.015 mL) was added via syringe with stirring at rt for 2 h, resulting in rigorous effervescence and a yellow solution with yellow precipitate. All volatiles were removed under vacuo and the residue dissolved in dichloromethane (1 mL) followed by addition of triethylamine (1.53 mmol, 0.155 g) via syringe under argon. A dichloromethane solution of mono Boc protected cis-1,3-diaminocyclohexane (0.980 mmol, 0.210 g) was added dropwise to the reaction mixture, the vessel sealed and stirred overnight at ambient temperature affording an orange solution with precipitate formation. The reaction was diluted with dichloromethane (250 mL), washed with brine (2×50 mL), water (50 mL), then brine (50 mL), the organic layer dried over sodium sulfate, filtered and the solvent removed by rotovaporation. Purification by silica chromatography (15:1:1 ethyl acetate:hexane) afforded an off white solid (0.216, 89% yield). IR ($cm^{-1}$) 3307, 3060, 2967, 2934, 2853, 1682, 1639, 1600, 1520, 1450, 868; $^1$H NMR (400 MHz, $CDCl_3$) δ 7.70 (bs, 4H, ArH), 7.25 (bs, 4H, ArH) 4.73 (bs, 4H, ArC(O)NH), 4.05 (m, 4H, $ArOCH_2$—), 3.99 (bs, 4H, $CHNHC(O)O^t$-Bu), 3.69 (m, 4H, $ArOCH_2CH_2$—), 3.60 (bs, 4H, $ArOCH_2CH_2OCH_2CH_2OCH_2CH_2OAr$), 3.53 (bs, 4H, cyclohexane), 2.30 (m, 4H, cyclohexane), 2.02 (m, 7H, cyclohexane), 1.83, 1.80 (m, s 11H, cyclohexane), 1.43 (bs, 36H $NHC(O)OC(CH_3)_3$), 1.20-1.00 (m, 10H, cyclohexane); ESIMS (MNa+)=1314 m/z.

Bridged macrocyclic module (6): To a 15 mL round bottom flask with stirbar under argon 5 (0.0107 mmol, 0.0138 g) was added. The vessel was evacuated and backfilled with argon (3×). The substrate was dissolved in dichloromethane (0.712 mL, 0.015 M). Anhydrous trifluoroacetic acid (0.356 mL) was added via syringe, the vessel sealed under argon with a glass stopper and stirred at rt for ca. 1 h. All volatiles were removed under vacuo followed by addition of ca. 1 mL of diethyl ether. Next, anhydrous NEt₃ (0.020 mL) was added via syringe under argon at rt and the mixture stirred for ca. 2 h. The resulting precipitate was washed with anhydrous diethyl ether (4×2 mL), followed by cannula filtration and drying in vacuo to afford a light yellow solid. In a nitrogen atmosphere glovebag, the solid was dissolved in CD₃OD (2 mL) and transferred to a vial containing 2-hydroxy-5-methyl-1,3-benzenedicarboxaldehyde (0.0214 mmol, 0.0035 g). The reaction mixture was transferred to a J-Young tube, sealed and heated to 66° C. for 22 h. Purification by silica plug (4:2:0.3 chloroform: hexane: triethylamine) afforded a yellow-green solid (0.0103 g, 84% yield). ¹H NMR (400 MHz, CDCl₃) δ 8.70 (bs, 1H, —N═CH—), 8.69 (bs, 1H, —N═CH—), 7.70 (bs, 1H, —N═CH—), 7.69 (bs, 1H, —N═CH—), 7.65-7.35 (m, 4H, ArH), 7.11 (bs, 4H, ArH), 5.54 (bs, 4H, CHNHC(O)Ar), 4.07 (m, 4H, ArOCH₂CH₂—), 3.93 (m, 4H, CHNHC(O)O$^t$-Bu), 3.80-3.69 (m, 4H, ArOCH₂CH₂—), 3.62 (bs, 4H, ArOCH₂CH₂OCH₂CH₂OCH₂CH₂OAr), 2.50 (bs, 4H, cyclohexane), 2.34, 2.33, 2.28, 2.23 (bs, 12H, ArMe), 2.00 (m, 7H, cyclohexane), 1.89 (m, s 11H, cyclohexane), 1.20-1.00 (m, 10H, cyclohexane); ESIMS (MH⁺)=1148.9 m/z.

Example 2

Bridged macrocyclic module compound 12 was made according to Scheme 16.

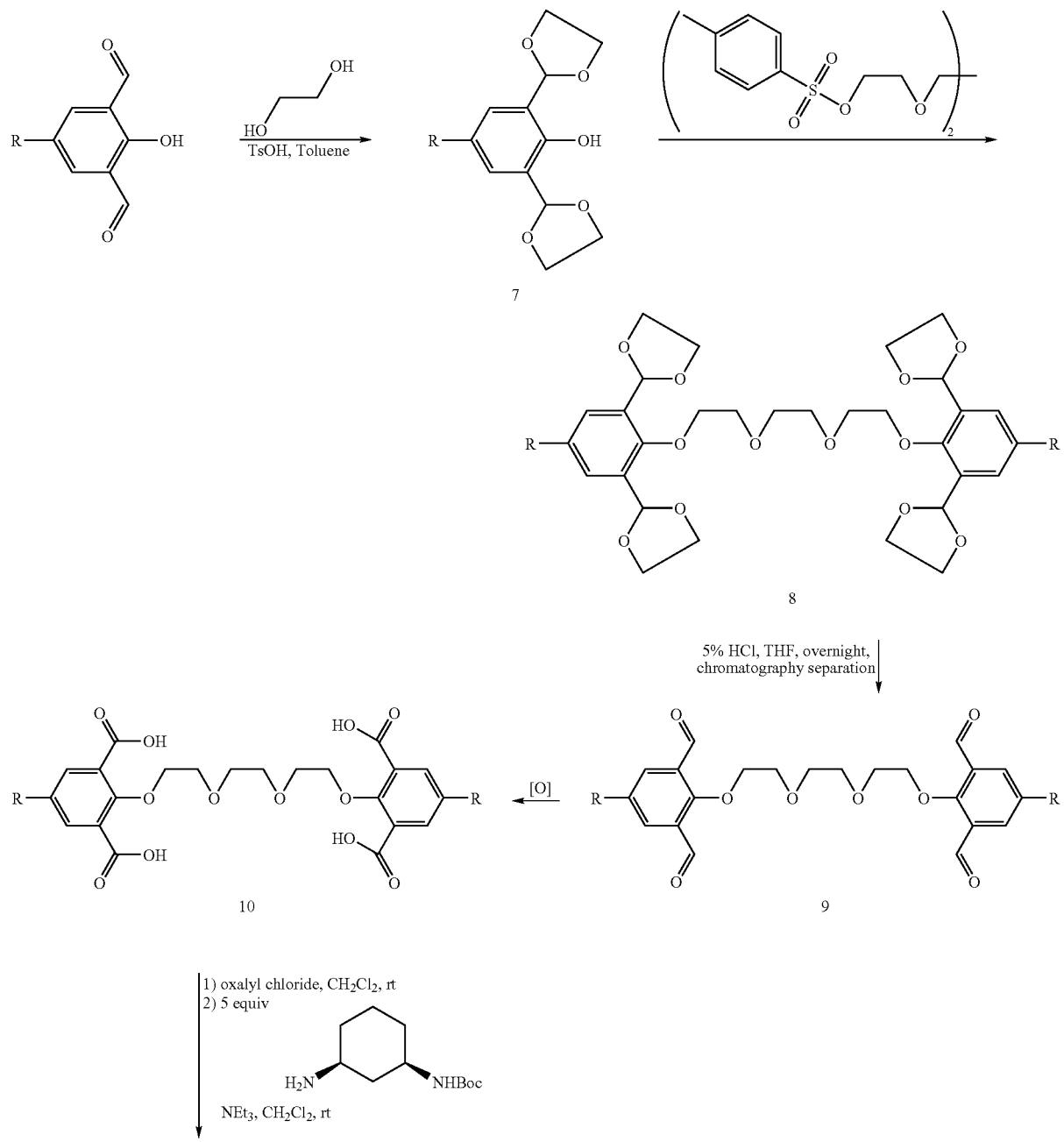

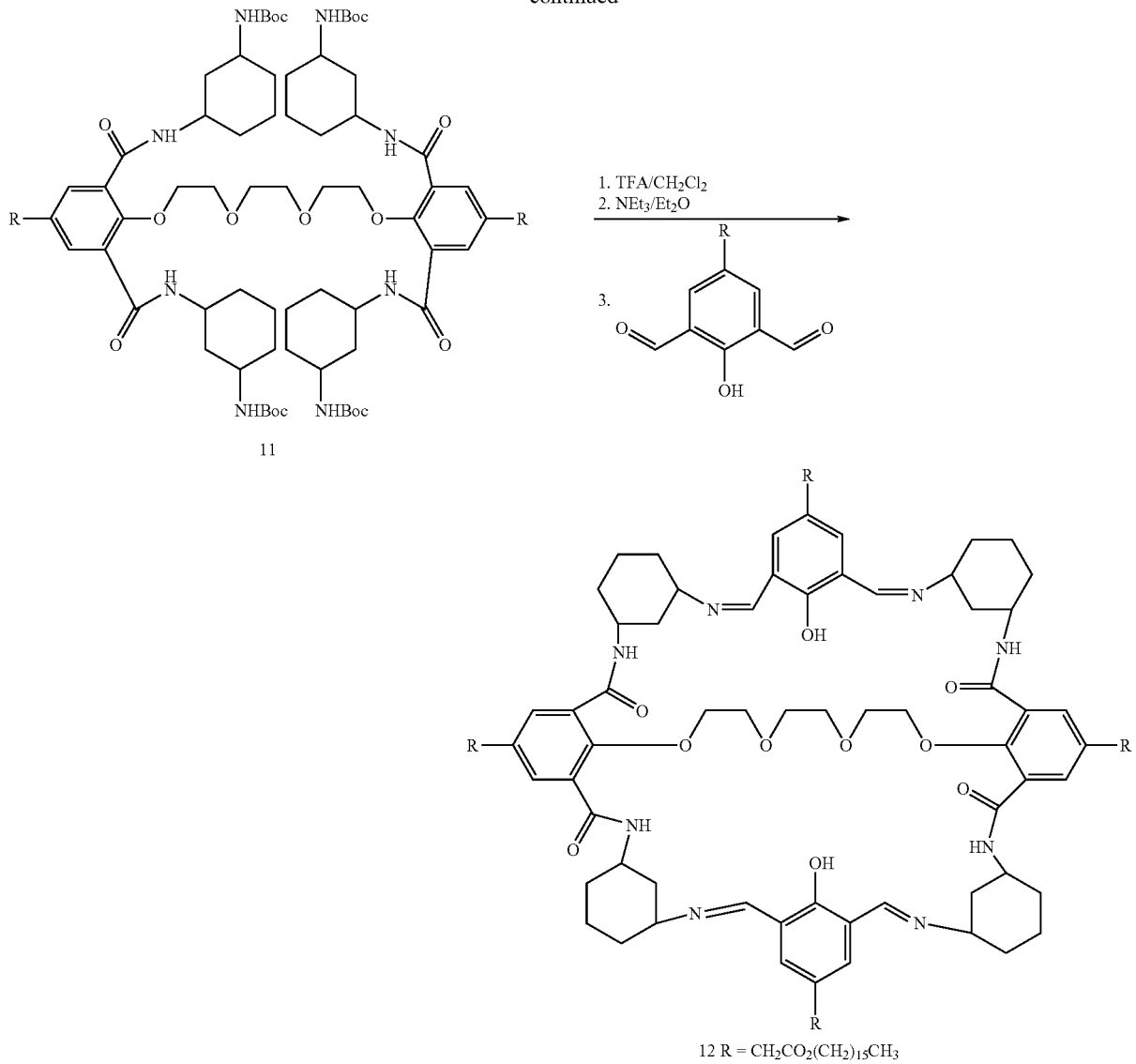

In Scheme 16, R is —CH$_2$CO$_2$(CH$_2$)$_{15}$CH$_3$.

Diprotected Dialdehyde j (7). To a 250 mL Schlenk flask with stirbar under argon dialdehyde j (2,6-diformyl-4-hexadecyl benzylphenyl carboxylate) (2.31 mmol, 1.0 g) was added, and the flask evacuated and backfilled with argon 3×. Anhydrous benzene (100 mL) was cannula transferred, followed by stirring at ambient temperature. Next, anhydrous ethylene glycol (30.48 mmol, 1.9 g) was added via syringe under argon followed by TsOH (0.089 mmol, 0.017 g). The reaction vessel was fitted with a Dean-Stark trap and reflux condenser and the reaction refluxed for ca. 23 h. The reaction was complete as assessed by TLC (Rf=0.63, 1:1 hexane:ethyl acetate, KMnO$_4$ stain). Purification by silica gel chromatography (2:1 hexane:ethyl acetate) afforded a white solid (0.770 g; 64% yield). IR (cm$^{-1}$) 3389, 2917, 2850, 1729, 1627, 1615 $^1$H NMR (400 MHz, CDCl$_3$) δ 8.19 (s, 1H, OH), 7.32 (s, 2H, ArH), 6.06 (s, 2H, ArCHO$_2$), 4.2-4.00 (m, 8H, OCH$_2$CH$_2$O), 3.54 (s, 2H, CH$_2$C(O)OCH$_2$(CH$_2$)$_{14}$CH$_3$), 1.61 (t, 2H, $^3$J=6.6 Hz CH$_2$C(O)OCH$_2$(CH$_2$)$_{14}$CH$_3$), 1.27 (m, 28H, CH$_2$C(O)OCH$_2$(CH$_2$)$_{14}$CH$_3$), 0.89 (t, 3H, $^3$J=6.6 Hz CH$_2$C(O)OCH$_2$(CH$_2$)$_{14}$CH$_3$); {$^1$H}

$^{13}$C NMR (100 MHz, CDCl$_3$) 171.9, 153.1, 129.5, 125.5, 123.5, 101.9, 65.2, 40.7, 32.1, 29.92, 29.89, 29.88, 29.81, 29.7, 29.6, 29.5, 28.8.

Triethylene glycol tethered Diprotected Dialdehyde j (8). To a 25 mL Schlenk flask with Kontes valve and stirbar under argon 7 (2.04 mmol, 1.06 g) was added and the flask evacuated and backfilled with argon 3×. Anhydrous DMF (14.9 mL) was added via syringe and the solution stirred at rt. Next, anhydrous CsCO$_3$ (4.28 mmol, 1.39 g) was added, followed by triethylene glycol ditosylate (0.983 mmol, 0.451 g) and the mixture stirred at rt. The vessel was closed, stirred and heated to 70° C. for ca. 12 h. The reaction was allowed to cool to rt then diluted with ethyl acetate (10 mL), filtered and the solid washed with ethyl acetate (3×100 mL) and filtered. The organic extracts were combined and washed with saturated NH$_4$Cl(aq) (75 mL), then washed with brine (3×75 mL), dried over Na$_2$SO$_4$, filtered and rotovapped to afford the crude product. Purification by column chromatography (2:1 ethyl acetate:hexane) afforded a white solid (1.035 g; 91% yield). IR (cm$^{-1}$) 2954, 2916, 2849, 1739, 1602; $^1$H NMR (400 MHz, CDCl$_3$) δ 7.50 (s, 4H, ArH), 6.15 (s, 4H, ArCHO$_2$), 4.20 (t, 4H, $^3$J=4.8 Hz, ArOCH$_2$—), 4.15-3.70 (m, 16H, OCH$_2$CH$_2$O), 3.84 (t, 4H, $^3$J=4.8 Hz, ArOCH$_2$CH$_2$—), 3.78 (s, 4H, CH$_2$C(O)OCH$_2$(CH$_2$)$_{14}$CH$_3$), 3.59 (s, 4H, ArOCH$_2$CH$_2$OCH$_2$CH$_2$OCH$_2$CH$_2$OAr), 1.60 (t, 4H, $^3$J=6.8 Hz CH$_2$C(O)OCH$_2$(CH$_2$)$_{14}$CH$_3$), 1.26 (m, 56H, CH$_2$C(O)OCH$_2$(CH$_2$)$_{14}$CH$_3$), 0.88 (t, 6H, $^3$J=6.6 Hz CH$_2$C(O)OCH$_2$(CH$_2$)$_{14}$CH$_3$); {$^1$H} $^{13}$C NMR (100 MHz, CDCl$_3$) 171.5, 155.7, 131.5, 130.3, 129.5, 99.1, 76.1, 71.0, 70.5, 65.5, 65.3, 41.0, 32.1, 29.89(br), 29.86, 29.80, 29.7, 29.6, 29.5, 28.7.

Triethylene glycol tethered Dialdehyde j (9). To a 200 mL pear-shaped flask and stirbar under argon 8 (0.89 mmol, 1.03 g) was added. The substrate was dissolved in THF (79.4 mL), then 5% HCl (28.4 mL, aq) was added and the mixture stirred for 12 h resulting in a white precipitate. The reaction mixture was poured into a separatory funnel containing 50 mL of NaHCO$_3$ (sat, aq) the reaction vessel rinsed with 100 mL of ethyl acetate and poured into the separatory funnel with an additional 250 mL of ethyl acetate, and the aqueous layer extracted, separated and washed with brine (3×50 mL). The organic layer was dried over Na$_2$SO$_4$, filtered and the solvent removed by rotovaporation. Purification by silica gel column chromatography (3:1 hexane:ethyl acetate) afforded a white solid (0.864 g, 99%). IR (cm$^{-1}$) 2956, 2917, 2851, 1720, 1694, 1683; $^1$H NMR (400 MHz, CDCl$_3$) δ 10.4 (s, 4H, ArCHO), 7.98 (s, 4H, ArH), 4.33 (t, 4H, $^3$J=4.4 Hz, ArOCH$_2$CH$_2$—), 4.09 (t, 4H, $^3$J=6.8 Hz CH$_2$C(O)OCH$_2$(CH$_2$)$_{14}$CH$_3$), 3.84 (t, 4H, $^3$J=4.4 Hz, ArOCH$_2$CH$_2$—), 3.67 (s, 4H, ArOCH$_2$CH$_2$OCH$_2$CH$_2$OCH$_2$CH$_2$OAr), 3.65 (s, 4H, CH$_2$C(O)OCH$_2$(CH$_2$)$_{14}$CH$_3$), 1.60 (dt, 4H, $^3$J=6.8 Hz CH$_2$C(O)OCH$_2$CH$_2$(CH$_2$)$_{13}$CH$_3$), 1.25 (m, 52H, CH$_2$C(O)OCH$_2$CH$_2$(CH$_2$)$_{13}$CH$_3$), 0.88 (t, 6H, $^3$J=6.6 Hz CH$_2$C(O)OCH$_2$(CH$_2$)$_{14}$CH$_3$); {$^1$H} $^{13}$C NMR (100 MHz, CDCl$_3$) 189.2, 170.8, 163.4, 135.9, 131.4, 130.4, 78.6, 70.9, 70.4, 65.7, 65.3, 40.2, 32.1, 29.89(br), 29.88, 29.86, 29.8, 29.7, 29.6, 29.4, 28.7.

Triethylene glycol tethered Dicarboxylic acid j (10). To a 100 mL round bottom flask and stirbar under argon 9 (0.204 mmol, 0.200 g) was added. The substrate was dissolved in 1,4-dioxane (21 mL), then sonicated until homogeneous. Buffer, NaH$_2$PO$_4$ (3.19 mmol, 382 mg) and sulfamic acid (1.23 mmol, 0.119 mg) were dissolved in de-ionized H$_2$O in a 25 mL Erlenmeyer flask with a 'flea' stirbar, then transferred to the stirring solution of the substrate by syringe. The heterogeneous solution was sonicated again until the mixture was nearly homogeneous. Sodium chlorite (NaClO$_2$, 1.06 mmol, 0.96 mg) was dissolved in a de-ionized H$_2$O (1 mL) and added dropwise via syringe to the stirring solution resulting in a yellow homogeneous solution. After ca. 3.5 h the reaction was complete as assessed by TLC. Sodium sulfite (0.98 mmol, 124 mg) was added and the reaction stirred for ca. 1 h giving a colorless solution. The reaction mixture was diluted with CH$_2$Cl$_2$ (200 mL), poured into a separatory funnel and the pH adjusted to ca. 1-2 with 4 M HCl. The aqueous layer was extracted with CH$_2$Cl$_2$ (2×50 mL). The organic layer was separated and washed with brine (3×50 mL). The organic layer was separated and the solvent removed by rotovaporation and then put under vacuo to remove the remaining H$_2$O, affording a white solid (0.211 g, 99% yield). IR (cm$^{-1}$) 3193, 2953, 2917, 2850, 1734 (br), 1607, 1582, 1467; $^1$H NMR (400 MHz, DMSO-d$_6$) δ 13.18 (bs, 4H, ArCOOH), 7.70 (s, 4H, ArH), 4.08 (t, 4H, $^3$J=5.1 Hz, ArOCH$_2$CH$_2$—), 4.04 (t, 4H, $^3$J=6.8 Hz CH$_2$C(O)OCH$_2$(CH$_2$)$_{14}$CH$_3$), 3.69 (t, 4H, 3J=5.1 Hz, ArOCH$_2$CH$_2$—), 3.57 (s, 4H, ArOCH$_2$CH$_2$OCH$_2$CH$_2$OCH$_2$CH$_2$OAr), 3.54 (s, 4H, CH$_2$C(O)OCH$_2$(CH$_2$)$_{14}$CH$_3$), 1.54 (tt, 4H, $^3$J=6.8 Hz CH$_2$C(O)OCH$_2$CH$_2$(CH$_2$)$_{13}$CH$_3$), 1.22 (m, 52H, CH$_2$C(O)OCH$_2$CH$_2$(CH$_2$)$_{13}$CH$_3$), 0.84 (t, 6H, $^3$J=6.6 Hz CH$_2$C(O)OCH$_2$(CH$_2$)$_{14}$CH$_3$); {$^1$H} $^{13}$C NMR (100 MHz, DMSO-d$_6$) 171, 166.9, 155.6, 134.4, 129.8, 127.6, 74.4, 69.6, 69.5, 66.4, 64.4, 31.3, 29.08 (br), 29.05, 29.0, 28.9, 28.8, 28.7, 28.1, 25.3, 22.1, 14.0.

Triethylene glycol tethered Diamide tetra-Boc-protected-cis-1,3-diaminocyclohexane j (11). To a 50 mL round bottom Schlenk flask with Kontes valve and stirbar under argon 10 (0.096 mmol, 0.100 g) was added., The vessel was evacuated and backfilled with argon (3×). Oxalyl chloride (2.0 M) in dichloromethane (0.985 mmol, 0.480 mL) was added via syringe. Next a catalytic amount of DMF (0.015 mL) was added via syringe with stirring at rt for 2 h, resulting in rigorous effervescence and a yellow solution with yellow precipitate. All volatiles were removed under vacuo and the residue dissolved in dichloromethane (1 mL) followed by addition of triethylamine (1.53 mmol, 0.155 g) via syringe under argon. A dichloromethane solution of mono-Boc-protected-cis-1,3-diaminocyclohexane (0.980 mmol, 0.210 g) was added dropwise to the reaction mixture, the vessel sealed and stirred overnight at ambient temperature, affording an orange solution with precipitate formation. The reaction was diluted with dichloromethane (250 mL), washed with brine (2×50 mL), water (50 mL), then brine (50 mL), the organic layer dried over sodium sulfate, filtered and the solvent removed by rotovaporation. Purification by silica chromatography (2.5:1 ethyl acetate:hexane) afforded an off white solid (0.154 mg, 88% yield). IR (cm$^{-1}$) 3360, 3320, 3053, 2924, 2854, 1710, 1696, 1642, 1520, 903, 874; $^1$H NMR (400 MHz, CDCl$_3$) δ 7.80 (bs, 4H, ArH), 7.21 (bs, 4H, ArC(O)NH), 4.75 (bs, 4H, CHNHC(O)O$^t$-Bu), 4.06 (m, 4H, ArOCH$_2$CH$_2$—), 3.99 (m, 4H, CH$_2$C(O)OCH$_2$(CH$_2$)$_{14}$CH$_3$), 3.70 (m, 4H, ArOCH$_2$CH$_2$—), 3.59 (bs, 4H, ArOCH$_2$CH$_2$OCH$_2$CH$_2$OCH$_2$CH$_2$OAr), 3.54 (bs, 4H, CH$_2$C(O)OCH$_2$(CH$_2$)$_{14}$CH$_3$), 2.31 (m, 4H, cyclohexane), 2.02 (m, 7H, cyclohexane), 1.81, 1.71 (m, s 11H, cyclohexane), 1.61 (m, 4H CH$_2$C(O)OCH$_2$CH$_2$(CH$_2$)$_{13}$CH$_3$), 1.26 (m, 52H, CH$_2$C(O)OCH$_2$CH$_2$(CH$_2$)$_{13}$CH$_3$), 1.20-1.00 (m, 10H, cyclohexane), 0.88 (m, 6H, $^3$J=6.6 Hz CH$_2$C(O)OCH$_2$(CH$_2$)$_{14}$CH$_3$); {$^1$H} $^{13}$C NMR (100 MHz, CDCl$_3$) 171.3, 164.6, 155.3, 153.3, 134.6, 130.9, 129.0, 70.3, 70.0, 65.6, 48.8, 48.2, 40.2, 39.8, 32.9, 32.2, 32.1, 29.92(br), 29.88, 29.83, 29.7, 29.6, 29.5, 28.7, 28.6, 26.1 23.2, 22.9, 14.4; ESIMS (MH$^+$)=1829.5 m/z.

Octamer IV pjs (12). To a 50 mL round bottom Schlenk flask with Kontes valve and stirbar under argon 11 (0.0107 mmol, 0.0195 g) was added. The vessel was evacuated and backfilled with argon (3×). The substrate was dissolved in dichloromethane (0.712 mL, 0.015 M). Anhydrous trifluoroacetic acid (0.356 mL) was added via syringe, the vessel sealed under argon with a glass stopper, and stirred at rt for ca. 1 h. All volatiles were removed under vacuo, followed by addition of about 1 mL of diethyl ether. Next, anhydrous NEt$_3$ (0.020 mL) was added via syringe under argon at rt, and the mixture stirred for ca. 2 h. The resulting precipitate was washed with anhydrous diethyl ether (3×2 mL), followed by cannula filtration and drying in vacuo to afford a light yellow solid. In a nitrogen atmosphere glovebag, the solid was dissolved in CD$_3$OD (2 mL) and transferred to a vial containing dialdehyde j (2,6-diformyl-4-hexadecyl benzylphenyl carboxylate) (0.0214 mmol, 0.0092 g). The reaction mixture was transferred to a J-Young tube, sealed and heated to 66° C. for 22 h. Purification by silica plug (4:2:0.3 chloroform:hexane:triethylamine) afforded a yellow-green solid (0.018 g, 76% yield). $^1$H NMR (400 MHz, CDCl$_3$) δ 8.77 (bs, 1H, —N═CH—), 8.75 (bs, 1H, —N═CH$_7$), 7.82 (bs, 1H, —N═CH—), 7.81 (bs, 1H, —N═CH—), 7.78-7.54 (m, 4H, ArH), 7.25 (bs, 4H, ArH), 5.60 (bs, 4H, CHNHC(O)Ar), 4.08-3.5 (m, 4H, ArOCH$_2$CH$_2$—; m, 4H, CH$_2$C(O)OCH$_2$(CH$_2$)$_{14}$CH$_3$; m, 4H cyclohexane; m, 4H, ArOCH$_2$CH$_2$—), 3.63 (bs, 4H, ArOCH$_2$CH$_2$OCH$_2$CH$_2$OCH$_2$CH$_2$OAr), 3.54 (bs, 4H, CH$_2$C(O)OCH$_2$(CH$_2$)$_{14}$CH$_3$), 2.36 (m, 4H, cyclohexane), 2.00, 2.35, 2.20, (m, 7H, cyclohexane), 1.95, 1.92 (m, s 11H, cyclohexane), 1.61 (m, 4H CH$_2$C(O)OCH$_2$CH$_2$(CH$_2$)$_{13}$CH$_3$), 1.28 (m, 52H, CH$_2$C(O)OCH$_2$CH$_2$(CH$_2$)$_{13}$CH$_3$), 1.20-1.00 (m, 10H, cyclohexane), 0.89 (m, 6H, $^3J$=6.6 Hz CH$_2$C(O)OCH$_2$(CH$_2$)$_{14}$CH$_3$); MALDITOFMS (MH$^+$)= 2222 m/z, (MH+H$_2$O)=2240 m/z, (MH+2H$_2$O)=2258 m/z, (MH+3H$_2$O)=2266 m/z. (MH+3 dihydroxybenzoic acid matrix)=2680 m/z.

Example 3

Bridged macrocyclic module compound 13 is prepared according to a stepwise synthesis method as shown in Scheme 17.

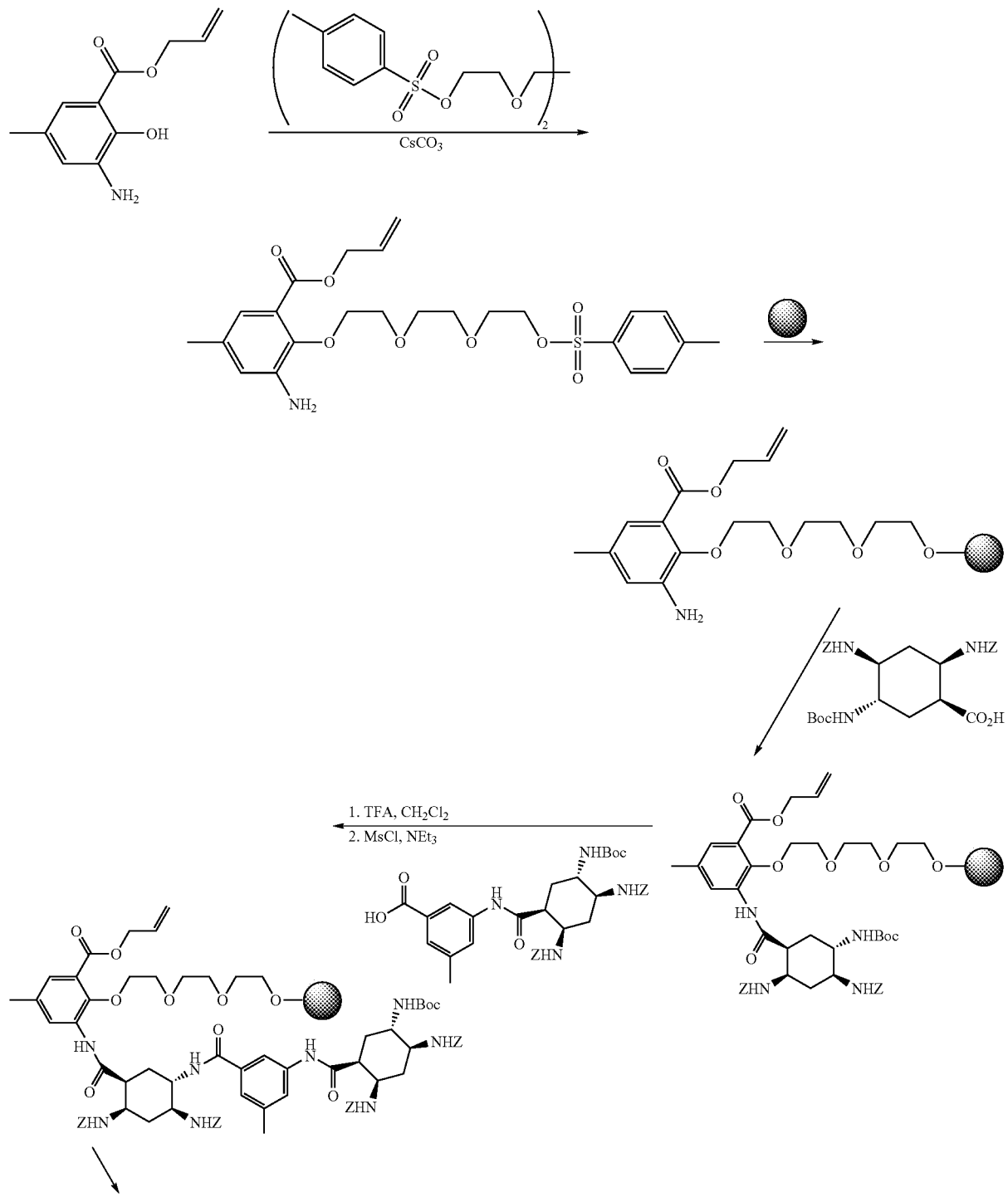

-continued
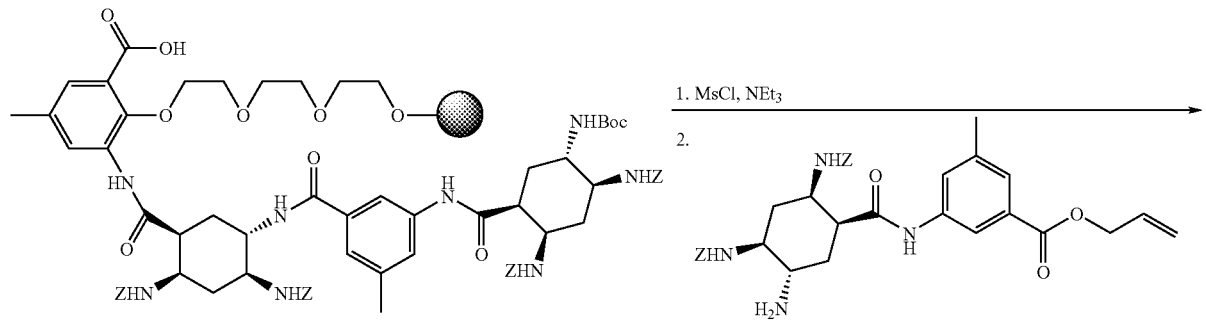
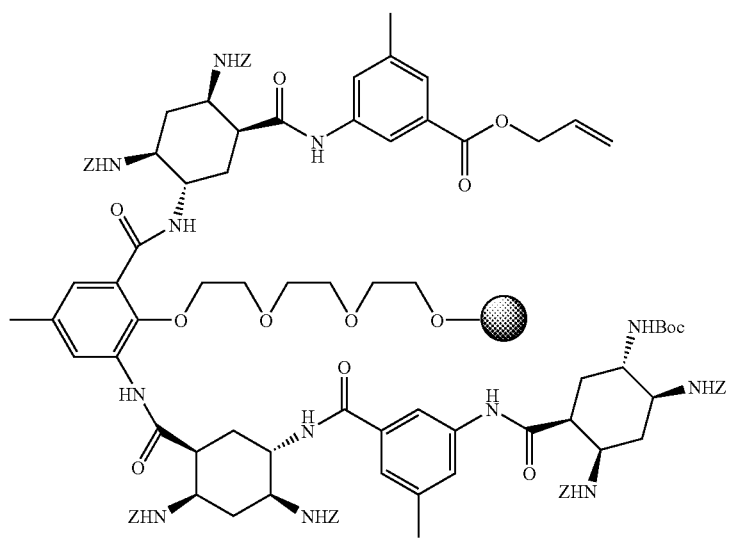
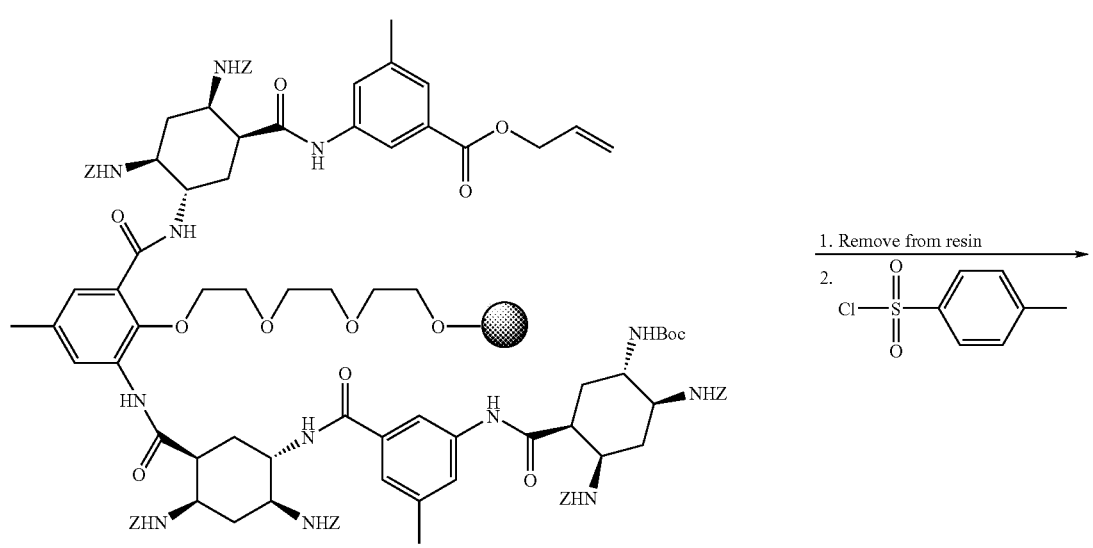

-continued
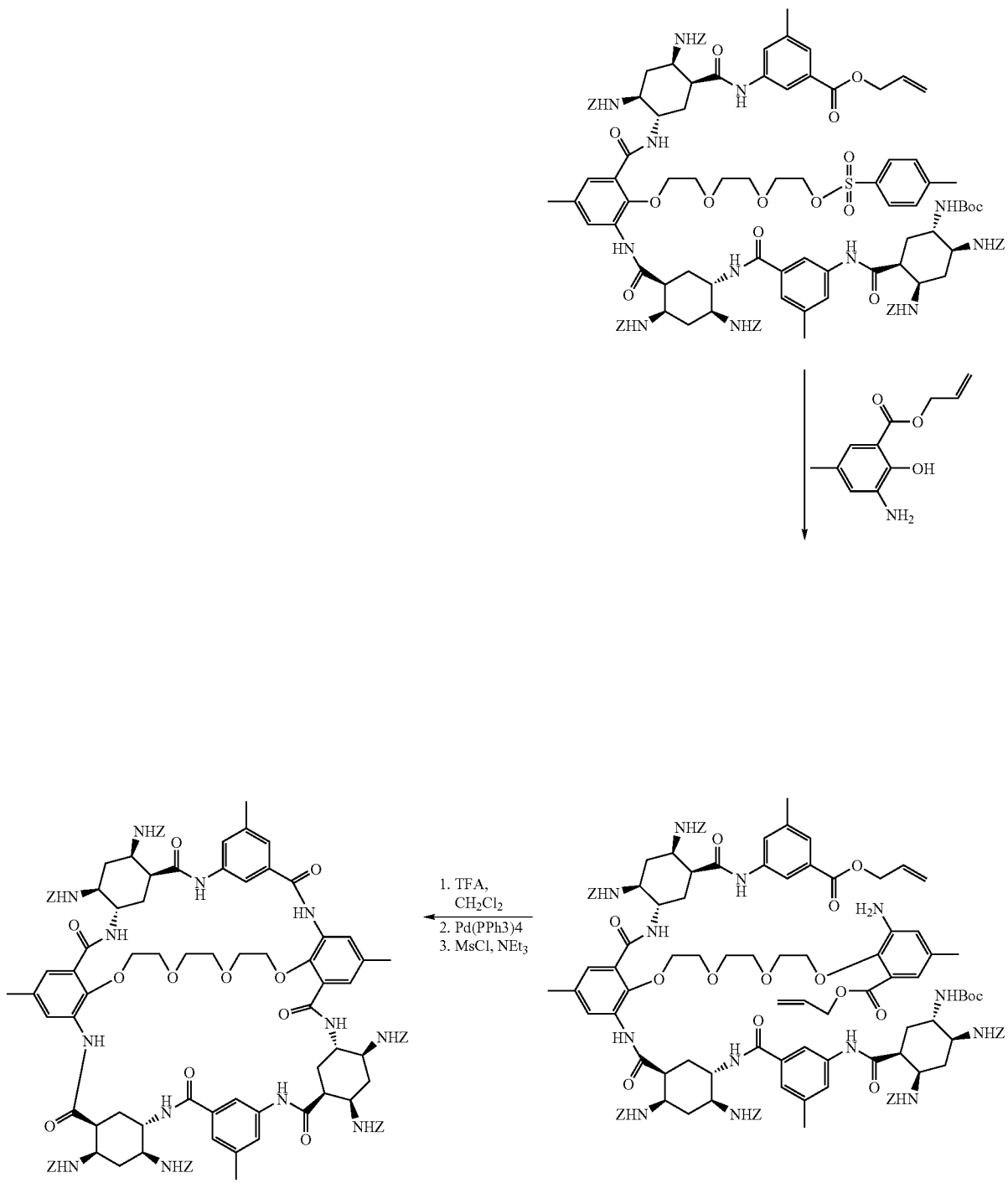

Example 4
Bridged macrocyclic module 14 is prepared by a convergent synthesis method as shown in Schemes 18 and 19.
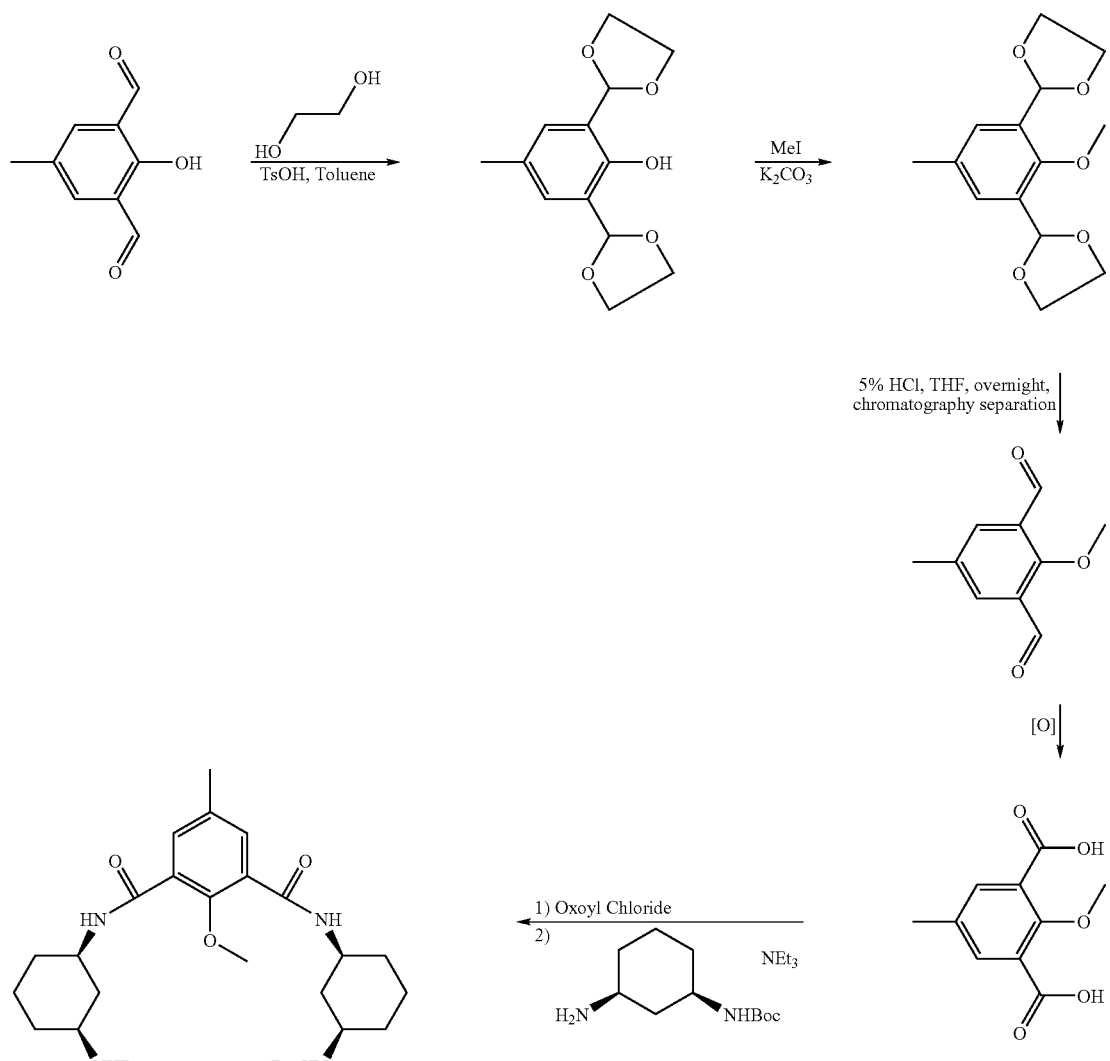
The N-protected synthon trimer A is prepared as shown above in Scheme 18.
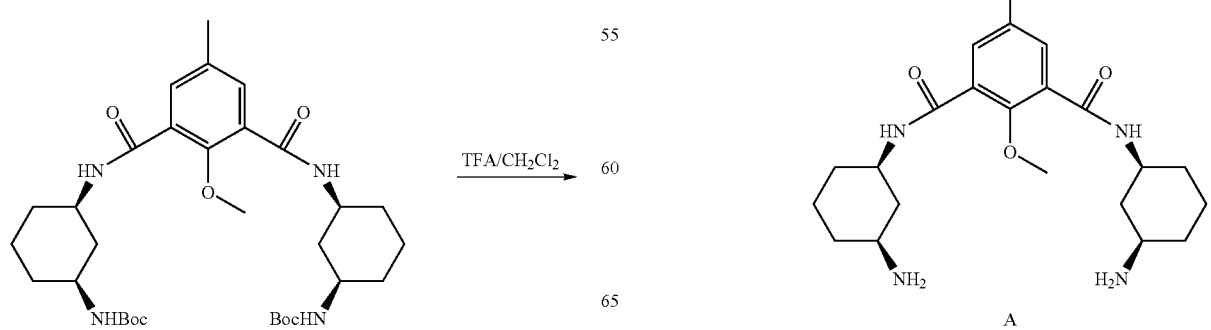

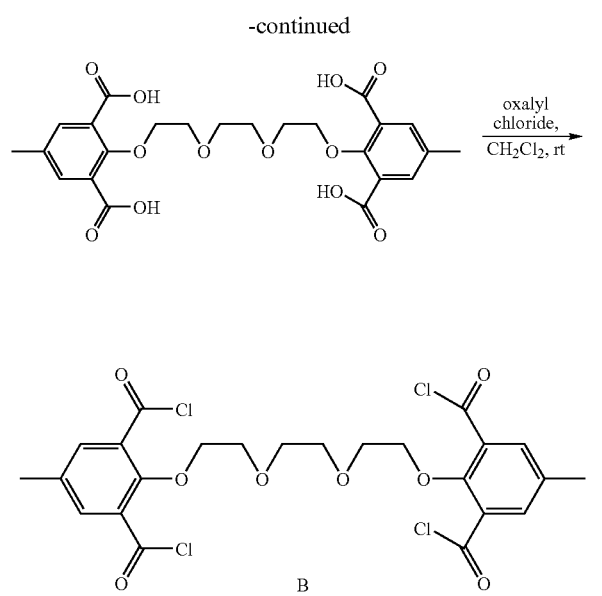
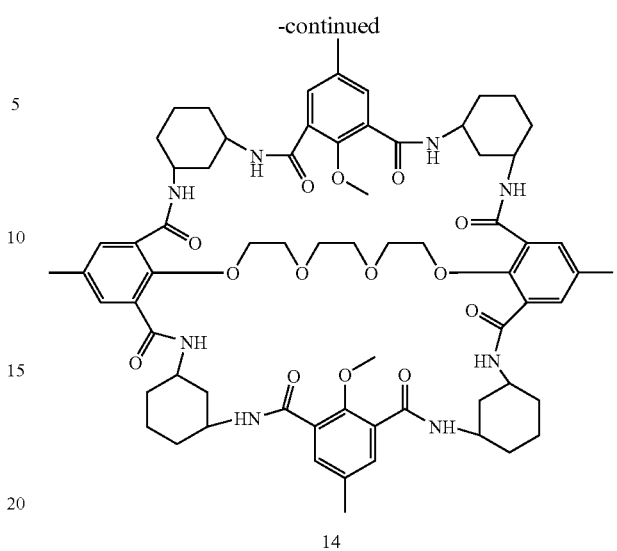
N-protected synthon trimer A is converted to the activated synthon trimer A, which is combined with bridged program director compound B to produce bridged macrocyclic module compound 14.
Example 5
Bridged Macrocyclic Module 15 is prepared according to Scheme 20.
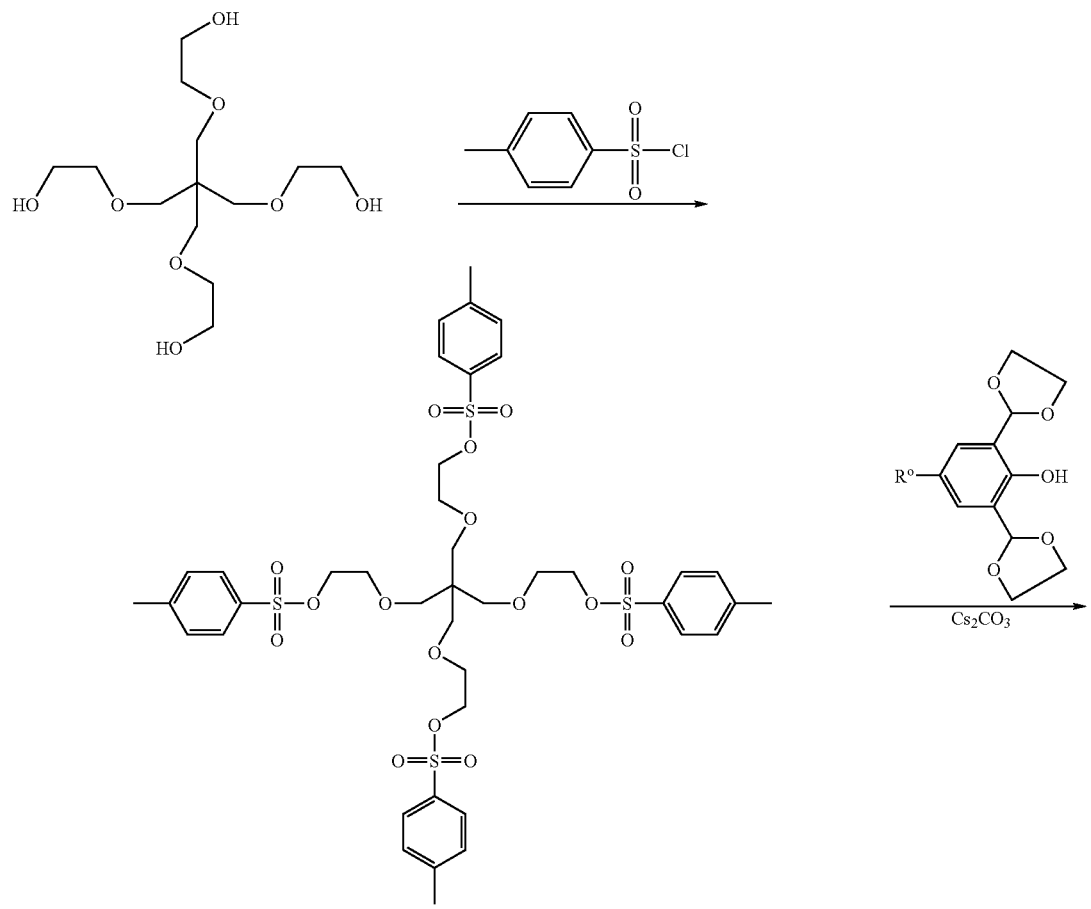

-continued

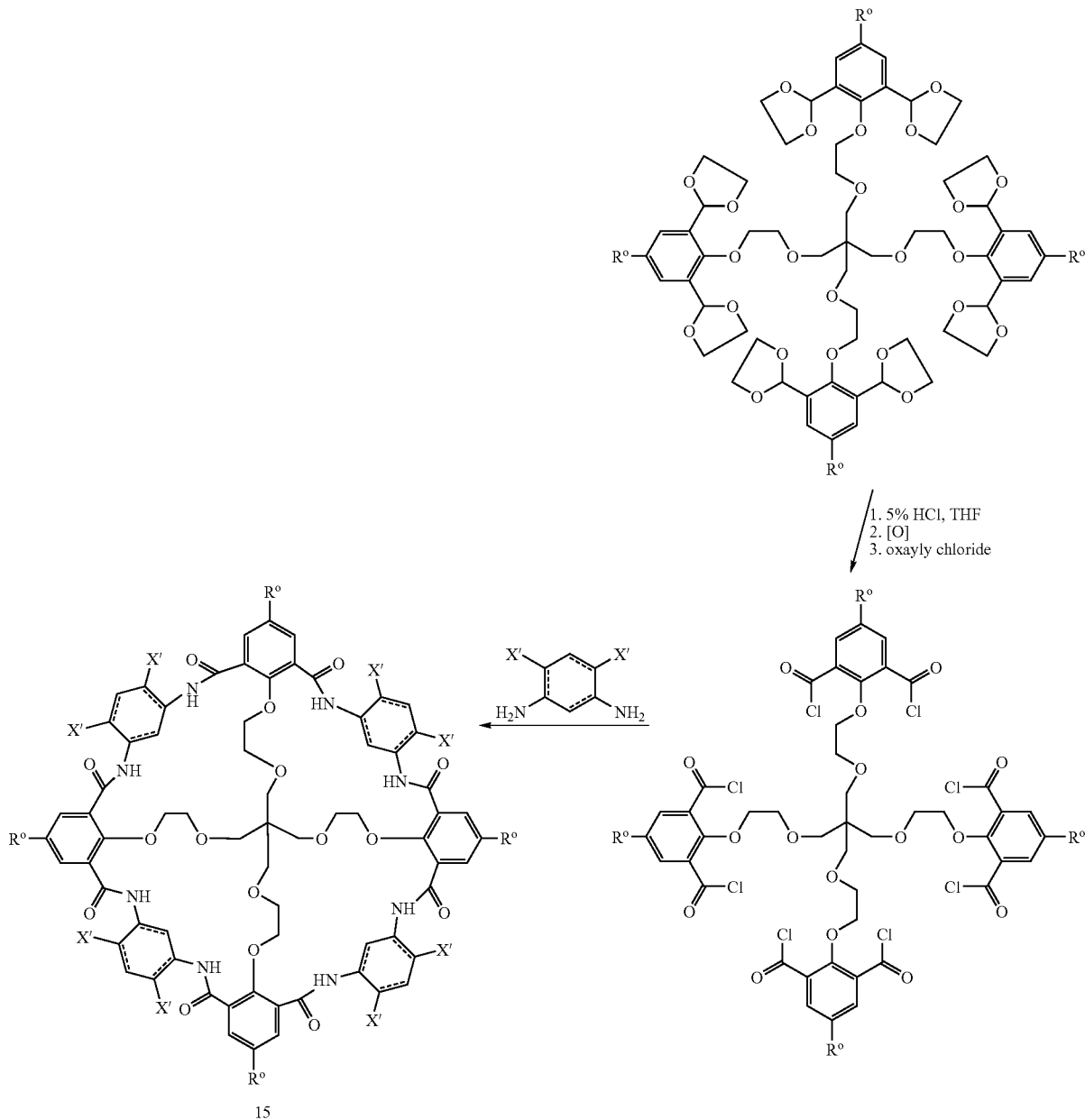

Example 6

Transport properties for bridged macrocyclic module 12 (Octamer IV pjs). The dimensions of macrocyclic module and bridged macrocyclic module pores may be measured by electrical conductance in a voltage-clamped lipid bilayer test. Bridged macrocyclic modules 12 were dissolved into a phosphatidylcholine-phosphatidylethanolamine lipid bilayer. On one side of the bilayer was placed a solution containing a test cationic species. On the other side was placed a solution containing a cationic species known to be able to pass through the module pore. Anions required for charge neutrality were selected such that they would not pass through the module pore (Cl⁻ in this example). When a positive potential was created in the solution on the side of the lipid bilayer containing the test species, if the test cations were of such a size that they could not pass through the pores in the modules, no current would be detected. The voltage was then reversed to create a positive potential on the side of the lipid bilayer having the solution containing the cationic species known to be able to traverse the pore. Observation of the expected current confirmed the integrity of the lipid bilayer and the availability of the module pores as transporters of cations of the known size and smaller.

The selective permeability of bridged macrocyclic module 12 (Octamer IV pjs) is shown in Table 9. "Yes" indicates permeation of the solute, "No" indicates rejection of the solute. Permeation and rejection are indicators of clearance. The clamp voltage was 50 mV. Transport properties of two hexameric macrocyclic modules are shown for comparison.

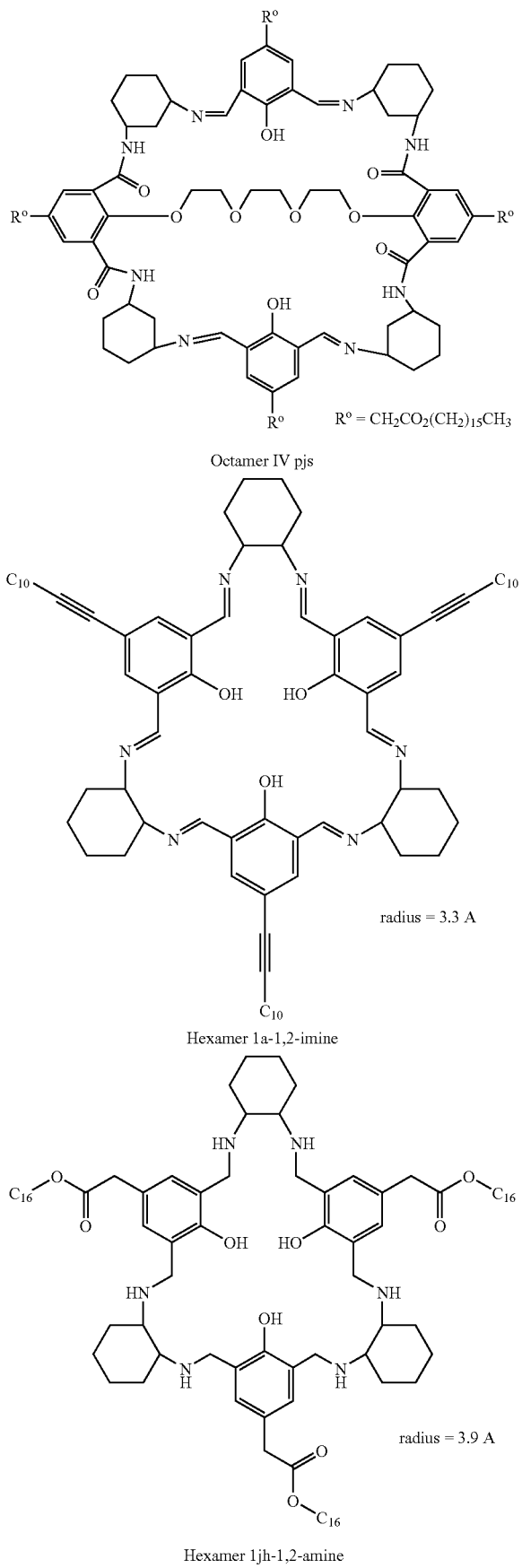

TABLE 9

Transport properties for bridged and non-bridged macrocyclic modules

| Solute | Solute Radius | Solute Hydration Radius (2nd shell) | Hexamer $I_a$ (1,2-imine) Radius 3.3 Å | Hexamer $I_{jh}$ (1,2-amine) Radius 3.9 Å | Bridged macrocyclic module 12 (amide-imine) |
|---|---|---|---|---|---|
| $Li^+$ | 0.6 | 2.0 (5.6) | No | Yes | Yes |
| $Na^+$ | 1.0 | 2.2 | Yes | Yes | Yes |
| $K^+$ | 1.3 | 2.7 | Yes | Yes | Yes |
| $Ca^{2+}$ | 1.0 | 2.7 | Yes | Yes | No-blocker |
| $Mg^{2+}$ | 0.7 | 2.8 (5.5) | No | Yes | No |
| $NH_3^+$ | 1.9 | 2.9 | Yes | Yes | Yes |
| $Cs^+$ | 1.7 | 3 | Yes | Yes | Yes |
| $MeNH_3^+$ | 2 | 3 | Yes | Yes | No |
| $EtNH_3^+$ | 2.6 | 3.6 | No | Yes | No |
| $NMe_4^+$ | 2.6 | 3.6 | No | Yes | No |
| Amino-guanidine | 3.1 | 4.1 | No | Yes | No |
| Choline | 3.8 | 4.8 | No | Yes | No |
| $NEt_4^+$ | 3.9 | 4.4 | No | No | No |
| Glucosamine | 4.2 | 5.2 | No | No | No |
| $NPr_4^+$ | — | — | — | No | — |

In Table 9, "No-blocker" indicates that the ion did not traverse the module, but was trapped in the module. The results in Table 9 show that the cut-off for passage through the pores in the selected bridged macrocyclic module is a van der Waals radius of between about 1.8-2. Without wishing to be bound by theory, and recognizing that several factors influence pore transport, the observed ability of hydrated ions to pass through the pore may be due to partial dehydration of the species to enter the pore, transport of water molecules and ions through the pore separately or with reduced interaction during transport, and re-coordination of water molecules and ions after transport. The details of pore structure, composition, and chemistry, the flexibility of the module, and other interactions may affect the transport process. Without wishing to be bound by theory, $Mg^{2+}$ and $Ca^{2+}$ ions may be bound by the PEG bridge moiety in bridged macrocyclic module 12.

Example 7

Preparation of nanofilm of Octamer IV pjs. 25 μl of a 1 mg/ml solution of Octamer IV pjs in chloroform was spread on a 100 mM $NaH_2PO_4$ buffered subphase (pH 7.0, T=22° C.). After waiting for 19 minutes to allow for spreading solvent evaporation, the monolayer was compressed at 1 mN/m. The monolayer exhibited a collapse pressure of approximately 30 mN/m and the entire isotherm indicated that the module was highly compressible. The corresponding composite isotherm data (i.e., from several Langmuir film runs) is shown in FIG. 1.

The inflection point at approximately 50 Å indicates that the molecule occupies a much smaller space per molecule than expected. This was more than half of the expected area from molecular mechanics computations.

Example 8

Figure 2:
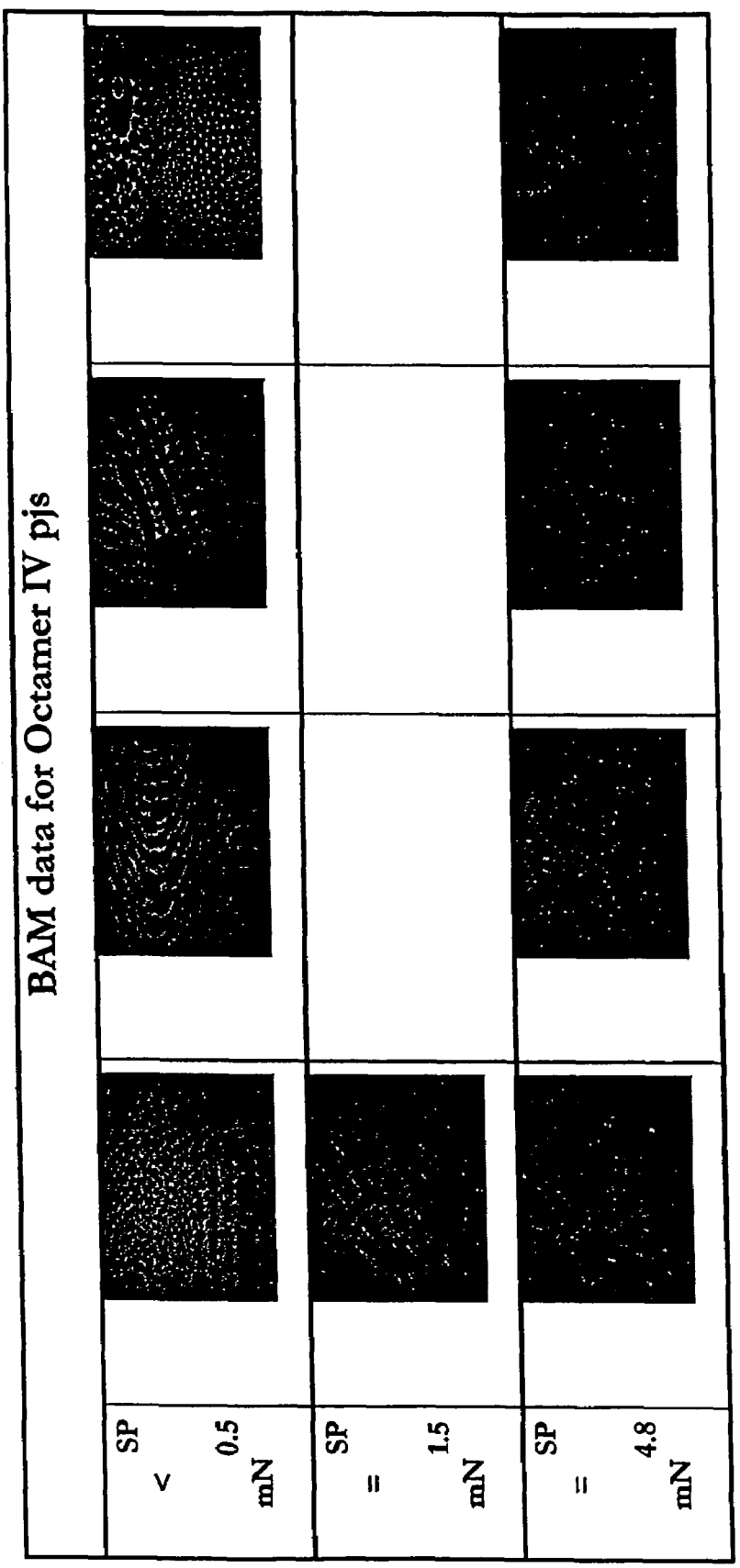
FIG. 2 shows examples of Brewster Angle Microscopy (BAM) data for a nanofilm of Octamer IV pjs.

Brewster Angle Microscopy (BAM) evaluation of nanofilms from Octamer IV pjs. Nanofilms produced on a Langmuir trough interface at different surface pressures were evaluated by BAM, as shown in FIG. 2. In FIG. 2, SP indicates surface pressure. Thus, at moderate surface pressures, the Octamer IV pjs appears to make a homogenous film on the Langmuir trough.

Example 9

Quantum mechanical (QM) and molecular mechanical (MM) computations for approximation of module pore size. Without intending to be bound by any one particular theory, one method to approximate pore size of a macrocyclic module or bridged macrocyclic module is quantum mechanical (QM) and molecular mechanical (MM) computations. For the purposes of QM and MM computations, the root mean square deviations in the pore areas were computed over dynamic runs.

For QM, each module was first optimized using the MM+force field approach of Allinger (JACS, 1977, 99:8127) and Burkert, et al., (Molecular Mechanics, ACS Monograph 177, 1982). They were then re-optimized using the AM1 Hamiltonian (Dewar, et al., JACS, 1985, 107:3903; Dewar, et al., JACS, 1986, 108:8075; Stewart, J. Comp. Aided Mol. Design, 1990, 4:1). To verify the nature of the potential energy surface in the vicinity of the optimized structures, the associated Hessian matrices were computed using numerical double-differencing.

For MM, the OPLS-AA force field approach (Jorgensen, et al., JACS, 1996, 118:11225) was used. For imine linkages, the dihedral angle was confined to 180°±10°. The structures were minimized and equilibrated for one picosecond using 0.5 femtosecond time steps. Then a 5 nanosecond dynamics run was carried out with a 1.5 femtosecond time step. Structures were saved every picosecond.

Figure 3:
FIG. 3 shows the conformation of Octamer IV pjs after molecular dynamics simulation.

While not wishing to be bound by theory, the molecular dynamics data for Octamer IV pjs indicated that there is a bending effect along the axis of the bridge moiety (FIG. 3), which may account for the unexpectedly low molecular area observed in the Langmuir isotherm.

Figure 4A:
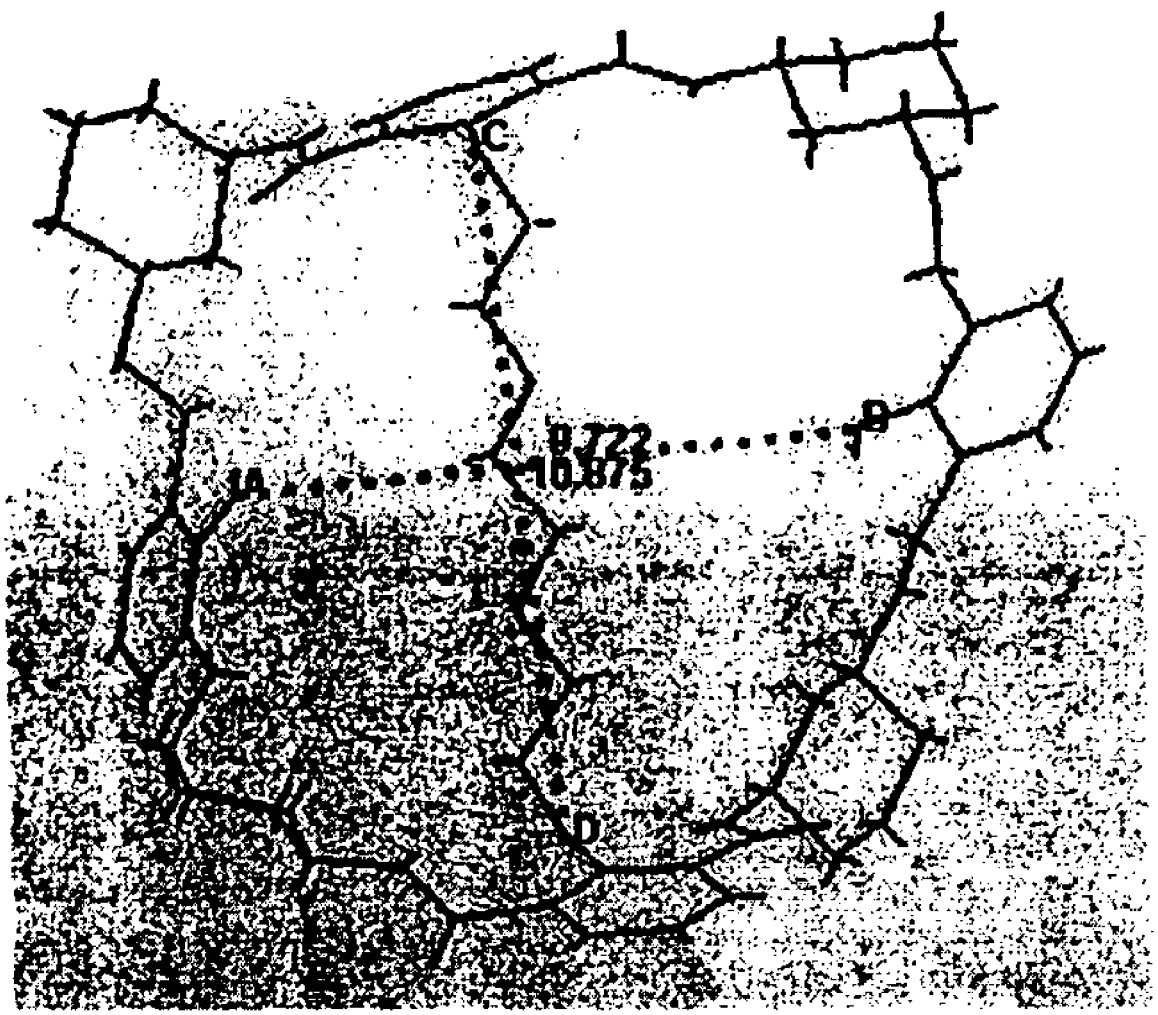
FIG. 4A shows the conformation of Octamer IV pjs before molecular mechanics annealing routines.
Figure 4B:
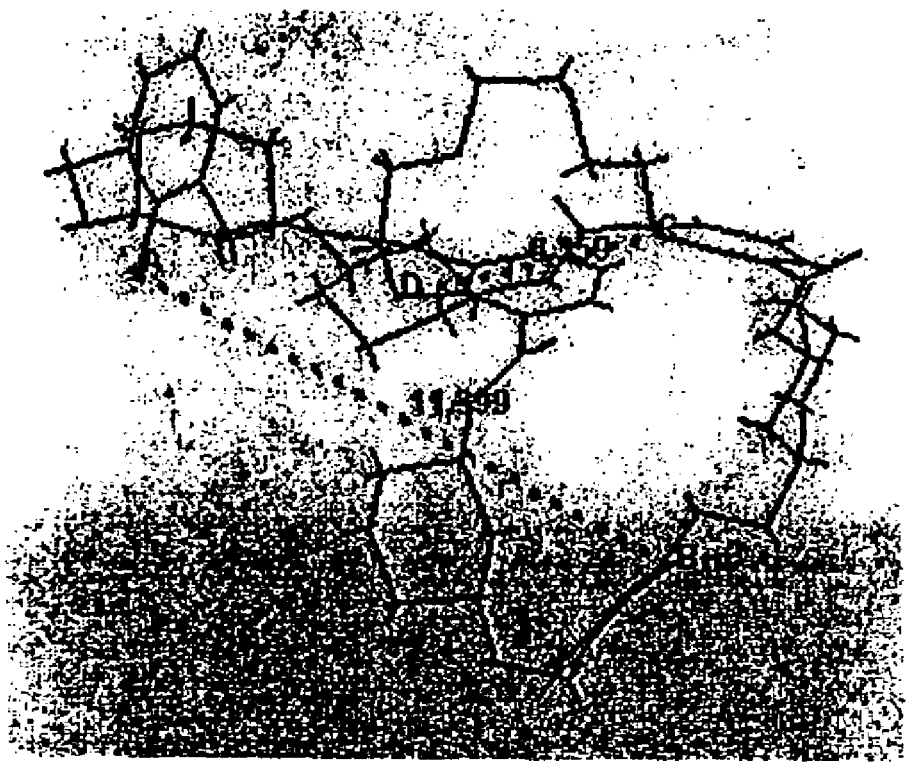
FIG. 4B shows two views of the conformation of Octamer IV pjs after molecular mechanics annealing routines.
Figure 4B:
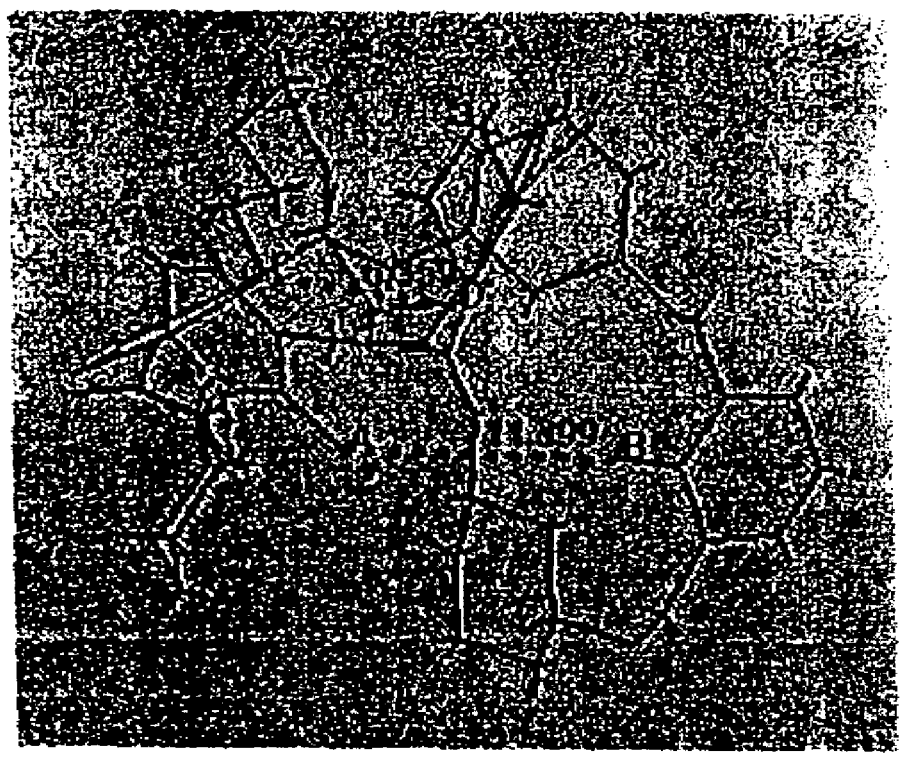

Molecular mechanics computations further indicated that the molecule will bend along the axis of the bridge moiety in solvents of low dielectric constant. The temperature was set at 300 K for this simulation. FIGS. 4A and 4B show the molecule before and after the simulation, with the indicated distances between atoms monitored.

Figure 5A:
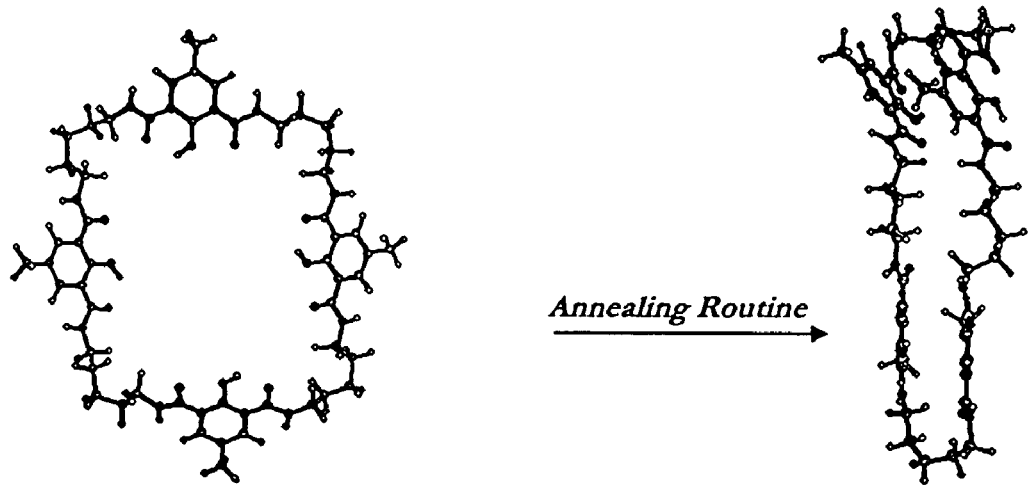
FIG. 5A shows the conformation of a molecule of Octamer IV pjs without the bridge moiety before and after a molecular mechanics annealing routine.
Figure 5B:
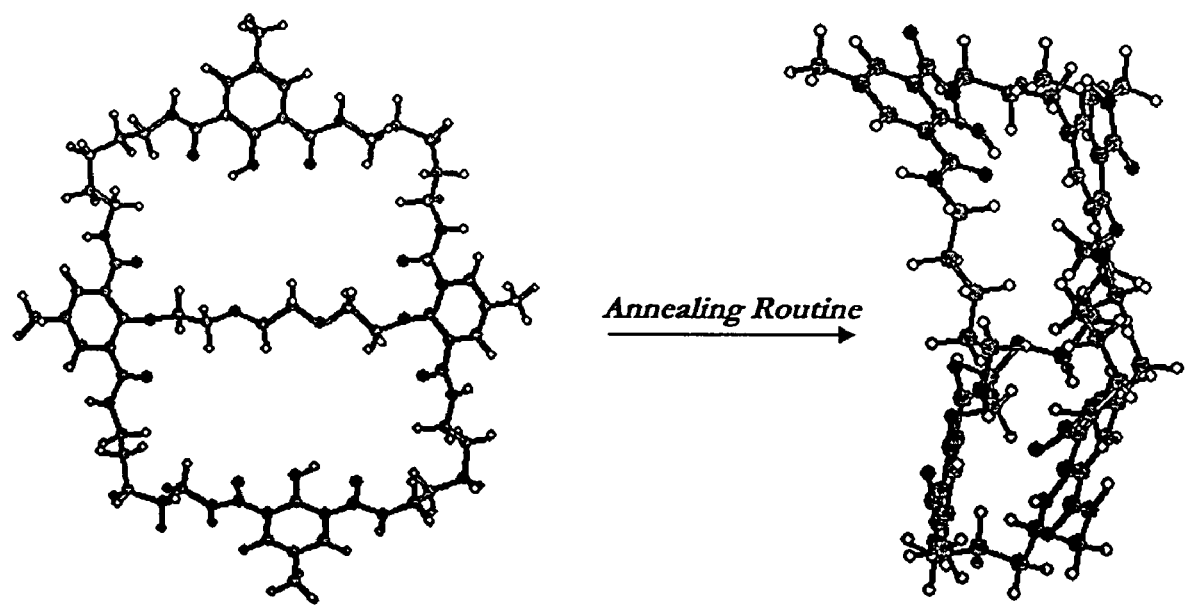
FIG. 5B shows the conformation of Octamer IV pjs before and after a molecular mechanics annealing routine.

A further molecular mechanics simulation included an annealing and cooling routine in a vacuum. Octamer IV pjs and a identical module without the bridge moiety were subject to 1 ps simulated annealing (T=1000K to 298K) in 10K temperature steps, and subsequently, 5 ps running at T=298K, and finally, 1 ps simulated annealing (T-298K to 0K) in 10K temperature steps. FIGS. 5A and 5B show the structures before and after the annealing routine (with optimization performed after the molecular dynamics).

Example 10

Derivatization of SiO$_2$ substrates with methylacryloxymethyltrimethoxysilane (MAOMTMOS). SiO$_2$ substrates were first sonicated in a piranha solution (3:1 ratio of H$_2$SO$_4$:30% H$_2$O$_2$) for 15 minutes, followed by a 15 minute sonication in Milli-Q water (>18 MgΩ-cm). The derivatization step was done in a glove bag under N$_2$ atmosphere. 0.05 mL MAOMTMOS and 0.05 mL pyridine were added to 9 mL of toluene. Immediately following mixing, the freshly cleaned SiO$_2$ substrates were immersed in the MAOMTMOS solution for 10 min. Substrates were washed with copious amounts of toluene and then dried with N$_2$. Deposited MAOMTMOS films showed a range of thickness values from 0.8 to 1.3 nm.

Example 11

Deposition of Octamer IV pjs-acrylamide nanofilm on MAOMTMOS modified SiO$_2$ substrates.

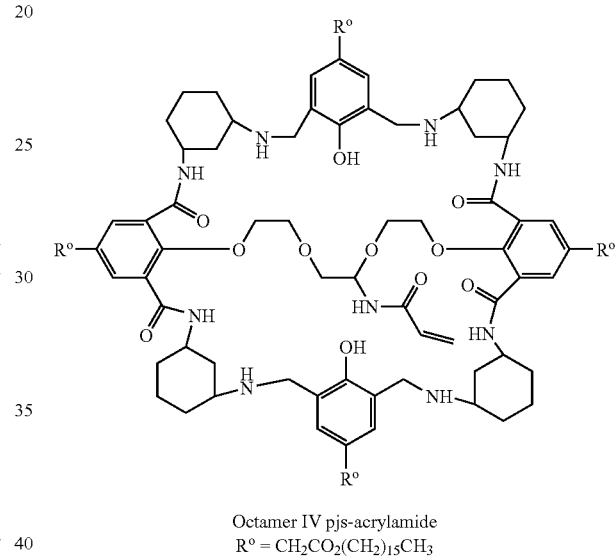

Octamer IV pjs-acrylamide
R° = CH$_2$CO$_2$(CH$_2$)$_{15}$CH$_3$

Octamer IV pjs-acrylamide is synthesized by addition of acrylamide to Octamer IV pjs.

The derivatized SiO$_2$ substrates are lowered into a pH 5, 22° C. aqueous subphase. 170 µl of Octamer IV pjs-acrylamide (1 mg/mL CHCl$_3$ solution) is spread at the air/water interface of a Langmuir trough. After 10 min the film is compressed to 5 mN/m at a rate of 2 mm/min. Prior to film collapse, the substrates are raised out of the subphase at a rate of 2 mm/min, resulting in the deposition of one layer of Octamer IV pjs-acrylamide. Following deposition some samples are irradiated (254 nm) for 40 or 220 min to induce coupling between the surface acryl groups (MAOMTMOS) and the acrylamide group of Octamer IV pjs-acrylamide. Samples are sonicated in CHCl$_3$ following the UV cure to determine the extent of surface attachment. If the film did not react with the surface, this treatment should result in the removal of the film.

Example 12

Selective filtration and relative clearance of solutes by various nanofilms which are contemplated to be produced by compounds of the invention. In Table 10, the heading "high permeability" indicates a clearance of greater than about 70-90% of the solute. The heading "medium permeability" indicates a clearance of less than about 50-70% of the solute. The heading "low permeability" indicates a clearance of less than about 10-30% of the solute.

TABLE 10

Clearance of solutes by nanofilms

| Nanofilm | high permeability | medium permeability | low permeability |
|---|---|---|---|
| water nanofilm | $H_2O$ | Glucose, $Na^+$, $K^+$, phosphate | $Ca^{2+}$, $Mg^{2+}$, $Li^+$, urea, creatinine |
| ion nanofilm | $H_2O$, $Na^+$, $K^+$, phosphate | Glucose | $Ca^{2+}$, $Mg^{2+}$, $Li^+$, urea, creatinine |
| glucose nanofilm | $H_2O$, $Na^+$, $K^+$, Glucose | Phosphate | $Ca^{2+}$, $Mg^{2+}$, $Li^+$, urea, creatinine |
| G nanofilm | $H_2O$, $Na^+$, $K^+$, phosphate, Glucose, $Ca^{2+}$, $Mg^{2+}$, $Li^+$, urea, creatinine | Vitamin $B_{12}$, Insulin, $\beta_2$ Microglobulin | Myglobin, Ovalbumin, Albumin, |
| gas nanofilm | He, $H_2$ | — | $H_2O$ and larger, liquids in general |
| anion nanofilm | $Cl^-$ | $HCO_3^-$, Phospate | — |

Example 13

Nanofilm filtration function of various nanofilms. The approximate diameter of some various species to be considered in a filtration process are illustrated in Table 11.

TABLE 11

Size of various species of interest for filtration

| solute | molecular weight (Da) | diameter (Å) |
|---|---|---|
| virus | $10^6$ | 133 |
| immunoglobulin G (IgG) | $10^5$ | 60 |
| albumin | $50 \times 10^4$ | 50 |
| $\beta_2$-Microglobulin | $10^3$ | 13 |
| urea | 60 | — |
| $Na^+$ | 23 | — |

The filtration function of a membrane may be described in terms of its solute rejection profile. The filtration function of some nanofilm membranes which are contemplated to be produced by the compounds of the invention are exemplified in Tables 12-13.

TABLE 12

Example filtration function of a G-membrane

| SOLUTE | MOLECULAR WEIGHT | PASS/NO PASS |
|---|---|---|
| Albumin | 68 kDa | NP |
| Ovalbumin | 44 kDa | P |
| Myoglobin | 17 kDa | P |
| $\beta_2$-Microglobulin | 12 kDa | P |
| Insulin | 5.2 kDa | P |
| Vitamin $B_{12}$ | 1350 Da | P |
| Urea, $H_2O$, ions | <1000 Da | P |

TABLE 13

Example filtration function of a T-membrane

| SOLUTE | MOLECULAR WEIGHT | PASS/NO PASS |
|---|---|---|
| $\beta_2$-Microglobulin | 12 kDa | NP |
| Insulin | 5.2 kDa | NP |
| Vitamin $B_{12}$ | 1350 Da | NP |
| Glucose | 180 Da | NP |
| Creatinine | 131 Da | NP |
| $H_2PO_4^-$, $HPO_4^{2-}$ | ≈97 Da | NP |
| $HCO_3^-$ | 61 Da | NP |
| Urea | 60 Da | NP |
| K+ | 39 Da | P |
| Na+ | 23 Da | P |

The passage or exclusion of a solute is measured by its clearance, which reflects the portion of solute that actually passes through the membrane. The no pass symbol in Tables 12-13 indicates that the solute is partly excluded by the nanofilm, sometimes less than 90% rejection, often at least 90% rejection, sometimes at least 98% rejection. The pass symbol indicates that the solute is partly cleared by the nanofilm, sometimes less than 90% clearance, often at least 90% clearance, sometimes at least 98% clearance.

Synthon and Macrocyclic Module Synthesis Methods

All chemical structures illustrated and described in this specification, both in the description above and the examples below, as well as in the figures, are intended to encompass and include all variations and isomers of the structure which are foreseeable, including all stereoisomers and constitutional or configurational isomers when the illustration, description, or figure is not explicitly limited to any particular isomer.

Methods for Preparing Cyclic Synthons

To avoid the need to separate single configurational or enantiomeric isomers from complex mixtures resulting from non-specific reactions, stereospecific or at least stereoselective coupling reactions may be employed in the preparation of the synthons of this invention. The following are examples of synthetic schemes for several classes of synthons useful in the preparation of macrocyclic modules of this invention. In general, the core synthons are illustrated, and lipophilic moieties are not shown on the structures, however, it is understood that all of the following synthetic schemes might encompass additional lipophilic or hydrophilic moieties used to prepare amphiphilic and other modified macrocyclic modules. Species are numbered in relation to the scheme in which they appear; for example, "S21-1" refers to the structure 1 in Scheme 21.

An approach to preparing synthons of 1,3-Diaminocyclohex-5-ene is shown in Scheme 21. Enzymatically assisted partial hydrolysis of the

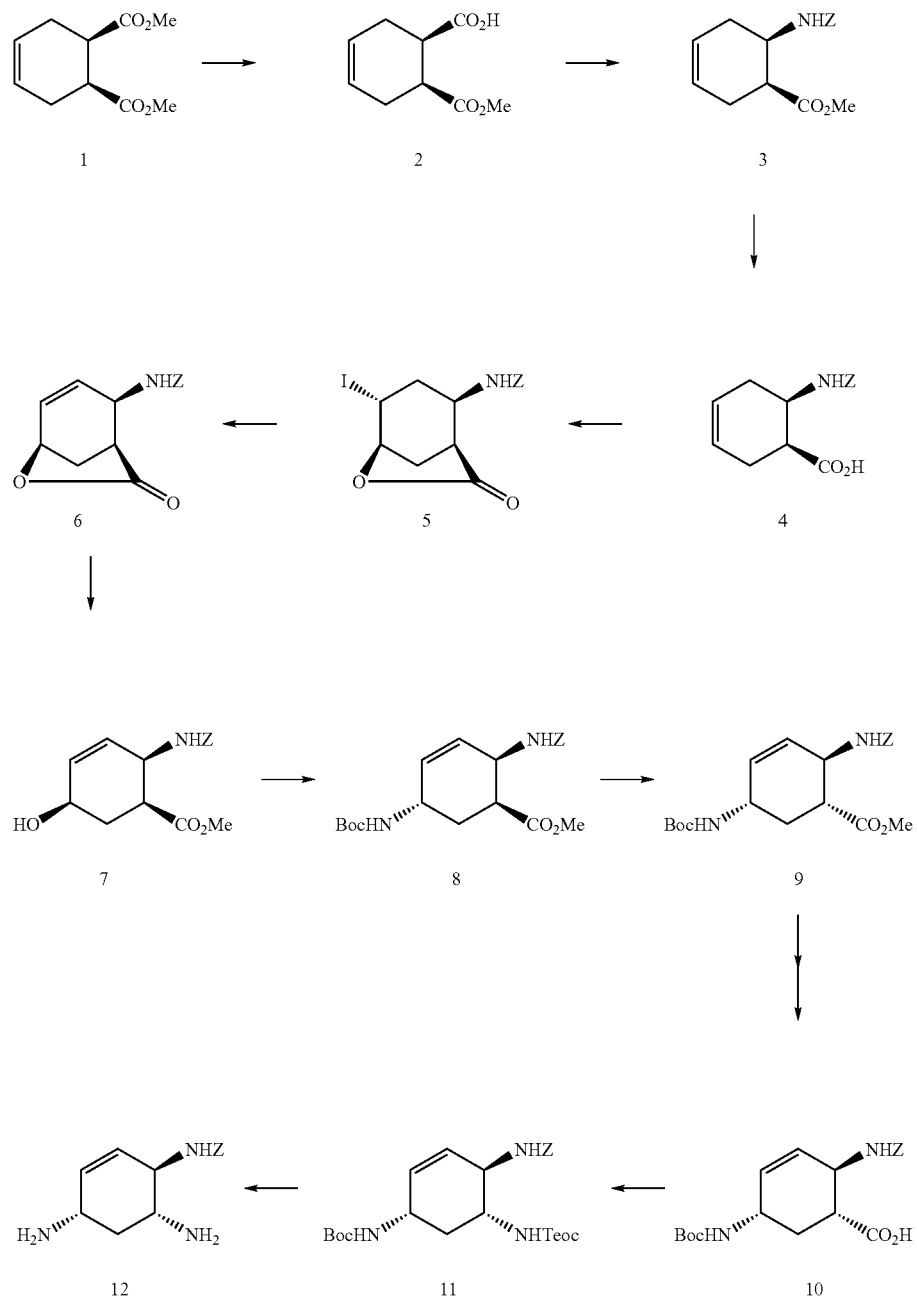

SCHEME 21 symmetrical diester S21-1 is used to give enantiomerically pure S21-2. S21-2 is subjected to the Curtius reaction and then quenched with benzyl alcohol to give protected amino acid S21-3. Iodolactonization of carboxylic acid S21-4 followed by dehydrohalogenation gives unsaturated lactone S21-6. Opening of the lactone ring with sodium methoxide gives alcohol S21-7, which is converted with inversion of configuration to S21-8 in a one-pot reaction involving mesylation, $SN_2$ displacement with azide, reduction and protection of the resulting amine with di-tert-butyl dicarbonate. Epimerization of S21-8 to the more stable diequatorial configuration followed by saponification gives carboxylic acid S21-10. S21-10 is subjected to the Curtius reaction. A mixed anhydride is prepared using ethyl chloroformate followed by reaction with aqueous $NaN_3$ to give the acyl azide, which is thermally rearranged to the isocyanate in refluxing benzene. The isocyanate is quenched with 2-trimethylsilylethanol to give differentially protected tricarbamate S21-11. Reaction with trifluoroacetic acid (TFA) selectively deprotects the 1,3-diamino groups to provide the desired synthon S21-12.

In another variation, an approach to preparing synthons of 1,3-Diaminocyclohexane is shown in Scheme 21a.

SCHEME 21a

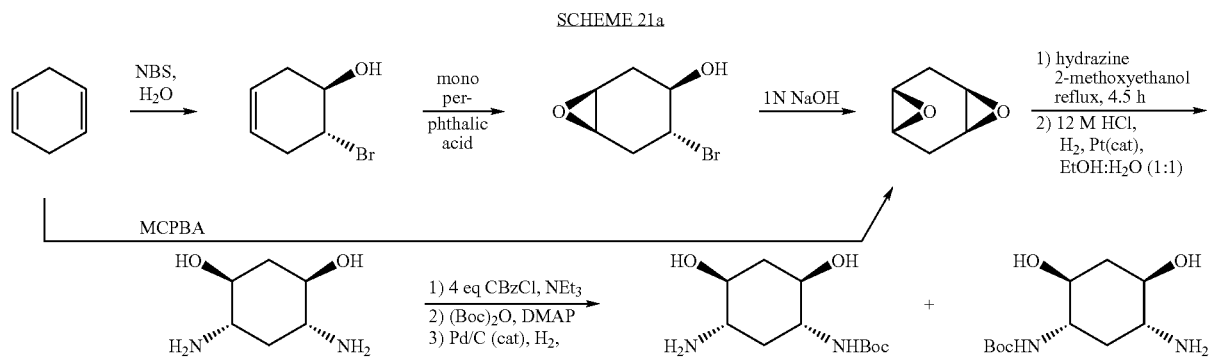

Some aspects of these preparations are given in Suami et al., *J. Org. Chem.* 1975, 40, 456 and Kavadias et al. *Can. J. Chem.* 1978, 56, 404.

In another variation, an approach to preparing synthons of 1,3-substituted cyclohexane is shown in Scheme 21b.

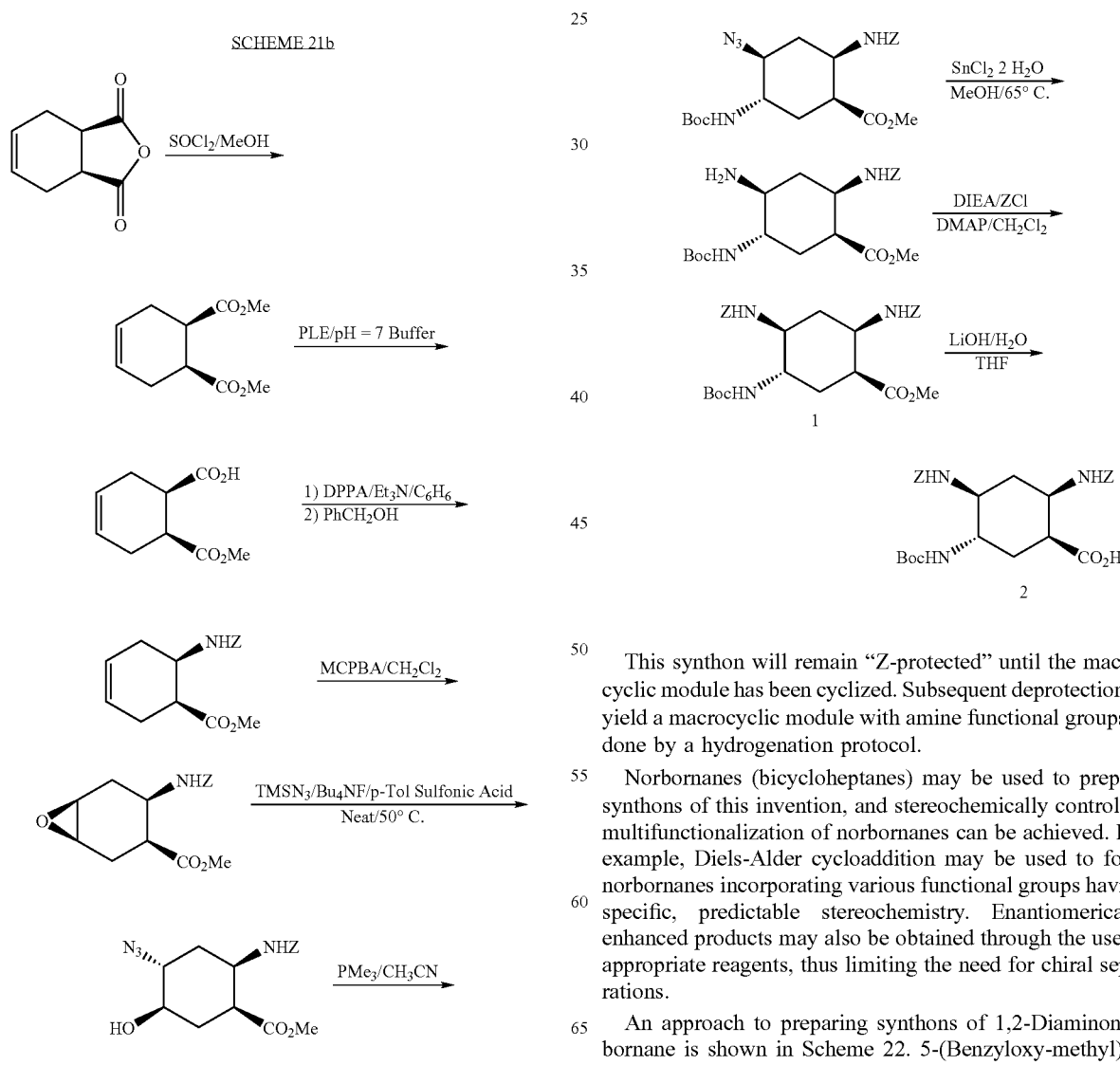

This synthon will remain "Z-protected" until the macrocyclic module has been cyclized. Subsequent deprotection to yield a macrocyclic module with amine functional groups is done by a hydrogenation protocol.

Norbornanes (bicycloheptanes) may be used to prepare synthons of this invention, and stereochemically controlled multifunctionalization of norbornanes can be achieved. For example, Diels-Alder cycloaddition may be used to form norbornanes incorporating various functional groups having specific, predictable stereochemistry. Enantiomerically enhanced products may also be obtained through the use of appropriate reagents, thus limiting the need for chiral separations.

An approach to preparing synthons of 1,2-Diaminonorbornane is shown in Scheme 22. 5-(Benzyloxy-methyl)-1,3-cyclopentadiene (S22-13) is reacted with

SCHEME 22

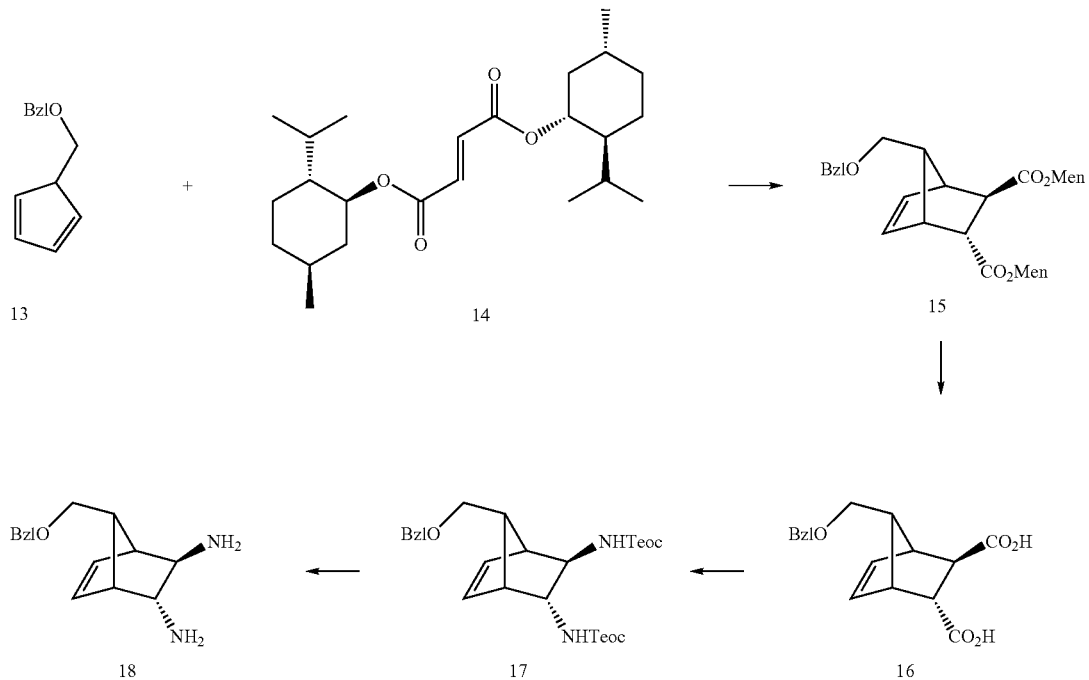

diethylaluminum chloride Lewis acid complex of di-(l)-menthyl fumarate (S22-14) at low temperature to give the diastereomerically pure norbornene S22-15. Saponification with potassium hydroxide in aqueous ethanol gives the diacid S22-16, which is subjected to a tandem Curtius reaction with diphenylphosphoryl azide (DPPA), the reaction product is quenched with 2-trimethylsilylethanol to give the biscarbamate S22-17. Deprotection with TFA gives diamine S22-18.

Another approach to this synthon class is outlined in Scheme 23. Opening of anhydride S23-19 with methanol in the presence of quinidine gives the enantiomerically pure ester acid S23-20. Epimerization of the ester group with sodium methoxide (NaOMe) gives S23-21. A Curtius reaction with DPPA followed by quenching with trimethylsilylethanol gives carbamate S23-22. Saponification with NaOH gives the acid S23-23, which undergoes a Curtius reaction,

SCHEME 23

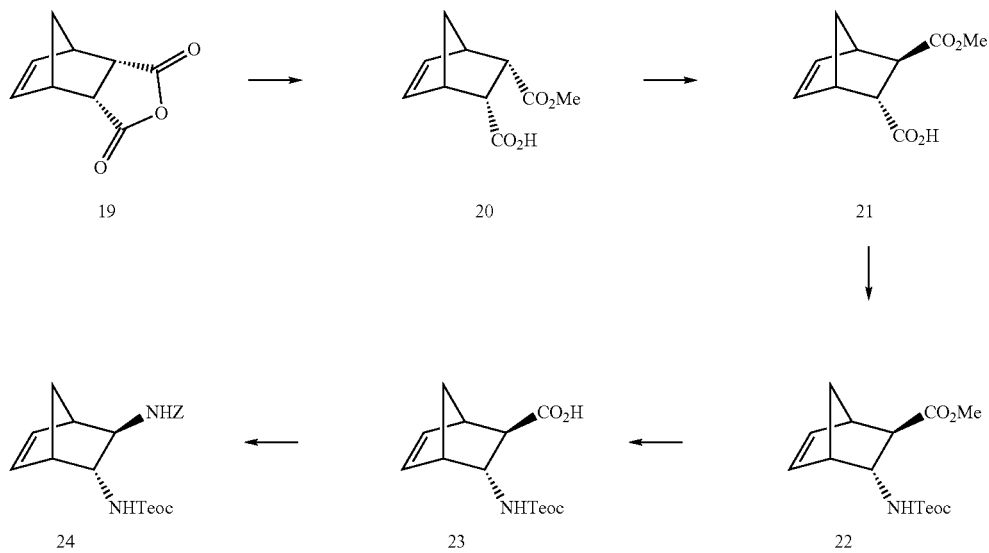

then quenched with benzyl alcohol to give differentially protected biscarbamate S23-24. Compound S23-24 can be fully deprotected to provide the diamine or either of the carbamates can be selectively deprotected.

An approach to preparing synthons of endo,endo-1,3-Diaminonorbornane is shown in Scheme 24. 5-Trimethylsilyl-1,3-cyclopentadiene (S24-25) is reacted with the diethylaluminum chloride Lewis acid complex of di-(1)-menthyl fumarate at low temperature to give nearly diastereomerically pure norbornene S24-26. Crystallization of S24-26 from alcohol results in recovery of greater than 99% of the single diastereomer. Bromolactonization followed by silver mediated rearrangement gives mixed diester S24-28 with an alcohol moiety at the 7-position. Protection of the alcohol with benzyl bromide and selective deprotection of the methyl ester gives the free carboxylic acid S24-30. A Curtius reaction results in trimethylsilylethyl carbamate norbornene S24-31. Biscarbonylation of the olefin in methanol, followed by a single-step deprotection and dehydration gives the mono-anhydride S24-33. Quinidine mediated opening of the anhydride with methanol gives S24-34. Curtius transformation of S24-34 gives the biscarbamate S24-35, which is deprotected with TFA or tetrabutylammonium fluoride (TBAF) to give diamine S24-36.

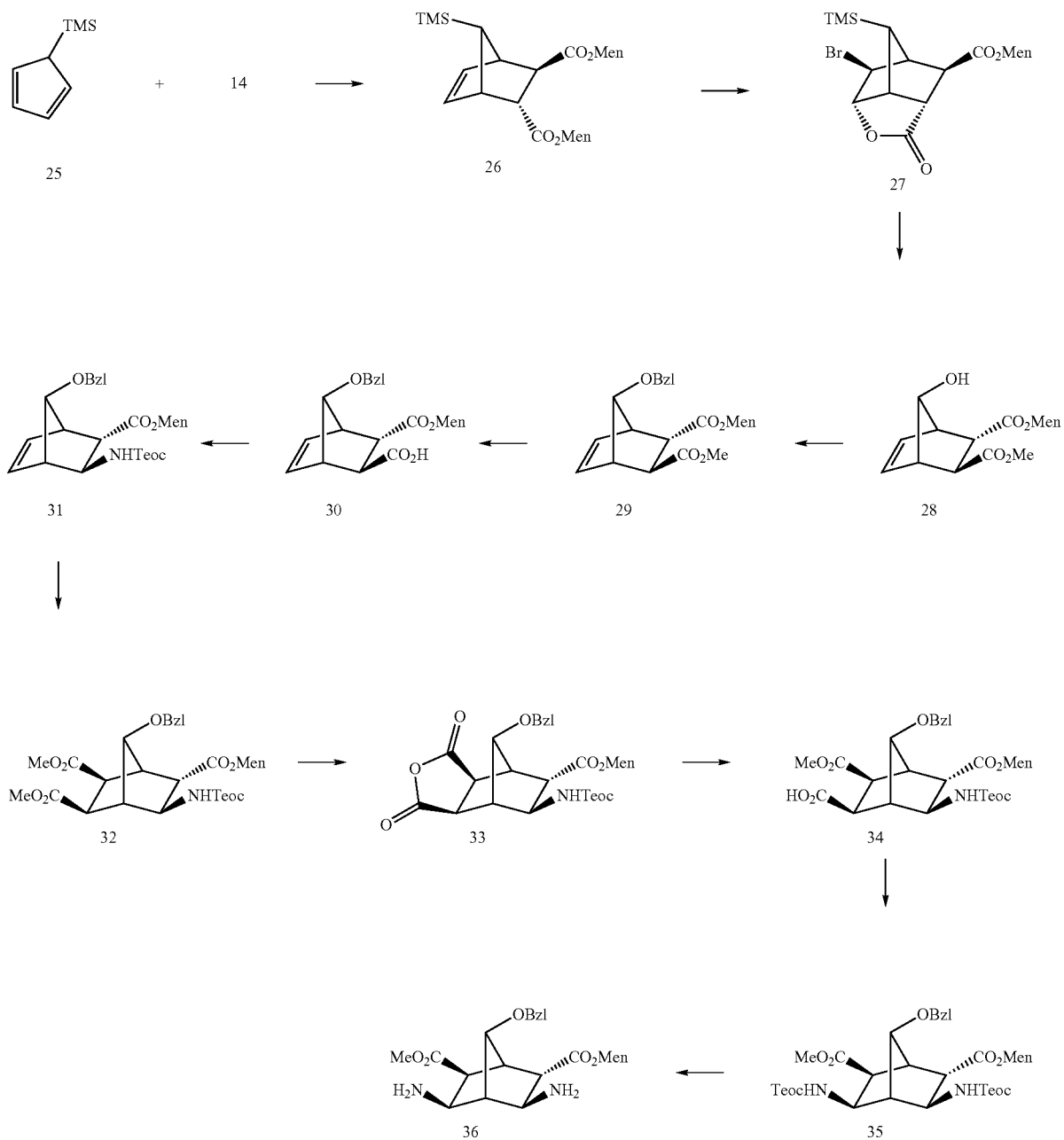

Another approach to this class of synthons is outlined in Scheme 25. Benzyl alcohol opening of S23-19 in the presence of quinidine gives S25-37 in high enantiomeric excess. Iodolactonization followed by NaBH$_4$ reduction gives lactone S25-39. Treatment with NaOMe liberates the methyl ester and the free alcohol to generate S25-40. Transformation of the alcohol S25-40 to the inverted t-butyl carbamate protected amine S25-41 is accomplished in a one-pot reaction by azide deplacement of the mesylate S25-40 followed by reduction to the amine, which is protected with di-tert-butyl dicarbonate. Hydrogenolytic cleavage of the benzyl ester and epimerization of the methyl ester to the exo configuration is followed by protection of the free acid with benzyl bromide to give S25-44. Saponification of the methyl ester followed by a trimethylsilylethanol quenched Curtius reaction

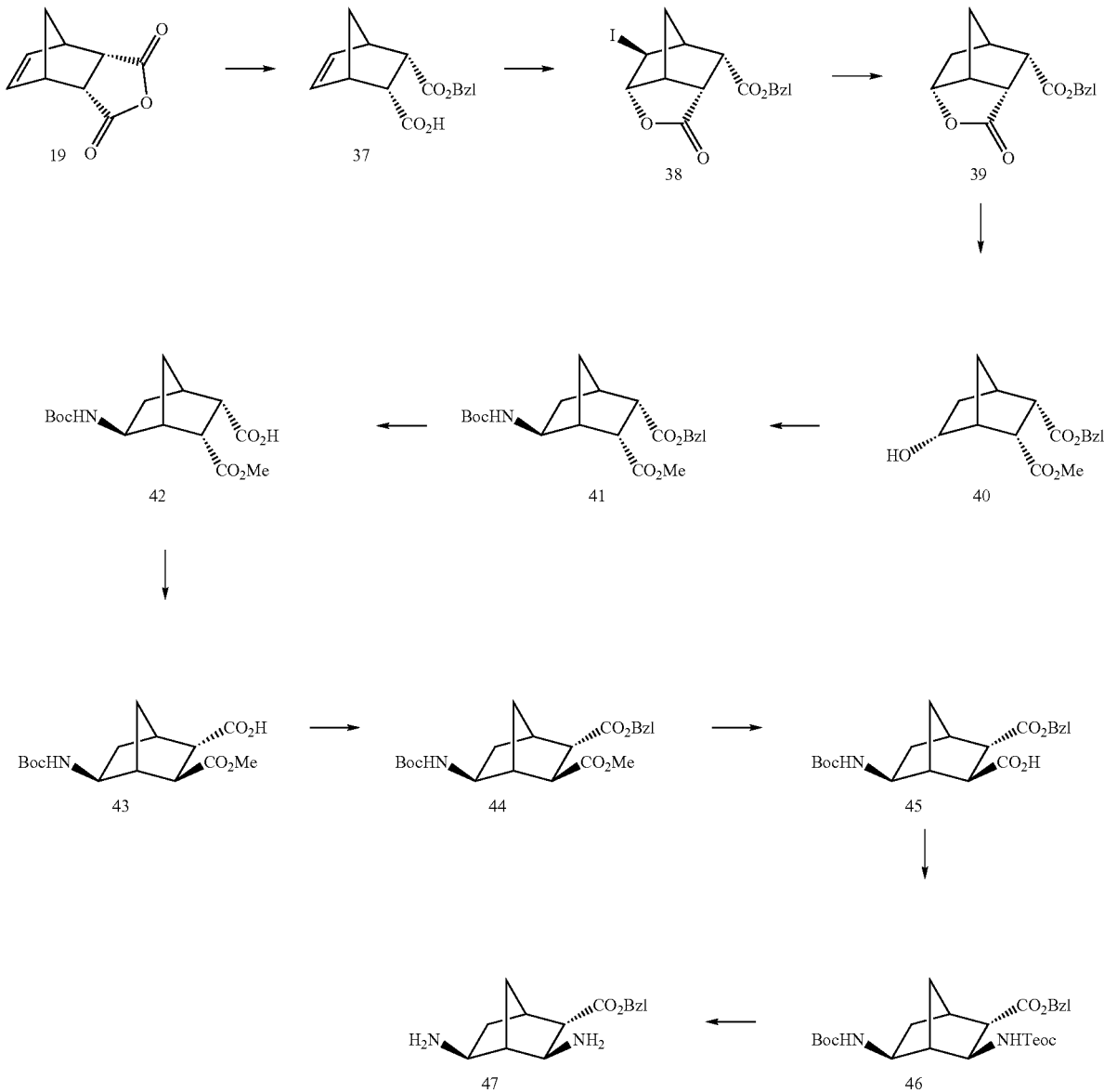

gives the biscarbamate S25-46, which is cleaved with TFA to give the desired diamine S25-47.

An approach to preparing synthons of exo, endo-1,3-Diaminonorbornane is shown in Scheme 26. p-Methoxybenzyl alcohol opening of norbornene anhydride S23-19 in the presence of quinidine gives monoester S26-48 in high enantiomeric excess. Curtius reaction of the free acid gives protected all endo monoacid-monoamine S26-49. Biscarbonylation and anhydride formation gives exo-monoanhydride S26-51. Selective methanolysis in the presence of quinine gives S26-52. A trimethylsilylethanol quenched Curtius reaction gives biscarbamate S26-53. Epimerization of the two esters results in the more sterically stable S26-54. Cleavage of the carbamate groups provides synthon S26-55.

When two types of synthons are used, a macrocyclic module may be formed having alternating synthons of different types. Scheme 27 illustrates a concerted module synthesis.

Referring to Scheme 27, 1,2-Diaminocyclohexane, S27-1, is a synthon having two amino functional groups for coupling to other synthons, and 2,6-diformyl-4-dodec-1-ynylphenyl, S27-2, is a synthon having two formyl groups

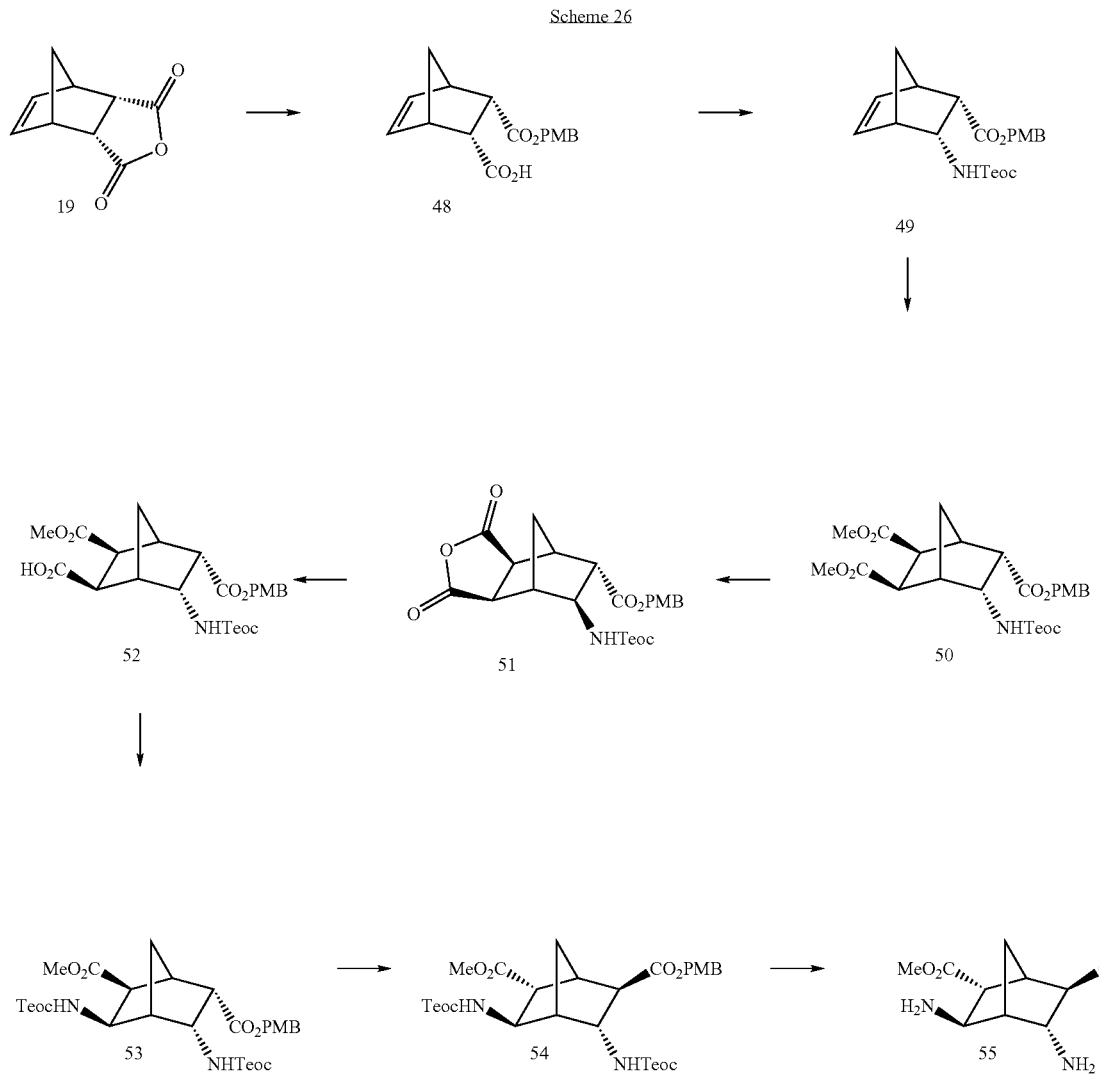

Methods for Preparing Macrocyclic Modules

Synthons may be coupled to one another to form macrocyclic modules. In one variation, the coupling of synthons may be accomplished in a concerted scheme. Preparation of a macrocyclic module by the concerted route may be performed using, for example, at least two types of synthons, each type having at least two functional groups for coupling to other synthons. The functional groups may be selected so that a functional group of one type of synthon can couple only to a functional group of the other type of synthon.

for coupling to other synthons. An amino group may couple with a formyl group to form an imine linkage. In Scheme 27, a concerted product hexamer macrocyclic module is shown.

In one variation, a mixture of tetramer, hexamer, and octamer macrocyclic modules may be formed in the concerted scheme. The yields of these macrocyclic modules can be varied by changing the concentration of various synthons in the reagent mixture, and among other factors, by changing the solvent, temperature, and reaction time.

SCHEME 27

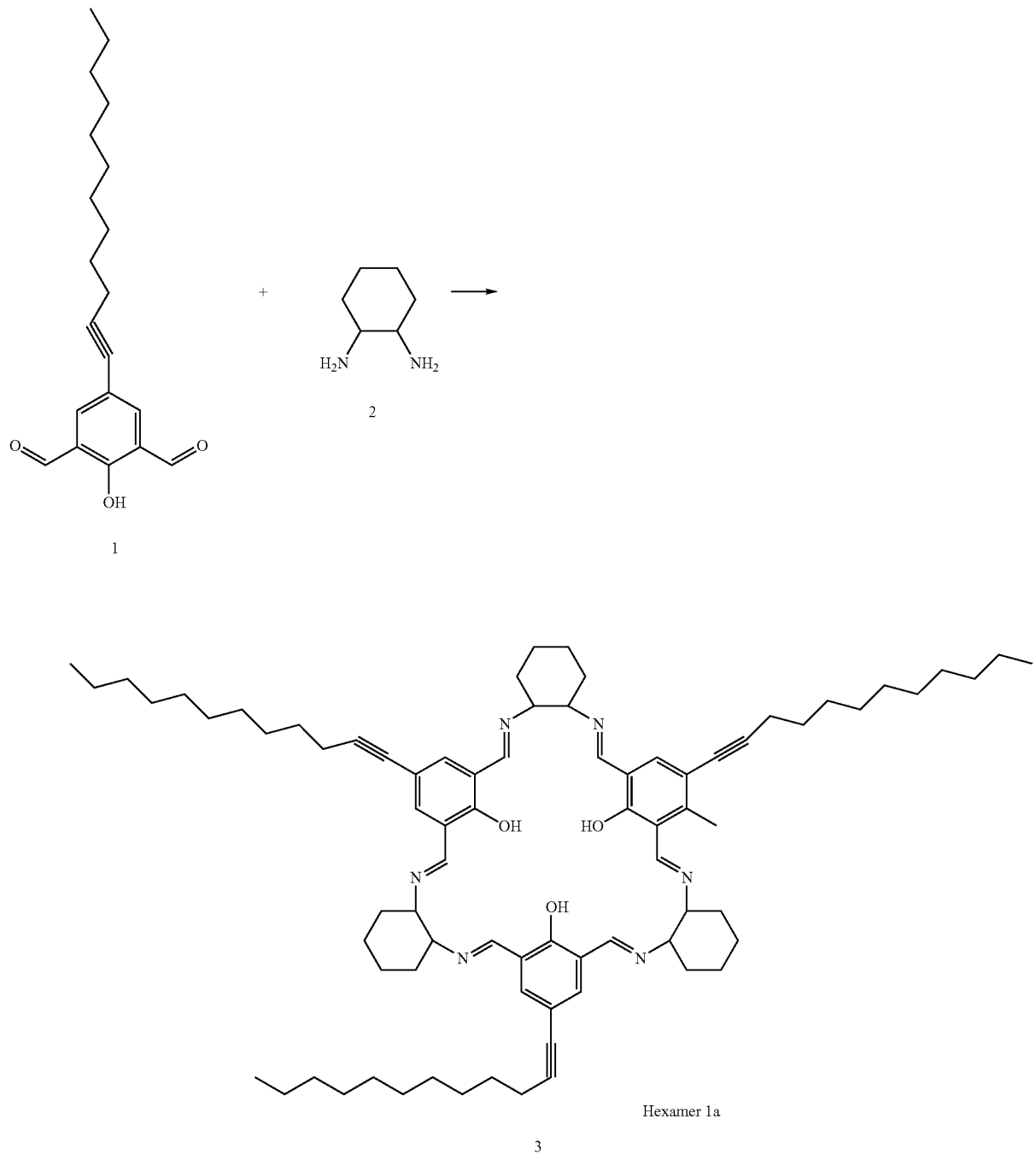

Hexamer 1a

The imine groups of S27-3 can be reduced, e.g. with sodium borohydride, to give amine linkages. If the reaction is carried out using 2,6-di(chlorocarbonyl)-4-dodec-1-ynylphenyl instead of 2,6-diformyl-4-dodec-1-ynylphenyl, the resulting module will contain amide linkages. Similarly, if 1,2-dihydroxycyclohexane is reacted with 2,6-di(chlorocarbonyl)4-dodec-1-ynylphenyl, the resulting module will contain ester linkages.

In some variations, the coupling of synthons may be accomplished in a stepwise scheme. In an example of the stepwise preparation of macrocyclic modules, a first type of synthon is substituted with one protected functional group and one unprotected functional group. A second type of synthon is substituted with an unprotected functional group that will couple with the unprotected functional group on the first synthon. The product of contacting the first type of synthon with the second type of synthon may be a dimer, which is made of two coupled synthons. The second synthon may also be substituted with another functional group which is either protected, or which does not couple with the first synthon when the dimer is formed. The dimer may be isolated and purified, or the preparation may proceed as a one-pot method. The dimer may be contacted with a third synthon having two functional groups, only one of which may couple with the remaining functional group of either the first or second synthons to form a trimer, which is made of three coupled synthons. Such stepwise coupling of synthons may be repeated to form macrocyclic modules of various ring sizes. To cyclize or close the ring of the macrocyclic module, the n$^{th}$ synthon which was coupled to the product may be substituted with a second functional group which may couple with the second functional group of a previously coupled synthon that has not been coupled, which may be deprotected for that step. The stepwise method may be carried out with synthons on solid phase support. Scheme 28 illustrates a stepwise preparation of module S28-1.

Compound S28-2 is reacted with S28-3, in which the phenyl is protected as the benzyl ether and the nitrogen is shown as protected with a group "P," which can be any of a large number of protecting groups well-known in the art, in the presence of methanesulfonyl chloride (Endo, K.; Takahashi, H. *Heterocycles,* 1999, 51, 337), to give S28-4. Removal of the N-protecting group give the free amine S28-5, which can be coupled with synthon S28-6 using any standard peptide coupling reaction such as BOP/HOBt to give S28-7. Deprotection/coupling is repeated, alternating synthons S28-3 and S28-6 until a linear construct with eight residues is obtained. The remaining acid and amine protecting groups on the 8-mer are removed and the oligomer is cyclized, see e.g., Caba, J. M., et al., *J. Org. Chem.,* 2001, 66:7568 (PyAOP cyclization) and Tarver, J. E. et al., *J. Org. Chem.,* 2001, 66:7575 (active ester cyclization). The R group is H or an alkyl group coupled via a functional group to the benzene ring, and X is N, O, or S. Examples of solid supports include Wang resin, hydrogels, silica gels, sepharose, sephadex, agarose, and inorganic solids. Using a solid support might simplify the procedure by obviating purification of intermediates along the way. The final cyclization may be done in a solid phase mode. A "safety-catch linker" approach (Bourne, G. T., et al., *J. Org. Chem.,* 2001, 66:7706) may be used to obtain cyclization and resin cleavage in a single operation.

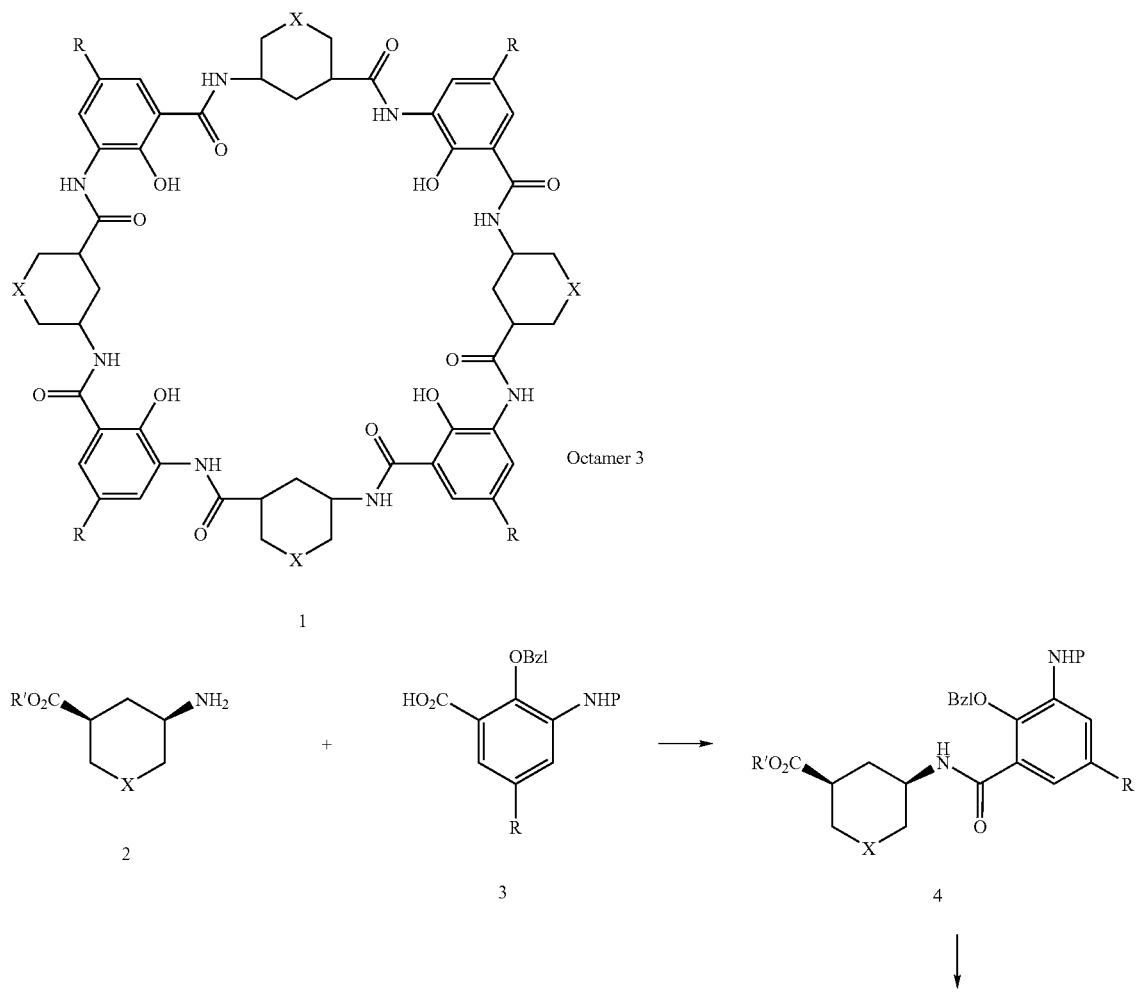

Scheme 28

-continued

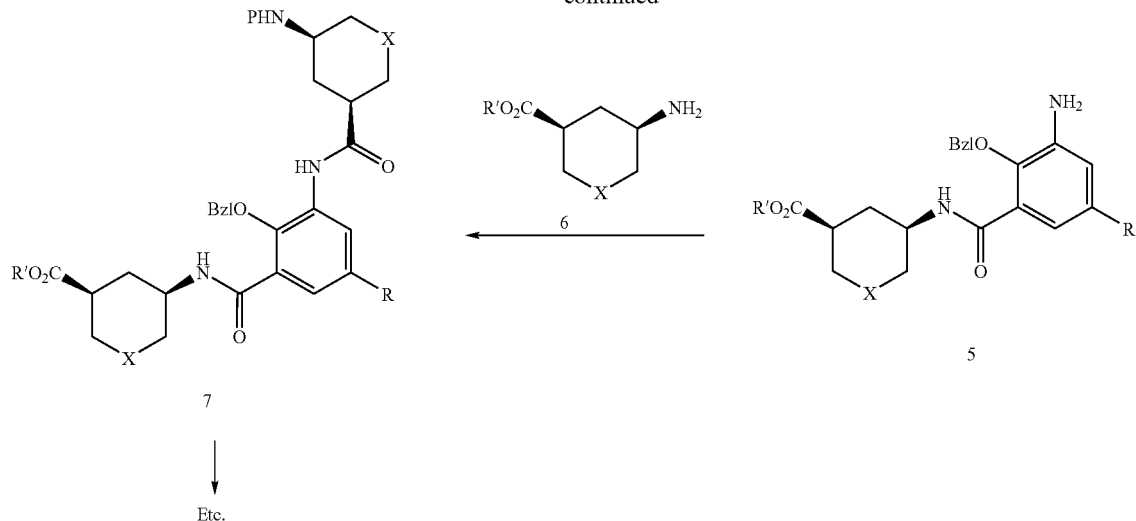

In another variation, a concerted method involves contacting two or more different synthons and a linker molecule as shown in Scheme 29, where R may be an alkyl group or other lipophilic group.

SCHEME 29

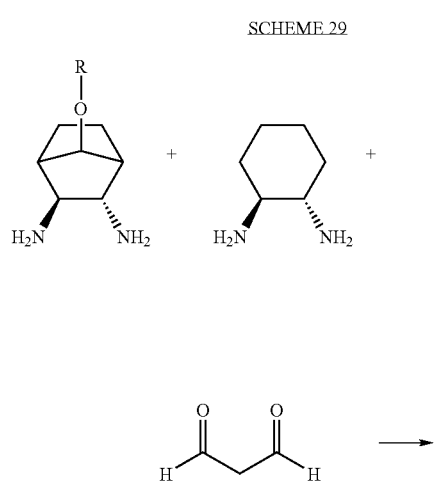

-continued

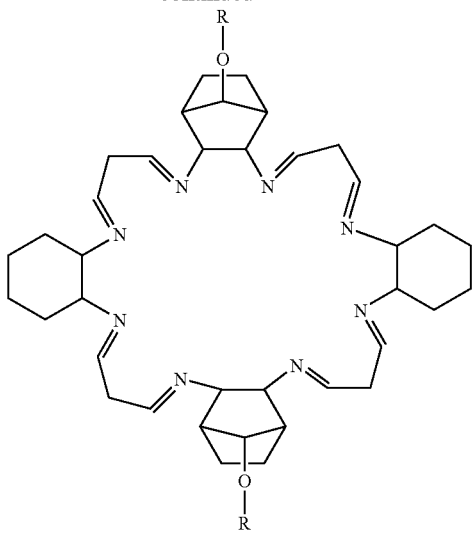

Tetramer-monobicycloheptane

In another variation, a stepwise linear method involves various synthons and a solid phase support as shown in Scheme 30.

SCHEME 30

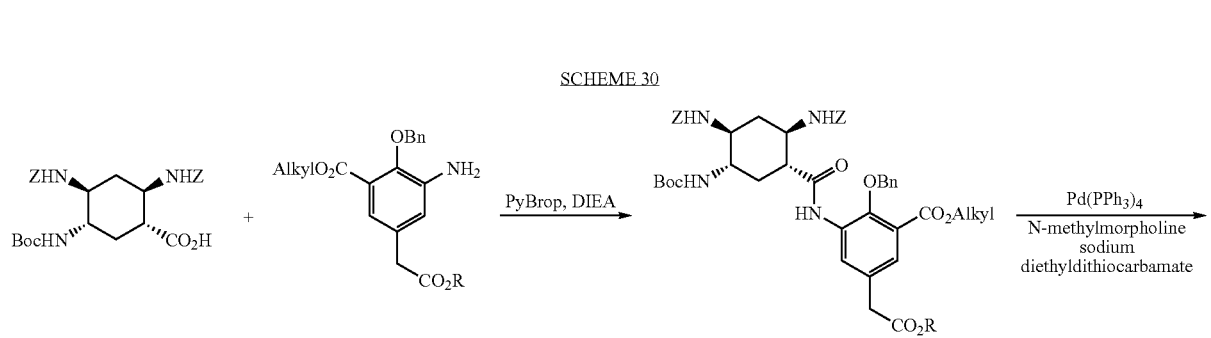

-continued
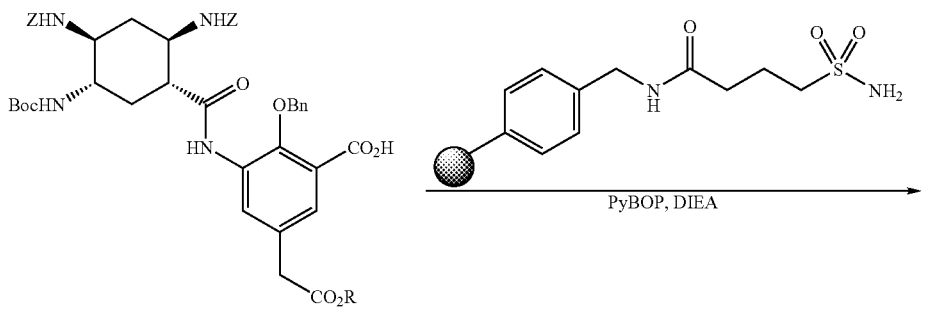
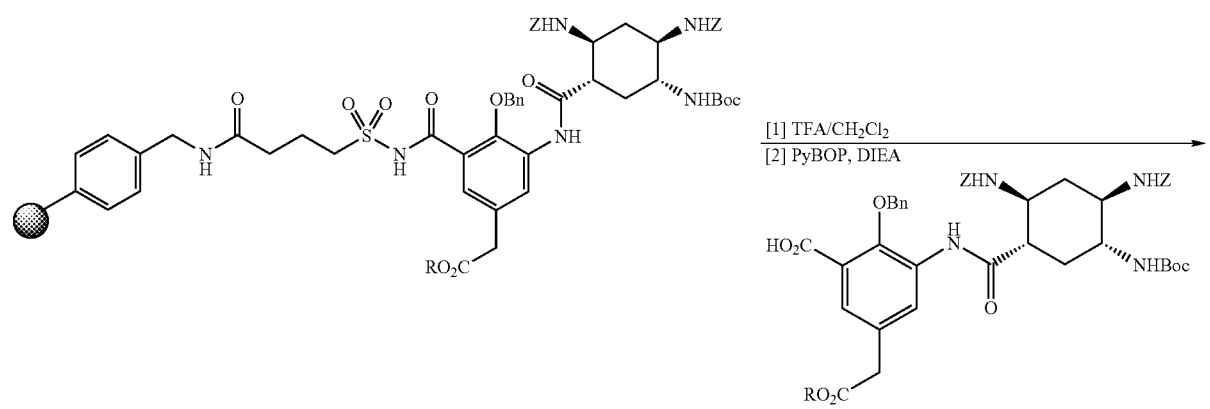
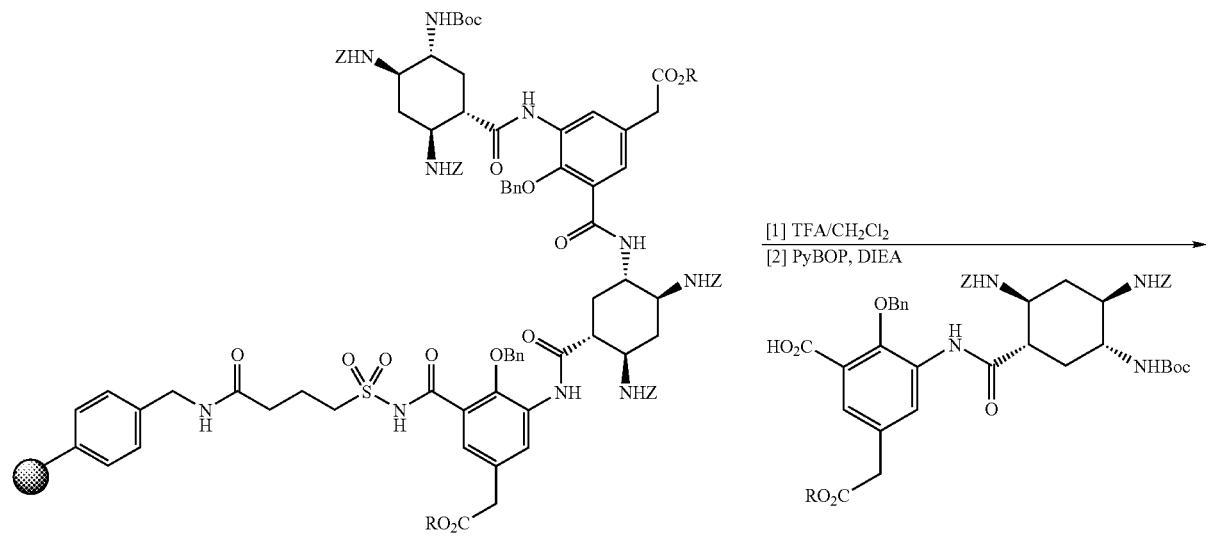

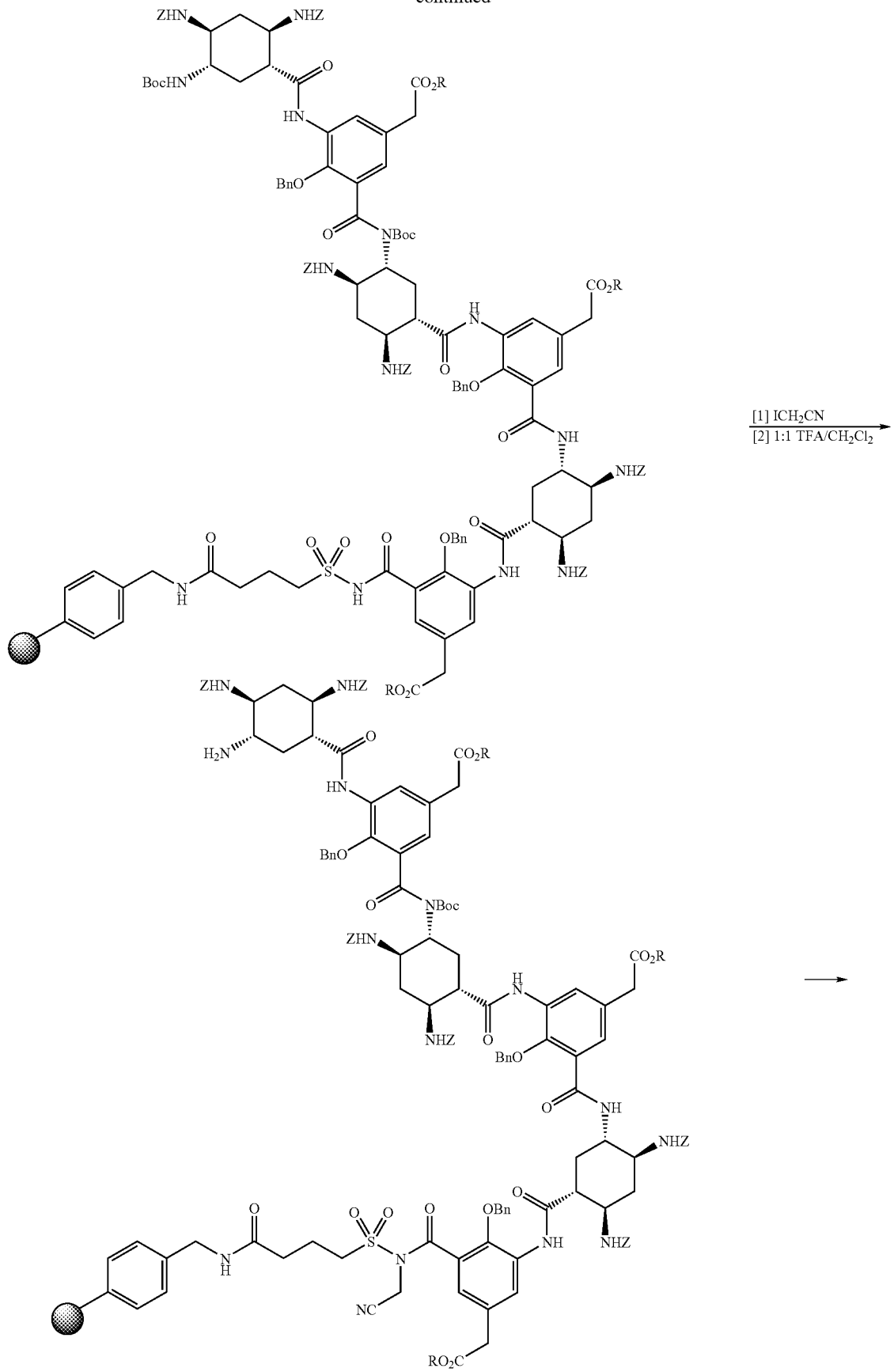

-continued
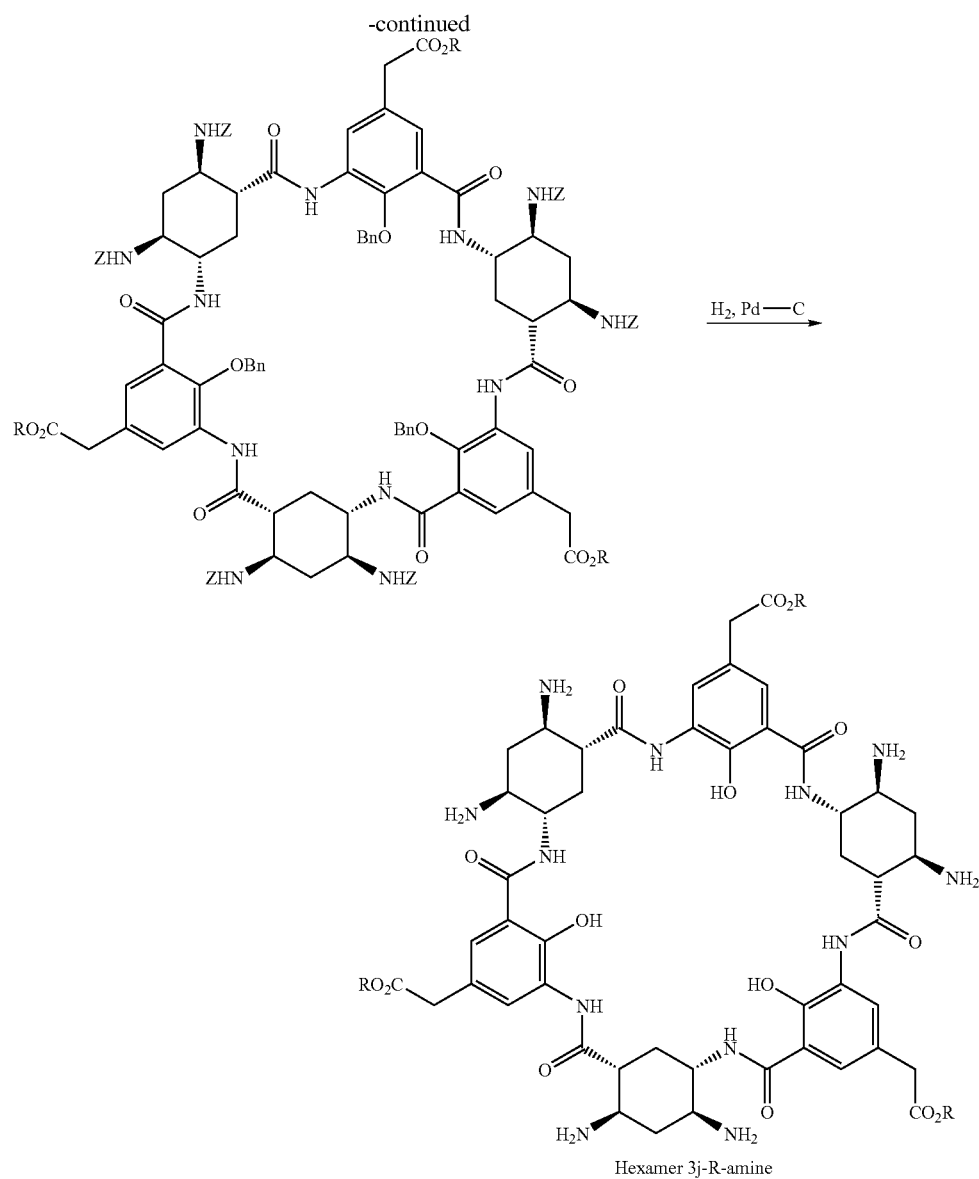
Hexamer 3j-R-amine
In another variation, a stepwise convergent method involves synthon trimers and a solid phase support as shown in Scheme 31. This method can also be done without the solid phase support using trimers in solution.
SCHEME 31
-continued
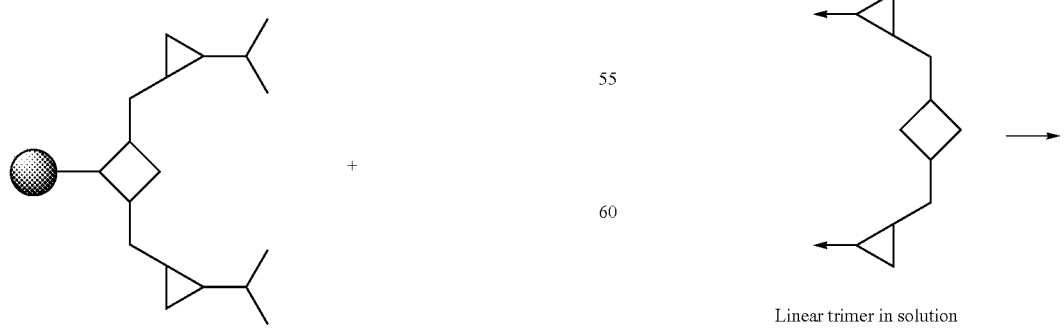
Linear trimer on resin
Linear trimer in solution

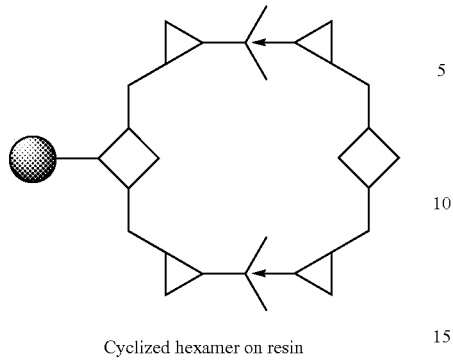
Cyclized hexamer on resin
In another variation, a template method involves synthons brought together by a template as shown in Scheme 32. Some aspects of this approach (and an $Mg^{2+}$ template) are given in Dutta et al. *Inorg. Chem.* 1998, 37, 5029.
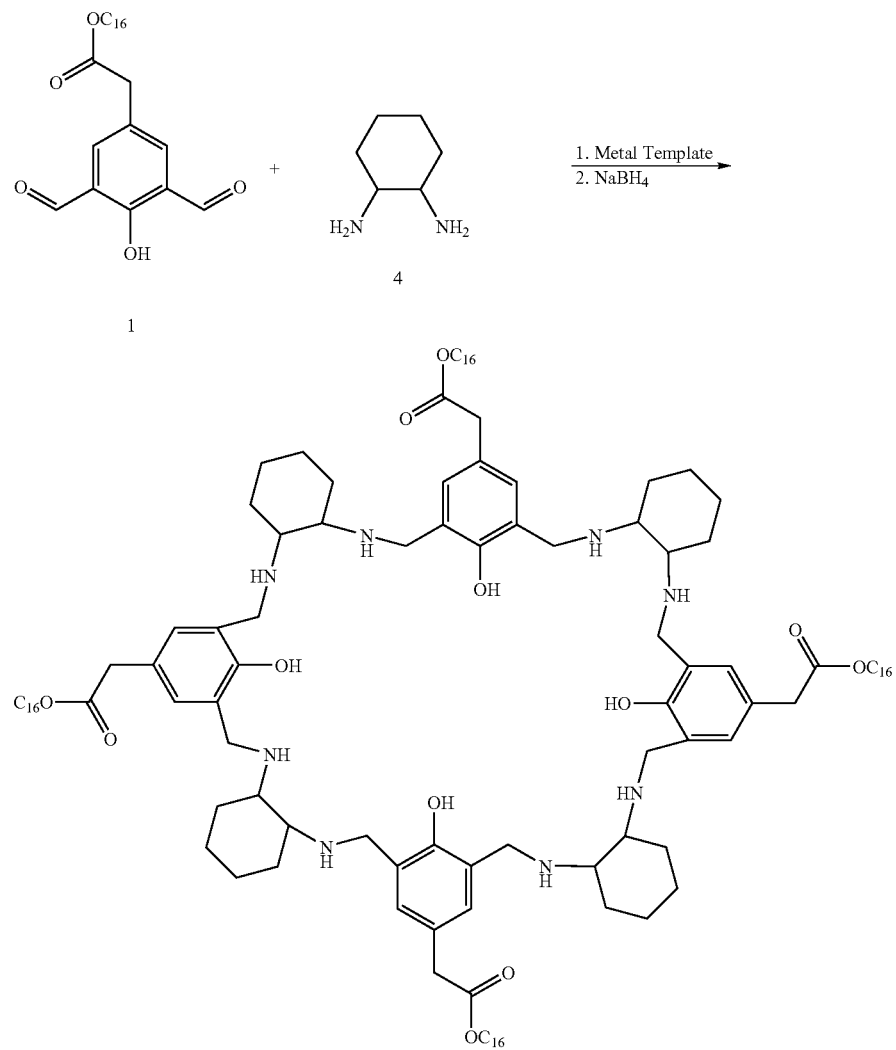
Octmaer 4jh In another variation, a linker molecule method involves cyclizing synthons in solution as shown in Scheme 33.

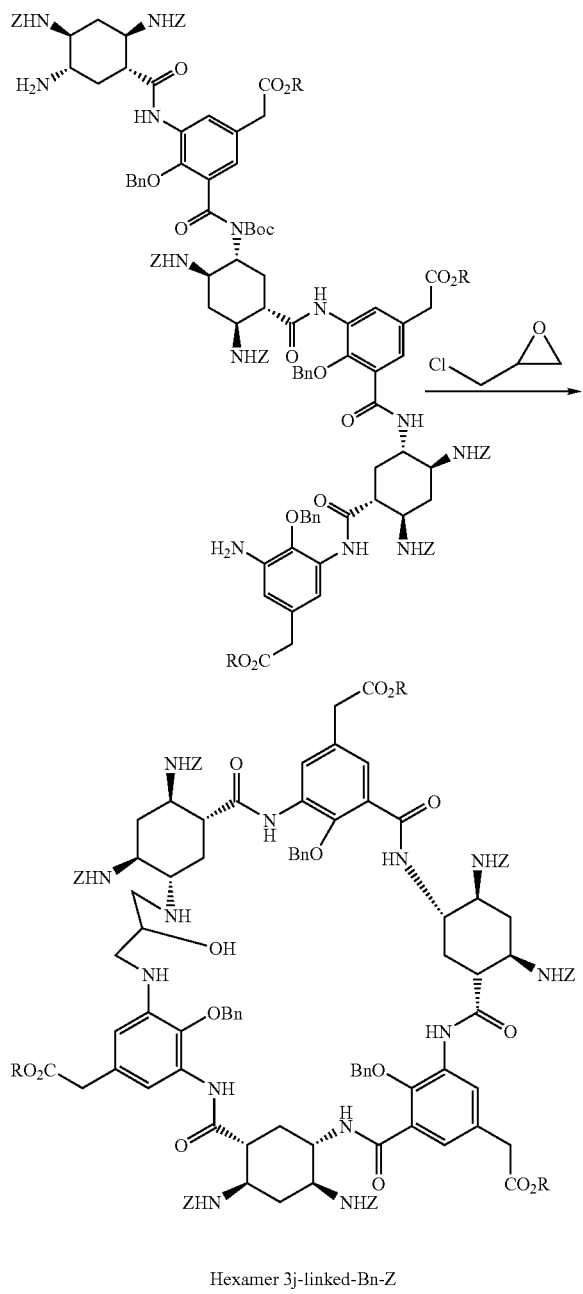

Hexamer 3j-linked-Bn-Z

Reagents for the following examples were obtained from Aldrich Chemical Company and VWR Scientific Products. All reactions were carried out under nitrogen or argon atmosphere unless otherwise noted. Solvent extracts of aqueous solutions were dried over anhydrous $Na_2SO_4$. Solutions were concentrated under reduced pressure using a rotary evaporator. Thin layer chromatography (TLC) was done on Analtech Silica gel GF (0.25 mm) plates or on Machery-Nagel Alugram Sil G/UV (0.20 mm) plates. Chromatograms were visualized with either UV light, phosphomolybdic acid, or $KMnO_4$. All compounds reported were homogenous by TLC unless otherwise noted. HPLC analyses were performed on a Hewlett Packard 1100 system using a reverse phase C-18 silica column. Enantiomeric excess was determined by HPLC using a reverse phase (l)-leucine silica column from Regis Technologies. All $^1[H]$ and $^{13}[C]$ NMR spectra were collected at 400 MHz on a Varian Mercury system. Electrospray mass spectra were obtained by Synpep Corp., or on a Thermo Finnigan LC-MS system.

Example 14

2,6-Diformyl-4-bromophenyl

Hexamethylenetetramine (73.84 g, 526 mmol) was added to TFA (240 mL) with stirring. 4-Bromophenyl (22.74 g, 131 mmol) was added in one portion and the solution heated in an oil bath to 120° C. and stirred under argon for 48 h. The reaction mixture was then cooled to ambient temperature. Water (160 mL) and 50% aqueous $H_2SO_4$ (80 mL) were added and the solution stirred for an additional 2 h. The reaction mixture was poured into water (1600 mL) and the resulting precipitate collected on a Büchner funnel. The precipitate was dissolved in ethyl acetate (EtOAc) and the solution was dried over $MgSO_4$. The solution was filtered and the solvent removed on a rotary evaporator. Purification by column chromatography on silica gel (400 g) using a gradient of 15-40% ethyl acetate in hexanes resulted in a isolation of the product as a yellow solid (18.0 g, 60%).

$^1$HNMR (400 MHz, $CDCl_3$) δ 11.54 (s, 1H, OH), 10.19 (s, 2H, CHO), 8.08 (s, 2H, ArH).

Example 15

2,6-Diformyl-4-(dodecyn-1-yl)phenyl 2,6-Diformyl-4-bromophenyl (2.50 g, 10.9 mmol), 1-dodecyne (2.00 g, 12.0 mmol), CuI (65 mg, 0.33 mmol), and bis(triphenylphosphine)palladium)II)dichloride were suspended in degassed acetonitrile (MeCN) (5 mL) and degassed benzene (1 mL). The yellow suspension was sparged with argon for 30 min and degassed $Et_3N$ (1 mL) was added. The resulting brown suspension was sealed in a pressure vial, warmed to 80° C. and held there for 12 h. The mixture was then partitioned between EtOAc and $KHSO_4$ solution. The organic layer was separated, washed with brine, dried ($MgSO_4$) and concentrated under reduced pressure. The dark yellow oil was purified by column chromatography on silica gel (25% $Et_2O$ in hexanes) to give 1.56 g (46%) of the title compound.

$^1$H NMR (400 MHz, $CDCl_3$) δ11.64 (s, 1H, OH), 10.19 (s, 2H, CHO), 7.97 (s, 2H, ArH), 2.39 (t, 2H, J=7.2 Hz, propargylic), 1.59 (m, 3H, aliphatic), 1.43, (m, 2H, aliphatic), 1.28 (m, 11H, aliphatic), 0.88 (t, 3H, J=7.0 Hz, $CH_3$). $^{13}$C NMR (400 MHz, $CDCl_3$) δ 192.5, 162.4, 140.3, 122.8, 116.7, 91.4, 77.5, 31.9, 29.6, 29.5, 29.3, 29.1, 28.9, 28.5, 22.7, 19.2, 14.1. MS (FAB): Calcd. for $C_{20}H_{27}O_3$ 315.1960; found 315.1958 $[M+H]^+$.

Example 16

2,6-Diformyl-4-(dodecen-1-yl)phenyl 2,6-Diformyl-4-bromophenyl (1.00 g, 4.37 mmol), 1-dodecene (4.8 mL, 21.7 mmol), 1.40 g tetrabutylammonium bromide (4.34 mmol), 0.50 g $NaHCO_3$ (5.95 mmol), 1.00 g LiCl (23.6 mmol) and 0.100 g palladium diacetate ($Pd(OAc)_2$) (0.45 mmol) were combined in 30 mL degassed anhydrous dimethylformamide (DMF). The mixture was sparged with argon for 10 min and then sealed in a pressure vial which was warmed to 82° C. and held for 40 h. The crude reaction mixture was partitioned between $CH_2Cl_2$ and 0.1 M HCl solution. The organic layer was washed with 0.1 M HCl (2×), brine (2×), and saturated aqueous $NaHCO_3$ (2×), dried over $MgSO_4$ and concentrated under reduced pressure. The dark yellow oil was purified by column chromatography on silica gel (25% hexanes in $Et_2O$) to give 0.700 g (51%) of the title compound as primarily the Z isomer.

$^1$H NMR (400 MHz, $CDCl_3$) δ 11.50 (s, 1H, OH), 10.21 (s, 2H, CHO), 7.95 (s, 2H, ArH), 6.38 (d, 1H, vinyl), 6.25 (m, 1H, vinyl), 2.21 (m, 2H, allylic), 1.30-1.61 (m, 16H, aliphatic), 0.95 (t, 3H, J=7.0 Hz, $CH_3$). MS (FAB): Calcd. for $C_{20}H_{27}O_3$ 315.20; found 315.35 $[M-H]^-$.

Example 17

(1R,6S)-6-Methoxycarbonyl-3-cyclohexene-1-carboxylic Acid (S21-2)

S21-1 (15.0 g, 75.7 mmol) was suspended in pH 7 phosphate buffer (950 mL). Pig liver esterase (2909 units) was added, and the mixture stirred at ambient temperature for 72 h with the pH maintained at 7 by addition of 2M NaOH. The reaction mixture was washed with ethyl acetate (200 mL), acidified to pH 2 with 2M HCl, and extracted with ethyl acetate (3×200 mL). The extracts were combined, dried, and evaporated to afford 13.8 g (99%) of S21-2.

$^1$H NMR: ($CDCl_3$) δ 2.32 (dt, 2H, $2_{ax}$- and $5_{ax}$-H's), 2.55 (dt, 2H, $2_{eq}$ and $5_{eq}$-H's), 3.00 (m, 2H, 1- and 6-H's), 3.62 (s, 3H, $CO_2Me$), 5.61 (m, 2H, 3- and 4-H's).

Example 18

Methyl (1S,6R)-6-Benzyloxycarbonylaminocyclohex-3-enecarboxylate (S21-3)

S21-2 (10.0 g, 54.3 mmol) was dissolved in benzene (100 mL) under $N_2$. Triethylamine (13.2 g, 18.2 mL, 130.3 mmol) was added followed by DPPA (14.9 g, 11.7 mL, 54.3 mmol). The solution was refluxed for 20 h. Benzyl alcohol (5.9 g, 5.6 mL, 54.3 mmol) was added and reflux continued for 20 h. The solution was diluted with EtOAc (200 mL), washed with saturated aqueous $NaHCO_3$ (2×50 mL), water (20 mL), and saturated aqueous NaCl (20 mL), dried and evaporated to give 13.7 g (87%) of S21-3.

$^1$H NMR: ($CDCl_3$) δ 2.19 (dt, 1H, $5_{ax}$-H), 2.37 (tt, 2H, $2_{ax}$- and $5_{eq}$-H's), 2.54 (dt, 1H, $2_{eq}$-H), 2.82 (m, 1H, 1-H), 3.65 (s, 3H, $CO_2Me$), 4.28 (m, 1H, 6-H), 5.08 (dd, 2H, $CH_2Ar$), 5.42 (d, 1H, NH), 5.62 (ddt, 2H, 3- and 4-H's), 7.35 (m, 5H, Ar H's).

Example 19

(1S,6R)-6-Benzyloxycarbonylaminocyclohex-3-enecarboxylic acid (S21-4)

S21-3 (23.5 g, 81.3 mmol) was dissolved in MeOH (150 mL) and the solution cooled to 0° C. 2M NaOH (204 mL, 0.41 mol) was added, the mixture allowed to come to ambient temperature and then it was stirred for 48 h. The reaction mixture was diluted with water (300 mL), acidified with 2M HCl, and extracted with dichloromethane (250 mL), dried, and evaporated. The residue was recrystallized from diethyl ether to give 21.7 (97%) of S21-4.

$^1$H NMR: ($CDCl_3$) δ 2.20 (d, 1H, $5_{ax}$-H), 2.37 (d, 2H, $2_{ax}$- and $5_{eq}$-H's), 2.54 (d, 1H, $2_{eq}$-H), 2.90 (br s, 1H, 1-H), 4.24 (br s, 1H, 6-H), 5.08 (dd, 2H, $CH_2Ar$), 5.48 (d, 1H, NH), 5.62 (dd, 2H, 3- and 4-H's), 7.35 (m, 5H, Ar H's).

Example 20

(1S,2R,4R,5R)-2-Benzyloxycarbonylamino-4-iodo-7-oxo-6-oxabicyclo[3.2.1]octane (S21-5)

S214 (13.9 g, 50.5 mmol) was dissolved in dichloromethane (100 mL) under $N_2$, 0.5 M $NaHCO_3$ (300 mL), KI (50.3 g, 303.3 mmol), and iodine (25.6 g, 101 mmol) were added and the mixture stirred at ambient temperature for 72 h. The mixture was diluted with dichloromethane (50 mL) and the organic phase separated. The organic phase was washed with saturated aqueous $Na_2S_2O_3$ (2×50 mL), water (30 mL), and saturated aqueous NaCl (20 mL), dried and evaporated to afford 16.3 g (80%) of S21-5.

$^1$H NMR: ($CDCl_3$) δ 2.15 (m, 1H, $8_{ax}$-H), 2.42 (m, 2H, $3_{ax}$- and $8_{eq}$-H's), 2.75 (m, 2H, 1- and $3_{eq}$-H's), 4.12 (br s, 1H, 2-H), 4.41 (t, 1H, 4-H), 4.76 (dd, 1H, 5-H), 4.92 (d, 1H, NH), 5.08 (dd, 2H, $CH_2Ar$), 7.35 (m, 5H, Ar H's).

Example 21

(1S,2R,5R)-2-Benzyloxycarbonylamino-7-oxo-6-oxabicyclo[3.2.1]oct-3-ene (S21-6)

S21-5 (4.0 g, 10 mmol) was dissolved in benzene (50 mL) under $N_2$. 1,8-Diazabicyclo[5.4.0]undec-7-ene (DBU) (1.8 g, 12 mmol) was added and the solution refluxed for 16 h. The precipitate was filtered and the filtrate was diluted with EtOAc (200 mL). The filtrate was washed with 1M HCl (20 mL), saturated aqueous $Na_2S_2O_3$ (20 mL), water (20 mL), and saturated aqueous NaCl (20 mL), dried and evaporated to give 2.2 g (81%) S21-6.

$^1$HNMR: ($CDCl_3$) δ 2.18 (d, 1H, $8_{ax}$-H), 2.39 (m, 1H, $8_{eq}$-H), 3.04 (t, 1H, 1-H), 4.70 (m, 1H, 5-H), 4.82 (t, 1H, 2-H), 5.15 (dd, 3H, $CH_2Ar$ and NH), 5.76 (d, 1H, 4-H), 5.92 (m, 1H, 3-H), 7.36 (s, 5H, Ar H's).

Example 22

(1S,2R,5R)-Methyl 2-Benzyloxycarbonylamino-5-hydroxycyclohex-3-enecarboxylate (S21-7)

S21-6 (9.0 g, 33 mmol) was suspended in MeOH (90 mL) and cooled to 0° C. NaOMe (2.8 g, 52.7 mmol) was added and the mixture stirred for 3 h during which time a solution gradually formed. The solution was neutralized with 2M HCl, diluted with saturated aqueous NaCl (200 mL), and extracted with dichloromethane (2×100 mL). The extracts were combined, washed with water (20 mL) and saturated aqueous NaCl (20 ml), dried, and evaporated. The residue was flash chromatographed (silica gel (250 g), 50:50 hexane/EtOAc) to give 8.5 g (85%) of S21-7.

$^1$H NMR: ($CDCl_3$) δ 1.90 (m, 1H, $6_{ax}$-H), 2.09 (m, 1H, $6_{eq}$-H), 2.81 (m, 1H, 1-H), 3.55 (s, 3H, $CO_2Me$), 4.15 (m, 1H, 5-H), 4.48 (t, 1H, 2-H), 5.02 (dd, 2H, $CH_2Ar$), 5.32 (d, 1H, NH), 5.64 (dt, 1H, 4-H), 5.82 (dt, 1H, 3-H), 7.28 (s, 5H, Ar H's).

Example 23

(1S,2R,5S)-Methyl 2-Benzyloxycarbonylamino-5-t-butoxycarbonylaminocyclohex-3-enecarboxylate (S21-8)

S21-7 (7.9 g, 25.9 mmol) was dissolved in dichloromethane (150 mL) and cooled to 0° C. under $N_2$. Triethylamine (6.3 g, 8.7 mL, 62.1 mmol) and methanesulfonyl chloride (7.1 g, 62.1 mmol) were added and the mixture stirred at 0° C. for 2 h. (n-Bu)$_4$NN$_3$ (14.7 g, 51.7 mmol) in dichloromethane (50 mL) was added and stirring continued at 0° C. for 3 h followed by 15 h at ambient temperature. The mixture was cooled to 0° C. and P(n-Bu)$_3$ (15.7 g, 19.3 mL, 77.7 mmol) and water (1 mL) were added and the mixture stirred at ambient temperature for 24 h. Di-tert-butyl dicarbonate (17.0 g, 77.7 mmol) was added and stirring continued for 24 h. The solvent was removed, the residue dissolved in 2:1 hexane/EtOAc (100 mL), the solution filtered, and evaporated. The residue was flash chromatographed (silica gel (240 g), 67:33 hexane/EtOAc) to give 5.9 g (56%) of S21-8.

$^1$H NMR: (CDCl$_3$) δ 1.40 (s, 9H, Boc H's), 1.88 (m, 1H, 6$_{ax}$-H), 2.21 (m, 1H, 6$_{eq}$-H), 2.95 (m, 1H, 1-H), 3.60 (s, 3H, CO$_2$Me), 4.15 (d, 1H, Boc NH), 4.50 (m, 2H, 2- and 5-H's), 5.02 (s, 2H, CH$_2$Ar), 5.38 (d, 1H, Z NH), 5.65 (m, 2H, 3- and 4-H's), 7.30 (s, 5H, Ar H's).

Example 24

(1R,2R,5S)-Methyl 2-Benzyloxycarbonylamino-5-t-butoxycarbonylaminocyclohex-3-enecarboxylate (S21-9)

S21-8 (1.1 g, 2.7 mmol) was suspended in MeOH (50 mL). NaOMe (0.73 g, 13.6 mmol) was added and the mixture refluxed for 18 h after which 0.5 M NH$_4$Cl (50 mL) was added and the resulting precipitate collected. The filtrate was evaporated and the residue triturated with water (25 mL). The insoluble portion was collected and combined with the original precipitate to give 0.85 g (77%) of S21-9.

$^1$H NMR: (CDCl$_3$) δ 1.38 (s, 9H, Boc H's), 1.66 (m, 1H, 6$_{ax}$-H), 2.22 (d, 1H, 6$_{eq}$-H), 2.58 (t, 1H, 1-H), 3.59 (3, 3H, CO$_2$Me), 4.22 (br s, 1H, Boc NH), 4.50 (m, 2H, 2- and 5-H's), 4.75 (d, 1H, Z NH), 5.02 (s, 2H, CH$_2$Ar), 5.62 (s, 2H, 3- and 4-H's), 7.30 (s, 5H, Ar H's).

Example 25

(1R,2R,5S)-2-Benzyloxycarbonylamino-5-t-butoxycarbonylaminocyclohex-3-enecarboxylic acid (S21-10)

S21-9 (0.85 g, 2.1 mmol) was suspended in 50:50 MeOH/dichloromethane (5 mL) and cooled to 0° C. under N$_2$ after which 2M NaOH (2.0 mL) was added and the mixture stirred at ambient temperature for 16 h. The mixture was acidified with 2M HCl upon which a white precipitate formed. The precipitate was collected, washed with water and hexane, and dried to give 0.74 g (90%) of S21-10.

$^1$H NMR: (CD$_3$OD) δ 1.42 (s, 9H, Boc H's), 1.66 (m, 1H, 6$_{ax}$-H), 2.22 (d, 1H, 6$_{eq}$-H), 2.65 (t, 1H, 1-H), 4.18 (m, 1H, 5-H), 4.45 (m, 1H, 5-H), 5.04 (s, 2H, CH$_2$Ar), 5.58 (m, 2H, 3- and 4-H's), 7.35 (s, 5H, Ar H's).

Example 26

(1R,2R,5S)-2-Benzyloxycarbonylamino-5-t-butoxycarbonylamino-1-(2-trimethylsilyl)ethoxycarbonylaminocyclohex-3-ene (S21-11)

S21-10 (3.1 g, 7.9 mmol) was dissolved in THF (30 mL) under N$_2$ and cooled to 0° C. Triethylamine (1.6 g, 2.2 mL, 15.9 mmol) was added followed by ethyl chloroformate (1.3 g, 1.5 mL, 11.8 mmol). The mixture was stirred at 0° C. for 1 h. A solution of NaN$_3$ (1.3 g, 19.7 mmol) in water (10 mL) was added and stirring at 0° C. was continued for 2 h. The reaction mixture was partitioned between EtOAc (50 mL) and water (50 mL). The organic phase was separated, dried, and evaporated. The residue was dissolved in benzene (50 mL) and refluxed for 2 h. 2-Trimethylsilylethanol (1.0 g, 1.2 mL, 8.7 mmol) was added and reflux continued for 3 h. The reaction mixture was diluted with EtOAc (200 mL), washed with saturated aqueous NaHCO$_3$ (50 mL), water (20 mL), and saturated aqueous NaCl (20 mL), dried and evaporated. The residue was flash chromatographed (silica gel (100 g), 67:33 hexane/EtOAc) to give 3.1 g (77%) of S21-11.

$^1$H NMR: (CDCl$_3$) δ-0.02 (s, 9H, TMS), 0.90 (t, 3H, CH$_2$TMS), 1.40 (s, 9H, Boc H's), 2.38 (m, 1H, 6$_{eq}$-H), 3.62 (m, 1H, 1-H), 4.08 (m, 2H, OCH$_2$CH$_2$TMS), 4.18 (m, 1H), 4.38 (m, 1H), 4.62 (m, 1H), 5.07 (dd, 2H, CH$_2$Ar), 5.18 (m, 1H), 5.26 (m, 1H), 5.58 (d, 1H, olefinic H), 5.64 (d, 2H, olefinic H), 7.30 (s, 5, Ar H's).

Example 27

(1R,2R,5S)-2-Benzyloxycarbonylamino-1,5-diaminocyclohex-3-ene (S21-12)

S21-11 (2.5 g, 4.9 mmol) was added to TFA (10 mL) and the solution stirred at ambient temperature for 16 h after which the solution was evaporated. The residue was dissolved in water (20 mL), basified to pH 14 with KOH and extracted with dichloromethane (3×50 mL). The extracts were combined, washed with water (20 mL), dried and evaporated to give 1.1 g (85%) of S21-12.

$^1$H NMR: (CDCl$_3$) δ 1.30 (m, 1H, 6$_{eq}$-H), 2.15 (br d, 1H, 6$_{eq}$-H), 2.68 (m, 1H, 1-H), 3.42 (br s, 1H, 5-H), 3.95 (m, 1H, 2-H), 4.85 (d, 1H, Z NH), 5.08 (t, 2H, CH$_2$Ar), 5.45 (d, 1H, 4-H), 5.62 (d, 1H, 3-H), 7.32 (s, 5H, Ar H's). ESCI MS m/e 262 M+1.

Example 28

Isolation of S21b-2 was accomplished using the following procedure: Using Schlenk technique 5.57 g (10.0 mmol) of methyl ester compound, S21b-1, was dissolved in 250 mL of THF. In another flask LiOH (1.21 g, 50.5 mmol) was dissolved in 50 mL water and de-gassed by bubbling N$_2$ through the solution using a needle for 20 minutes. The reaction was started transferring the base solution into the flask containing S21b-1 over one minute with rapid stirring. The mixture was stirred at room temperature and work-up initiated when the starting material S21b-1 was completely consumed (Using a solvent system of 66% EtOAc/33% Hexane and developing with phosphomolybdic acid reagent (Aldrich #31,927-9) the starting material S21b-1 has an Rf of 0.88 and the product streaks with an Rf of approx. 0.34 to 0.64.). The reaction usually takes 2 days. Work-Up: The THF was removed by vacuum transfer until about the same volume is left as water added to the reaction, in this case 50 mL. During this the reaction solution forms a white mass that adheres to the stir bar surrounded by clear yellow solution. As the THF is being removed a separatory funnel is set up including a funnel to pour in the reaction solution and an Erlenmeyer flask is placed underneath the separatory funnel. Into the Erlenmeyer flask is added some anhydrous Na$_2$SO$_4$. This apparatus should be set up before acidification is started. (It is important to set up the separatory funnel and Erlenmeyer flask etc. before acidification of the reaction solution to enable separation of phases and extraction of the product away from the acid quickly once the solution attains a pH close to 1. If the separation is not preformed rapidly the Boc functional group will be hydrolyzed significantly reducing the yield.) Once the volatiles are sufficiently removed, CH$_2$Cl$_2$ (125 mL) and water (65 mL) are added and the reaction flask cooled in an ice bath. The solution is stirred rapidly and 5 mL aliquots of 1N HCl are added by syringe and the reaction solution tested with pH paper. Acid is added until the spot on the pH paper shows red (not orange) around the edge indicating a pH is 1 to 2 has been achieved (The solution being tested is a mixture of CH$_2$Cl$_2$ and water so the pH paper will show the accurate measurement at the edge of the spot and not the center.) and the phases are separated by quickly pouring the solution into the separatory funnel. As the phases separate the stopcock is turned to release the $CH_2Cl_2$ phase (bottom) into the Erlenmeyer flask and swirl the flask to allow the drying agent to absorb water in the solution. (At this scale of this procedure 80 mL of 1N HCl was used.) Soon after phase separation the aqueous phase is extracted with $CH_2Cl_2$ (2×100 mL), dried over anhydrous $Na_2SO_4$ and the volatiles removed to produce 5.37 g/9.91 mmoles of a beautiful white microcrystals reflecting a 99.1% yield. This product can not be purified by chromatography since that process would also hydrolyze the Boc functional group on the column.

$^1$H NMR (400 MHz, $CDCl_3$) δ7.33, 7.25 (5H, m, Ph), 6.30 (1H, d, NH), 5.97 (1H, d, NH), 5.10 (2H, m, $CH_2Ph$), 4.90 (1H, d, NH), 3.92, 3.58, 3.49 (1H, m, CHNH), 2.96, 2.48, 2.04, 1.95, 1.63 (1H, m, $CH_2CHNH$), 1.34 (9H, s, $CCH_3$).

IR (crystalline, $cm^{-1}$) 3326 br w, 3066 w, 3033 w, 2975 w, 2940 w sh, 1695 vs, 1506 vs, 1454 m sh, 1391 w, 1367 m, 1300 m sh, 1278 m sh, 1236 s, 1213 w sh, 1163 vs, 1100 w, 1053 m, 1020 m, 981 w sh, 910 w, 870 m, 846 w, 817 w, 775 w sh, 739 m, 696 m.

Example 29

Di-(l)-menthyl bicyclo[2.2.1]hept-5-ene-7-anti-(trimethylsilyl)-2-endo-3-exo-dicarboxylate (S24-26)

To a solution of S24-25 (6.09 g, 0.0155 mol) in toluene (100 mL) was added diethylaluminum chloride (8.6 mL of a 1.8 M solution in toluene) at −78° C. under nitrogen and the mixture was stirred for 1 hour. To the resulting orange solution was added S22-14 (7.00 g, 0.0466 mol) dropwise as a −78° C. solution in toluene (10 mL). The solution was kept at −78° C. for 2 hours, followed by slow warming to room temperature overnight. The aluminum reagent was quenched with a saturated solution of ammonium chloride (50 mL). The aqueous layer was separated and extracted with methylene chloride (100 mL) which was subsequently dried over magnesium sulfate. Evaporation of the solvent left a yellow solid that was purified by column chromatography (10% ethyl acetate/hexanes) to give S24-26 as a while solid (7.19 g, 0.0136 mol, 87% yield).

$^1$H NMR: ($CDCl_3$) δ-0.09 (s, 9H, $SiMe_3$), 0.74-1.95 (multiplets, 36H, menthol), 2.72 (d, 1H, α-menthyl carbonyl CH), 3.19 (bs, 1H, bridgehead CH), 3.30 (bs, 1H, bridgehead CH), 3.40 (t, 1H, α-menthyl carbonyl CH), 4.48 (d of t, 1H, α-menthyl ester CH), 4.71 (d of t, 1H, α-menthyl ester CH), 5.92 (d of d, 1H, CH=CH), 6.19 (d of d, 1H, CH=CH).

Example 30

5-exo-Bromo-3-exo-(l)-menthylcarboxybicyclo[2.2.1]heptane-7-anti-(trimethylsilyl)-2,6-carbolactone (S24-27)

A solution of bromine (3.61 g, 0.0226 mol) in methylene chloride (20 mL) was added to a stirring solution of S24-26 (4.00 g, 0.00754 mol) in methylene chloride (80 mL). Stirring was continued at room temperature overnight. The solution was treated with 5% sodium thiosulfate (150 mL), and the organic layer separated and dried over magnesium sulfate. The solvent was evaporated at reduced pressure, and the crude product purified by column chromatography (5% ethyl acetate/hexanes) to give S24-27 as a white solid (3.53 g, 0.00754 mol, 99% yield).

$^1$H NMR: ($CDCl_3$) δ -0.19 (s, 9H, $SiMe_3$), 0.74-1.91 (multiplets, 18H, menthol), 2.82 (d, 1H, α-lactone carbonyl CH), 3.14 (bs, 1H, lactone bridgehead CH), 3.19 (d of d, 1H, bridgehead CH), 3.29 (t, 1H, α-menthyl carbonyl CH), 3.80 (d, 1H, α-lactone ester), 4.74 (d of t, 1H, α-menthyl ester CH), 4.94 (d, 1H, bromo CH).

Example 31

Bicyclo[2.2.1]hept-5-ene-7-syn-(hydroxy)-2-exo-methyl-3-endo-(l)-menthyl dicarboxylate (S24-28)

S24-27 (3.00 g, 0.00638 mol) was dissolved in anhydrous methanol (150 mL), silver nitrate (5.40 g, 0.0318 mol) added and the suspension refluxed for 3 days. The mixture was cooled, filtered through Celite and the solvent evaporated to give an oily residue. Purification by column chromatography gave S24-28 as a light yellow oil (1.72 g, 0.00491 mol, 77% yield).

$^1$H NMR: ($CDCl_3$) δ 0.75-2.02 (multiplets, 18H, menthol), 2.83 (d, 1H, α-menthyl carbonyl CH), 3.03 (bs, 1H, bridgehead CH), 3.14 (bs, 1H, bridgehead CH), 3.53 (t, 1H, α-methyl carbonyl CH), 3.76 (s, 3H, $CH_3$), 4.62 (d of t, 1H, α-menthyl ester CH), 5.87 (d of d, 1H, CH=CH), 6.23 (d of d, 1H, CH=CH).

Example 32

2-exo-Methyl-3-endo-(l)-menthylbicyclo[2.2.1]hept-5-ene-7-syn-(benzyloxy) dicarboxylate (S24-29)

Benzyl bromide (1.20 g, 0.0070 mol) and silver oxide (1.62 g, 0.0070 mol) were added to a stirring solution of S24-28 (0.490 g, 0.00140 mol) in DMF (25 mL). The suspension was stirred overnight and then diluted with ethyl acetate (100 mL). The solution was washed repeatedly with water followed by 1 N lithium chloride. The organic layer was separated and dried with magnesium sulfate. The solvent was evaporated under reduced pressure and the crude product was purified by column chromatography on silica gel to give S24-29 as an oil (0.220 g, 0.000500 mol, 36% yield).

$^1$H NMR: ($CDCl_3$) δ 0.74-2.08 (multiplets, 18H, menthol), 2.83 (d, 1H, α-menthyl carbonyl CH), 3.18 (bs, 1H, bridgehead CH), 3.44 (bs, 1H, bridgehead CH), 3.52 (t, 1H, bridge CH), 3.57 (s, 3H, $CH_3$), 3.68 (t, 1H, α-methyl carbonyl CH), 4.42 (d of d, 2H, benzyl —$CH_2$—), 4.61 (d of t, 1H, α-menthyl ester CH), 5.89 (d of d, 1H, CH=CH), 6.22 (d of d, 1H, CH=CH), 7.25-7.38 (m, 5H, $C_6H_5$).

Example 33

Bicyclo[2.2.1]hept-5-ene-7-syn-(benzyloxy)-2-exo-carboxy-3-endo-(l)-menthyl carboxylate (S24-30)

S24-29 (0.220 g, 0.00050 mol) was added to a mixture of tetrahydrofuran (1.5 mL), water (0.5 mL), and methanol (0.5 mL). Potassium hydroxide (0.036 g, 0.00065 mol) was added and the solution stirred at room temperature overnight. The solvent was evaporated under reduced pressure and the residue purified by column chromatography (10% ethyl acetate/hexanes) to give S24-30 (0.050 g, 0.00012 mol, 23% yield).

$^1$H NMR: ($CDCl_3$) δ 0.73-2.01 (multiplets, 18H, menthol), 2.85 (d, 1H, α-menthyl carbonyl CH), 3.18 (bs, 1H, bridgehead CH), 3.98 (bs, 1H, bridgehead CH), 3.53 (bs, 1H, bridge CH), 3.66 (t, 1H, α-methyl carbonyl CH), 4.44 (d of d, 2H, benzyl —$CH_2$—), 4.63 (d of t, 1H, α-menthyl ester CH), 5.90 (d of d, 1H, CH=CH), 6.23 (d of d, 1H, CH=CH), 7.25-7.38 (m, 5H, $C_6H_5$).

Mass Spec: calculated for $C_{26}H_{34}O_5$ 426.24; found 425.4 (M−1) and 851.3 (2M−1).

Example 34

Bicyclo[12.2.11]hept-5-ene-7-syn-(benzyloxy)-2-exo-(trimethylsilylethoxycarbonyl)-amino-3-endo-(l)-menthyl carboxylate (S24-31)

To a solution of S24-30 in benzene is added triethylamine and diphenylphosphoryl azide. The solution is refluxed for 24 hours then cooled to room temperature. Trimethylsilylethanol is added, and the solution refluxed for an additional 48 hours. The benzene solution is partitioned between ethyl acetate and 1 M sodium bicarbonate. The organic layers are combined, washed with 1 M sodium bicarbonate and dried over sodium sulfate. The solvent is evaporated under reduced pressure to give the crude Curtius reaction product.

Example 35

Bicyclo[2.2.1]heptane-7-syn-(benzyloxy)-2-exo-(trimethylsilylethoxycarbonyl)-amino-3-endo-(l)-menthyl-5-exo-methyl-6-exo-methyl tricarboxylate (S24-32)

S24-31, dry copper(II) chloride, 10% Pd/C, and dry methanol are added to a flask with vigorous stirring. After degassing, the flask is charged with carbon monoxide to a pressure just above 1 atm., which is maintained for 72 hours. The solids are filtered and the residue worked up in the usual way to afford the biscarbonylation product.

Example 36

Bicyclo[2.2.1]heptane-7-syn-(benzyloxy)-2-exo-(trimethylsilylethoxycarbonyl)-amino-3-endo-(l)-menthylcarbox-5-exo-6-exo-dicarboxylic anhydride (S24-33)

A mixture of S24-32, formic acid, and a catalytic amount of p-toluenesulfonic acid is stirred at 90° C. overnight. Acetic anhydride is added and the reaction mixture refluxed for 6 hours. Removal of the solvents and washing with ether gives the desired anhydride.

Example 37

Bicyclo[2.2.1]heptane-7-syn-(benzyloxy)-2-exo-(trimethylsilylethoxycarbonyl)-amino-3-endo-(l)-menthyl-6-exo-carboxy-5-exo-methyl dicarboxylate (S24-33)

To a solution of S24-32 in equal amounts of toluene and carbon tetrachloride is added quinidine. The suspension is cooled to −65° C. and stirred for 1 hour. Three equivalents of methanol are slowly added over 30 minutes. The suspension is stirred at −65° C. for 4 days followed by removal of the solvents under reduced pressure. The resulting white solid is partitioned between ethyl acetate and 2M HCl. The quinine is recovered from the acid layer and S24-33 obtained from the organic layer.

Example 38

Bicyclo[2.2.1]heptane-7-syn-(benzyloxy)-2-exo-(trimethylsilylethoxycarbonyl)-amino-3-endo-(l)-menthyl-6-exo-(trimethylsilylethoxycarbonyl)amino-5-exo-methyl dicarboxylate (S24-35)

To a solution of S24-34 in benzene is added triethylamine and diphenylphosphoryl azide. The solution is refluxed for 24 hours. After cooling to room temperature, 2-trimethylsilylethanol is added and the solution refluxed for 48 hours. The benzene solution is partitioned between ethyl acetate and 1M sodium bicarbonate. The organic layers are combined, washed with 1M sodium bicarbonate, and dried over sodium sulfate. The solvent is evaporated under reduced pressure to give the crude Curtius reaction product.

Example 39 endo-Bicyclo[2.2.1]hept-5-ene-2-benzylcarboxylate-3-carboxylic acid (S25-37)

Compound S23-19 (4.00 g, 0.0244 mol) and quinidine (8.63 g, 0.0266 mol) were suspended in equal amounts of toluene (50 mL) and carbon tetrachloride (50 mL). The suspension was cooled to −55° C. after which benzyl alcohol (7.90 g, 0.0732 mol) was added over 15 minutes. The reaction mixture became homogenous after 3 hours and was stirred at −55° C. for an additional 96 hours. After removal of the solvents, the residue was partitioned between ethyl acetate (300 mL) and 2M hydrochloric acid (100 mL). The organic layer was washed with water (2×50 mL) and saturated aqueous sodium chloride (1×50 mL). Drying over magnesium sulfate and evaporation of the solvent gave S25-37 (4.17 g, 0.0153 mol, 63% yield).

$^1$H NMR: ($CDCl_3$) δ 1.33 (d, 1H, bridge $CH_2$), 1.48 (d of t, 1H, bridge $CH_2$), 3.18 (bs, 1H, bridgehead CH), 3.21 (bs, 1H, bridgehead CH), 3.33 (t, 2H, α-acid CH), 4.98 (d of d, 2H, $CH_2Ph$), 6.22 (d of d, 1H, CH=CH), 6.29 (d of d, 1H, CH=CH), 7.30 (m, 5H, $C_6H_5$).

Example 40

2-endo-Benzylcarboxy-6-exo-iodobicyclo[2.2.1]heptane-3,5-carbolactone (S25-38)

S25-37 (4.10 g, 0.0151 mol) was dissolved in 0.5 M sodium bicarbonate solution (120 mL) and cooled to 0° C. Potassium iodide (15.0 g, 0.090 mol) and iodine 7.66 g, 0.030 mol) were added followed by methylene chloride (40 mL). The solution was stirred at room temperature overnight. After dilution with methylene chloride (100 mL), sodium thiosulfate was added to quench the excess iodine. The organic layer was separated and washed with water (100 mL) and sodium chloride solution (100 mL). Drying over magnesium sulfate and evaporation of the solvent gave S25-38 (5.44 g, 0.0137 mol, 91% yield).

$^1$H NMR: ($CDCl_3$) δ 1.86 (d of q, 1H, bridge —$CH_2$—), 2.47 (d of t, 1H, bridge —$CH_2$—), 2.83 (d of d, 1H, α-lactone carbonyl CH), 2.93 (bs, 1H, lactone bridgehead CH), 3.12 (d of d, 1H, α-benzyl ester CH), 3.29 (m, 1H, bridgehead CH), 4.63 (d, 1H, α-lactone ester CH), 5.14 (d of d, 2H, $CH_2Ph$), 5.19 (d, 1H, iodo CH), 7.38 (m, 5H, $C_6H_5$).

Example 41

2-endo-Benzylcarboxy-bicyclo[2.2.1]heptane-3,5-carbolactone (S25-39)

S25-38 (0.30 g, 0.75 mmol) was placed in DMSO under $N_2$, $NaBH_4$ (85 mg, 2.25 mmol) added and the solution stirred at 85° C. for 2 h. The mixture was cooled, diluted with water (50 mL) and extracted with dichloromethane (3×20 mL). The extracts were combined, washed with water (4×15 mL) and saturated aqueous NaCl (10 mL), dried, and evaporated to give 0.14 g (68%) of S25-39.

Example 42

5-endo-hydroxybicyclo[2.2.1]heptane-2-endo-benzyl-3-endo-methyl dicarboxylate (S25-40)

Compound S25-39 is dissolved in methanol and sodium methoxide added with stirring. Removal of the solvent gives S25-40.

Example 43

Bicyclo[2.2.1]heptane-2-endo-benzyl-3-endo-methyl-5-exo-(t-butoxycarbonyl)-amino dicarboxylate (S25-41)

In a one-pot reaction S25-40 is converted to the corresponding mesylate with methanesulfonyl chloride, sodium azide added to displace the mesylate to give exo-azide, which is followed by reduction with tributyl phosphine to give the free amine, which is protected as the t-Boc derivative to give S25-41.

Example 44

Bicyclo[2.2.1]heptane-2-endo-carboxy-3-exo-methyl-5-exo-(t-butoxycarbonyl)-amino carboxylate (S25-42)

The benzyl ether protecting group is removed by catalytic hydrogenolysis of S25-41 with 10% Pd/C in methanol at room temperature for 6 hours. Filtration of the catalyst and removal of the solvent yields crude S25-42.

Example 45

Bicyclo[2.2.1]heptane-2-endo-carboxy-3-exo-methyl-5-exo-(t-butoxycarbonyl)-amino carboxylate (S25-43)

Sodium is dissolved in methanol to generate sodium methoxide. S25-42 is added and the mixture stirred at 62° C. for 16 hr. The mixture is cooled and acetic acid added with cooling to neutralize the excess sodium methoxide. The mixture is diluted with water and extracted with ethyl acetate. The extract is dried and evaporated to give S25-43.

Example 46

Bicyclo[2.2.1]heptane-2-endo-benzyl-3-exo-methyl-5-exo-(t-butoxycarbonyl)amino dicarboxylate (S25-44)

Compound S25-43 is reacted with benzyl bromide and cesium carbonate in tetrahydrofuran at room temperature to give benzyl ester S25-44, which is isolated by acid work-up of the crude reaction mixture.

Example 47

Bicyclo[2.2.1]heptane-2-endo-benzyl-3-exo-carboxy-5-exo-(t-butoxycarbonyl)-amino carboxylate (S25-45)

Compound S25-44 is dissolved in methanol and cooled to 0° C. under $N_2$. 2M NaOH (2 equivalents) is added dropwise, the mixture allowed to come to ambient temperature and is stirred for 5 h. The solution is diluted with water, acidified with 2M HCl and extracted with ethyl acetate. The extract is washed with water, saturated aqueous NaCl, dried and evaporated to give S25-45.

Example 48

Bicyclo[2.2.1]heptane-2-endo-benzyl-3-exo-(trimethylsilylethoxycarbonyl)amino-5-exo-(t-butoxycarbonyl)amino carboxylate (S25-46)

To a solution of S25-45 in benzene is added triethylamine and diphenylphosphoryl azide. The solution is refluxed for 24 hours and then cooled to room temperature. Trimethylsilylethanol is added and the solution refluxed for 48 hours. The solution is partitioned between ethyl acetate and 1M sodium bicarbonate. The organic layer is washed with 1M sodium bicarbonate and dried over sodium sulfate. The solvent is evaporated under reduced pressure to give crude Curtius product S25-46.

Example 49 endo-Bicyclo[2.2.1]hept-5-ene-2-(4-methoxy)benzylcarboxylate-3-carboxylic acid (S26-48)

Compound S23-19 and quinidine are suspended in equal amounts of toluene and carbon tetrachloride and cooled to −55° C. p-Methoxybenzyl alcohol is added over 15 minutes and the solution stirred at −55° C. for 96 hours. After removal of the solvents, the residue is partitioned between ethyl acetate and 2 M hydrochloric acid. The organic layer is washed with water and saturated aqueous sodium chloride. Drying over magnesium sulfate and removal of the solvent gives S26-48.

Example 50 endo-Bicyclo[2.2.1]hept-5-ene-2-(4-methoxy)benzyl-3-(trimethylsilylethoxy-carbonyl)amino carboxylate (S26-49)

To a solution of S26-48 in benzene is added triethylamine and diphenylphosphoryl azide. The solution is refluxed for 24 hours, cooled to room temperature, trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give crude Curtius product S26-49.

Example 51

Bicyclo[2.2.1]heptane-2-endo-(4-methoxy)benzyl-3-endo-(trimethylsilylethoxycarbonyl)amino-5-exo-methyl-6-exo-methyl tricarboxylate (S26-50)

S26-49, copper(II) chloride, 10% Pd/C, and dry methanol are added to a flask with vigorous stirring. After degassing the suspension, the flask is charged with carbon monoxide to a pressure just above 1 atm. The pressure of carbon monoxide is maintained over 72 hours. The solids are filtered off, and the crude reaction mixture worked up in the usual way to afford S26-50.

Example 52

Bicyclo[2.2.1]heptane-2-endo-(4-methoxy)benzyl-3-endo-(trimethylsilylethoxycarbonyl)amino-5-exo-6-exo-dicarboxylic anhydride (S26-51)

S26-50, formic acid, and a catalytic amount of p-toluenesulfonic acid is heated at 90° C. overnight. Acetic anhydride is added to the reaction mixture, and it is refluxed for an additional 6 hours. Removal of the solvents and washing with ether affords S26-51.

Example 53

Bicyclo[2.2.1]heptane-2-endo-(4-methoxy)benzyl-3-endo-(trimethylsilylethoxycarbonyl)amino-5-exo-carboxy-6-exo-methyl dicarboxylate (S26-52)

To a solution of S26-51 in equal amounts of toluene and carbon tetrachloride is added quinine. The suspension is cooled to −65° C. and stirred for 1 hour. Three equivalents of methanol are added slowly over 30 minutes. The suspension is stirred at −65° C. for 4 days followed by removal of the solvents. The resulting white solid is partitioned between ethyl acetate and 2 M HCl, with S26-52 worked up from the organic layer.

Example 54

Bicyclo[2.2.1]heptane-2-endo-(4-methoxy)benzyl-3-endo-(trimethylsilylethoxycarbonyl)amino-5-exo-(trimethylsilylethoxycarbonyl)amino-6-exo-methyl Dicarboxylate (S26-53)

To a solution of S26-52 in benzene is added triethylamine and diphenylphosphoryl azide. The solution is refluxed for 24 hours then cooled to room temperature. 2-Trimethylsilylethanol is added, and the solution is refluxed for an additional 48 hours. The benzene solution is partitioned between ethyl acetate and 1 M sodium bicarbonate. The organic layers are combined, washed with 1 M sodium bicarbonate, and dried with sodium sulfate. The solvent is evaporated under reduced pressure to give S26-53.

Example 55

Bicyclo[2.2.1]heptane-2-exo-(4-methoxy)benzyl-3-endo-(trimethylsilylethoxycarbonyl)amino-5-exo-(trimethylsilylethoxycarbonyl)amino-6-endo-methyl dicarboxylate (S26-54)

To a solution of S26-53 in tetrahydrofuran is carefully added potassium tert-butoxide. The basic solution is refluxed for 24 hours followed by addition of acetic acid. Standard extraction methods give the double epimerized product S26-54.

Example 56

Preparation of Hexamer:

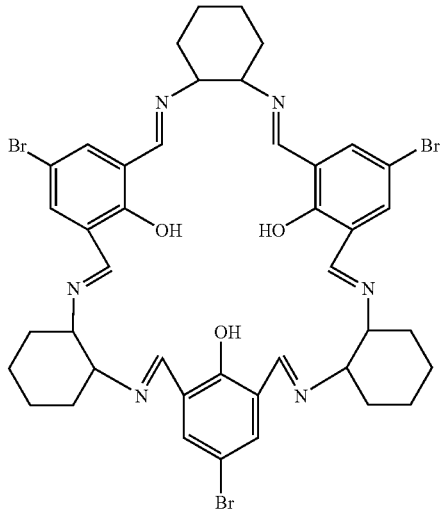

Hexamer 1a-Br

To 0.300 g (1R,2R)-(−)-trans-1,2-diaminocyclohexane (2.63 mmol) in 5 mL $CH_2Cl_2$ at 0° C. was added 0.600 g of 2,6-diformyl-4-bromophenyl (2.62 mmol) in 5 mL of $CH_2Cl_2$. The yellow solution was allowed to warm to room temperature and stirred for 48 hours. The reaction solution was decanted, and added to 150 mL of methanol. After standing for 30 minutes, the yellow precipitate was collected, washed with methanol, and air-dried (0.580 g; 72% yield).
$^1$H NMR (400 MHz, $CDCl_3$) δ 14.31 (s, 3H, OH), 8.58 (s, 3H, CH=N), 8.19 (s, 3H, CH=N), 7.88 (d, 3H, J=2.0 Hz, ArH), 7.27 (d, 3H, J=2.0 Hz, ArH), 3.30-3.42 (m, 6H, $CH_2$—CH—N), 1.41-1.90 (m, 24H, aliphatic). MS (FAB): Calcd for $C_{42}H_{46}N_6O_3Br_3$ 923.115; found 923.3 $[M+H]^+$.

Example 57

Preparation of Hexamer:

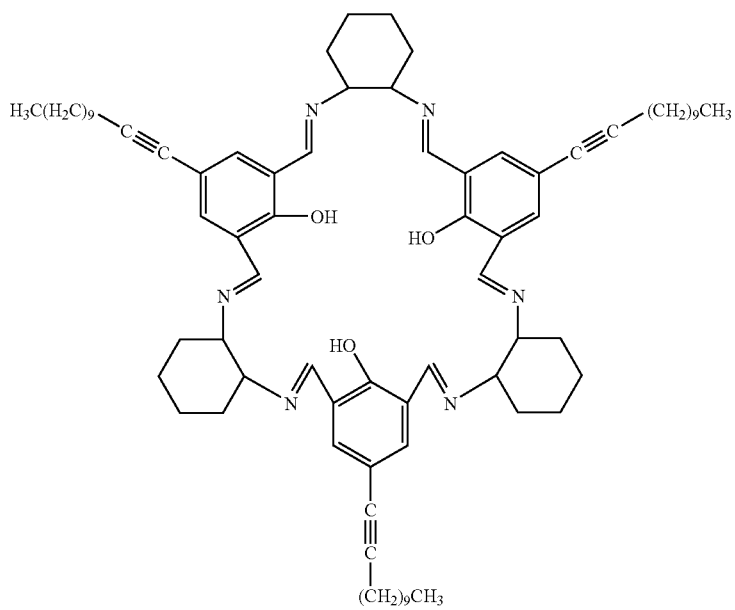

Hexamer 1a

To 0.300 g (1R,2R)-(−)-trans-1,2-diaminocyclohexane (2.63 mmol) in 6 mL $CH_2Cl_2$ at 0° C. was added 0.826 g of 2,6-diformyl-4-(1-dodec-1-yne)phenyl (2.63 mmol) in 6 mL of $CH_2Cl_2$. The orange solution was stirred at 0° C. for 1 hour and then allowed to warm to room temperature after which stirring was continued for 16 hours. The reaction solution was decanted and added to 150 mL of methanol. A sticky yellow solid was obtained after decanting the methanol solution. Chromatographic cleanup of the residue gave a yellow powder.

$^1$H NMR (400 MHz, $CDCl_3$) δ 14.32 (s, 3H, OH), 8.62 (s, 3H, CH=N), 8.18 (s, 3H, CH=N), 7.84 (d, 3H, J=2.0 Hz, ArH), 7.20 (d, 3H, J=2.0 Hz, ArH), 3.30-3.42 (m, 6H, $CH_2$—CH—N), 2.25 (t, 6H, J=7.2 Hz, propargylic), 1.20-1.83 (m, 72H, aliphatic), 0.85 (t, 9H, J=7.0 Hz, $CH_3$). $^{13}$C NMR (400 MHz, $CDCl_3$) δ 163.4, 161.8, 155.7, 136.9, 132.7, 123.9, 119.0, 113.9, 88.7, 79.7, 75.5, 73.2, 33.6, 33.3, 32.2, 29.8, 29.7, 29.6, 29.4, 29.2, 29.1, 24.6, 24.5, 22.9, 19.6, 14.4. MS (FAB): Calcd for $C_{78}H_{109}N_6O_3$ 1177.856; found: 1177.8 $[M+H]^+$.

Example 58

Preparation of Hexamer:

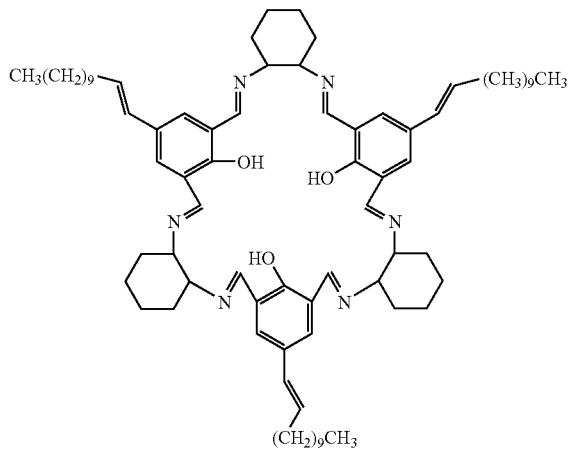

Hexamer 1d-C12

To 0.240 g of 2,6-diformyl-4-(1-dodecene)phenyl (0.76 mmol) in 10 mL of benzene was added a 10 mL benzene solution of (1R,2R)-(−)-trans-1,2-diaminocyclohexane (0.087 g, 0.76 mmol). The solution was stirred at room temperature for 48 hours shielded from the light. The orange solution was taken to dryness and chromatographed (silica, 50/50 acetone/$Et_2O$) to give a yellow sticky solid (33% yield).

$^1$H NMR (400 MHz, $CDCl_3$) δ 14.12 (s, 3H, OH), 8.62 (s, 3H, CH=N), 8.40 (s, 3H, CH=N), 7.82 (d, 3H, J=2.0 Hz, ArH), 7.28 (d, 3H, J=2.0 Hz, ArH), 6.22 (d, 3H, vinyl), 6.05 (d, 3H, vinyl), 3.30-3.42 (m, 6H, $CH_2$—CH—N), 1.04-1.98 (m, 87H, aliphatic). MS (FAB): Calcd for $C_{78}H_{15}N_6O_3$ 1183.90; found: 1184.6 $[M+H]^+$.

Example 59

Preparation of Tetramer:

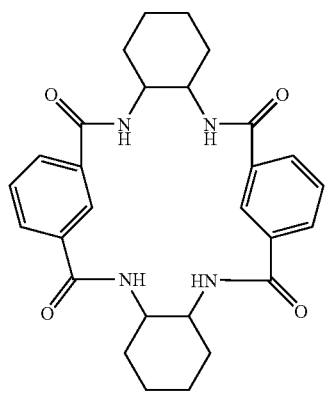

Tetramer 2-phenyl

Preparation of Hexamer:

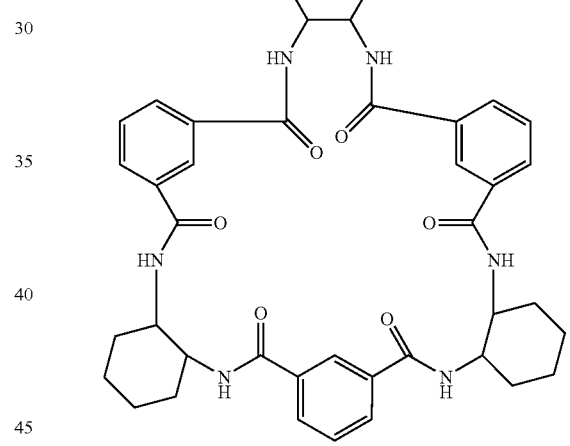

Hexamer 6-phenyl

Triethylamine (0.50 mL, 3.59 mmol) and (1R,2R)-(−)-trans-1,2-diaminocyclohexane (0.190 g, 1.66 mmol) were combined in 150 mL EtOAc and purged with $N_2$ for 5 minutes. To this solution was added 0.331 g isophthaloyl chloride (1.66 mmol) dissolved in 100 mL EtOAc dropwise over six hours. The solution was filtered and the filtrate taken to dryness. TLC (5% methanol/$CH_2Cl_2$) shows the product mixture to be primarily composed of two macrocyclic compositions. Chromatographic separation (silica, 5% methanol/$CH_2Cl_2$) gave the above tetramer (0.020 g, 5% yield) and hexamer (about 10%).

Tetramer:

$^1$H NMR (400 MHz, $CDCl_3$) δ 7.82 (s, 1H), 7.60 (br s, 2H), 7.45 (br s, 2H), 7.18 (br s, 1H), 3.90 (br s, 2H), 2.22 (d, 2H), 1.85 (m, 4H), 1.41 (m, 4H). MS (ESI): Calcd for $C_{28}H_{33}N_4O_4$ 489.25; found 489.4 $[M+H]^+$.

Hexamer:

MS (ESI): Calcd for $C_{42}H_{49}N_6O_6$ 733.37; found 733.5 $[M+H]^+$.

Example 60
Preparation of Macrocyclic Modules from Benzene and Cyclohexane Cyclic Synthons:

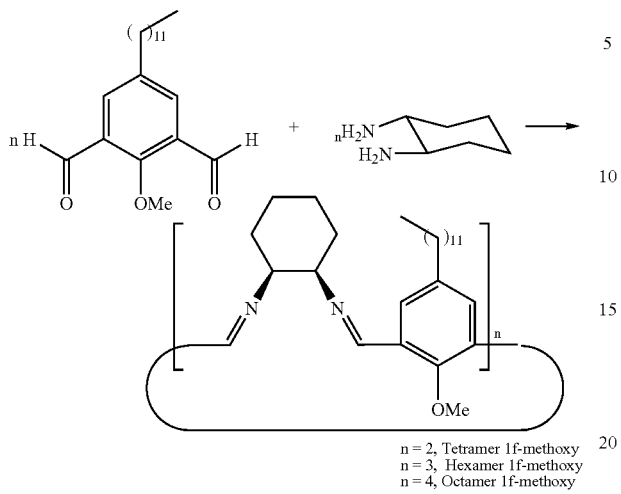

n = 2, Tetramer 1f-methoxy
n = 3, Hexamer 1f-methoxy
n = 4, Octamer 1f-methoxy

To a 5 mL dichloromethane solution of 4-dodecyl-2,6-diformyl anisole (24 mg; 0.072 mmol) was added a 5 mL dichloromethane solution of (1R,2R)-(−)-trans-1,2-diaminocyclohexane (8.5 mg; 0.074 mmol). This solution was stirred at room temperature for 16 hours and then added to the top of a short silica column. Elution with diethyl ether and then removal of solvent led to the isolation of 22 mg of an off-white solid. Positive ion electrospray mass spectrometry demonstrated the presence of the tetramer (m/z 822, MH$^+$), hexamer (m/z 1232, MH$^+$), and the octamer (m/z 1643, MH$^+$) in the off-white solid. Calculated molecular weights were as follows: tetramer+H($C_{54}H_{85}N_4O_2$, 821.67); hexamer+H($C_{81}H_{127}N_6O_3$, 1232.00); octamer+H ($C_{108}H_{169}N_8O_4$, 1643.33).

Example 61

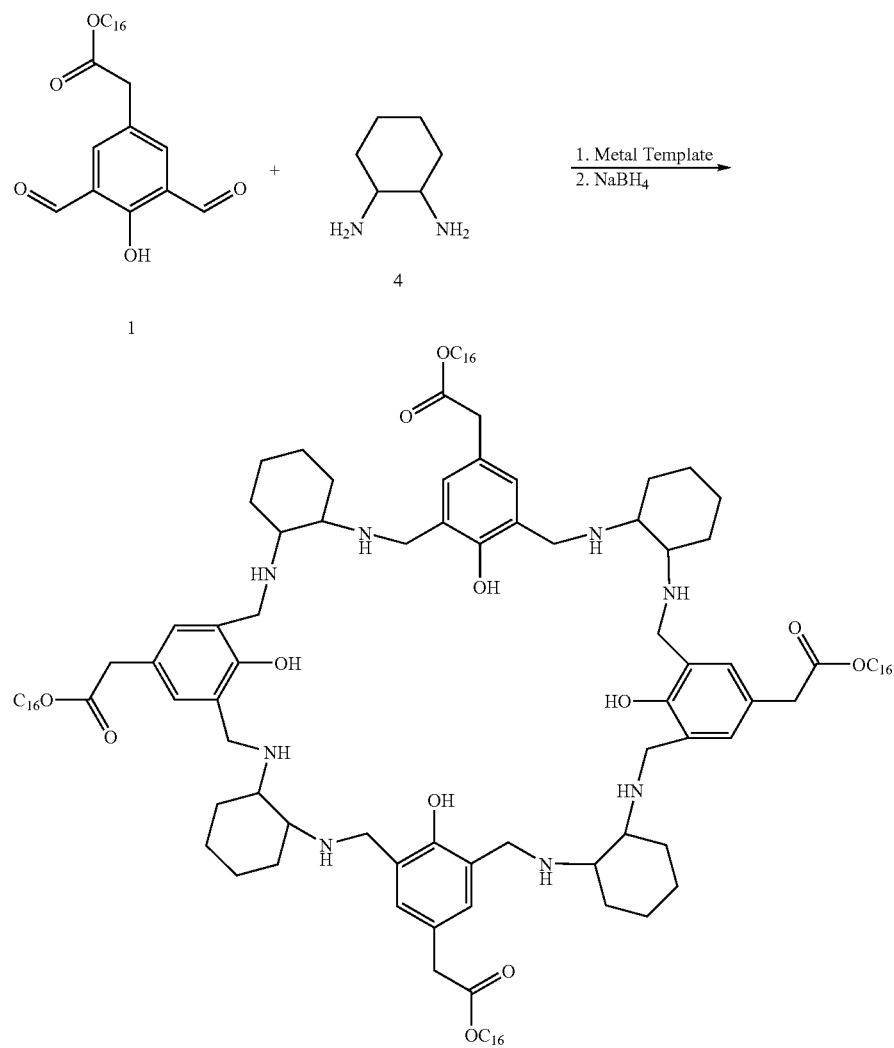

Octmaer 4jh

Templated Imine Octamer. To a 3 neck 100 mL round bottomed flask with stirbar, fitted with condenser and addition funnel under argon, amphiphilic dialdehyde phenyl 1 (500 mg, 1.16 mmol) was added. Next, $Mg(NO_3)_2 \cdot 6H_2O$ (148 mg, 0.58 mmol) 2 and $Mg(OAc)_2 \cdot 4H_2O$ (124 mg, 0.58 mmol) were successively added. The flask was put under vacuo and backfilled with argon 3×. Anhydrous methanol was transferred to the flask via syringe under argon and the resulting suspension stirred. The mixture was then refluxed for 10 min affording a homogeneous solution. The reaction was allowed to cool to room temperature under positive argon pressure. (1R,2R)-(−)-trans-1,2-diaminocyclohexane 4 was added to the addition funnel followed by cannula transfer of anhydrous MeOH (11.6 mL) under argon. The diamine/MeOH solution was added to the stirred homogeneous metal template/dialdehyde solution drop wise over a period of 1 h affording an orange oil. The addition funnel was replaced with a glass stopper and the mixture was refluxed for 3 days. The solvent was removed in vacuo affording a yellow crystalline solid that was used without further purification.

Amine Octamer. To a 50 mL schlenk flask with stirbar under argon Imine Octamer (314 mg, 0.14 mmol) was added. Next anhydrous THF (15 mL) and MeOH (6.4 mL) were added via syringe under argon and the suspension stirred at room temperature. To the homogeneous solution, $NaBH_4$ (136 mg, 3.6 mmol) was added in portions and the mixture stirred at room temperature for 12 h. The solution was filtered, followed by addition of 19.9 mL $H_2O$. The pH was adjusted to ca. 2 by addition of 4 M HCl, then 6.8 mL of an ethylenediamine tetraacetic acid disodium salt dihydrate (0.13 M in $H_2O$) was added and the mixture stirred for 5 min. To the solution, 2.0% ammonium hydroxide was added and stirring continued for an additional 5 min. The solution was extracted with ethyl acetate (3×100 mL) the organic layer separated, dried over $Na_2SO_4$ and the solvent removed via rotoevaporation affording a pale yellow solid. Recrystallization from chloroform and hexanes afforded the Amine Octamer. Molecular weight was confirmed by ESIMS M+H=experimental=2058.7 m/z, calcd=2058.7 m/z.

Example 62

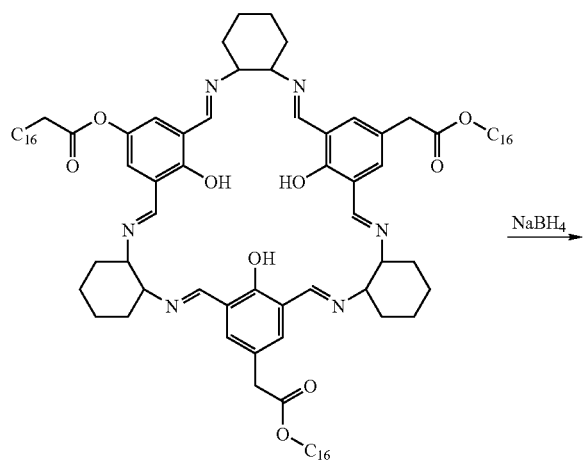

Hexamer 1j-1,2-imine

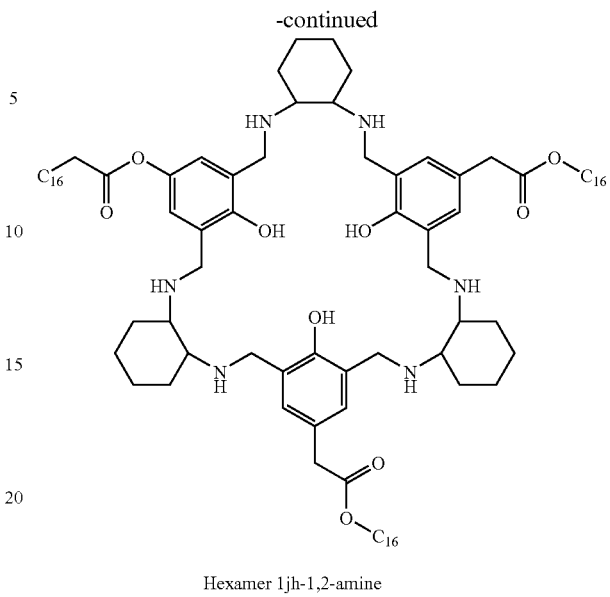

Hexamer 1jh-1,2-amine

Hexamer 1j. The two substrates, (−)-R,R-1,2-trans-diaminocyclohexane (0.462 mmol, 0.053 g) and 2,6-diformyl-4-hexadecyl benzylphenyl carboxylate (0.462 mmol, 0.200 g) were added to a 10 mL vial containing a magnetic stirbar followed by the addition of 2 mL of $CH_2Cl_2$. The yellow solution was stirred at room temperature. After 24 h the reaction solution was plugged through silica gel with diethyl ether, and the solvent removed via roto-evaporation. (232 mg; 98% yield). $^1$H NMR (400 MHz, $CDCl_3$): δ 14.11 (s, 3H, OH), 8.67 (s, 3H, CH=N), 8.23 (s, 3H, CH=N), 7.70 (s, 3H, ArH), 7.11 (s, 3H, ArH), 4.05-3.90 (t, 6H, $^3J$=6.6 Hz, $CH_2C(O)OCH_2(CH_2)_{14}CH_3$), 3.44 (s, 6H, $CH_2C(O)OCH_2(CH_2)_{14}CH_3$), 3.30-3.42 (m, 6H, $CH_2$—CH—N), 1.21-1.90 (m, 108H, aliphatic) 0.92-0.86 (t, 9H, $^3J$=6.6 Hz. ESIMS (+) Calcd for $C_{96}H_{11}N_6O_9$: 1533; Found: 1534 [M+H]$^+$.

Hexamer 1jh. To a 100 mL pear-shaped flask with magnetic stirbar under argon, Hexamer 1j (0.387 mmol, 0.594 g) was added and dissolved in THF:MeOH (7:3, 28:12 mL, respectively). Next, $NaBH_4$ (2.32 mmol, 0.088 g) was added slowly in portions at room temperature for 6.5 h. The solvent was removed by roto-evaporation, the residue dissolved in 125 mL ethyl acetate and washed 3×50 mL of $H_2O$. The organic layer was separated, dried over $Na_2SO_4$ and the solvent removed by roto-evaporation. The resulting residue was recrystallized from $CH_2Cl_2$ and MeOH affording a white solid (0.440 g; 74% yield). $^1$H NMR (400 MHz, $CDCl_3$): δ 6.86 (s, 6H, ArH), 4.10-4.00 (t, 6H, $^3J$=6.6 Hz, $CH_2C(O)OCH_2(CH_2)_{14}CH_3$), 3.87-3.69 (dd, 6H, $^3J$=13.7 Hz, $^3J$ (CNH)=42.4 Hz $CH_2$—CH—N), 3.43 (s, 6H, $CH_2C(O)OCH_2(CH_2)_{14}CH_3$), 2.40-2.28 (m, 6H, aliphatic), 2.15-1.95 (m, 6H, aliphatic), 1.75-1.60 (m, 6H, aliphatic), 1.60-1.55 (m, 6H, aliphatic) 1.37-1.05 (m, 84H, aliphatic) 0.92-0.86 (t, 9H, $^3J$=6.8 Hz. ESIMS (+) Calcd for $C_{96}H_{163}N_6O_9$: 1544; Found: 1545 [M+H]$^+$.

Example 63

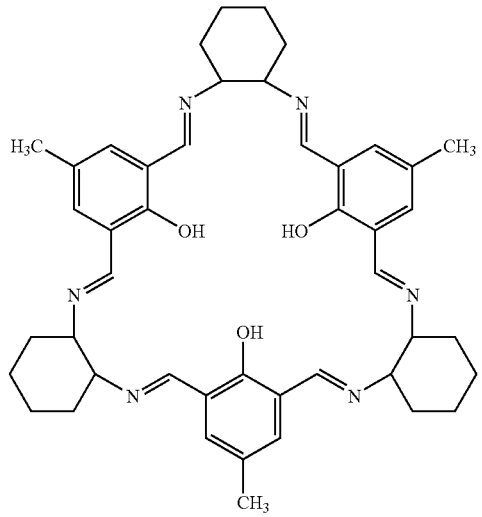

Hexamer 1a-Me-1,2-imine

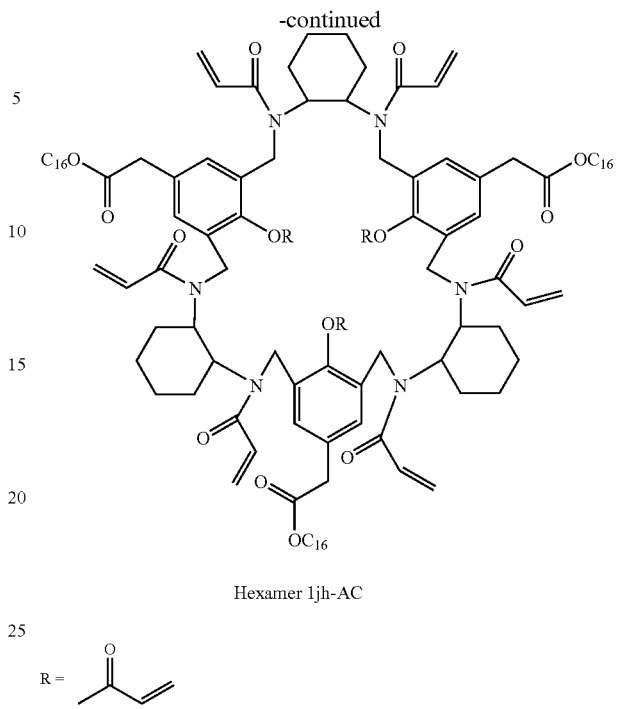

Hexamer 1jh-AC

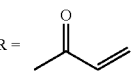

Hexamer 1A-Me. A solution of 2-hydroxy-5-methyl-1,3-benzenedicarboxaldehye (53 mg, 0.32 mmol) in dichloromethane (0.6 mL) was added to a solution of (1R,2R)-(−)-1,2-diaminocyclohexane (37 mg, 0.32 mmol) in dichloromethane (0.5 mL). The mixture was stirred at ambient temperature for 16 h, added dropwise to methanol (75 mL) and chilled (4° C.) for 4 h. The precipitate was collected to afford 71 mg (92%) of hexamer 1A-Me. $^1$H NMR (CDCl$_3$): δ 13.88 (s, 3H, OH), 8.66 (s, 3H, ArCH=N), 8.19 (s, 3H, ArCH=N), 7.52 (d, 3H, J=2 Hz, Ar H), 6.86 (d, 3H, J=2 Hz, Ar H), 3.35 (m, 6H, cyclohexane 1,2-H's), 2.03 (3, 9H, Me), 1.6-1.9 (m, 18H, cyclohexane 3,6-H$_2$ and 4$_{eq}$,5$_{eq}$-H's), 1.45 (m, 6H, cyclohexane 4$_{ax}$,5$_{ax}$-H's); $^{13}$C NMR δ 63.67, 159.55, 156.38, 134.42, 129.75, 127.13, 119.00, 75.68, 73.62, 33.68, 33.41, 24.65, 24.57, 20.22; ESI(+) MS m/e (%) 727 M+H (100); IR 1634 cm$^{-1}$.

Example 64

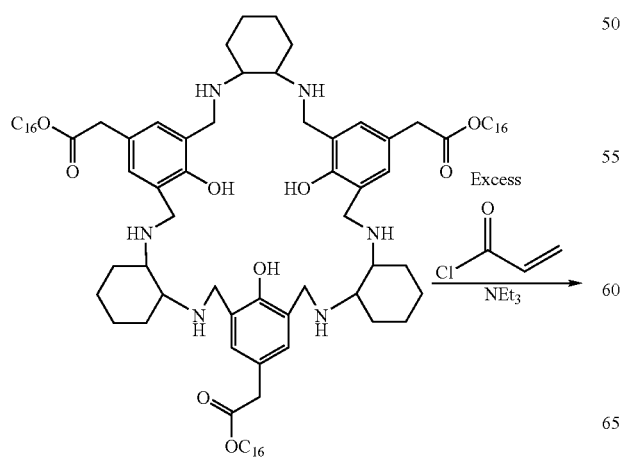

32.7 mg Hexamer 1jh (recrystallized times) was added to 30 mL dry THF. 100 μL triethylamine and 100 μL acryloyl chloride (freshly distilled) were added subsequently to the THF mixture using Schlenk technique. Solution was stirred for 18 hrs in an acetone/dry ice bath. After removal of solvent a white precipitate remained. The precipitate was redissolved in CH$_2$Cl$_2$ and filtered through a fritted funnel. CH$_2$Cl$_2$ solution was added to the separatory funnel and washed one time with water followed by two brine (NaCl) washes. The CH$_2$Cl$_2$ solution was dried over MgSO$_4$ and then filtered to remove MgSO$_4$. A yellow precipitate remained after solvent removal. $^1$H NMR (CDCl$_3$): δ-0.867-0.990 (3H), 1.259 (21.8H), 1.39 (1.86H), 1.64 (12.7H), 2.8 (1.25H), 3.46-3.62 (2.47H), 3.71 (0.89H), 3.99 (2.46H), 5.06 (0.71H), 5.31 (3.80H), 5.71 (1.43H), 5.90 (0.78H), 6.2-6.4 (2.49H), 6.59 (0.80H), 6.78 (0.47H), 6.98 (0.28H). FTIR-ATR: 3340, 2926 (—CH$_2$—), 2854 (—CH$_2$—), 1738 (Ester Carbonyl), 1649 and 1613 (Acrylate), 983 (=CH), 959 sh (=CH$_2$). ESI-MS: 1978.5 (Hex1JhAC+8-AC), 1948.8 (Hex1JhAC+7-AC+Na$^+$), 1923.3 (Hex1JhAC+7-AC), 1867.6 (Hex1JhAC+6-AC), 1842.6, 1759.7 (Hex1JhAC+4-AC).

We claim:

1. A bridged macrocyclic module compound of the formula:

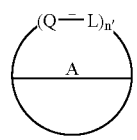

wherein each Q is a synthon independently selected from: benzene, cyclohexadiene, cyclopentadiene, naphthalene, biphenyl, cyclohexane, cyclohexene, decalin, cyclopentane, and cyclopentene, wherein each synthon Q is optionally substituted with one or more functional groups for coupling the synthon to at least a second bridged macrocyclic module or to a substrate;

wherein each synthon Q is optionally substituted with one or more groups chosen from lipophilic groups and hydrophilic groups;

wherein each L is a linkage moiety independently selected from: —N(R)—, —NRC(O)—, —C(O)NR—, —CH=N—, and —N=CH—;

wherein R is H, aryl, heteroaryl, cyclic hydrocarbon, —NH$_2$, —OH, —CN, —NO$_2$, —COOH, or —CHO;

wherein the bridge moiety A is selected from:
—O(CH$_2$)$_m$—O—;
—O(CH$_2$CH$_2$O)$_m$—;
—(OCH(CH$_3$)CH$_2$)$_m$O—;

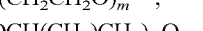

wherein n' is 4 to 16; and wherein m is 2 to 14.

2. The compound of claim 1, wherein the bridged macrocyclic module compound is selected from:

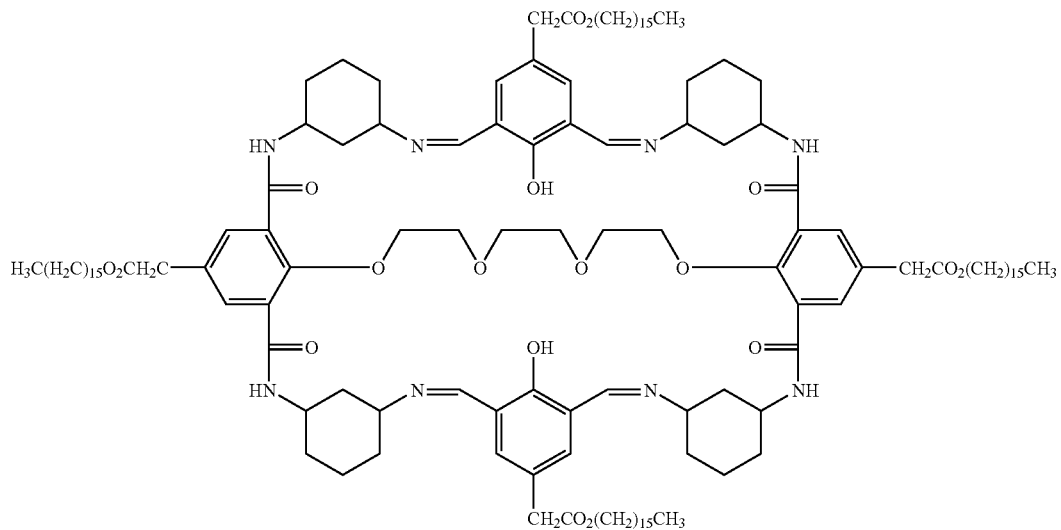

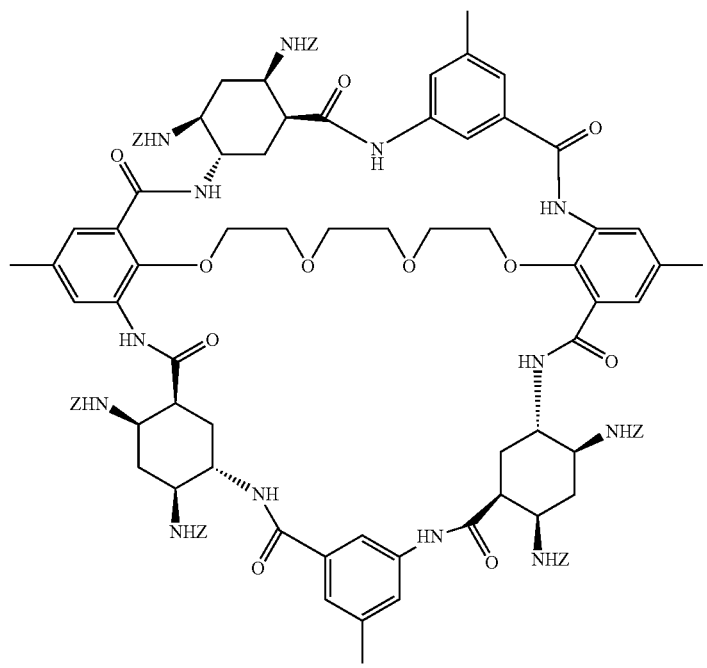

wherein each Z is independently H, a lipophilic group, or a hydrophilic group.

3. The compound of claim 1, wherein n' is from 4 to 12.

4. The compound of claim 1, wherein n' is from 6 to 12.

5. The compound of claim 1, having the formula:

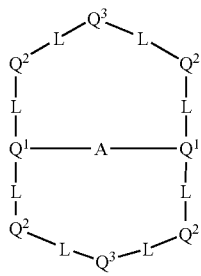

wherein Q1, Q2, and Q3 are Q, wherein each Q is a synthon independently selected from: benzene, cyclohexadiene, cyclopentadiene, naphthalene, biphenyl, cyclohexane, cyclohexene, decalin, cyclopentane, and cyclopentene, wherein each synthon Q is optionally substituted with one or more functional groups for coupling the synthon to at least a second bridged macrocyclic module or to a substrate;

wherein each synthon Q is optionally substituted with one or more groups chosen from lipophilic groups and hydrophilic groups;

wherein each L is a linkage moiety independently selected from: —N(R)—, —NRC(O)—, —C(O)NR—, —CH=N—, and —N=CH—;

wherein R is H, aryl, heteroaryl, cydic hydrocarbon, —NH$_2$, —OH, —CN, —NO$_2$, —COCH, or —CHO;

wherein the bridge moiety A is selected from:
—O(CH$_2$)$_m$—O—;
—O(CH$_2$CH$_2$O)$_m$—;
—(OCH(CH$_3$)CH$_2$)$_m$O—;

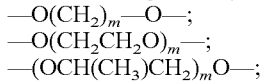

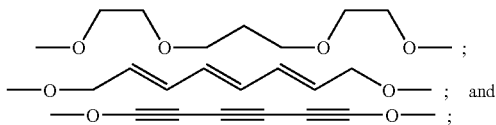

and
wherein m is 2 to 14.

6. The compound of claim 5, wherein each Q$^1$ is the same synthon.

7. The compound of claim 5, wherein each Q$^2$ is the same synthon.

8. The compound of claim 5, wherein each Q$^3$ is the same synthon.

9. The compound of claim 5, wherein each L between the synthons is the same.

10. A nanofilm comprising a plurality of bridged macrocyclic modules of claim 1.

11. The nanofilm of claim 10, wherein the thickness of the nanofilm composition is less than about 30 nanometers.

12. The nanofilm of claim 10, wherein the thickness of the nanofilm composition is less than about 6 nanometers.

13. The nanofilm of claim 10, wherein the nanofilm is impermeable to viruses and larger species.

14. The nanofilm of claim 10, wherein the nanofilm is impermeable to immunoglobulin G and larger species.

15. The nanofilm of claim 10, wherein the nanofilm is impermeable to albumin and larger species.

16. The nanofilm of claim 10, wherein the nanofilm is impermeable to β2-Microglobulin and larger species.

17. The nanofilm of claim 10, wherein the nanofilm is permeable only to water and smaller species.

18. The nanofilm of claim 10, wherein the nanofilm has a molecular weight cut-off of 13 kDa.

19. The nanofilm of claim 10, wherein the nanofilm has a molecular weight cut-off of 190 Da.

20. The nanofilm of claim 10, wherein the nanofilm has a molecular weight cut-off of 100 Da.

21. The nanofilm of claim 10, wherein the nanofilm has a molecular weight cut-off of 45 Da.

22. The nanofilm of claim 10, wherein the nanofilm has a molecular weight cut-off of 20 Da.

23. The nanofilm of claim 10, wherein the nanofilm has high permeability for water molecules and Na+, K+, and Cs+ in water.

24. The nanofilm of claim 10, wherein the nanofilm has low permeability for glucose and urea.

25. The nanofilm of claim 10, wherein the nanofilm has high permeability for water molecules and Cl– in water.

26. The nanofilm of claim 10, wherein the nanofilm has high permeability for water molecules and K+ in water, and low permeability for Na+ in water.

27. The nanofilm of claim 10, wherein the nanofilm has high permeability for water molecules and Na+ in water, and low permeability for K+ in water.

28. The nanofilm of claim 10, wherein the nanofilm has low permeability for urea, creatinine, Li+, Ca2+, and Mg2+ in water.

29. The nanofilm of claim 10, wherein the nanofilm has high permeability for Na+, K+, hydrogen phosphate, and dihydrogen phosphate in water.

30. The nanofilm of claim 10, wherein the nanofilm has high permeability for Na+, K+, and glucose in water.

31. The nanofilm of claim 10, wherein the nanofilm has low permeability for myoglobin, ovalbumin, and albumin in water.

32. The nanofilm of claim 10, wherein the nanofilm has high permeability for organic compounds and low permeability for water.

33. The nanofilm of claim 10, wherein the nanofilm has low permeability for organic compounds and high permeability for water.

34. The nanofilm of claim 10, wherein the nanofilm has low permeability for water molecules and high permeability for helium and hydrogen gases.

* * * * *